US012616848B2

(12) United States Patent
Bourke, Jr. et al.

(10) Patent No.: US 12,616,848 B2
(45) **Date of Patent: *May 5, 2026**

(54) ENERGY AUGMENTATION STRUCTURES, ENERGY EMITTERS OR ENERGY COLLECTORS CONTAINING THE SAME, AND THEIR USE IN SOLAR CELLS AND OTHER ENERGY CONVERSION DEVICES

(71) Applicant: IMMUNOLIGHT, LLC, Detroit, MI (US)

(72) Inventors: Frederic A. Bourke, Jr., Aspen, CO (US); Harold Walder, Oak Island, NC (US); Zakaryae Fathi, Raleigh, NC (US); Wayne F. Beyer, Jr., Ivanhoe, VA (US); Ronald A. Rudder, Clarksville, VA (US); Daniel I. Becker, Detroit, MI (US); Joseph H. Simmons, Tucson, AZ (US)

(73) Assignee: IMMUNOLIGHT, LLC, Detroit, MI (US)

( * ) Notice: Subject to any disclaimer, the term of this patent is extended or adjusted under 35 U.S.C. 154(b) by 35 days.

This patent is subject to a terminal disclaimer.

(21) Appl. No.: 18/541,531

(22) Filed: Dec. 15, 2023

(65) Prior Publication Data

US 2024/0115878 A1 Apr. 11, 2024

Related U.S. Application Data

(63) Continuation of application No. 17/433,827, filed as application No. PCT/US2020/020118 on Feb. 27, 2020, now Pat. No. 11,998,760.
(Continued)

(51) Int. Cl.
*H10F 77/42* (2025.01)
*A61K 35/12* (2015.01)
(Continued)

(52) U.S. Cl.
CPC .............. *A61N 5/062* (2013.01); *A61K 35/12* (2013.01); *A61K 41/00* (2013.01);
(Continued)

(58) Field of Classification Search
CPC .................. H02S 40/20–22; H10F 77/40–496
(Continued)

(56) References Cited

U.S. PATENT DOCUMENTS

| | | | |
|---|---|---|---|
| 4,940,495 | A | 7/1990 | Weber |
| 7,538,641 | B2 | 5/2009 | Puente Baliarda et al. |

(Continued)

FOREIGN PATENT DOCUMENTS

| | | | |
|---|---|---|---|
| CN | 205881926 U * | 1/2017 | |
| EP | 1 917 556 B1 | 5/2008 | |

(Continued)

OTHER PUBLICATIONS

CN-205881926-U English (Year: 2017).*
(Continued)

*Primary Examiner* — Bach T Dinh
(74) *Attorney, Agent, or Firm* — TUCKER ELLIS LLP; J. Derek Mason

(57) ABSTRACT

An emission enhancement structure having at least one energy augmentation structure; and an energy converter capable of receiving energy from an energy source, converting the energy and emitting therefrom a light of a different energy than the received energy. The energy converter is disposed in a vicinity of the at least one energy augmentation structure such that the emitted light is emitted with an intensity larger than if the converter were remote from the at least one energy augmentation structure. Also described are various uses for the energy emitters, energy augmentation
(Continued)

structures and energy collectors in a wide array of fields, especially in the field of solar cells and other energy conversion devices.

71 Claims, 93 Drawing Sheets

Related U.S. Application Data

(60) Provisional application No. 62/955,533, filed on Dec. 31, 2019, provisional application No. 62/946,648, filed on Dec. 11, 2019, provisional application No. 62/897,677, filed on Sep. 9, 2019, provisional application No. 62/855,508, filed on May 31, 2019, provisional application No. 62/813,390, filed on Mar. 4, 2019.

(51) Int. Cl.

| | |
|---|---|
| ***A61K 41/00*** | (2020.01) |
| ***A61N 5/06*** | (2006.01) |
| ***A61N 5/067*** | (2006.01) |
| ***C09J 133/08*** | (2006.01) |
| ***C09K 11/02*** | (2006.01) |
| ***C12N 15/01*** | (2006.01) |
| ***F21K 2/00*** | (2006.01) |
| ***F21S 11/00*** | (2006.01) |
| ***F21V 9/40*** | (2018.01) |
| ***H10F 10/10*** | (2025.01) |
| ***H10F 77/14*** | (2025.01) |
| *A23B 2/50* | (2025.01) |
| *H10F 77/45* | (2025.01) |

(52) U.S. Cl.
CPC ........ *A61K 41/0057* (2013.01); *A61N 5/0601* (2013.01); *A61N 5/067* (2021.08); *C09J 133/08* (2013.01); *C09K 11/025* (2013.01); *C12N 15/01* (2013.01); *F21K 2/00* (2013.01); *F21S 11/007* (2013.01); *F21V 9/40* (2018.02); *H10F 10/10* (2025.01); *H10F 77/14* (2025.01); *H10F 77/147* (2025.01); *H10F 77/42* (2025.01); *A23B 2/50* (2025.01); *A61N 2005/0661* (2013.01); *A61N 2005/0662* (2013.01); *A61N 2005/0663* (2013.01); *H10F 77/45* (2025.01)

(58) Field of Classification Search
USPC .................................................. 136/243–265
See application file for complete search history.

(56) References Cited

U.S. PATENT DOCUMENTS

| | | | | |
|---|---|---|---|---|
| 8,376,013 | B2 | 2/2013 | Bourke | |
| 8,389,958 | B2 | 3/2013 | Vo-Dinh | |
| 8,618,509 | B2 | 12/2013 | Vo-Dinh | |
| 8,658,086 | B2 | 2/2014 | Bourke | |
| 8,927,615 | B2 | 1/2015 | Bourke | |
| 9,004,131 | B2 | 4/2015 | Bourke | |
| 9,005,406 | B2 | 4/2015 | Bourke | |
| 9,023,249 | B2 | 5/2015 | Fathi | |
| 9,174,190 | B2 | 11/2015 | Bourke | |
| 9,232,618 | B2 | 1/2016 | Bourke | |
| 9,278,331 | B2 | 3/2016 | Bourke | |
| 9,488,916 | B2 | 11/2016 | Bourke | |
| 9,526,914 | B2 | 12/2016 | Vo-Dinh | |
| 9,579,523 | B2 | 2/2017 | Bourke | |
| 9,630,022 | B2 | 4/2017 | Bourke | |
| 9,649,832 | B2 | 5/2017 | Fathi | |
| 9,662,389 | B2 | 5/2017 | Vo-Dinh | |
| 9,676,918 | B2 | 6/2017 | Fathi | |
| 9,701,102 | B2 | 7/2017 | Fathi | |
| 9,715,159 | B1 | 7/2017 | Akselrod et al. | |
| 9,907,976 | B2 | 3/2018 | Bourke | |
| 9,937,695 | B2 | 4/2018 | Fathi | |
| 10,026,711 | B2 | 7/2018 | Fathi | |
| 10,029,117 | B2 | 7/2018 | Bourke | |
| 10,074,627 | B2 | 9/2018 | Fathi | |
| 10,080,275 | B2 | 9/2018 | Bourke | |
| 10,087,343 | B2 | 10/2018 | Fathi | |
| 10,093,784 | B2 | 10/2018 | Fathi | |
| 10,201,796 | B2 | 2/2019 | Bourke | |
| 10,213,763 | B2 | 2/2019 | Bourke | |
| 10,283,476 | B2 | 5/2019 | Fathi | |
| 10,363,541 | B2 | 7/2019 | Bourke | |
| 10,410,991 | B2 | 9/2019 | Fathi | |
| 10,494,500 | B2 | 12/2019 | Fathi | |
| 10,575,541 | B2 | 3/2020 | Bourke | |
| 10,593,642 | B2 | 3/2020 | Fathi | |
| 10,682,624 | B2 | 6/2020 | Bourke | |
| 10,717,062 | B2 | 7/2020 | Bourke | |
| 10,734,353 | B2 | 8/2020 | Fathi | |
| 10,748,868 | B2 | 8/2020 | Fathi | |
| 10,847,666 | B2 | 11/2020 | Bourke | |
| 10,874,123 | B2 | 12/2020 | Bourke | |
| 10,899,907 | B2 | 1/2021 | Fathi | |
| 10,974,493 | B2 | 4/2021 | Fathi | |
| 11,173,467 | B2 | 11/2021 | Bourke | |
| 11,270,973 | B2 | 3/2022 | Fathi | |
| 11,278,861 | B2 | 3/2022 | Bourke | |
| 11,345,833 | B2 | 5/2022 | Fathi | |
| 11,476,222 | B2 | 10/2022 | Fathi | |
| 11,589,432 | B2 | 2/2023 | Bourke | |
| 11,648,750 | B2 | 5/2023 | Fathi | |
| 11,678,682 | B2 | 6/2023 | Bourke | |
| 11,998,760 | B2 * | 6/2024 | Bourke, Jr. | H10F 77/147 |
| 2004/0233512 | A1 | 11/2004 | Fujioka | |
| 2008/0057000 | A1 | 3/2008 | Loveridge | |
| 2008/0248001 | A1 | 10/2008 | Bourke | |
| 2009/0078316 | A1 | 3/2009 | Khazeni | |
| 2009/0159510 | A1 | 6/2009 | Haushalter | |
| 2009/0314333 | A1 | 12/2009 | Shepard | |
| 2010/0188171 | A1 | 7/2010 | Mohajer-Iravani et al. | |
| 2010/0261263 | A1 | 10/2010 | Vo-Dinh et al. | |
| 2010/0284086 | A1 * | 11/2010 | Novack | H01Q 1/248 359/580 |
| 2011/0063189 | A1 * | 3/2011 | Cohen | H01Q 19/00 343/899 |
| 2011/0126889 | A1 * | 6/2011 | Bourke, Jr. | H10F 77/45 362/552 |
| 2011/0226317 | A1 | 9/2011 | Xu | |
| 2012/0139349 | A1 | 6/2012 | Fornage | |
| 2013/0019945 | A1 | 1/2013 | Hekmatshoar-Tabari | |
| 2013/0056712 | A1 | 3/2013 | Jain | |
| 2013/0171060 | A1 | 7/2013 | Vo-Dinh | |
| 2014/0269806 | A1 | 9/2014 | Bora et al. | |
| 2014/0272030 | A1 | 9/2014 | Bourke | |
| 2014/0277294 | A1 | 9/2014 | Jones | |
| 2014/0323946 | A1 | 10/2014 | Bourke, Jr. | |
| 2015/0014022 | A1 | 1/2015 | Young | |
| 2015/0314526 | A1 * | 11/2015 | Cohen | H01Q 9/40 343/907 |
| 2016/0027949 | A1 | 1/2016 | Cooke | |
| 2016/0181456 | A1 | 6/2016 | Zhang | |
| 2017/0154866 | A1 | 6/2017 | Fathi et al. | |
| 2017/0167977 | A1 | 6/2017 | Rivera | |
| 2017/0239489 | A1 | 8/2017 | Bourke, Jr. | |
| 2018/0269174 | A1 | 9/2018 | Fathi et al. | |
| 2018/0271121 | A1 | 9/2018 | Bourke, Jr. et al. | |
| 2018/0317307 | A1 | 11/2018 | Bourke, Jr. et al. | |
| 2018/0358327 | A1 | 12/2018 | Fathi et al. | |
| 2020/0295461 | A1 | 9/2020 | Luk | |
| 2020/0323711 | A1 | 10/2020 | Bourke | |
| 2020/0357943 | A1 | 11/2020 | Rotschild | |
| 2021/0353954 | A1 | 11/2021 | Bourke | |
| 2022/0146076 | A1 | 5/2022 | Bourke | |
| 2022/0148997 | A1 | 5/2022 | Bourke | |
| 2022/0181292 | A1 | 6/2022 | Fathi | |

(56) References Cited

U.S. PATENT DOCUMENTS

| | | | |
|---|---|---|---|
| 2022/0275914 | A1 | 9/2022 | Bourke |
| 2022/0315809 | A1 | 10/2022 | Bourke |
| 2023/0191747 | A1 | 6/2023 | Fathi |

FOREIGN PATENT DOCUMENTS

| | | | |
|---|---|---|---|
| EP | 2 028 225 A1 | 2/2009 | |
| KR | 10-1928757 | 1/2014 | |
| WO | WO 99/11727 | 3/1999 | |
| WO | WO 2010/107720 A2 | 9/2010 | |

OTHER PUBLICATIONS

Examination Report issued Mar. 28, 2025, in European Patent Application No. 20 765 910, filed Feb. 28, 2020.

International Search Report and Written Opinion issued on Aug. 12, 2020 in PCT/US2020/020118 filed Feb. 27, 2020.

Abdellatif, S., et al., "Nanowire Photovotaic Efficiency Enhancement Using Plasmonic Coupled Nano-Fractal Antennas", Optics Letters, vol. 38, No. 18, 2013, pp. 3680-3683, 5 pp.

Zhu et al., Broadband Absorption and Efficiency Enhancement of an Ultra-Thin Silicon Solar Cell With a Plasmonic Fractal, Optics Express, vol. 21, No. S3 (2013).

P. Jung, et al., "Progress in Superconducting Metamaterials", Superconductor Science and Technology, 27, 2014, 13pp.

P. Cai, et al., "Synthesis and Realization of Novel Ultra-Wideband Bandpass Filters Using 3/4 Wavelength Parallel-Coupled Line Resonators", Proceedings of Asia-Pacific Microwave Conference, 2006, 4pp.

Search Report issued Mar. 14, 2023, in European Patent Application No. 20766537.3.

Search Report issued Mar. 24, 2023, in European Patent Application No. 20766868.2.

Search Report issued Feb. 17, 2023, in European Patent Application No. 20765906.1.

Search Report issued Feb. 21, 2023, in European Patent Application No. 20767183.5.

K. Watanabe, et al., "A Microstrip Uwb Bandpass Filter Using a Stub-Loaded Dual-Mode Ring Resonator and a Step Impedance Two-Mode Resonator", Microwave Conference, 2008, 4pp. XP031636965.

L. Snehalatha, et al., "A Compact Half-Wave Folded Waveguide Resonator for Dual-Band Applications", National Conference on Recent Advances in Electronics & Computer Engineering, 2015, 4pp., XP032923138.

* cited by examiner array of fractal antennas 32

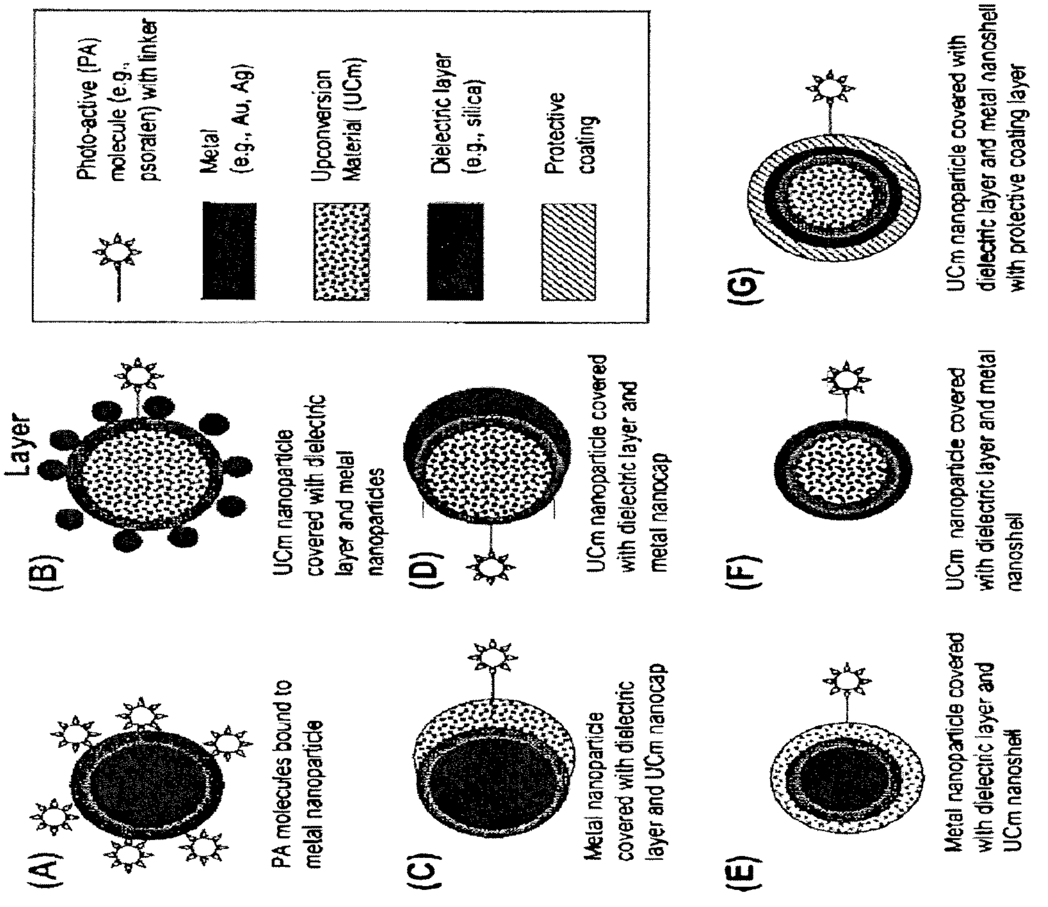

Figure 41B

UC Plasmonics Photo-active Probes With Dielectric Layer

Photo-active (PA) molecule (e.g., psoralen) with linker

Metal (e.g., Au, Ag)

Upconversion Material (UCm)

Dielectric layer (e.g., silica)

Protective coating (A) PA molecules bound to metal nanoparticle (B) UCm nanoparticle covered with dielectric layer and metal nanoparticles (C) Metal nanoparticle covered with dielectric layer and UCm nanocap (D) UCm nanoparticle covered with dielectric layer and metal nanocap (E) Metal nanoparticle covered with dielectric layer and UCm nanoshell (F) UCm nanoparticle covered with dielectric layer and metal nanoshell (G) UCm nanoparticle covered with dielectric layer and metal nanoshell with protective coating layer

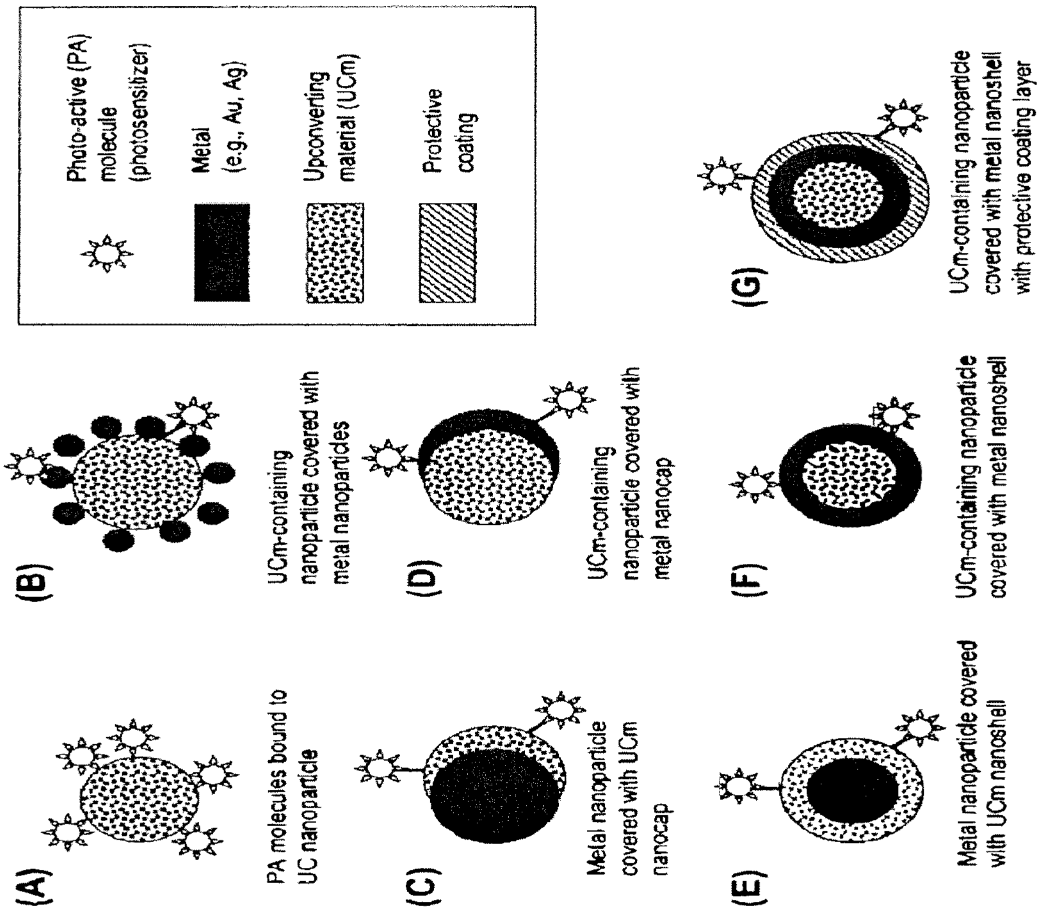

Figure 41D

Photo-active (PA) molecule (photosensitizer)

Metal (e.g., Au, Ag)

Upconverting material (UCm)

Protective coating (A) PA molecules bound to UC nanoparticle (B) UCm-containing nanoparticle covered with metal nanoparticles (C) Metal nanoparticle covered with UCm nanocap (D) UCm-containing nanoparticle covered with metal nanocap (E) Metal nanoparticle covered with UCm nanoshell (F) UCm-containing nanoparticle covered with metal nanoshell (G) UCm-containing nanoparticle covered with metal nanoshell with protective coating layer Solar or Non-solar energy source Power converter with or without spectrum converter Light controller with or without spectrum converter Controller Fiber Bundle Interface Fiber Bundles Room #1

Room #2

Room #3

Figure 43

| Module Cost Per Watt | | | | | | | |
|---|---|---|---|---|---|---|---|
| Technology | Substrate | Junctio n | Module Efficienc y | Cost Per Watt 2011 | Cost Per Watt 2016 | Cost Per Watt 2021 | Production |
| a-Si (1x) | rigid glass | Single | 0.06 | $ 1.41 | $ 1.07 | $ 0.83 | Hi Volume |
| a-Si (3x) | flexible steel | Triple | 0.078 | $ 1.42 | $ 1.08 | $ 0.85 | Hi Volume |
| aSi/mcSi (2x) | rigid glass | Dual | 0.085 | $ 1.08 | $ 0.79 | $ 0.63 | Hi Volume |
| CdTe | rigid glass | Single | 0.095 | $ 0.98 | $ 0.71 | $ 0.54 | Hi Volume |
| CIGS | rigid glass | Single | 0.1 | $ 1.19 | $ 0.81 | $ 0.62 | Limited |
| CIGS | flexible steel | Single | 0.095 | $ 1.25 | $ 0.83 | $ 0.62 | N/A |
| Organic Dye | rigid flexible | Single | 0.05 | - | - | - | N/A |
| c-Si | Rigid Si wafers | Single | 0.131 | $ 1.20 | $ 1.38 | $ 1.10 | Hi Volume |

PRIOR ART

Stacked array of folded resonators

ENERGY AUGMENTATION STRUCTURES, ENERGY EMITTERS OR ENERGY COLLECTORS CONTAINING THE SAME, AND THEIR USE IN SOLAR CELLS AND OTHER ENERGY CONVERSION DEVICES

CROSS REFERENCE TO RELATED APPLICATIONS

This application is a Continuation of U.S. Ser. No. 17/433,827, filed Aug. 25, 2021, pending, which is a 371 of international PCT application PCT/US2020/020118, filed Feb. 27, 2020, the entire disclosures of each of which are incorporated herein by reference. This application is related to, and claims priority to, provisional application U.S. Ser. No. 62/955,533, filed Dec. 31, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/946,648, filed Dec. 11, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/897,677, filed Sep. 9, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/855,508, filed May 31, 2019, entitled ENERGY AUGMENTATION STRUCTURE; ENERGY COLLECTOR CONTAINING THE SAME; AND COLOR ENHANCEMENT UTILIZING AT LEAST ONE ENERGY AUGMENTATION STRUCTURE, the entire disclosure of which is hereby incorporated by reference. This application is related to, and claims priority to, provisional application U.S. Ser. No. 62/813,390, filed Mar. 4, 2019, entitled COLOR ENHANCEMENT UTILIZING AT LEAST ONE ENERGY AUGMENTATION STRUCTURE, the entire disclosure of which is hereby incorporated by reference. This application is related to U.S. application Ser. No. 16/599,732, filed Oct. 11, 2019, pending, which claims priority to provisional application U.S. Ser. No. 62/745,057, filed Oct. 12, 2018, the entire contents of each of which are hereby incorporated by reference. This application is related to U.S. Ser. No. 13/204,355 filed Aug. 5, 2011, the entire disclosures of which are hereby incorporated by reference. This application is related to U.S. provisional patent application 61/371,549, filed Aug. 6, 2010. This application is related to U.S. provisional patent application 61/161,328, filed Mar. 18, 2009 and to U.S. provisional patent application 61/259,940, filed Nov. 10, 2009, the entire disclosures of which are hereby incorporated by reference. This application is related to U.S. Ser. No. 12/725,108, the entire disclosures of which are hereby incorporated by reference.

This application is related to Provisional Application Ser. No. 60/954,263, filed Aug. 6, 2007, and 61/030,437, filed Feb. 21, 2008, and U.S. application Ser. No. 12/059,484, filed Mar. 31, 2008, the contents of which are hereby incorporated herein by reference. This application is also related to U.S. application Ser. No. 11/935,655, filed Nov. 6, 2007; and Provisional Application Ser. No. 61/042,561, filed Apr. 4, 2008; 61/035,559, filed Mar. 11, 2008, and 61/080,140, filed Jul. 11, 2008, the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009, the entire disclosures of which are hereby incorporated by reference.

BACKGROUND OF THE INVENTION

Field of the Invention

The invention relates to methods, systems, and devices for energy augmentation, with and without an energy modulation agent/energy conversion agent present, and uses particularly for generating or enhancing photon or electron emission and/or for enhancing light or photon collection, especially in the area of solar cells and other energy conversion devices.

Discussion of the Background

Presently, light (i.e., electromagnetic radiation from the radio frequency through the visible to the X-ray wavelength range) is used in a number of industrial, communication, electronic, and pharmaceutical processes. Light in the infrared and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged particles, such as parts of molecules (or adjacent atoms) with high thermal energy, or electrons in atoms (or molecules).

For reference purposes, infra-red (IR) radiation just beyond the red end of the visible region; and, ultra-violet (UV) radiation has a shorter wavelength than violet light. The UV portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including W-filaments, halogen-protected W-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ ($lm/m^2$) in a certain direction per steradian (unit of solid angle) and the irradiance (illuminance) of a surface in $W/m^2$ ($lm/m^2$ or lux).

With the development of ultraviolet sources, ultraviolet radiation is being increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

With the development of infrared radiation sources, infrared radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many, if not all, of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Indeed, workers have studied the phenomenon of photoluminescence and fluorescence, which is the ability of certain solids to emit light when driven or charged by an external energy source. Many well-known phosphors and fluorescors are triggered by high-energy electrons or photons and emit photons of lower energy. It has been recognized that certain infrared phosphors can convert infrared light to light in the visible range (violet through red).

The properties of light such as its radiance is particularly important in reading or display applications where the human eye has to perceive and discern temporary images or permanent images (as for example shown by road and highway signs) formed with visible light. Televisions, computer monitors, displays, and signs use a cathode ray technology (CRT) technology where high energy electrons impinge on phosphors that emit visible light. Televisions, computer monitors, displays, and signs more recently have used liquid crystal display or plasma display technology to generate visible images discernable to the human eye.

In these and other reading or display applications, attempts have been made to develop displays with relatively high contrast images while minimizing the amount of broadband light emitted or reflected from a display, which may detract from the contrast of the image displayed.

In general, the up conversion and the down conversion discussed above have been used in a number of fields to in effect convert an incident wavelength of light to a different wavelength. In one example, high energy photons such as X-rays are converted by absorption in phosphors of the x-ray energy, and luminescence from the phosphors in the ultraviolet, visible, and/or near infrared spectrum has been used for driving photoactive reactions. In other examples, infrared or near infrared light has been up converted by absorption in phosphors of the infrared or near infrared light, and luminescence from the phosphors in the visible and/or ultraviolet spectrum. In other examples, light within the visible region can be down converted or up converted (depending on the phosphors chosen) to a different band within the visible wavelengths. This shifting (energy conversion) can be for color enhancement and can be used in solar cells to convert one part of the solar spectrum to another part more favorable for a photovoltaic device to generate power.

In many of these prior applications, metallic structures have been placed on the phosphors or in a vicinity of the phosphors to generate a plasmonics effect which essentially is an amplification of the local field very nearby the outside of the metallic structures. Plasmonic effects can enhance coupling of incident light into the phosphors and/or enhance the reactivity of the converted light tons nearby receptor. While the plasmons in the metal can propagate along the metal, the plasmons decay evanescently in the z direction normal to the metal/dielectric interface with 1/e decay length of the order of half the wavelength (~200 nm for wavelengths in the visible range).

In some prior applications, photonic band gap structures have been used. In a photonics band gap structure, the materials thereof consist or photonic crystals (PhCs) are materials with a periodic dielectric profile, which can prevent light of certain frequencies or wavelengths from propagating in one, two or any number of directions within the materials. In this way, light not suitable or detrimental to a process can be rejected while light more suitable for a process can be confined within the photonic band gap structure or better confined within the photovoltaic converter.

A conventional solar cell uses monocrystalline silicon to convert solar radiation into usable energy. Other semiconductor materials besides silicon can be used, and these materials (including silicon) can exist in the solar cell in amorphous or polycrystalline form. Organic materials can also be used for solar cell conversion. Tandem solar cell arrangements are also used which include different semiconductor materials where each layer in the tandem is made of a specific band gap material designed to "match" better the solar cell the sun's spectrum of light.

A solar cell covered on monocrystalline silicon is usually a p-type semi-conductive monocrystalline silicon wafer, which is realized by doping boron compound into a monocrystalline silicon. Antimony or other suitable n-type dopant is included in the silicon to form a form p-n junction typically a layer on or near the silicon surface to be exposed to the sun's light. The thickness of n-type layer is usually from 0.5-3 μm. The n-type layer is connected to a contact electrode (e.g., gold or an alloy thereof or a transparent metal oxide such as indium tin oxide) on its front surface. The back of the silicon wafer is usually completely covered with a metal electrode or silver deposited electrode.

When a solar cell device is excited by the radiation of the sun or artificial light, the photons absorbed by semiconductor material result in unbalanced hole-electron pair production. At this moment, the electrons in the p-layer close to the p-n junction drift to the boundary at the p-n junction and are attracted into the n-type junction by the self-imposed electric field existing across the p-n junction. The holes (p-type carriers) in the n-type junction will partially drift into the interior, i.e. the p-type region. This drifts results in adding extra negative charges into the n-type material and adding extra positive charges into the p-type material, leading to a voltage for an outside circuit. A semiconductor power source of this kind has the n-type junction as the cathode and p-type junction as the anode.

The effective working efficiency of the simplest framework of this kind of solar cell assembly is 15 to 16%.

According to the solar radiation spectrum measured in the medium latitude region (at northern latitude 48°, for example), when the Sun is 450 above the horizon, the maximum-energy wavelength of the solar spectrum reaching the earth surface is between 290-1060 nm. When a solar cell works in the near-space environment, the complete spectrum also contains the short-wavelength radiation of UV and VUV and the medium-wavelength radiation of far-red longer than 1065 nm.

However, the energy distribution of the solar radiation spectrum is uneven. The maximum energy of the solar radiation appears in the blue light (λ=470 nm). The solar radiation is reduced by 20% in the main section of visible light between the wavelength 500-600 nm, and the corresponding radiation is half at λ=720 nm. Furthermore, the radiation at λ=1000 nm=1 μm is only ⅕ of the maximum value.

At a wavelength range between λ=950~980 nm, the silicon solar cell assembly is most responsive with the maximum sensitivity because the energy band structure of the monocrystalline silicon has a bandgap Eg of 1.21 ev, which corresponds to the wavelength of λ=950 nm. On the other hand, the solar cell assembly is virtually non-responsive to the ultraviolet (λ<4 00 nm), i.e. silicon cannot efficiently convert this ultraviolet light.

Solar cells operate as quantum energy conversion devices, and are therefore subject to the "Thermodynamic Efficiency Limit." Photons with an energy below the band gap of the absorber material cannot generate a hole-electron pair, and so their energy is not converted to useful output and only generates heat if absorbed. For photons with an energy above the band gap energy, only a fraction of the energy above the band gap can be converted to useful output. When a photon of greater energy is absorbed, the excess energy above the band gap is converted to kinetic energy of the carrier combination. The excess kinetic energy is converted to heat through phonon interactions as the kinetic energy of the carriers slows to equilibrium velocity.

The overall effect of temperature on cell efficiency can be computed. Most crystalline silicon solar cells decline in efficiency by 0.50%/° C. and most amorphous cells decline by 0.15-0.25%/° C.

Solar cell efficiencies vary from 6% for amorphous silicon-covered solar cells to 40.7% with multiple-junction (or tandem) cells and 42.8% with multiple dies assembled into a hybrid package Solar cell energy conversion efficiencies for commercially available multicrystalline Si solar cells are around 14-19%. The highest efficiency cells have not always been the most economical—for example a 30% efficient multijunction cell covered on materials such as gallium arsenide or indium selenide and produced in low volume might well cost one hundred times as much as an 8% efficient amorphous silicon cell in mass production, while only delivering about four times the electrical power.

However, there is a way to "boost" solar power. By increasing the light intensity, typically photo generated carriers are increased, resulting in increased efficiency by up to 15%. These so-called "concentrator systems" have only begun to become cost-competitive as a result of the development of high efficiency GaAs cells. The increase in intensity is typically accomplished by using concentrating optics. A typical concentrator system may use a light intensity 6-400 times the sun, and increase the efficiency of a one sun GaAs cell from 31% at AM 1.5 to 35%. Most commercial producers are developing systems that concentrate between 400 and 1000 suns.

For a long time, researchers have strived to overcome the defects and limitations described above. In one prior approach, a solar cell is covered with a layer of monocrystalline ruby including Cr+3, which can enhance the absorption of the solar radiation in the wavelength range of 2.3 ev~3.2 ev. The physical significance of this design is that, by coating a solar cell with a layer of monocrystalline ruby, the absorption of the solar radiation in the range of 2.3 ev~3.2 ev will be enhanced, because the Cr+3 will be excited to induce d-d transitions and then cause the narrow band to emit light. The peak wavelength of Cr+3 in the ruby corresponds to λ=695 nm, and thus the original solar radiation is "moved" to a longer wavelength range by way of the short-wavelength range of the radiation being absorbed and re-emitted in the wavelength range of λ=700 nm.

Naum et al in U.S. Pat. Appl. Publ. Nos. 2007/0267058 and 2009/0156785 (the entire contents of which are incorporated herein by reference) describe a transparent light conversion film including phosphor materials to increase the overall efficiency of converting the incident solar light. Specifically, Naum et al focused only on the problem that, when the sunlight reaches the earth, about 6~8% of the energy is ultraviolet. The energy carried by ultraviolet cannot be absorbed by a solar cell to generate electric energy. Moreover, this energy can degrade and heat up the solar cell assembly, resulting in damaging the assembly and lowering its efficiency. Naum et al used a transparent phosphor powder which absorbed the ultraviolet in the wavelength λ<400 nm and re-radiated red light in the wavelength range λ=500~780 nm, thereby generating extra electricity and enhancing the conversion efficiency of the solar cell assembly.

Yet, in this work, only a portion of the solar spectrum above the band gap energy of the solar cell is converted.

In the field of solar cells, the addition of plasmonics, photonics band gap, and up and down conversion is known in the literature. Additionally, antireflection coatings and concentrators are well known in the literature.

The problem with the plasmonics effect is that, as noted above, the plasmons and the electric field enhancement decays rapidly with distance away from the metal structure meaning that the effect is only useful for a small volume of interaction.

The problem with antireflection coatings is that, although sun light is not scattered away as much as if there were no coatings, the light transmitted is still predominantly that of wavelengths that are not optimum for power generation.

The problem with concentrators is that, besides concentrating light which can be converted to power, a concentrator also concentrates light which does not generate power, which in general makes for waste heat.

While photonic band gap structures can serve to reflect or confine light, they have no effective way to gain power from the discarded light.

SUMMARY OF THE INVENTION

In one embodiment, there is provided an energy augmentation structure capable of capturing one or more wavelengths of electromagnetic energy, and augmenting the one or more wavelengths of electromagnetic energy in at least one property.

In one embodiment, the energy augmentation structure may be one or more of an electromagnetic resonator structure, a folded resonator structure, and a fractal structure having a region of an intensified electromagnetic field within the structure.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

In one embodiment, the energy converter noted above is disposed with an energy augmentation structure comprising one or more of an electromagnetic resonator structure, a folded resonator structure, and a fractal structure, any of which having a region of an intensified electromagnetic field within the resonating structures.

In one embodiment, the energy converter noted above includes one or more luminescing materials. As described herein, there are uses of the energy augmentation structure and/or energy collector embodiments which enhance bioluminescence, chemo-luminescence, photoluminescence, fluorescence, and mechano-luminescence.

In one embodiment, the energy converter noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter (e.g., the luminescent material) were remote from the at least one energy augmentation structure.

In one embodiment, the energy converter noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, UV-emitting bioluminescent materials can be used.

In additional embodiments, there are provided uses of the energy augmentation structure and energy collector embodiments in solar cells and other energy conversion devices and end uses.

In another embodiment, the energy converter noted above is disposed with an energy augmentation structure such that x-ray induced photoluminescence or fluorescence is higher compared to if the energy converter (e.g., x-ray induced photoluminescence or fluorescence materials) were remote from the at least one energy augmentation structure.

In another embodiment, there is provided a distributed energy collector having separate light collection components branched together for collecting solar light for conversion into electrical power.

In another embodiment, there is provided the above-noted distributed energy collector with separate light collection components collects solar light by directing the collected solar flux to a photovoltaic, thermoelectric, or thermionic emission cell.

In another embodiment, there is provided a distributed energy collector integrated with a photovoltaic at separate light collection components within the collector in order to convert solar light into electrical power at the light collection components.

In another embodiment, there is provided the above-noted distributed energy collector with separate light collection components and/or the above-noted energy augmentation structure having the region of the intensified electromagnetic field such that solar light heats a thermionic emission cell. When the region of the intensified electromagnetic field is disposed in a vicinity of the thermionic emission cell, the intensified electromagnetic field enhances thermionic emission.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 16 is a diagram showing a paired three-dimensional fractal structure with an intensified electric field in between;

FIG. 39A-1 is a schematic illustration of the capability to "tune" the metal shell to have a spectral overlap with the excitation and/or emission radiation wavelengths;

FIG. 41B is another schematic illustration of other various upconverter structures of the invention;

FIG. 41D is a schematic illustration of other plasmonics-active upconverter structures of the invention;

FIG. 43 is a table summarizing the cost per watt per module time over time for various PV technologies;

DETAILED DESCRIPTION OF THE INVENTION

Figure 1:
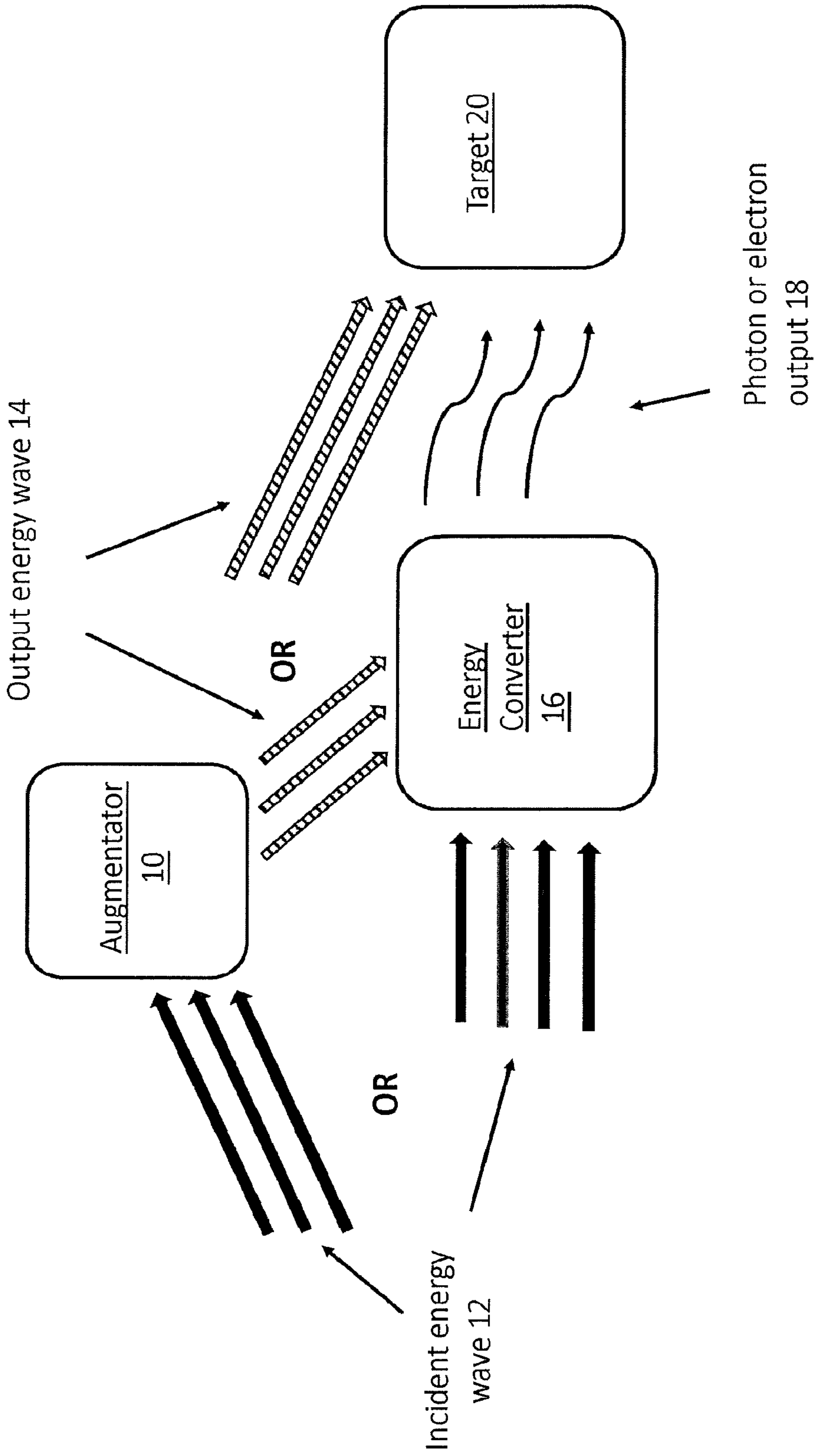
FIG. 1 is a schematic depicting an energy augmentator system of the invention with optional inclusion of an energy converter.

Reference will now be made in detail to a number of embodiments of the invention, examples of which are illustrated in the accompanying drawings, in which like reference characters refer to corresponding elements.

As noted above, energy converters such up conversion materials and down conversion materials have been used in a number of fields in effect to convert an incident wavelength of light to a different wavelength. Metallic structures have been placed on the phosphors or in a vicinity of the phosphors to generate a plasmonics effect which essentially is an amplification of the local field very nearby the outside of the metallic structures. In some applications, photonic band gap structures have been used in solar cell applications to prevent light of certain frequencies or wavelengths from propagating in one, two or any number of directions within the materials. Additionally, antireflection coatings and concentrators are well known in the literature.

The present inventors recognized that the shortcomings of these structures could be addressed by use of the energy augmentation structures described herein used separately or in conjunction with energy converters.

A. Energy Augmentation Structures

In the present invention, the term "energy augmentation" means effecting some change in one or more wavelengths of electromagnetic energy in at least one property, including, but not limited to, intensity, power, associated electrical field, associated magnetic field, wave amplitude, photonic flux, magnetic flux, phase, coherence, propagation direction, etc. The structure performing the energy augmentation can be termed an "energy augmentation structure" or an "energy augmentator". These terms are used interchangeably herein. Preferably the energy augmentation structure is a non-plasmonic structure (a structure that does not exhibit plasmonic properties).

The energy augmentator can take any desired form so long as it can perform the necessary function of augmenting the energy applied to it, causing a change in one or more wavelengths of electromagnetic energy in at least one property as noted above. Examples of such energy augmentators include, but are not limited to, at least one non-plasmonic member selected from the group consisting of resonators, fractal antennas, electrical grid patterns, antennas, cavities, etalons, nanoparticles, microparticles, nanostructures, and microstructures, just to name a few.

In one embodiment, as shown schematically in FIG. 1, an energy augmentator 10 is provided that is capable of receiving or capturing one or more wavelengths of electromagnetic energy representing an incident energy wave 12. Having received or captured the incident energy wave 12, the energy augmentator 10 is capable of augmenting the one or more wavelengths of received or captured energy wave flux 12 in at least one property. As shown in FIG. 1, in one embodiment, energy augmentator 10 then outputs an energy wave 14 with the at least one property augmented, with the augmented energy wave 14 incident on target 20. Details of the augmentation are described below.

In another embodiment, the output (augmented) energy wave 14 (i.e., one or more output wavelengths of electromagnetic energy) can be incident on an energy converter 16 (such as the up conversion materials and down conversion materials noted above). The energy converter 16 can output photons or electrons 18 which can be directed to target 20. In these embodiments, target 20 may receive the photons or electrons 18 or the output augmented energy wave 14 simultaneously or separately.

In one embodiment, the energy augmentator 10 may be one or more of an electromagnetic resonator structure, a folded resonator structure, and a fractal structure having a region of an intensified electromagnetic field within those structures.

Figure 2:
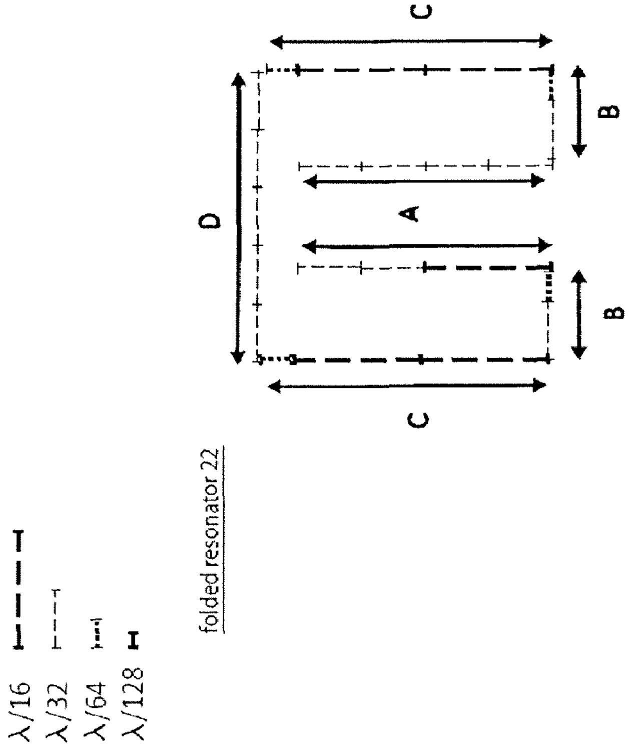
FIG. 2 is a schematic depicting a folded resonator as an illustrative energy augmentation structure of the invention.

FIG. 2 below is a diagram depicting a folded resonator structure 22 of this invention.

The resonator in one embodiment of the present invention is a $\frac{3}{4}\lambda$ metal structure bent, as shown in FIG. 2 having a "folded" structure making for opposing electrodes between which an intense electric field is developed. Exemplary characteristics of the "folded structure" antenna are listed in the following table:

TABLE 1

| | Wavelength (nm) | | | | | | | | | | |
|---|---|---|---|---|---|---|---|---|---|---|---|
| Antenna Side | 1400 | 1300 | 1200 | 1100 | 1000 | 900 | 800 | 700 | 600 | 500 | 400 |
| A | 175.0 | 162.5 | 150.0 | 137.5 | 125.0 | 112.5 | 100.0 | 87.5 | 75.0 | 62.5 | 50.0 |
| B | 65.6 | 60.9 | 56.3 | 51.6 | 46.9 | 42.2 | 37.5 | 32.8 | 28.1 | 23.4 | 18.8 |
| C | 196.9 | 182.8 | 168.8 | 154.7 | 140.6 | 126.6 | 112.5 | 98.4 | 84.4 | 70.3 | 56.3 |
| D | 218.8 | 203.1 | 187.5 | 171.9 | 156.3 | 140.6 | 125.0 | 109.4 | 93.8 | 78.1 | 62.5 |
| Total | 1093.8 | 1015.6 | 937.5 | 859.4 | 781.3 | 703.1 | 625.0 | 546.9 | 468.8 | 390.6 | 312.5 |
| ¾ lambda | 1050 | 975 | 900 | 825 | 750 | 675 | 600 | 525 | 450 | 375 | 300 |

The calculations of a theoretical $\frac{3}{4}\lambda$ and the slightly oversized antenna to account for all the bending corners involved in making the antenna would result in this structure having a size between the theoretical $0.75*\lambda$ and the upper oversized limit $0.78*\lambda$.

While the resonators shown in most of the drawings could be characterized as having a rectangular-shape loop connecting the opposing antenna sections or electrodes together, the invention is not so limited. Other "loop" shapes could be used, so long as the opposing electrodes are parallel and coplanar with one another, with the loop forming an electrical path having a length of $\frac{1}{2}\lambda$, with the opposing electrodes having a length of $\frac{1}{8}\lambda$ each, thereby making the $\frac{3}{4}\lambda$ resonator.

Figure 3:
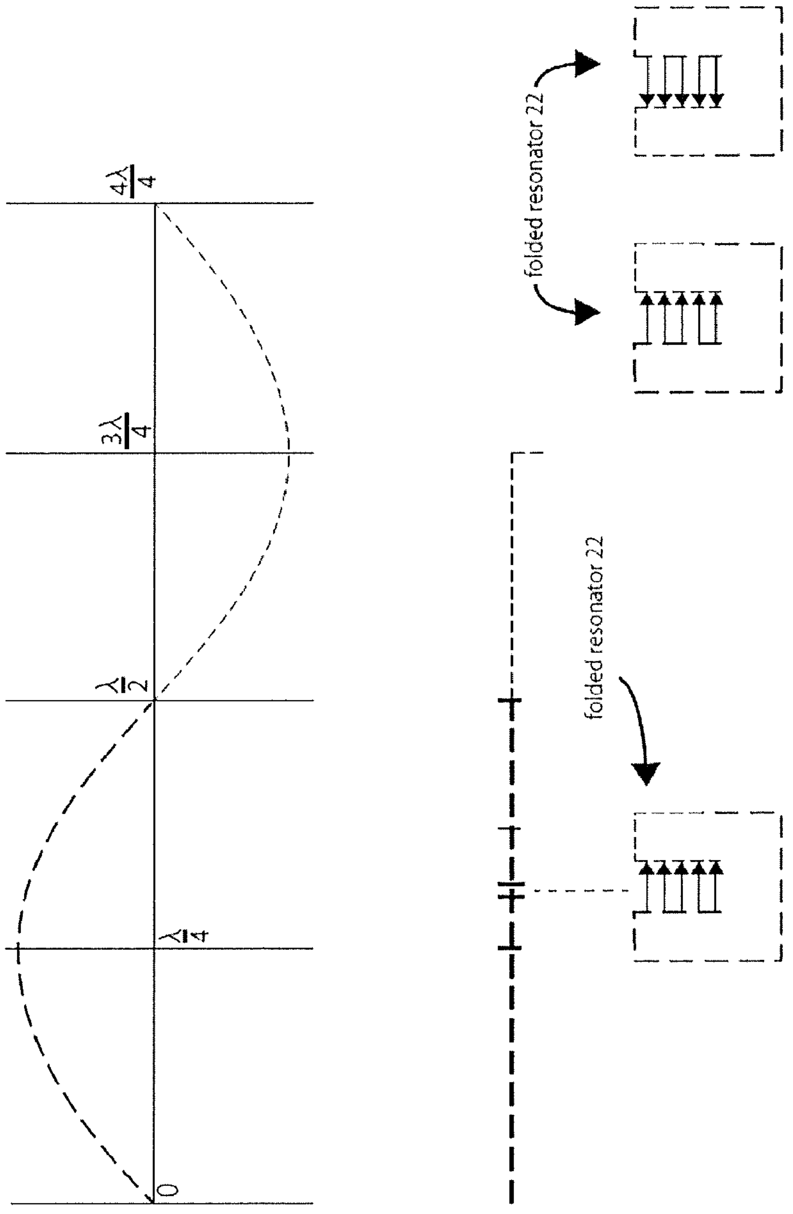
FIG. 3 is a diagram depicting the basic concepts underlying one of the energy augmentation structures of this invention.

FIG. 3 is a diagram depicting the basic concepts underlying one of the energy augmentation structures of this invention. In the depiction in FIG. 3 is a sinusoidal wave representing for example an instantaneous waveform of a light wave (an incident energy flux 12). The depiction shows the length of $\frac{3}{4}$ of the wavelength $\lambda$, and how in one embodiment a $\frac{3}{4}\lambda$ resonator is constructed with the open ends of the resonator "folded" together to form in this embodiment a $\frac{3}{4}\lambda$ folded resonator 22. As shown in FIG. 3, the folded ends form a region of an intensified, amplified electric field denoted by the horizontally directed arrows between the opposing open ends. When light nominally of a wavelength $\lambda$ (or harmonics thereof $2\lambda$, $3\lambda$, $4\lambda$, etc.) is incident on the folded antenna structure, a fraction-a of the light will be coupled into this structure establishing the amplified electric field. Since the light from sun comes continuously and at different rotational polarizations, subsequent light waves will continue to "pump" the electric fields in the resonant structure until some "loss" mechanism caps the strength of the electric fields. For resonators made of low loss materials, high Q-factors are obtained which, in this case, could mean that the electric field strength between the opposing electrodes may be for example 100 to 1000 times the peak amplitude of the electric field vector of the incident waveform.

Figure 4:
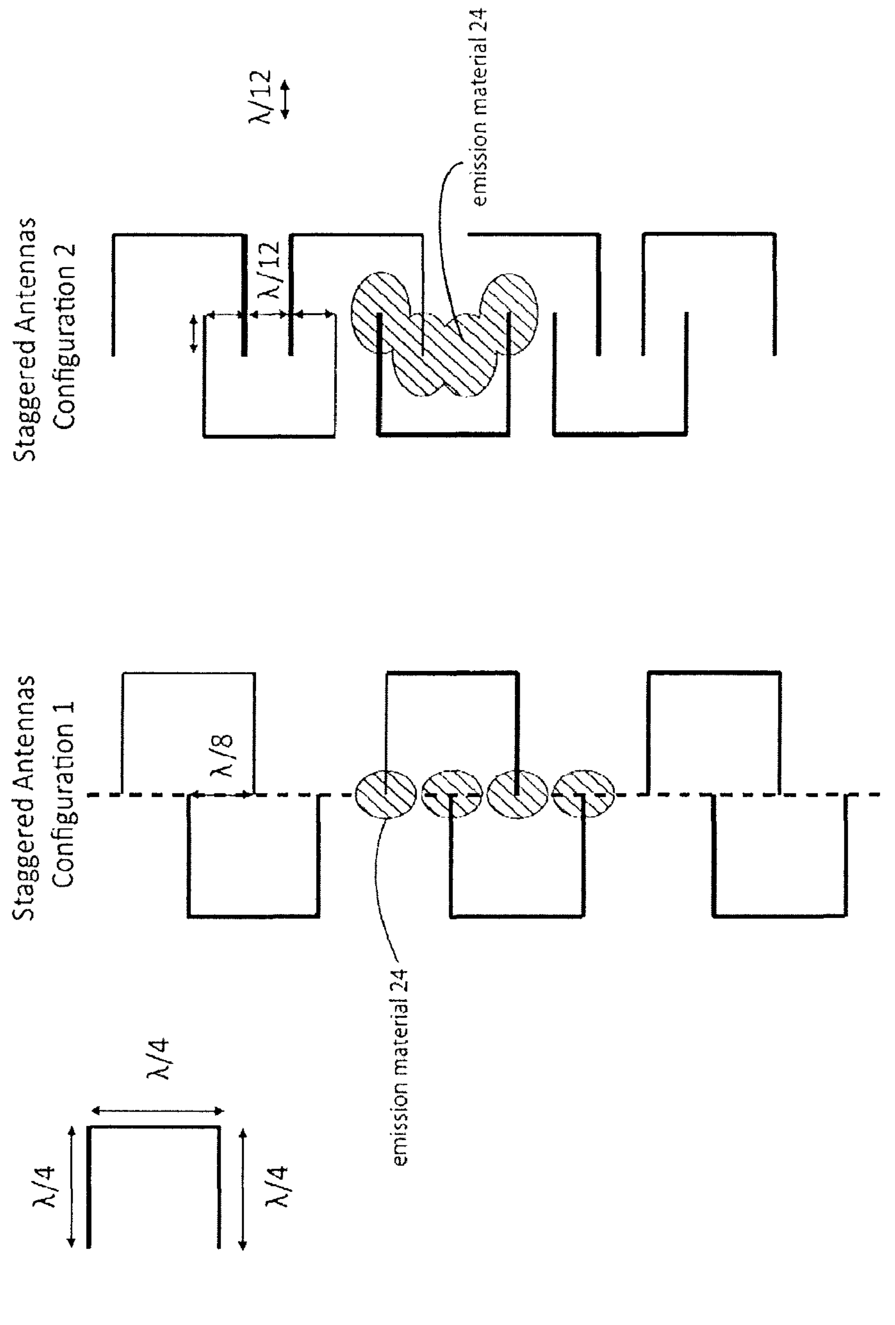
FIG. 4 is a schematic depicting a staggered antenna configuration as an illustrative energy augmentation structure of the invention.

In another embodiment, a resonating antenna could have the configuration below shown in FIG. 4. Here, the $\frac{3}{4}\lambda$ structures oppose and are interdigitated together without a "folded" structure. In the depiction in FIG. 4, the horizontal stubs are $\frac{1}{4}\lambda$ long, the vertical extending connectors are $\frac{1}{4}$ long, and the vertical spacing between the horizontal stubs and the extend of interdigitation varies as shown between configuration 1 and configuration 2. In one embodiment of the invention, an energy converter, a light or electron emitting material, or a color emitting or color converter material (i.e., emissive material 24) is placed inside or around the region of an intensified electric field, as shown in FIG. 4.

Figure 5:
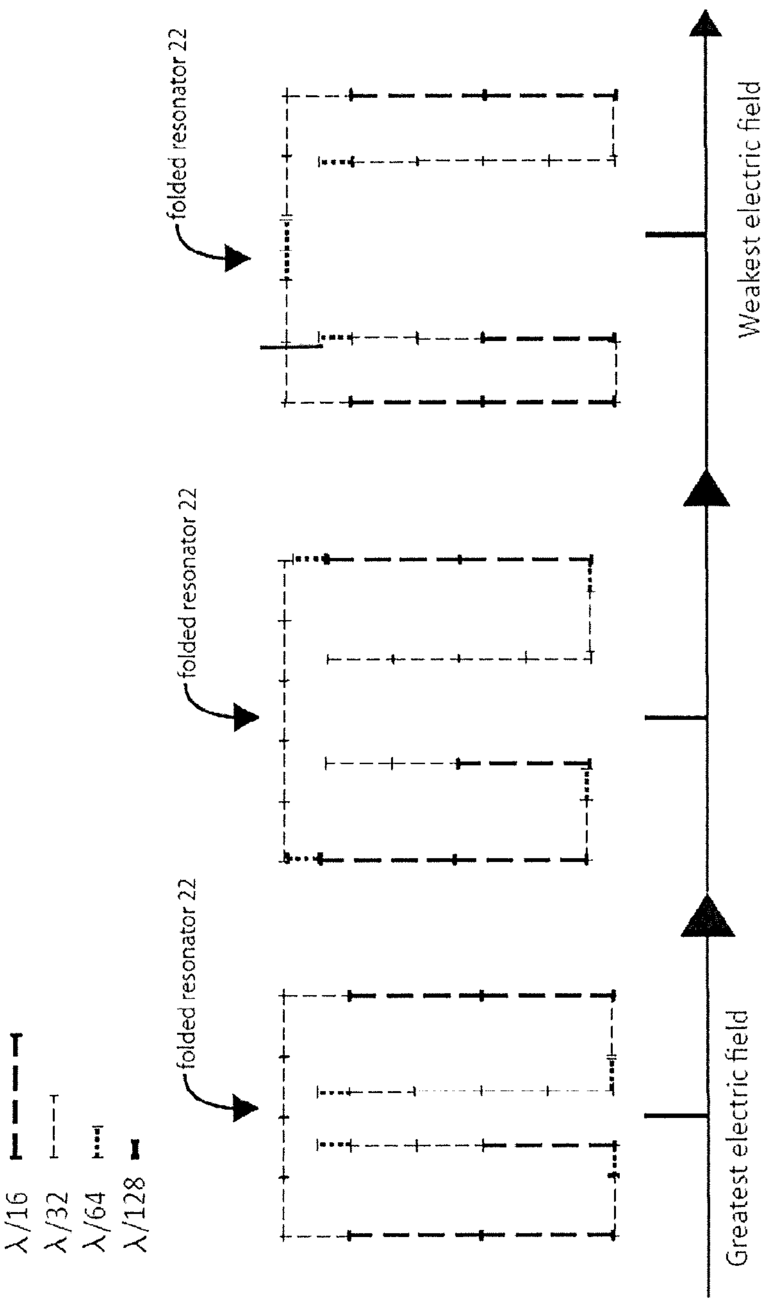
FIG. 5 is a schematic depicting the effect of electrode spacing in the folded resonator of the invention.

FIG. 5 shows that different $\frac{3}{4}\lambda$ folded resonators can be made having different distances between the opposing electrodes and thus different electric field strengths. In this way, the folded resonators of the invention can be adjusted such that the strength of the electric field between the opposing electrodes does not exceed the dielectric strength of any material in between. Exceeding the dielectric strength of any material in between could result in destruction of that material as intense current (e.g., a micro-arc) would flow during any time that the dielectric strength was exceeded, thus breaking the material down. As shown, here the opposing sides need not have an exact length of $\frac{1}{8}\lambda$.

In one embodiment of the invention, an energy converter, a light or electron emitting material, or a color emitting or color converter material (i.e., an emissive material) 24 is placed inside or around the regions of intensified electric field near/between the opposing electrodes. In one embodiment of the invention, the color emitting or color converter material may itself be absorbing a color light such as for example blue light and emitting lower energy, down-shifted red light. In this case, a red phosphor could be the color emitting or color converter material.

While the $\frac{3}{4}\lambda$ folded resonator in one embodiment could be designed to resonate at blue light ($\lambda$=420 to 440 nm), the resonator is preferably designed to resonate from light at a different frequency than the blue light that is being absorbed by the red phosphor. In one embodiment, for color enhancement for objects under solar light, the $\frac{3}{4}\lambda$ folded resonator could be designed to be driven by infrared light from the solar spectrum (e.g. $\lambda$=700 to 1000 nm) to generate the intensified electric field, and the red phosphor disposed in the region of intensified electric field would have a brighter red emission than if the intensified electric field were not present.

Figure 6:
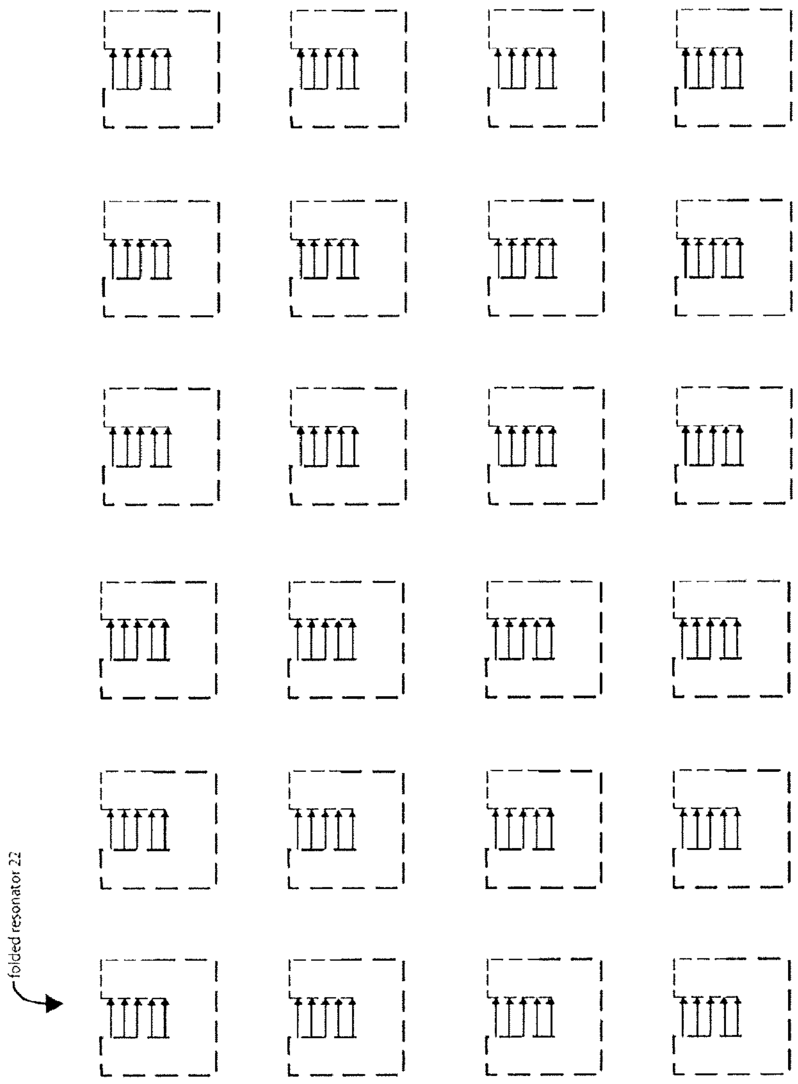
FIG. 6 is a diagram showing a pattern of ¾ λfolded resonators distributed in space.

FIG. 6 is diagram showing a pattern of ¾ λfolded resonators 22 distributed in space. As to be discussed in more detail later, there are numerous ways to distribute the ¾ λfolded resonators. The present invention is not limited to the regular, uniformly spaced and sized resonators shown in FIG. 6. There is no requirement that the distribution be regular, uniformly spaced, uniformly sized, or uniformly oriented. Differently sized, spaced, and oriented resonators may provide better utilization of the full spectrum of the sun or any other light source incident on the object.

FIG. 7 is diagram showing a pattern of ¾ λfolded resonators 22 distributed in a plane or otherwise along a surface of an object. In one embodiment, this pattern could be formed by lithographic or stamping processes onto a planar surface such as a glass plate or onto a curved sheet type product. In one embodiment, the glass plate could itself be a phosphorescent plate or could have sections of different phosphorescent material deposited in a pattern that would align/match the respective positions of the opposing electrodes on each resonator. In one embodiment, the sheet product could be a laminate type of product applied to for example a nominally white object. Upon solar irradiation, the infrared part of the solar spectrum (normally only heating the surface) would generate the intensified electric field regions. In those regions, down converting phosphors converting deep blue and ultraviolet light to visible light would convert the deep blue and ultraviolet light of the solar spectrum to visible light, and the intensified electric field would enhance greater visible light emission.

Figure 7A:
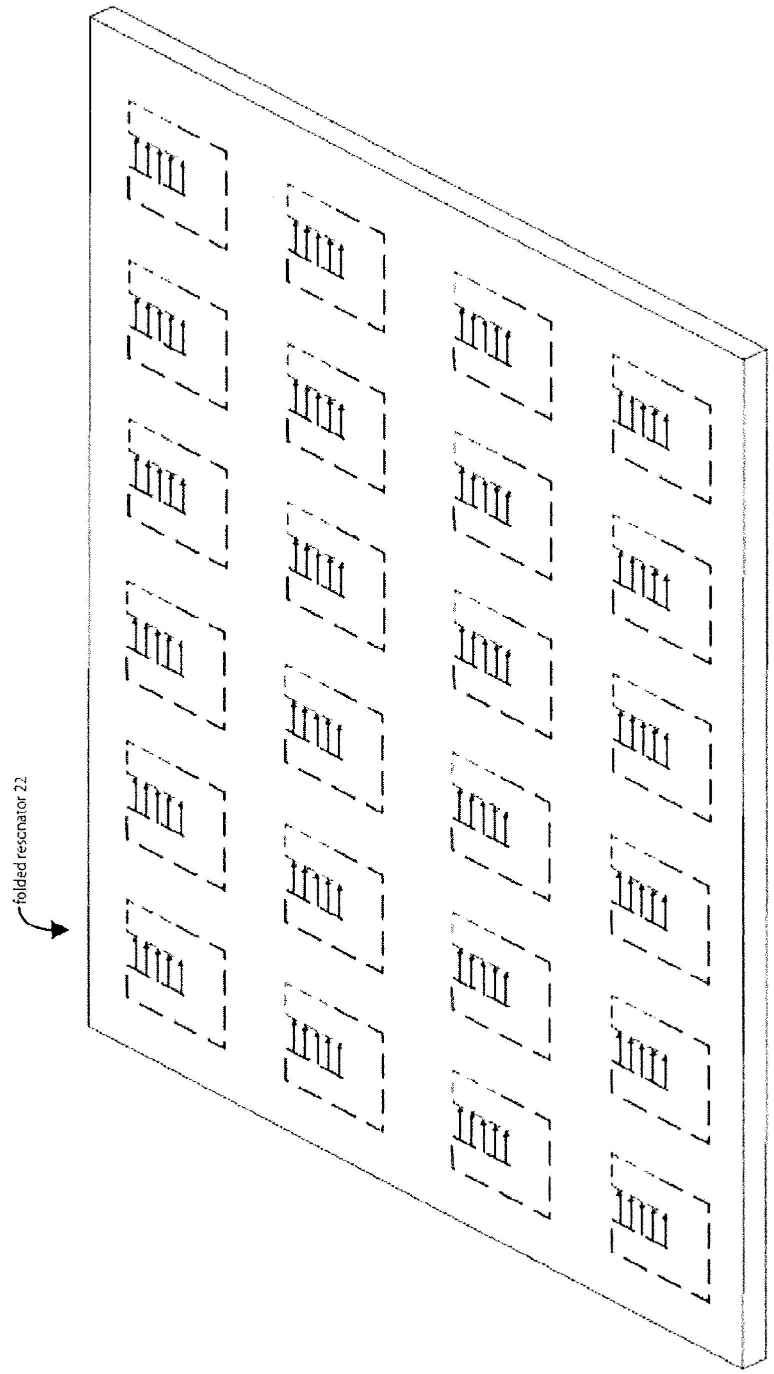
FIGS. 7A-7C is a diagram showing a pattern of ¾ λfolded resonators distributed in a plane or otherwise along a surface of an object.
Figure 7B:
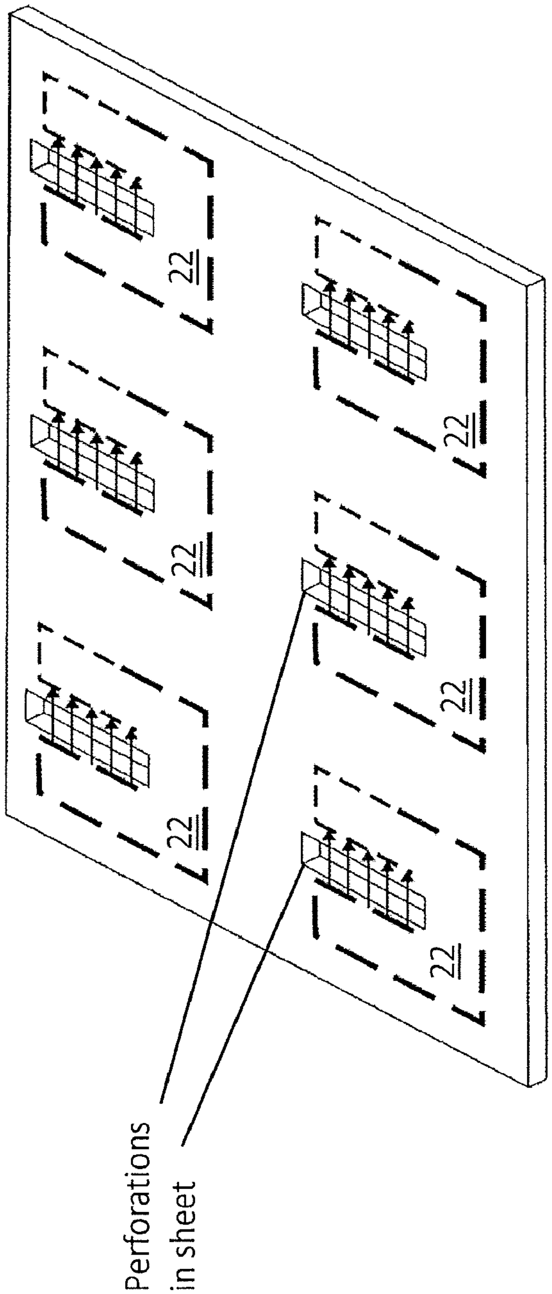

In one embodiment, the energy augmentators could be disposed on a perforated sheet, as shown in FIG. 7B. The perforations in one embodiment are in the regions of intensified electric field such that phosphors or other energy converting materials or devices could be disposed in the perforations.

In one embodiment (for color enhancement), the sheet product could be a laminate type of product applied to for example a nominally green object. Upon solar irradiation, the infrared part of the solar spectrum (normally only heating the surface) would generate the intensified electric field regions. In those regions, down converting phosphors converting blue, deep blue and ultraviolet light to green light would convert the blue, deep blue, and ultraviolet light of the solar spectrum to green light and the intensified electric field would enhance greater green light emission.

In one embodiment, the sheet product could be a laminate type of product applied to for example a nominally red object. Upon solar irradiation, the infrared part of the solar spectrum (normally only heating the surface) would generate the intensified electric field regions. In those regions, down converting phosphors converting green, blue, deep blue and ultraviolet light to red light would convert the green, blue, deep blue and ultraviolet light of the solar spectrum to red light and the intensified electric field would enhance greater red light emission.

Figure 7C:
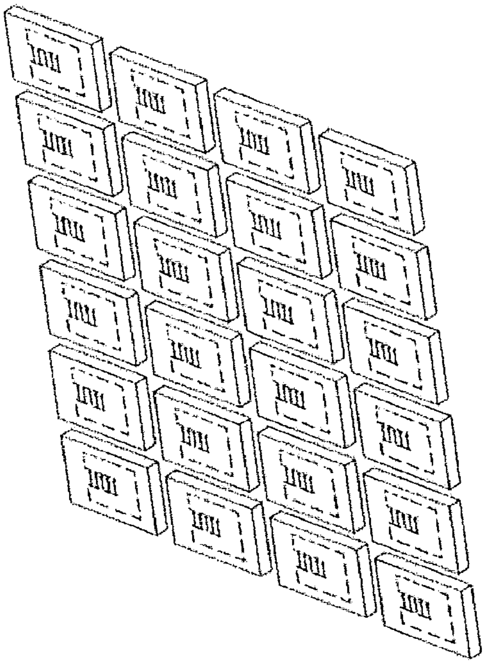

In one embodiment, the energy augmentators could be disposed on a sheet and then separated into distinct pieces, as shown in FIG. 7C, which could be readily added and mixed into a medium to be processed.

Figure 8:
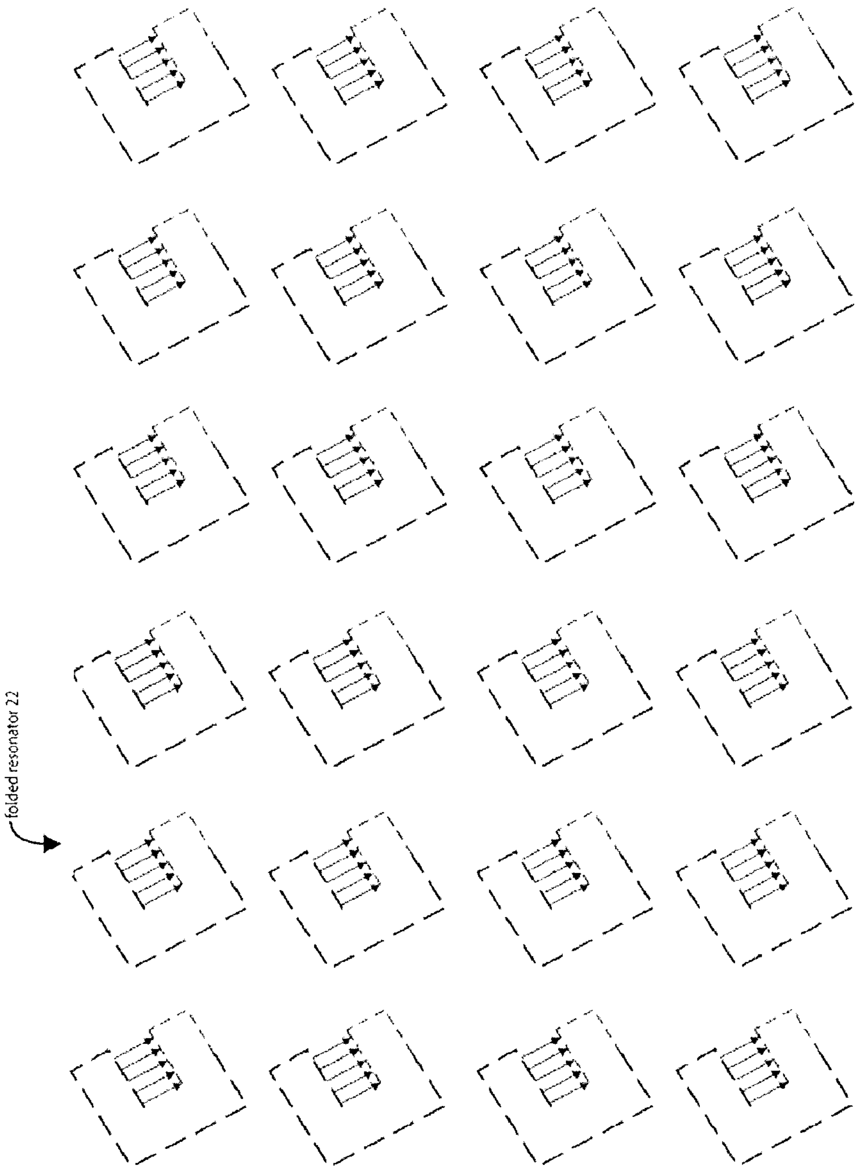
FIG. 8 is a diagram showing a pattern of ¾ λfolded resonators distributed in a plane or otherwise along a surface of an object and having a different orientation than in FIG. 7A.

FIG. 8 is a diagram showing a pattern of ¾ λfolded resonators 22 distributed in a plane or otherwise along a surface of an object and having a different orientation than in FIG. 7. By having different orientations, the rotating polarized sun light waves which may at one instance not have an electric field alignment conducive to driving the ¾ λfolded resonators, would have their electric field alignment conducive to driving resonators of a different orientation and therefore better aligned. Accordingly, if the sheet type products were used, layers of differently oriented % K folded resonators could be stacked together.

Figure 9:
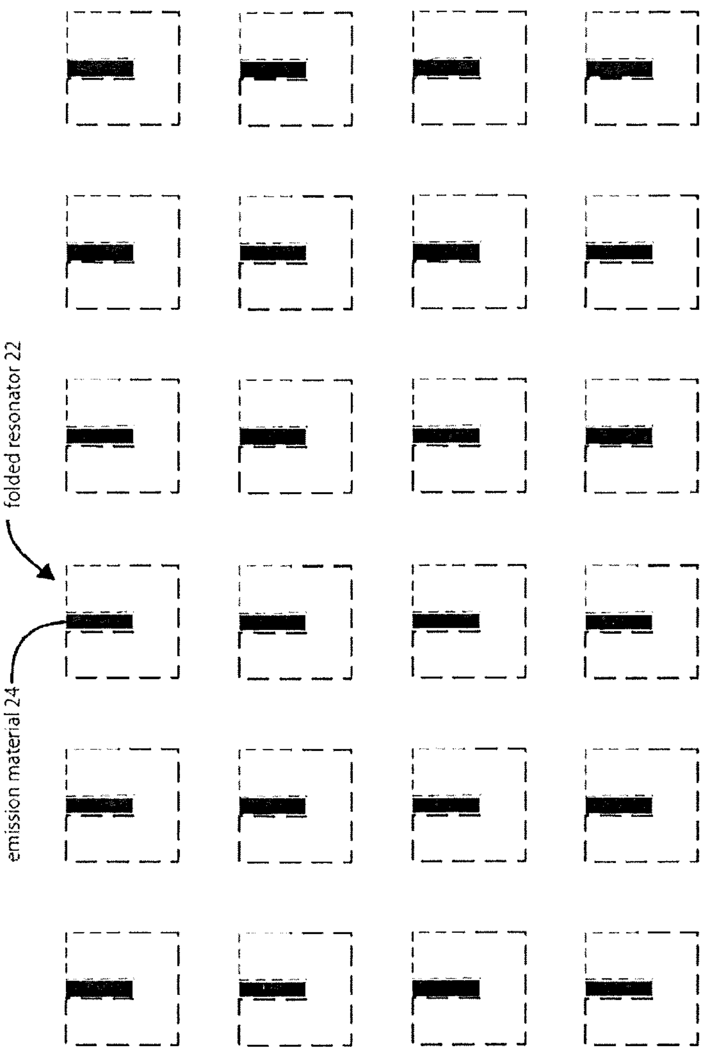
FIG. 9 is a diagram showing a pattern of ¾ λfolded resonators having a light or photon or electron emitting material deposited in the region of between the opposing electrodes.

FIG. 9 is a diagram showing a pattern of ¾ λfolded resonators 22 having an energy converter, a light or electron emitting material, or a color emitting or color converter material (i.e., emissive material 24) deposited in the region of between the opposing electrodes. Here, while shown in a plan view, the color converting or enhancing material deposited in the region of between the opposing electrodes may be deposited such that the color converting or enhancing material has an upper surface raised above the metal traces of the ¾ λfolded resonators. In this embodiment, the raised sections would intercept fringing fields of the intensified electric field between the opposing electrodes.

Figure 10:
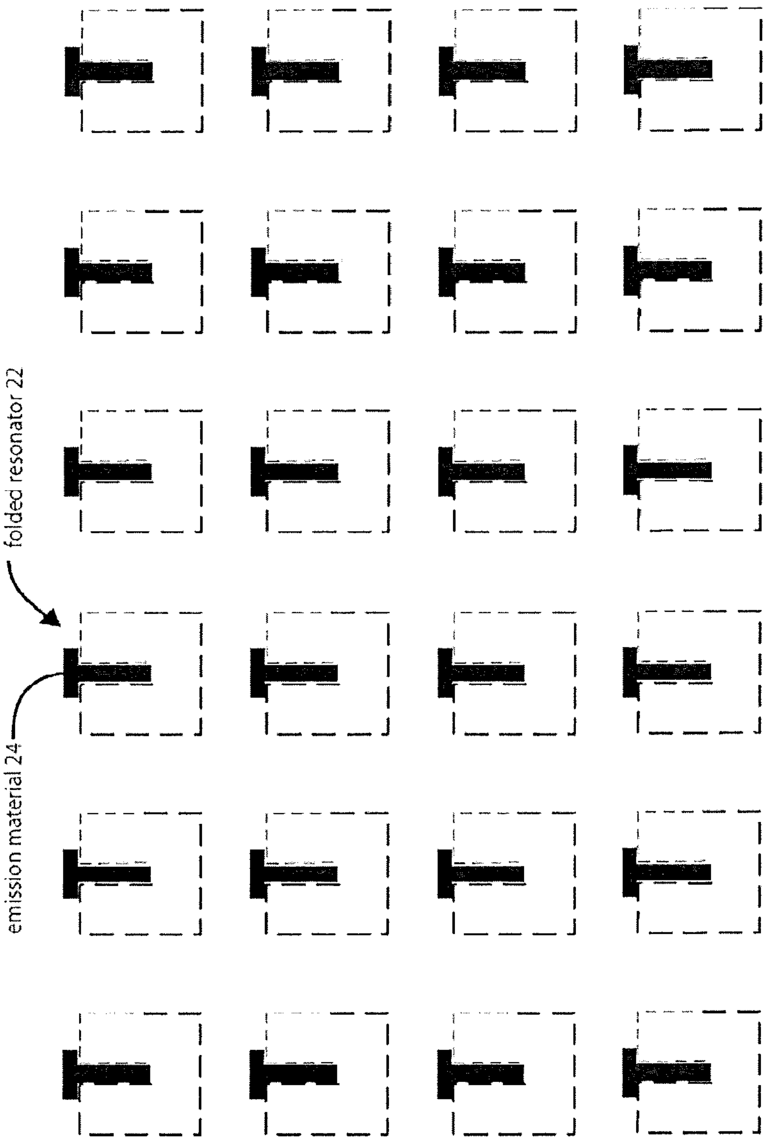
FIG. 10 is a diagram showing a pattern of ¾ λfolded resonators having a patterned deposit of a light or photon or electron emitting material in the region of between the opposing electrodes.

FIG. 10 is a diagram showing a pattern of ¾ λfolded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the ¾ λfolded resonators. In this embodiment, the raised sections would intercept fringing fields of the intensified electric field between the opposing electrodes. In this embodiment, the raised sections would extend around the corners where geometrically the corners would further intensify the electric field.

Figure 11:
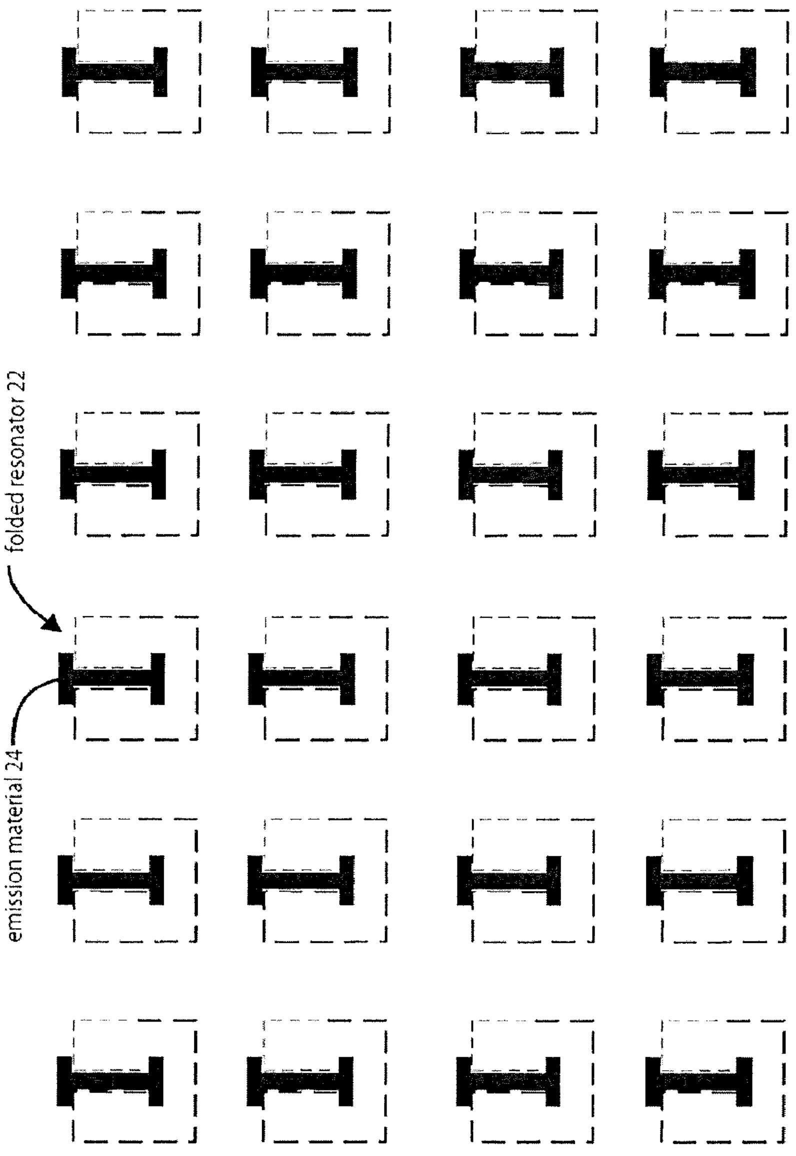
FIG. 11 is a diagram showing a pattern of ¾ λfolded resonators having a patterned deposit of a light or photon or electron emitting material in the region of between the opposing electrodes.

FIG. 11 is a diagram showing a pattern of ¾ λfolded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the ¾ λfolded resonators. In this embodiment, the raised sections would intercept fringing fields of the intensified electric field between the opposing electrodes. In this embodiment, the raised sections would extend around the corners where geometrically the corners would further intensify the electric field and would extend around the ends of the opposing electrodes.

In these embodiments shown in FIGS. 9, 10, and 11, the energy converters, or light or electron emitting materials, or color emitting or color converter materials (i.e., emissive materials 24) are disposed in a vicinity of one or more energy augmentation structures (i.e., the ¾ λfolded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters or color converting or enhancing materials disposed in a vicinity of one or more energy augmentation structures may have a physical conductive connection between the energy converter and the at least one energy augmentation structure. Alternatively, the coupling may be more that of radiatively or capacitively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

As used herein, in a vicinity of refers to the disposition of one thing inside the structure of another thing, outside and nearby or adjacent the structure of the other thing, and can include the disposition of one thing above or below the other thing in any three dimensional direction. Accordingly, in one embodiment of the present invention, the color converting or enhancing materials are disposed in a vicinity of the energy augmentation structures.

Figure 12:
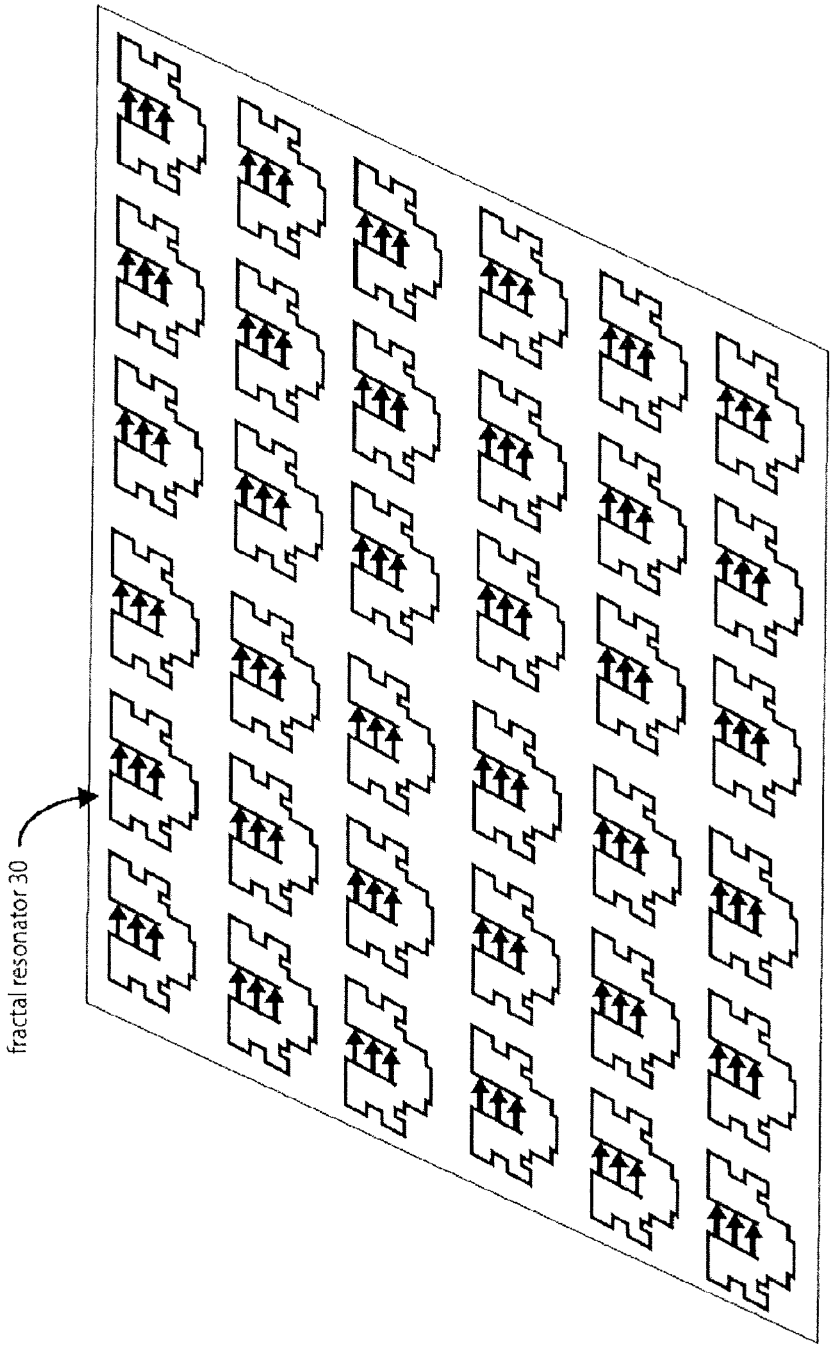
FIG. 12 is a diagram showing a pattern of ¾ λfolded resonators having for the metal traces a fractal pattern for the electrical path that loops around to connect the opposing electrodes.

FIG. 12 is a diagram showing a pattern of % k folded resonators 30 having for its metal traces a fractal pattern for the electrical path that loops around to connect the opposing electrodes. A fractal pattern for the electrical path with this pattern means that the metal trace can support various wavelengths resonating with the % k characteristics because of the multiplicity of possible loop paths available because the widths of each segment of the conductive path vary in width permitting electrical paths of different physical lengths to exist around the loop.

Figure 13:
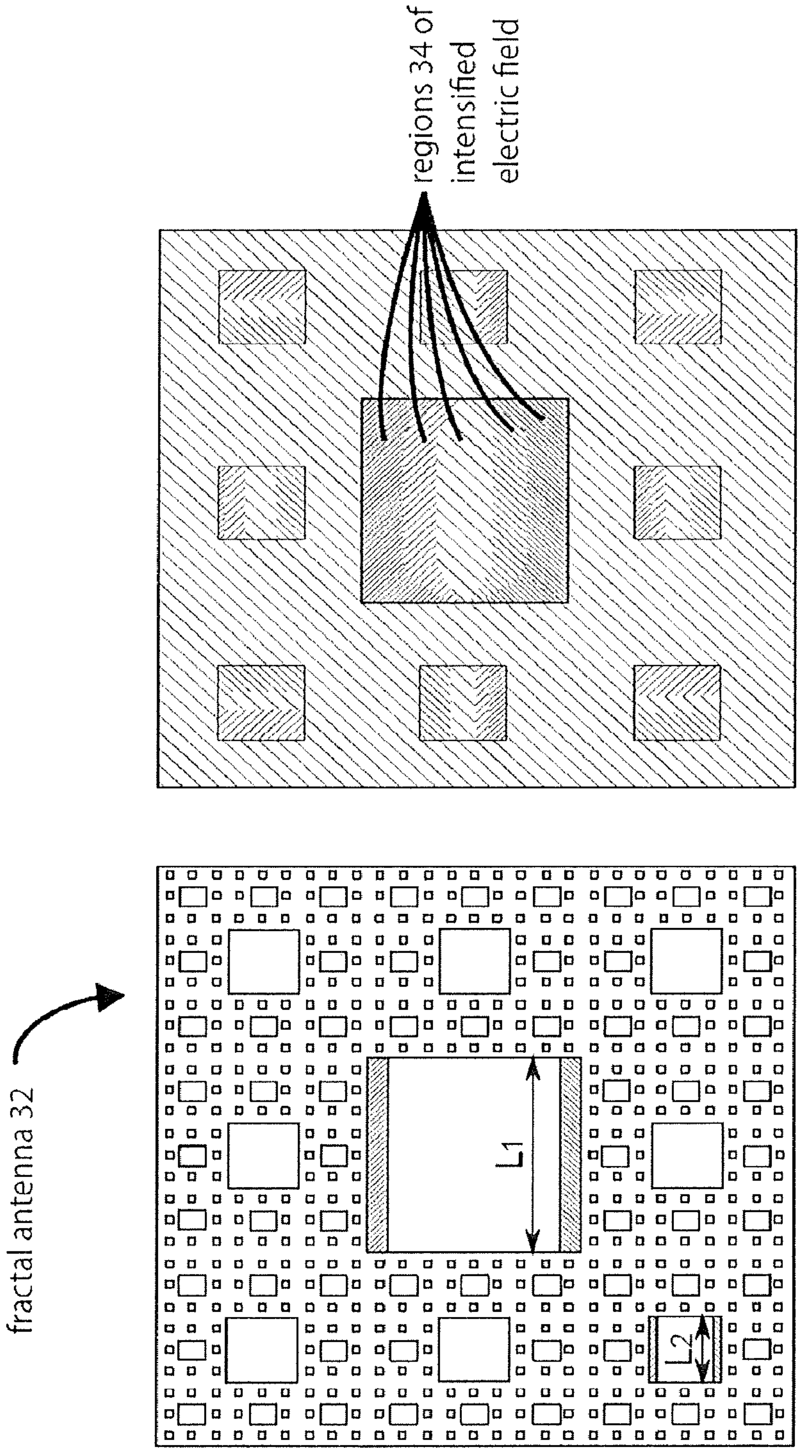
FIG. 13 is a diagram showing a fractal antenna segment where the straight-line sides of the metal pads have locally intensified electric field.

FIG. 13 is a diagram showing another fractal antenna segment 32 where the straight-line sides of the metal pads have regions 24 of locally intensified electric field. Here, in one embodiment, the fractal antenna segment is designed for resonance in the infrared range, with the intensifies electric field regions 34 (for example as shown toward the straight-line sides of the metal pads being the place where blue phosphors and red phosphors (or other emissive materials 24) would be deposited such that their emission, would be enhanced the intensified electric fields in those regions 34.

Figure 14:
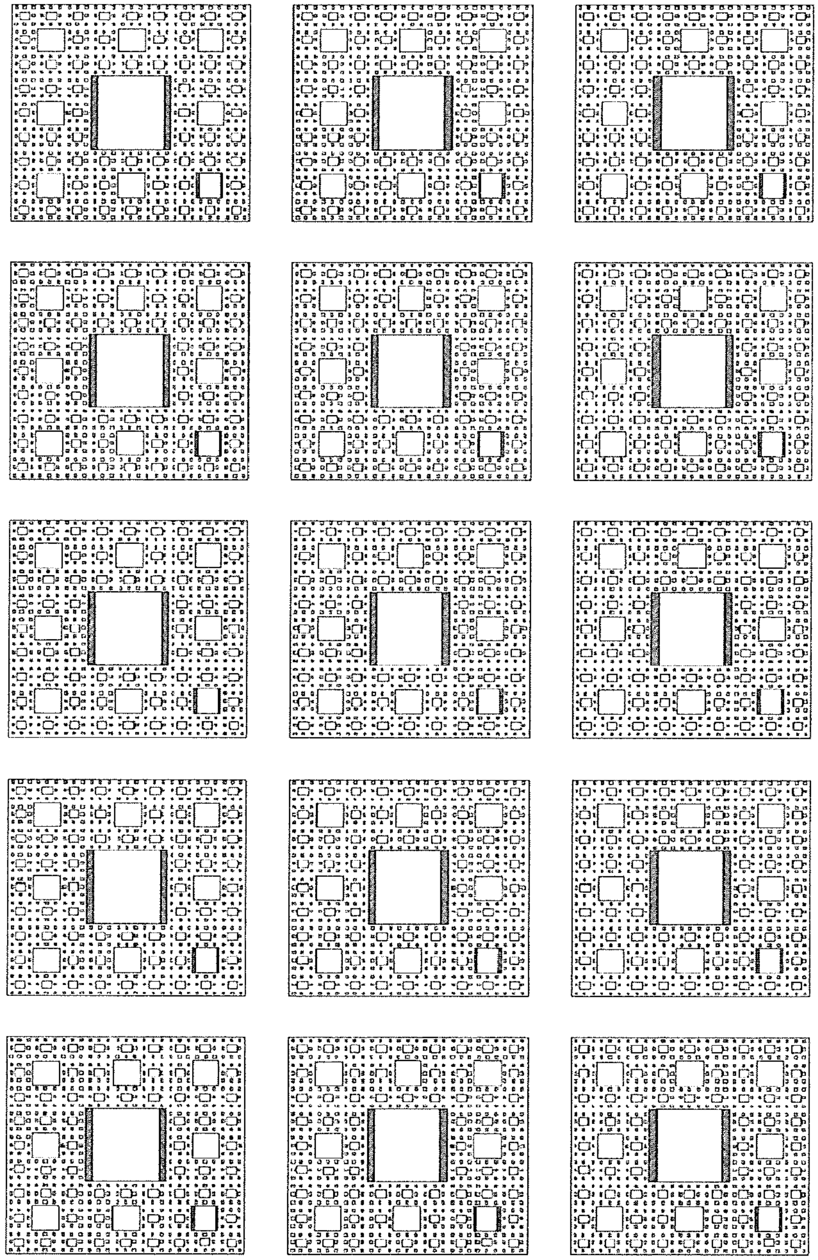
FIG. 14 is a diagram showing a repeated pattern of the fractal antenna segment of FIG. 13

FIG. 14 is a diagram showing a repeated pattern (array) of the fractal antenna segments 32 of FIG. 13.

Figure 15:
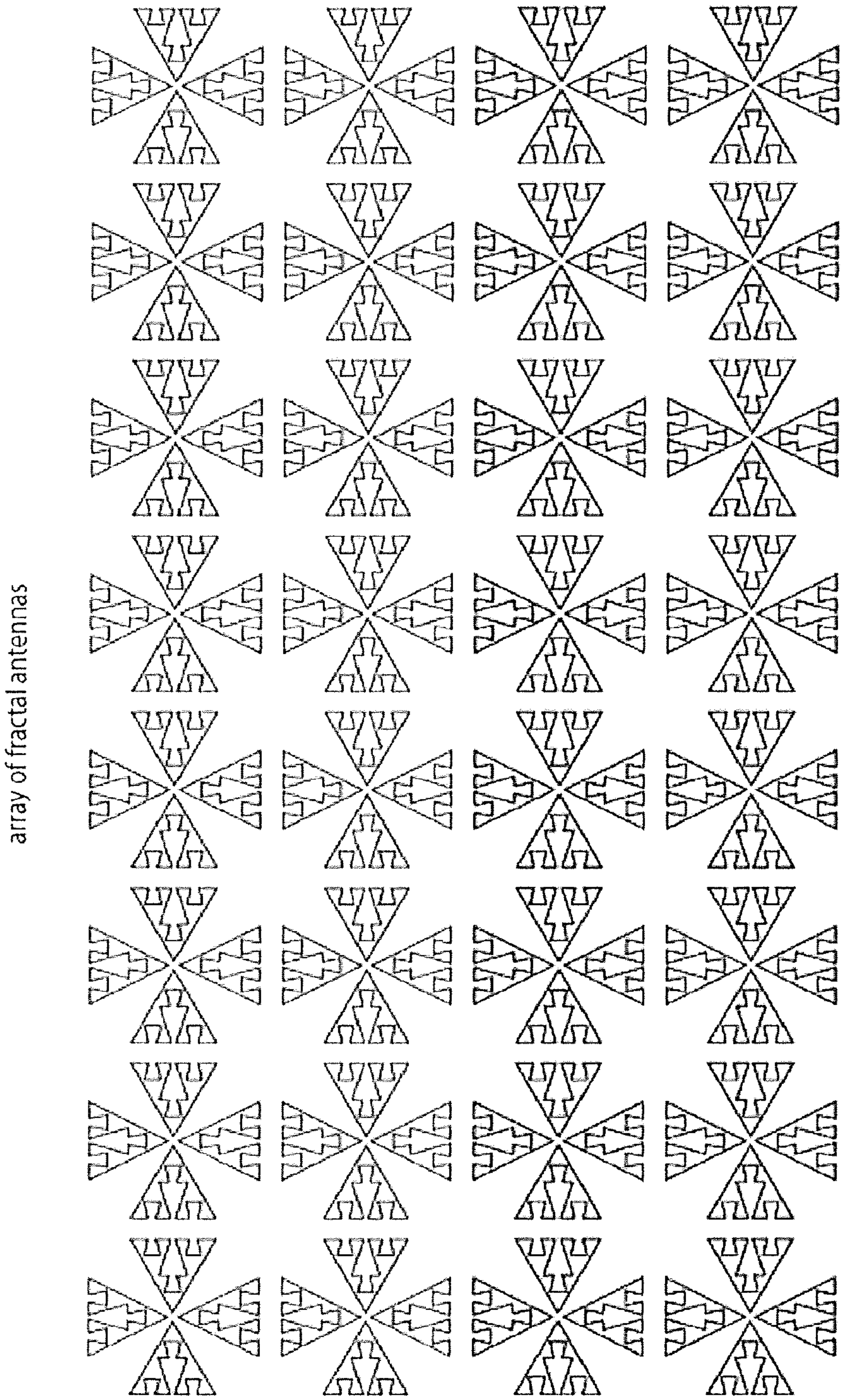
FIG. 15 is a diagram showing a pattern of bowtie fractal antenna segments.

FIG. 15 is a diagram showing a pattern (array) of bowtie fractal antenna segments, providing an alternative embodiment to the fractal antenna segments of FIG. 14.

In one embodiment of the invention, the resonant structures can comprise three-dimensional fractal patterns. Known in the art is the fabrication of three-dimensional fractal structures by nanoscale anisotropic etching of silicon such as described in Nanoscale etching of 3d fractal structures with many applications including 3d fractal antennas and structures for filters, by Brian Wang, Jun. 22, 2013, in the Journal of Micromechanics and Microengineering, (available at www.nextbigfuture.com/2013/06/nanoscale-etching-of-3d-fractal.html) the entire contents of which are incorporated herein by reference. In one embodiment of the invention, metal is deposited over a silicon three-dimensional fractal structure to form a multi-dimensional light collector.

Figure 16:
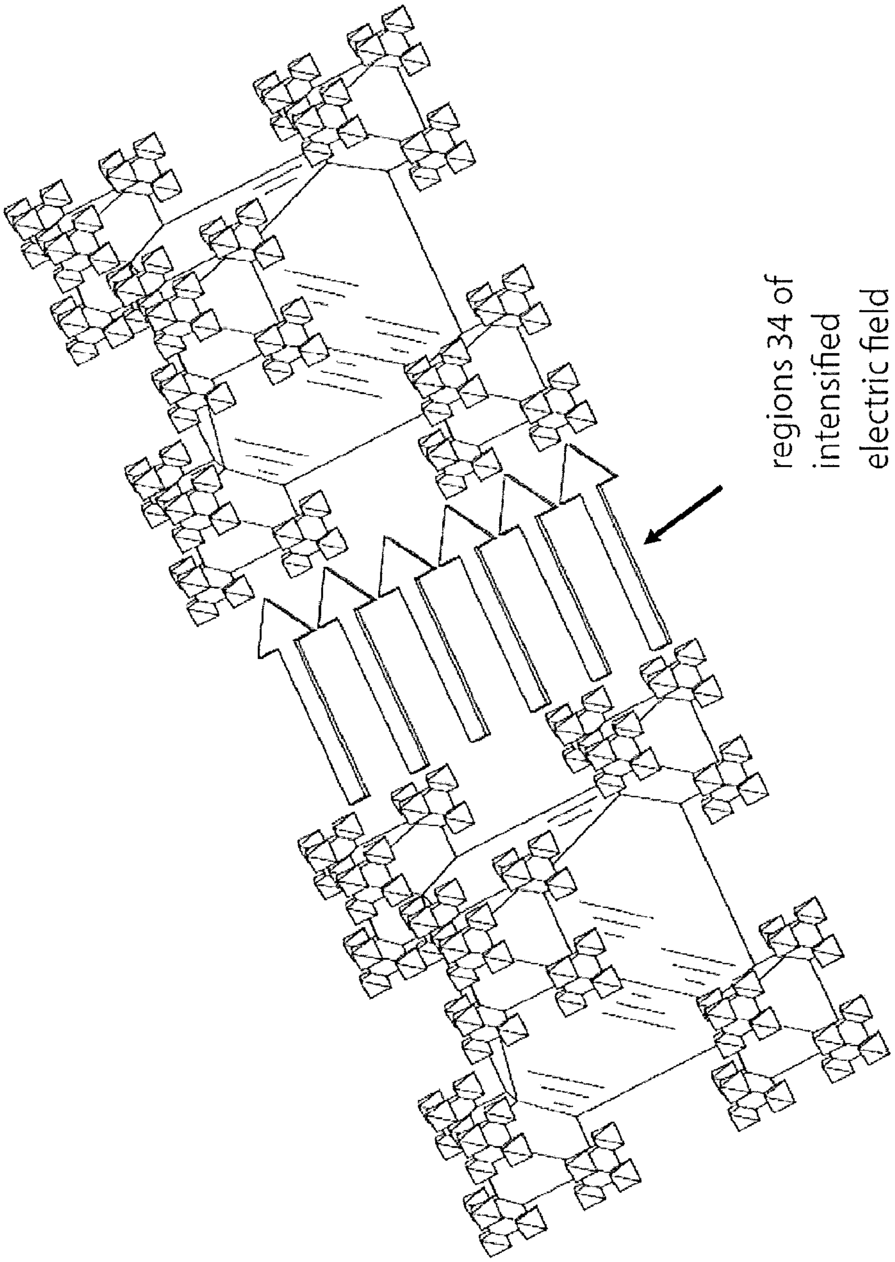

FIG. 16 is a diagram showing a paired three-dimensional fractal structure with regions 34 of an intensified electric field in between the pairs. The paired three-dimensional fractal structure is a color enhancement structure according to one embodiment of the invention. In one embodiment of the invention, these pyramidal type structures would be metallized with opposing faces metalized, a first loop conductor formed around the other sides of the first pyramid, then connecting across a region between the pair, and then a second loop formed around the sides of the second pyramid to the metallized opposing face of the second pyramid, to mimic (as seem from above) the ¾ λfolded resonators shown in FIG. 3.

In one embodiment, converter (emissive) materials 24 would be disposed nearby different sections of the pyramidal type structures and preferably between the opposing faces of the pair where the intensified electric field (depicted by the arrows) exists. With the three-dimensional aspect of this invention, red, yellow, green, and blue converters (or other designated emitters) could be disposed at different levels within this region of intensified electric field.

Figure 17:
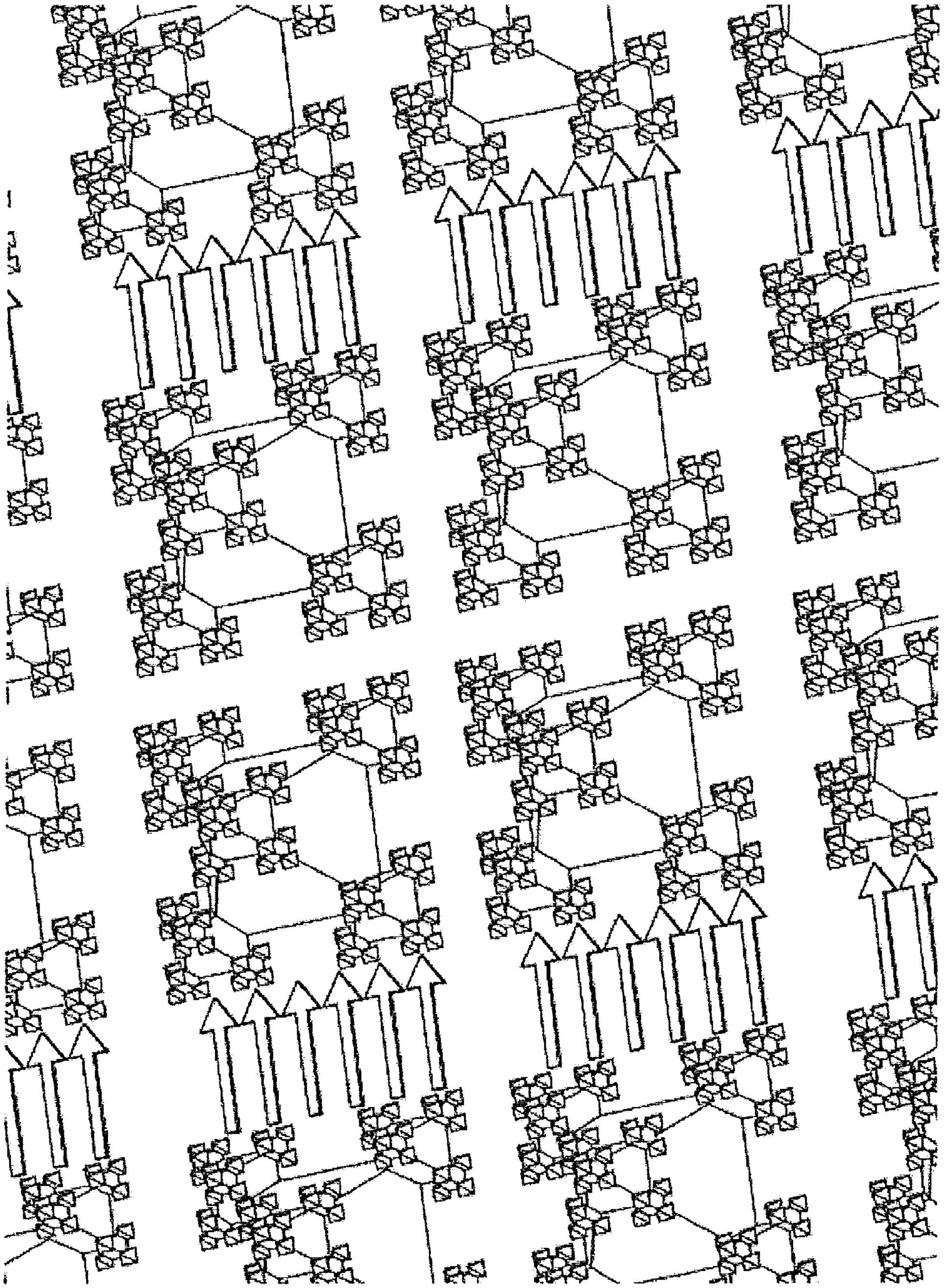
FIG. 17 is a diagram showing a pattern of the paired three-dimensional fractal structures.

FIG. 17 is a diagram showing a pattern (array) of the paired three-dimensional fractal structures of FIG. 16.

In these embodiments shown in FIGS. 12 to 17, the energy converters, or light or electron emitting materials, or color emitting or color converter materials (i.e., emissive materials 24) are disposed in a vicinity of one or more energy augmentation structures (i.e., the % k folded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters, or light or electron emitting materials, or color emitting or color converter materials disposed in a vicinity of one or more energy augmentation structures may have a physical conductive connection between the energy converter and the at least one energy augmentation structure. Alternatively, the coupling may be more that of radiatively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

Figure 18:
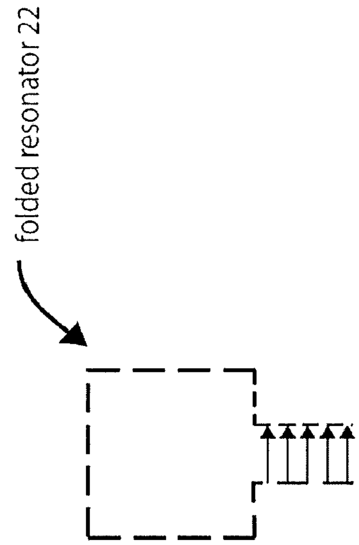
FIG. 18 is a diagram showing a ¾ wavelength resonator with the distal ends of the resonator antenna protruding outwardly while maintaining parallelism.

The energy augmentation structures are not limited to those shown above. Other variants are possible. Moreover, in one embodiment of the invention, the ¾ λfolded resonators need not to have the "folded sections" which fold inwards as shown in FIG. 3. Instead, as shown in FIG. 18, the ¾ λresonators of the invention can have folded sections which fold outward with the regions of intensified electric field being outside of the "loop" of the resonator. The distal ends of the antenna protrude outwardly while maintaining parallelism. Specifically, FIG. 8 is a schematic of a ¾ λ external-electrode folded resonator 22. This external, opposed electrode pair design follows the general apportioning, scaling aspects, converter material placement, etc., shown in FIGS. 5 through 11 but with the internal folded sections being replaced by the external-electrode pair.

Figure 19:
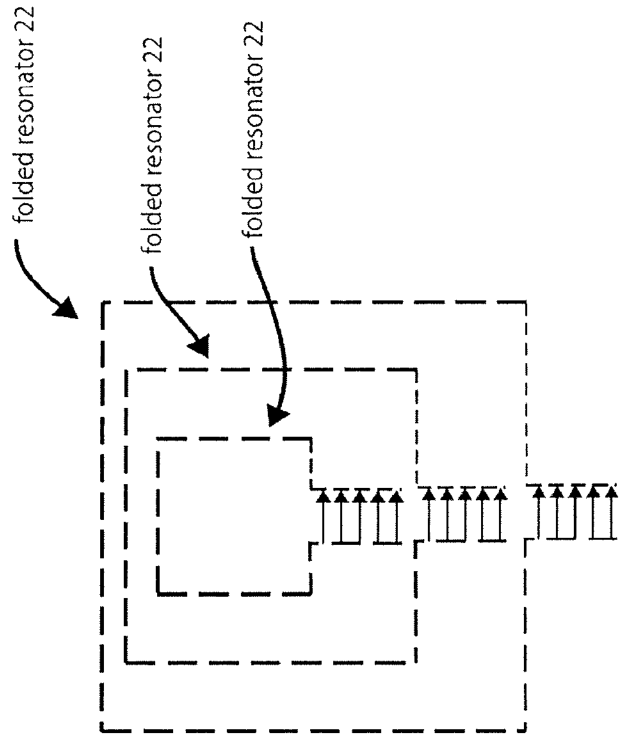
FIG. 19 is a diagram showing a packing configuration for three different % wavelength resonators, that are maintained in plane with no overlapping distal ends.

In one embodiment of the invention, the ¾ λexternal-electrode folded resonator 22 provides the capability to be packed in a concentric-type arrangement with progressively increasing or decreasing size resonators. These resonators are maintained in plane with no overlapping distal ends. FIG. 19 is a schematic of a plurality of concentric-type ¾ λ external-electrode folded resonators 22. Since each of the ¾ λexternal-electrode folded resonators 22 has a different electrical length, the plurality of concentric-type ¾ λexternal-electrode resonators will be "tuned" to the different wavelengths associated with the respective electrical lengths. Three different frequencies are therefore focused between the distal ends of the antennas.

Figure 20:
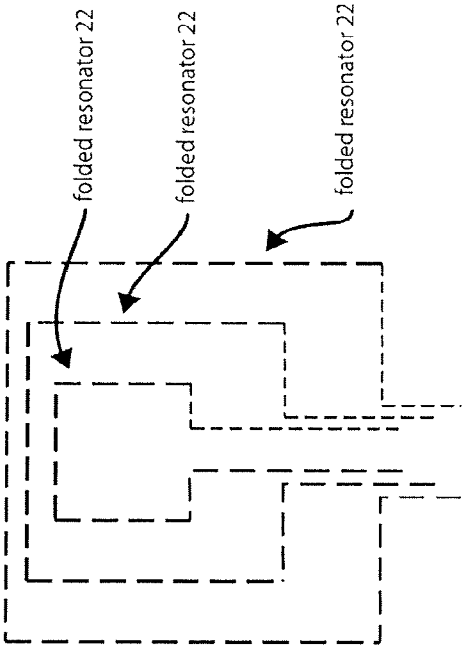
FIG. 20 is a diagram showing another packing configuration for three different % wavelength resonators, that are maintained in plane with overlapping distal ends.

In another embodiment, FIG. 20 is a schematic of a plurality of concentric-type ¾ λexternal-electrode folded resonators 22 with overlapping electrodes. In one embodiment, the overlapping provides a more concentrated/enhanced field region than in the non-overlapping arrangement of FIG. 19.

Figure 21:
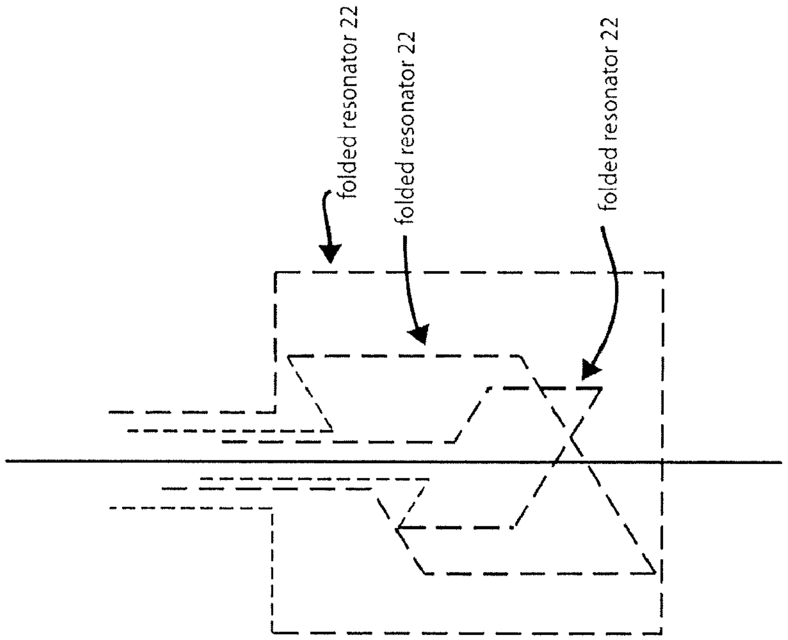
FIG. 21 is a diagram showing yet another packing configuration for the % wavelength resonators, with an off (or out of) plane axial symmetry.

The present invention is not limited to planar concentric type packing arrangements as shown in FIG. 19 or 20. The three different ¾ wavelength resonators in FIG. 20 are maintained in plane with overlapping distal ends. These antennas are inductively coupled. In one embodiment, the present invention utilizes an off plane configuration with axial symmetry where the antennas are in an axially rotated, multiple frequency, interleaved ¾ wave resonator structure. FIG. 21 is a schematic of an axially rotated, multiple frequency, interleaved ¾ wave resonators 22 showing (in this example) three differently sized resonators for multiple frequency resonance disposed about/along a common axis but axially rotated. In one embodiment, in this configuration, the resultant electric field is concentrated without one electrode section perturbing the electric fields from another.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Figure 22:
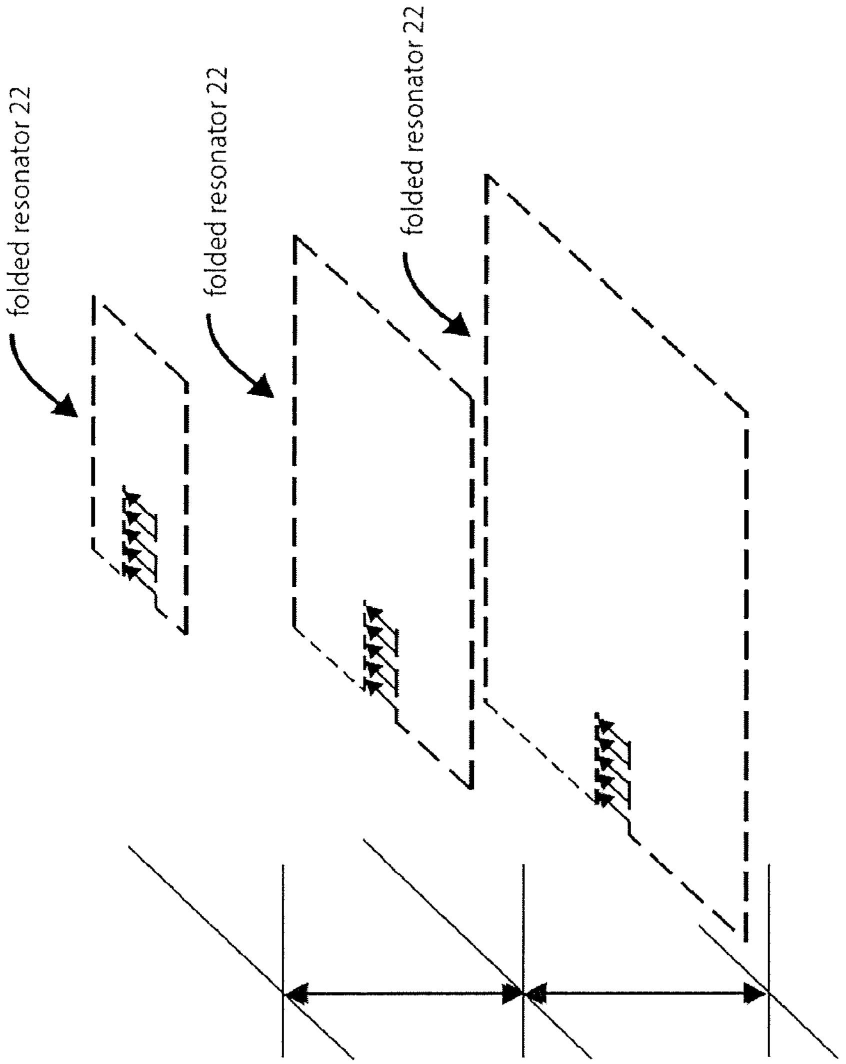
FIG. 22 is a diagram showing a multi-level packing configuration in parallel planes for the folded ¾ wavelength resonator shown.
Figure 23:
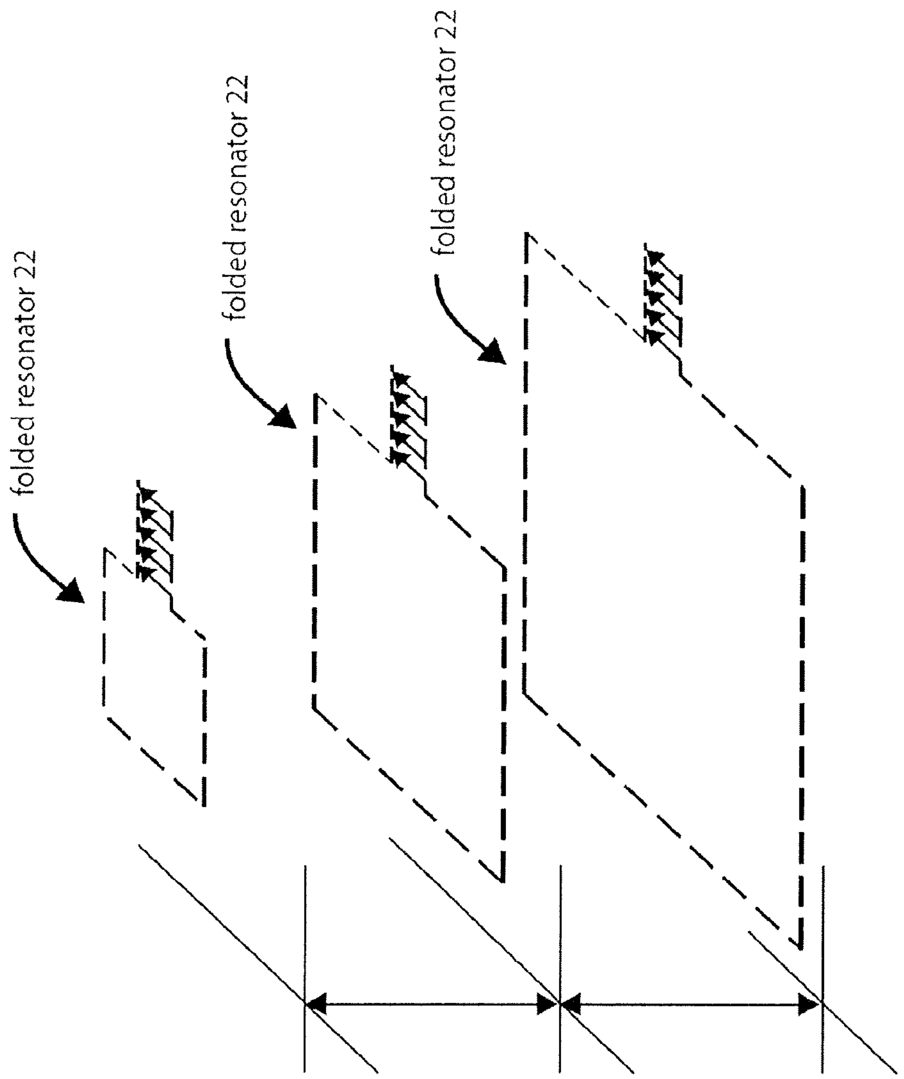
FIG. 23 is a diagram showing a multi-level packing configuration in parallel planes with distal ends protruding out for the % wavelength resonator in FIG. 22.

In one embodiment, the present invention can use different levels for disposing ¾ λresonators thereon regardless of the resonators being ¾ λinternally-folded resonators or ¾ λ external-electrode resonators. This packing is shown in FIGS. 22 and 23 for configuration in parallel planes with distal ends folded in or protruding out respectively.

Figure 24A:
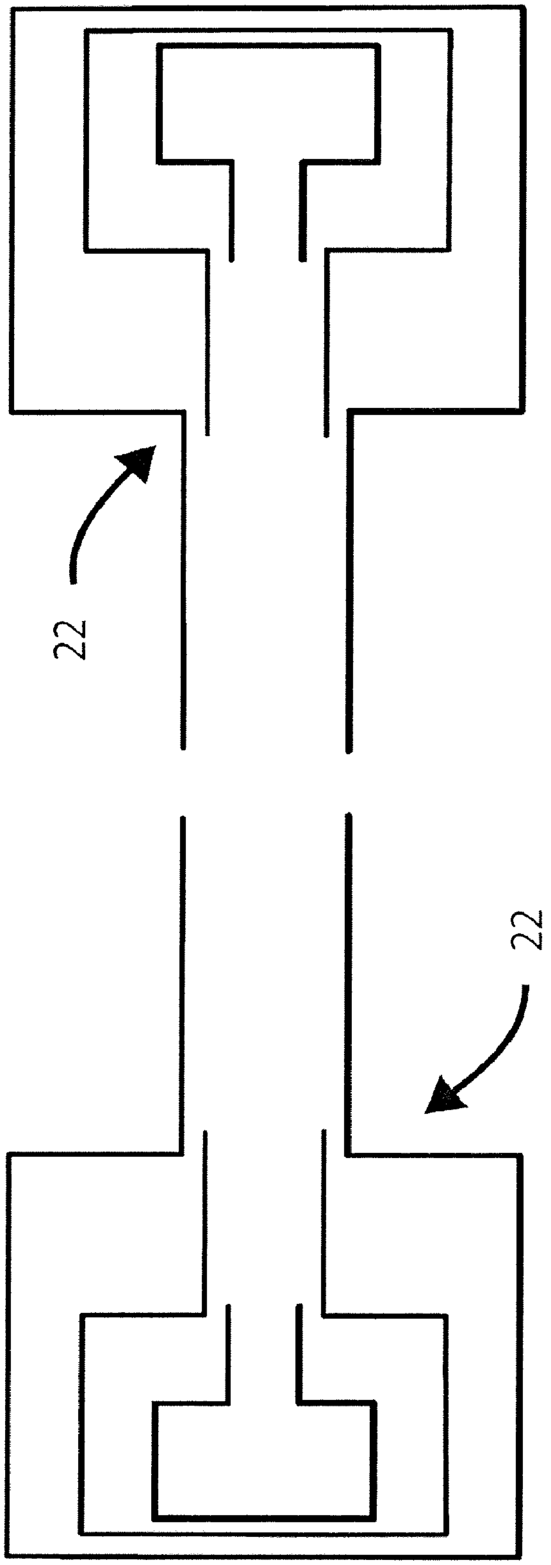
FIG. 24A is a diagram showing a different in-plane packing configuration.

In the embodiment of the invention depicted in FIG. 20 having a plurality of concentric-type ¾ λexternal-electrode resonators 22, the antennas are inductively decoupled. This configuration allows the electric field to be focused from three different frequencies in a longer path. This configuration can be used to create a mirror image configuration to extend the length of focused electric field as is illustrated in FIG. 24A.

Figure 24B:
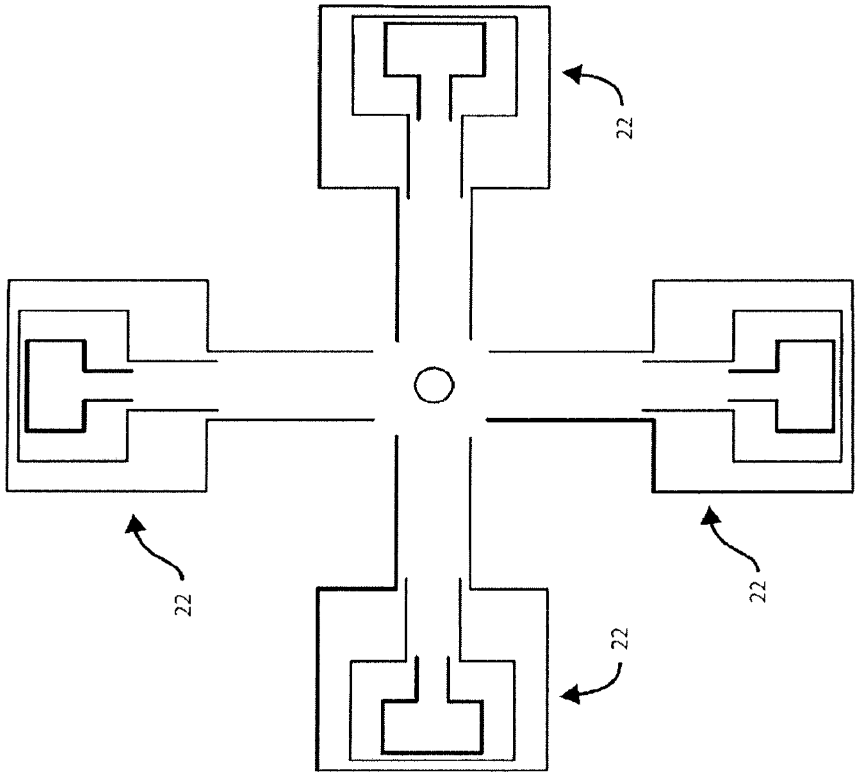
FIG. 24B is a diagram showing another different in-plane packing configuration.

The resonator configuration in this case is mirror imaged with another set of antennas (folded resonators 22) to create a longer path (doubled) of focused electric field. Furthermore, the resonator antenna configuration can be placed in more creative ways to enhance the electric field focusing around a target as is illustrated in the FIG. 24B.

The configuration in FIG. 25 allows the surrounding of a target within the plane of the resonator structure/antenna for the purpose of heating and focusing energy around the target. This prevents heat dissipation in silicon where the thermal conductivity is high. The silicon substrate in such an instance can be single crystalline, polycrystalline or amorphous.

In one embodiment of the present invention, an "energy augmentation structure" represents a structure whereby a spatial region of the energy collector contains a converter material (or other light or electron emitting material) exposed to energy which stimulates emission of light at a different energy (wavelength) from that to which it is exposed while being in a spatial area/volume (e.g., between or around or in a vicinity of the folded structures or the external-electrode pairs) where there is an artificially induced higher electrical field and/or a higher energy density. These artificial regions can be produced for example by use of structures including, but not limited to, multiple level collection optics, resonators, fractal antennas, and electrical grid (or electrode) patterns.

By having the light or electron emitting materials disposed in a vicinity of the energy augmentation structures of this invention, regardless of the whether the energy augmentation structure is in a region of intensified electric field or otherwise outside the region of intensified electric field, the energy augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

In one embodiment, the light or electron emitting materials noted above are disposed with an energy augmentation structure comprising one or more of an electromagnetic resonator structure, a folded resonator structure, and a fractal resonating structure, any of which having a region of an intensified electromagnetic field within the resonating structures.

In one embodiment, the energy converter or light or electron emitting materials noted above includes one or more luminescing materials. As described herein, there are uses of the energy augmentation structure and/or energy collector embodiments which enhance bioluminescence, chemo-luminescence, photoluminescence, fluorescence, mechano-luminescence, and/or electron emission.

In one embodiment, the energy converter or light emitting materials noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter (e.g., the luminescent material) were remote from the at least one energy augmentation structure.

In one embodiment, the bioluminescent materials are UV-emitting bioluminescent materials such as catalyzed luciferase and luminescent proteins.

In one embodiment, the energy converter or light emitting materials noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, UV-emitting bioluminescent materials can be used.

In some embodiments, metallic patterns form a folded resonator having opposing electrodes with electric fields directed in between, and a converter is positioned between the opposing electrodes or within fringing electric field of the opposing electrodes or otherwise in a vicinity of the opposing electrodes. In one example, the folded resonator is a % k folded resonator. In one example, metallic patterns comprise at least one of Au, Ag, Cu, Al, or transparent metal oxides. In another example, the metallic patterns can be formed with refractory metals such for example Ti, W, and Mo.

In some embodiments, the metallic patterns referenced above comprise an external external-electrode pair structure having opposing electrodes with electric fields directed in between, and a converter is positioned between the opposing electrodes or within fringing electric field of the opposing electrodes or otherwise in a vicinity of the opposing electrodes. In one example, the resonator is a ¾ λexternal-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments, plural resonators and plural converters are disposed at multiple positions throughout a light collector. In one example, the plural converters are positioned to convert light being internally scattered within the light collector.

In some embodiments of the energy augmentation structures, a first level of metallic patterns (or a second level of metallic patterns) comprises a metal core cladded with a high-K dielectric and a subsequent cladding of a low-K dielectric. In some embodiments of the energy augmentation structures, the first level of metallic patterns noted above (or the second level of metallic patterns) comprises a radial pattern of conductors. In some embodiments of the energy augmentation structures, the first level of metallic patterns noted above (or the second level of metallic patterns) comprises a fractal pattern. In one example, the fractal pattern is embedded within a dielectric material.

In some embodiments of the energy augmentation structures, the first level of metallic patterns noted above (or the second level of metallic patterns) comprises a three-dimensional fractal structure.

In some embodiments of the energy augmentation structures, there is provided a panel with the first level of metallic patterns and the second level of metallic patterns and optionally multiple converters formed therein or thereon. In some embodiments of the augmentation structures, there is provided a sheet with the first level of metallic patterns and the second level of metallic patterns and optionally multiple converters formed therein or thereon.

In some embodiments of the energy augmentation structures, the first level of metallic patterns noted above (or the second level of metallic patterns) is of different sizes and/or orientations to each other of the first level of metallic patterns or with respect to the second level of metallic patterns.

In another embodiment, the energy augmentator can collect or distribute light.

Figure 25A:
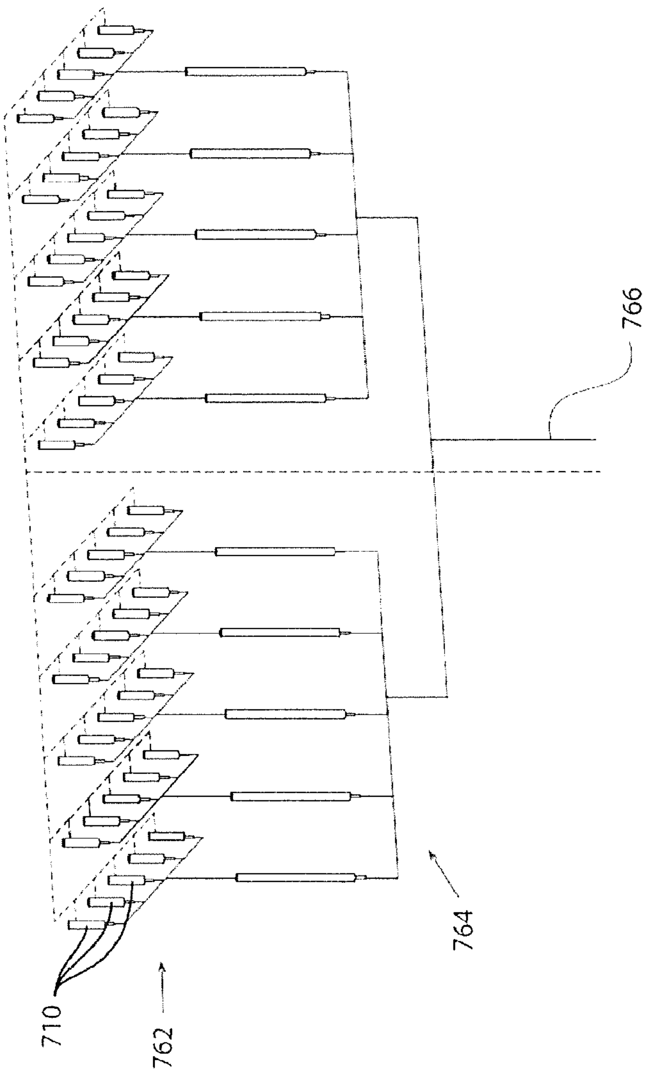
FIG. 25A is a schematic illustrating a distributed point light collector/transmitter of the invention.
Figure 25B:
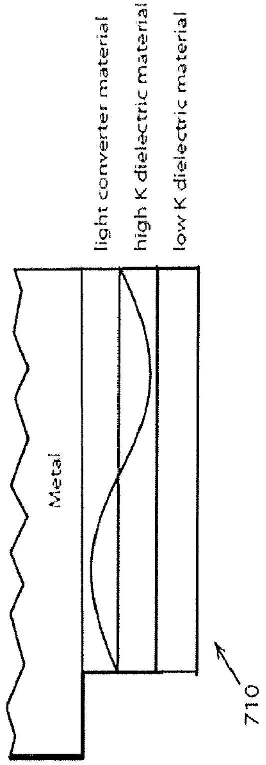
FIG. 25B is a schematic of a cross section of the collector/transmitter of FIG. 25A.

FIG. 25A is a schematic illustrating a distributed point light collector/transmitter of the invention showing a distribution of branches that can either collect light from distributed points 710 or conversely can distribute light from a central source 766 to the distributed points 710. The section of the collector/transmitter is shown in FIG. 25B showing a core metal, an optional light converter material, a high K dielectric, and a low K dielectric. In this arrangement, as shown, light is confined and not loss to scatter out of the collector/transmitter, except at the ends.

B. Energy Converters

In various embodiments of the invention, energy converters can be used with or without the energy augmentators described above. In some embodiments, the converters are for up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without the energy augmentators are included to enhance electromagnetic energy emission, preferably light or photon emission. When an energy augmentator is present, it may be separate from or connected to the energy converter. In certain embodiments, the energy converter can have the energy augmentator formed on its surface through chemical vapor deposition ("CVD") or physical vapor deposition ("PVD") processes or other nanoscale "printing" methods. Such embodiments may be particularly useful in methods for treating human or animal patients, in which having such energy augmentators "imprinted" on a surface of the energy converter can guarantee proximity between the energy augmentator and the energy converter to maximize the interaction with the energy being applied. Alternatively, the energy augmentator can be formed on a surface of an inert non-energy converting particle, formed, for example, from silica or formed from a non-energy converting particle coated with an biologically and/or chemically inert coating (such as, for example, diamond, diamond-like carbon, or similar inert materials). Such an energy augmentator can then be co-administered with the energy converter to the human or animal patient.

Suitable energy modulation agents or energy converters (the two terms are used interchangeably herein) of the invention include, but are not limited to, a biocompatible fluorescing metal nanoparticle, fluorescing dye molecule, gold nanoparticle, a water soluble quantum dot encapsulated by polyamidoamine dendrimers, a luciferase (bioluminescence), a biocompatible phosphorescent molecule, a combined electromagnetic energy harvester molecule, and a lanthanide chelate capable of intense luminescence.

Alternatively, the energy modulation agent or energy converter can emit energy in a form suitable for absorption at a target site or receptor. For example, the initiation energy source may be acoustic energy and one energy converter may be capable of receiving acoustic energy and emitting photonic energy (e.g. sonoluminescent molecules) to be received by another energy converter that is capable of receiving photonic energy. Other examples include energy converters that receive energy at x-ray wavelength and emit energy at UV wavelength, preferably at UV-A wavelength. A plurality of such energy converters may be used to form a cascade to transfer energy from initiation energy source via a series of energy converters.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a target site or a receptor such as a photoactivatable agent.

In a further embodiment, a biocompatible emitting source, such as a fluorescing metal nanoparticle or fluorescing dye molecule, is selected as an energy converter that emits in the UV-A band. In another embodiment, an energy converter comprising a UV-A emitting source can be a gold nanoparticle comprising for example a cluster of 5 gold atoms.

In another embodiment, an energy converter comprising a UV- or light-emitting luciferase is selected as the emitting source. A luciferase may be combined with ATP or another molecule, which may then be oxygenated with additional molecules to stimulate light emission at a desired wavelength. Alternatively, a phosphorescent emitting source may be used as the energy converter. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In one embodiment, the energy converters of the invention can include persistent after-glow phosphor materials emitting light in the visible to near ultraviolet and ultraviolet range. In one embodiment, Eu-doped strontium aluminate is used as an energy converter in which deep UV light or x-ray or electron beans "charge" the photoluminescence such that these phosphors can be charged outside for example a patient and then injected into target or diseased site where UV photons would be emitted. In another embodiment, gadolinium strontium magnesium aluminate is used as an energy converter in which deep UV light or x-ray or electron beans "charge" the photoluminescence such that these phosphors can be charged outside for example a patient and then injected into target or diseased site where UV photons would be emitted. U.S. Pat. Appl. Publ. No. 20070221883 (the entire contents of which are incorporated herein by reference) describes specifically gadolinium-activated strontium magnesium aluminate having an excitation maximum at about 172 nm, and which emits in a narrow-band UV emission at about 310 nm. The '883 publication also describes other useful energy converters for this invention, making note of emission spectra between 300 nm and 320 nm for a $Sr(Al,Mg)_{12}O_{19}$:Gd phosphor and two 312 nm line emitting phosphors, $YMgB_5O_{10}$:Gd, Ce and $YMgB_5O_{10}$: Gd, Ce, Pr. WO2016200349 (the entire contents of which are incorporated herein by reference) describes long lasting yellowish-green emitting phosphorescent pigments in the strontium aluminate (SrAl2O4) system, which could serve as energy converters in the present invention. WO 2016200348 (the entire contents of which are incorporated herein by reference) describes long lasting bluish-green emitting phosphorescent pigments in the strontium aluminate (Sr4Al14O25) system, which could serve as energy converters in the present invention. Xiong et al in "Recent advances in ultraviolet persistent phosphors," Optical Materials X 2 (2019) (the entire contents of which are incorporated herein by reference) describes a number of ultraviolet persistent phosphors that could as energy converters in the present invention. The table below provides a listing of such persistent phosphors:

| | | |
|---|---|---|
| $SrO:Pb^{2+}$ | 390 | >1 h |
| $CaAl_2O_4:Ce^{3+}\ Tb^{3+}$ | 400 | >10 h |
| $CaAl_2O_4:Ce^{3+}\ Tb^{3+}$ | 413 | >10 h |
| $Sr_2Al_2SiO_7:Ce^{3+}$ | 400 | several minutes |
| $SrZrO_3$ | 395 | <1000 s |
| $BaZrO_3:Mg^{2+}$ | 400 | >2400 s |
| $SrZrO_3:Pr^{3+}$ | 356 | |
| $CdSiO_3:Bi^{3+}$ | 360 | |
| $CdSiO_3:Bi^{3+}\ Dy^{3+}$ | 360 | |
| $CdSiO_3:Bi^{3+}\ Gd^{3+}$ | 344 | >6 h |
| $Sr_2MgGe_2O_7:Pb^{2+}$ | 370 | >12 h |
| $NaLuGeO_4:Bi^{3+}\ Eu^{3+}$ | 400 | >63 h |
| $CaZnGe_2O_6:Bi^{3+}$ | 300-700 | >12 h |
| $Cs_2NaYF_6:Pr^{3+}$ | 250 | >2 h |

In one embodiment, the phosphor described by Xiong et al as $CaAl_2O_4:Ce^{3+}$ having an emission peak of 400 nm and a persistent time of more than 10 h could be used, where it would be charged by x-ray irradiation outside a patient and then injected at a diseased site to provide internally generated UV light.

In one embodiment, the persistent phosphors noted could be activated ex vivo and introduced along with psoralen (or other photoactivatable drug) into the patient by exchange of a bodily fluid or for example by supplying the persistent phosphors and the photoactivatable drug into a patient's blood stream.

In one embodiment, the persistent phosphors noted could be activated in vivo by injection of the phosphors into a diseased site and then exposure to x-rays.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. In another embodiment, a Stokes shift of an emitting source or a series of emitting sources arranged in a cascade is selected to convert a shorter wavelength energy, such as X-rays, to a longer wavelength fluorescence emission such an optical or UV-A.

In one embodiment, a lanthanide chelate capable of intense luminescence is used as an energy converter. In another embodiment, a biocompatible, endogenous fluorophore emitter is selected as an energy converter.

In one embodiment, the energy converters of the invention can include visible and UV-light emitting bioluminescent materials. In one embodiment, bioluminescent materials such as coelenterate-type luciferin analogues could be used including amide monoanion known to emit at 480 nm and oxyluciferin known to emit at 395 nm.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance light or photon emission. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance light or photon emission can convert energy from one of ultraviolet light, x-rays, and high energy particles to visible light. The down conversion materials to enhance light or photon emission can convert energy from higher energy visible light to lower energy visible light.

In one embodiment of the invention, a quantum dot mixture with or without the energy augmentators can be used for the multiple nanoparticles. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted wavelength or energy emission. Quantum dots represent one way to down convert blue light of the spectrum to a targeted wavelength or energy emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

Specifically, in one embodiment of the invention, a quantum dot mixture (QDM) coating can be deposited using CVD and or sol-gel techniques using standard precipitation techniques. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials described here can be used with or without energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{2+}$ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$, and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers with or without energy augmentators are also suitable as conversion materials: poly(phenylene ethynylene), poly(phenylene vinylene), poly(p-phenylene), poly(thiophene), poly(pyridyl vinylene), poly(pyrrole), poly (acetylene), poly(vinyl carbazole), poly(fluorenes), and the like, as well as copolymers and/or derivatives thereof.

In various embodiments of the invention, the following materials with or without energy augmentators can be used similar to that detailed in U.S. Pat. No. 7,090,355, the entire contents of which are incorporated herein by reference. For down-conversion, the following materials can be used. Inorganic or ceramic phosphors or nano-particles, including but not limited to metal oxides, metal halides, metal chalcogenides (e.g. metal sulfides), or their hybrids, such as metal oxo-halides, metal oxo-chalcogenides. Laser dyes and small organic molecules, and fluorescent organic polymers. Semiconductor nano-particles, such as II-VI or III-V compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_mA_{1-m})_3(Al_nB_{1-n})_5O_{12}$, doped with Ce; where 0≤m, n≤1, where A includes other rare earth elements, B includes B, Ga. In addition, phosphors containing metal silicates, metal borates, metal phosphates, and metal aluminates hosts can be used. In addition, nano-particulates phosphors containing common rare earth elements (e.g. Eu, Tb, Ce, Dy, Er, Pr, and Tm) and transitional or main group elements (e.g. Mn, Cr, Ti, Ag, Cu, Zn, Bi, Pb, Sn, and Tl) as the fluorescent activators, can be used. Materials such as Ca, Zn, Cd in tungstates, metal vanadates, ZnO, etc. can be used.

The commercial laser dye materials obtained from several laser dye vendors, including Lambda Physik, and Exciton, etc. can also be used with or without energy augmentators. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in optoelectronic devices, such as polymer light emitting diodes (PLED). Such fluorescent polymers can be used directly as the fluorescent layer of the transparent 2-D display screen with and without energy augmentators.

As noted above, semiconductor nanoparticles (e.g., quantum dots) can be used with or without energy augmentators. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nanoparticle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion materials with or without energy augmentators.

Such molecules include a metal center of rare earth elements including Eu, Tb, Er, Tm, Ce protected with organic chelating groups. The metal center may also include transitional elements such as Zn, Mn, Cr, Ir, etc. and main group elements such as B, Al, Ga. Such organometallic molecules can readily dissolve in liquid or transparent solid host media. Some examples of such fluorescent organometallic molecules include: 1. Tris(dibenzoylmethane)mono(phenanthroline)europium(III); 2. Tris(8-hydroxyquinoline) erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. An europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue), or different wavelengths or energies of light. In embodiments, the conversion materials can be light emitting particles made of pure organic or organo-metallic dyes with or without energy augmentators.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials (which can be used with or without energy augmentators) include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties, as noted above. Examples of doped (or alloyed) glass systems suitable for the include $Y_2O_3$:Gd, $Y_2O_3$:Dy, $Y_2O_3$:Tb, $Y_2O_3$:Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$:Eu (red), $Y_2O_3$:Eu (red), $YVO_4$:Eu (red), and $Zn_2SiO_4$:Mn (green).

With regard more specifically to down converter materials suitable for the invention, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without energy augmentators. In one example, the infrared-triggered phosphors would be used in conjunction with the folded resonators, and the receipt of a microwave or IR signal would locally heat and trigger emission. (This application would be particularly well suited for color enhancement and/or security applications.)

In other embodiments of the invention, the down converter materials (or mixtures of down converters materials (which can be used with or without energy augmentators) can include $Y_2O_3$:Li. Sun et al "Luminescent properties of Li+ doped nanosized $Y_2O_3$:Eu," Solid State Comm. 119 (2001) 393-396 (the entire contents of which are incorporated herein by reference) describe such materials. Hou et al "Luminescent properties nano-sized $Y_2O_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria ($Y_2O_3$) powders have been successfully synthesized by a co-precipitation method. The powders were well crystallized, and the grains were almost spherical with good dispersibility. The quenching concentration of $Eu^{3+}$ ions is 9 mol % which is much higher than micro-scaled powders. The incorporation of Li+ ions greatly improved the luminescence intensity. The highest emission intensity was observed with 4 mol % Li+ doped $Y_2O_3$:Eu powder ($(Y_{0.87}Eu_{0.09}Li_{0.04})_2O_3$) and the fluorescence intensity was increased by as much as 79%. Yi et al "Improved cathodoluminescent characteristics of $Y_2O_3$:$Eu^{3+}$ thin films by Li-doping," Appl. Phys. A 87, 667-671 (2007) (the entire contents of which are incorporated herein by reference) describe cathodoluminescent spectra for both $Y_2O_3$:$Eu^{3+}$ and Li-doped $Y_2O_3$:$Eu^{3+}$ films and methods for making these materials.

Specific downconverting materials may also include at least one or more of $Y_2O_3$, $Y_2O_3$:Gd, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS, ZnSe, MgS, CaS, $Zn_2SiO_4$:Mn, LaOBr:Tm and alkali lead silicate including compositions of $SiO_2$, $B_2O_3$, $Na_2O$, $K_2O$, PbO, MgO, or Ag, and combinations or alloys or layers thereof. Furthermore, the down-converting materials can be sulfur containing phosphors, which can help for example in the rubber vulcanization or other photoactivated processes. An example of such a sulfur containing phosphor is: (Sr,Ca)$Ga_2S_4$. Other examples wherein said phosphor particles comprise a thiogallate host material selected from the group consisting of $SrGa_2S_4$, $CaGa_2S_4$ $BaGa_2S_4$, $MgGa_2S_4$ and solid solutions thereof. The particle size of such phosphor can be controlled from 25 nm to 300 microns in size as described in U.S. Pat. No. 6,153,123A. The downconverting materials can include a dopant including at least one of Er, Eu, Yb, Tm, Nd, Mn, Sb, Tb, Ce, Y, U, Pr, La, Gd and other rare-earth species or a combination thereof. The dopant can be included at a concentration of 0.01%-50% by mol concentration. At times it is preferable to have a combination of dopants rather than one dopant such is the case for a Mn and Sb in silicate matrices.

The invention in other embodiments can use a wide variety of up conversion materials (or mixtures of up converters) with or without the energy augmentators to enhance a particular wavelength or energy of light emitted from a material or surface. These up conversion materials can include similar materials as discussed above with regard to down conversion but typically included doped or impurity states in a host crystal that provide a mechanism for up conversion pumping. Accordingly, the up conversion materials to enhance wavelength or energy emission can convert energy from one of near infrared, infrared, and microwave irradiation. The upconversion materials to enhance color emission can convert energy from lower energy visible light to higher energy visible light.

In one example, a nanoparticle of a lanthanide doped oxide can be excited with near infrared light such as laser light at 980 nm and 808 nm to produce visible light in different parts of the red, green, blue spectrum (different wavelengths or energies) depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the $NaYF_4$ such that the $Yb^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention with or without the energy augmentators.

Further, materials specified for up conversion materials in the invention (with or without energy augmentation) include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\le 1$, and $0<y\le 1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\le 1$, $0<y\le 1$, $0<z\le 1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er;

CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . 0<z≤1, o<q≤1).

Some nanoparticles such as ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$ are known in the art to function for both down-conversion luminescence and upconversion luminescence and would be suitable for the invention with or without energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple wavelength or energy emissions from even the same dopants.

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a $Tm^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4$:$Yb^{3+}$, $Tm^{3+}$, and $YbPO_4$:$Er^{3+}$ nanocrystals in chloroform. Excitation at 975 nm has been shown by others to produce visible emission in the blue, green, or red spectral regions.

Tellurium and germanium oxides (tellurites and germanates) are also suitable upconverters. These glasses can be doped with Tm, Yb, Ho, Er, Pr, for example.

$Yb^{3+}$ doped $BaZrO_3$ is also suitable for upconversion. $Er^{3+}$ and/or $Tm^{3+}$ doping are also suitable for tailoring the emission wavelengths.

In another embodiment, $Nd^{3+}$:$Cs_2NaGdCl_6$ and $Nd^{3+}$, $Yb^{3+}$:$Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2-4I9/2), and (4G7/2→4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^{3+}$/$Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in $[Ru(dmb)_3]^{2+}$ (dmb=4,4'-dimethyl-2,2'-bipyridine) in the presence of anthracene or 9,10-diphenylanthracene have been reported to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

In certain embodiments, further energy converters include, but are not limited to, (not ranked by order of preference or utility):

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$, and $LuPO_4$:$Pr^{3+}$. Examples further include the alkali earth chalcogenide phosphors which are in turn exemplified by the following non-inclusive list: MgS:$Eu^{3+}$, CaS:$Mn^{2+}$, CaS:Cu, CaS:Sb, CaS:$Ce^{3+}$, CaS:$Eu^{2+}$, CaS:$Eu^{2+}$ $Ce^{3+}$, CaS:$Sm^{3+}$ CaS:$Pb^{2+}$, CaO:$Mn^{2+}$, CaO:$Pb^{2+}$.

Further examples include the ZnS type phosphors that encompass various derivatives: ZnS:Cu,Al(Cl), ZnS:Cl(Al), ZnS:Cu,I(Cl), ZnS:Cu, ZnS:Cu,In.

Also included are the compound IIIb-Vb phosphors which include the group IIIb and Vb elements of the periodic table. These semiconductors include BN, BP, BSb, AlN, AlP, AlAs, AlSb, GaN, GaP, GaAs, GaSb, InN, InP, InAs, InSb and these materials may include donors and acceptors that work together to induce light emission diodes. These donors include, but are not limited to, Li, Sn, Si, Li, Te, Se, S, O and acceptors include, but are not limited to, C, Be, Mg, Zn, Cd, Si, Ge. Further included are the major GaP light emitting diodes which include, but are not limited to, GaP:Zn,O, GaP:NN, Gap:N and GaP, which emit colors Red, Yellow, Green and Pure Green respectively.

The materials can further include such materials as GaAs with compositional variation of the following sort: $In_{1-y}(Ga_{1-x}Al_x)_yP$.

Also included is silicon carbide SiC, which has commercial relevancy as a luminescent platform in blue light emitting diodes. These include the polytypes 3C—SiC, 6H—SiC, 4H—SiC with donors such as N and Al and acceptors such as Ga and B.

Further examples include multiband luminescent materials include, but not limited to, the following compositions (Sr, Ca, Ba)$_5(PO_4)_3Cl:Eu^{2+}$, $BaMg_2Al_{16}O_{27}:Eu^{2+}$, $CeMgAl_{11}O_{19}:Ce^{3+}:Tb^{3+}$, $LaPO_4:Ce^{3+}:Tb^{3+}$, $GdMgB_5O_{10}:Ce_3:Tb^{3+}$, $Y_2O_3:Eu^{3+}$, $(Ba,Ca,Mg)_5(PO_4)_3Cl:Eu^{2+}$, $2SrO_{0.84}$P2O50.16B2O3:$Eu^{2+}$, $Sr_4Al_{14}O_{25}:Eu^{2+}$.

Materials typically used for fluorescent high pressure mercury discharge lamps are also included. These can be excited with X-Ray and are exemplified by way of family designation as follows: Phosphates (Sr, M)$(PO_4)_2:Sn^{2+}$, Mg or Zn activator, Germanate $4MgO{\cdot}GeO_2:Mn^{4+}$, 4(MgO, $MgF_2)GeO_2:Mn^{4+}$, Yttrate $Y_2O_3:Eu^{3+}$, Vanadate $YVO_4:Eu^{3+}$, $Y(P,V)O_4:Eu^{3+}$, $Y(P,V)O_4:In^{+}$, Halo-Silicate $Sr_2Si_3O_{82}SrCl_2:Eu^{2+}$, Aluminate $(Ba,Mg)_2Al_{16}O_{24}:Eu^{2+}$, (Ba, $Mg)_2Al_{16}O_{24}:Eu^{2+},Mn^{2+}$, $Y_2O_3Al_2O_3:Tb^{3+}$.

Another grouping by host compound includes chemical compositions in the halophosphates phosphors, phosphate phosphors, silicate phosphors, aluminate phosphors, borate phosphors, tungstate phosphors, and other phosphors. The halophosphates include, but are not limited to: $3Ca_3(PO_4)_2{\cdot}Ca(F,Cl)_2:Sb^{3+}$, $3Ca_3(PO_4)_2{\cdot}Ca(F,Cl)_2:Sb^{3+}/Mn^{2+}$, $Sr_{10}(PO_4)_6Cl_2:Eu^{2+}$, $(Sr,Ca)_{10}(PO_4)_6Cl_2:Eu^{2+}$, $(Sr,Ca)_{10}(PO_4)_6{\cdot}nB_2O_3:Eu^{3+}$, (Sr, $Ca,Mg)_{10}(PO_4)_6Cl_2:Eu^{2+}$. The phosphate phosphors include, but are not limited to: $Sr_2P_2O_7:Sn^{2+}$, $(Sr,Mg)_3(PO_4)_2:Sn^{2+}$, $Ca_3(PO_4)_2{\cdot}Sn^{2+}$, $Ca_3(PO_4)_2:Tl^{+}$, $(Ca,Zn)_3(PO_4)_2:Tl^{+}$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3{\cdot}0.2SiO_2{\cdot}0.9P_2O_5:Ce^{3+}{\cdot}Tb^{3+}$, $BaO{\cdot}TiO_2{\cdot}P_2O_5$. The silicate phosphors $Zn_2SiO_4:Mn^{2+}$, $CaSiO_3:Pb^{2+}/Mn^{2+}$, (Ba, Sr, $Mg){\cdot}3Si_2O_7:Pb^{2+}$, $BaSi_2O_5:Pb^{2+}$, $Sr_2Si_3O_8{\cdot}2SrCl_2:Eu^{2+}$, $Ba_3MgSi_2O_8:Eu^{2+}$, $(Sr,Ba)Al_2Si_2O_8:Eu^{2+}$.

The aluminate phosphors include, but are not limited to: $LiAlO_2:Fe^{3+}$, $BaAl_8O_{13}:Eu^{2+}$, $BaMg_2Al_{16}O_{27}:Eu^{2+}$, $BaMg_2Al_{16}O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include: $Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include, but are not limited to: $CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO{\cdot}As_2O_5:Mn^{2+}$, $3.5MgO{\cdot}0.5MgF_2{\cdot}GeO_2:Mn^{4+}$.

The activators to the various doped phosphors include, but are not limited to: $Tl^{+}$, $Pb^{2+}$, $Ce^{3+}$ $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$. The luminescence center $Tl^{+}$ is used with a chemical composition such as: $(Ca,Zn)_3(PO_4)_2:Tl^{+}$, $Ca_3(PO_4)_2:Tl^{+}$. The luminescence center $Mn^{2+}$ is used with chemical compositions such as $MgGa_2O_4:Mn^{2+}$, $BaMg_2Al_{16}O_{27}:Eu^{2+}/Mn^{2+}$, $Zn_2SiO_4:Mn^{2+}$, $3Ca_3(PO_4)_2{\cdot}Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$. The luminescence center Sn2+ is used with chemical compositions such as: $Sr_2P_2O_7:Sn^{2+}$, $(Sr,Mg)_3(PO_4)_2:Sn^{2+}$. The luminescence center $Eu^{2+}$ is used with chemical compositions such as: $SrB_4$O7F:$Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$. The luminescence center $Pb^{2+}$ is used with chemical compositions such as: $(Ba,Mg,Zn)_3Si_2O_7:Pb^{2+}$, $BaSi_2O_5:Pb^{2+}$, (Ba, $Sr)_3Si_2O_7:Pb^{2+}$.

The luminescence center $Sb^{2+}$ is used with chemical compositions such as: $3Ca_3(PO_4)_2{\cdot}Ca(F,Cl)_2:Sb^{3+}$, $3Ca_3(PO_4)_2{\cdot}Ca(F,Cl)_2:Sb^{3+}/Mn^{2+}$.

The luminescence center $Tb^{3+}$ is used with chemical compositions such as: $CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$. The luminescence center $Eu^{3+}$ is used with chemical compositions such as: $Y_2O_3:Eu^{3+}$, $Y(V,P)O_4:Eu^{3+}$. The luminescence center $Dy^{3+}$ is used with chemical compositions such as: $YVO_4:Dy^{3+}$. The luminescence center $Fe^{3+}$ is used with chemical compositions such as: $LiAlO_2:Fe^{3+}$. The luminescence center $Mn^{4+}$ is used with chemical compositions such as: $6MgO{\cdot}As_2O_5:Mn^{4+}$, $3.5MgO0.5MgF_2{\cdot}GeO_2:Mn^{4+}$. The luminescence center $Ce^{3+}$ is used with chemical compositions such as: $Ca_2MgSi_2O_7:Ce^{3+}$ and $Y_2SiO_5:Ce^{3+}$. The luminescence center $WO_4^{2-}$ is used with chemical compositions such as: $CaWO_4$, $(Ca,Pb)WO_4$, $MgWO_4$. The luminescence center $TiO_4^{4-}$ is used with chemical compositions such as: $BaO{\cdot}TiO_2{\cdot}P_2O_5$.

Additional phosphor chemistries of interest using X-Ray excitations include, but are not limited to, the k-edge of these phosphors. Low energy excitation can lead to intense luminescence in materials with low k-edge. Some of these chemistries and the corresponding k-edge are listed below:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4$:Nb | 67.42 keV |
| ZnS:Ag | 9.66 keV |
| (Zn, Cd)S:Ag | 9.66/26.7 keV |

These materials can be used alone or in combinations of two or more. A variety of compositions can be prepared to obtain the desired output wavelength or spectrum of wavelengths.

In the present invention, the phosphor selection could be chosen such that under x-ray or other high energy source irradiation, the light emitted from the phosphors could, for example, have exemplary characteristics including:

Emissions in 190-250 nm wavelength range;

Emissions in the 330-340 nm wavelength range.

Mechanoluminescent Materials (Organic and Inorganic):

In another embodiment of the invention, mechano-luminescent materials can be used as energy converters and optionally can be used with the energy augmentation structures described above.

Mechano-luminescent materials convert ultrasonic or mechanical energy (such as vibrations naturally existing on an article such as motor or vibrations from driven by transducers) into visible light. Here, for example, the mechano-luminescent materials would be placed in a vicinity (e.g., between or around or inside) the folded structures or the external-electrode pairs.

In one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

Various mechano-luminescent materials suitable for the present invention with or without energy augmentators include $ZnS{:}Mn^{2+}$, $SrAl_2O_4{:}Eu^{2+}$, ZnS:Cu, $SrAMgSi_2O_7{:}Eu^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_x$ ($x<1/4$), CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$ ($1\leq n\leq 2$), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ (x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, $(Ca, Sr, Ba)_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

In one embodiment, a europium-holmium co-doped strontium aluminate can be used as a mechano-luminescent material (i.e., an energy converter) alone or in conjunction with the energy augmentators. The europium-holmium co-doped strontium aluminate and the other mechano-luminescent materials convert sonic or acoustic energy into photon emissions which may or may not be placed in a vicinity of the energy augmentators.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention with or without energy augmentators, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light.

Electroluminescent and phosphorescent materials (organic and inorganic): The present invention in various embodiments can utilize organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used with or without energy augmentators for the electroluminescence and phosphorescent materials described below include but is not limited to the following inorganic electroluminescent phosphor materials:

$SrS{:}Ce^{3+}$
$CaGa_2S_4{:}Ce^{3+}$
$SrS{:}Cu^{+}$
$CaS{:}Pb^{2+}$
$BaAl_2S_4{:}Eu^{2+}$
$ZnS{:}Tb^{3+}$,
$ZnMgS{:}Mn^{2+}$
$SrGa_2S_4{:}Eu^{2+}$
$CaAl_2S_4{:}Eu^{2+}$
$BaAl_2S_4{:}Eu^{2+}$
$ZnS{:}Mn^{2+}$
$MgGa_2O_4{:}Eu^{3+}$
$(Ca, Sr)Y_2S_4{:}Eu^{2+}$
$BaAl_2S_4{:}Eu^{2+}$

Organic molecules that can phosphoresce under the influence of an electric field are also of interest in the present application. The organic fluorescent compounds with high quantum yield include by way of illustration:

Naphthalene,
Pyrene,
Perylene,
Anthracene,
Phenanthrene,
p-Terphenyl,
p-Quartphenyl,
Trans-stilbene,
Tetraphenylbutadiene,
Distyrylbenzene,
2,5-Diphenyloxazole,
4-Methyl-7-diethylaminocoumarin,
2-Phenyl-5-(4-biphenyl)-1,3,4-oxadiazole,
3-Phenylcarbostyryl,
1,3,5-Triphenyl-2-pyrazoline,
1,8-Naphthoylene-1',2'-bezimidazole,
4-Amino-N-phenyl-naphthalimide.

The inorganic fluorescent and phosphorescent materials detailed here are numerous, and various examples are given by way of illustration rather than limitation and can be used with or without energy augmentators. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$.

Further included are alkali earth chalcogenide phosphors which are in turn exemplified by the following non-inclusive list:

$MgS{:}Eu^{3+}$, $CaS{:}Mn^{2+}$, CaS:Cu, CaS:Sb, $CaS{:}Ce^{3+}$, $CaS{:}Eu^{2+}$, $CaS{:}Eu^{2+}Ce^{3+}$ $CaS{:}Sm^{3+}$, $CaS{:}Pb^{2+}$, $CaO{:}Mn^{2+}$, $CaO{:}Pb^{2+}$.

The examples include the ZnS type phosphors that encompass various derivatives:

ZnS:Cu,Al(Cl), ZnS:Cl(Al), ZnS:Cu,I(Cl), ZnS:Cu, ZnS:Cu,In.

Compound IIIb-Vb phosphors which include the group IIIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1−y(Ga1−xAlx)yP (provides a simple example). Silicon Carbide SiC as a luminescent platform has commercial relevancy if the blue light emitting diodes. These include the polytypes 3C—SiC, 6H—SiC, 4H—SiC with donors such as N and Al and acceptors such as Ga and B.

Multiband luminescent materials suitable for converter materials include for example the following compositions:

(Sr, Ca, Ba)$_5$(PO$_4$)$_3$Cl:Eu$^{2+}$, BaMg$_2$Al$_{16}$O$_{27}$:Eu$^{2+}$, CeMgAl$_{11}$O$_{19}$:Ce$^{3+}$:Tb$^{3+}$, LaPO$_4$:Ce$^{3+}$:Tb$^{3+}$, GdMgB$_5$O$_{10}$:Ce$^{3+}$:Tb$^{3+}$, Y$_2$O$_3$:Eu$^{3+}$, (Ba,Ca,Mg)$_5$(PO$_4$)$_3$Cl:Eu$^{2+}$, 2SrO$_{0.84}$P$_2$O$_5$·0.16B$_2$O$_3$:Eu$^{2+}$, Sr$_4$Al$_{14}$O$_{25}$:Eu$^{2+}$.

Other materials suitable for converter materials include those materials used for fluorescent high pressure mercury discharge lamps can be excited with X-Ray and are exemplified by way of family designation as follows:

Phosphates (Sr, M)(PO$_4$)$_2$:Sn$^{2+}$, Mg or Zn activator, Germanate 4MgO·GeO$_2$:Mn$^{4+}$, 4(MgO, MgF$_2$)GeO$_2$:Mn$^{4+}$, Yttrate Y$_2$O$_3$:Eu$^{3+}$, Vanadate YVO$_4$:Eu$^{3+}$, Y(P,V)O$_4$:Eu$^{3+}$, Y(P,V)O$_4$:In$^{+}$, Halo-Silicate Sr$_2$Si$_3$O$_8$·2SrCl$_2$:Eu$^{2+}$, Aluminate (Ba,Mg)$_2$Al$_{16}$O$_{24}$:Eu$^{2+}$, (Ba, Mg)$_2$Al$_{16}$O$_{24}$:Eu$^{2+}$,Mn$^{2+}$, Y$_2$O$_3$Al$_2$O$_3$:Tb$^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration:

3Ca$_3$(PO$_4$)$_2$·Ca(F,Cl)$_2$:Sb$^{3+}$, 3Ca$_3$(PO$_4$)$_2$·Ca(F,Cl)$_2$:Sb$^{3+}$ Mn$^{2+}$, Sr$_{10}$(PO$_4$)$_6$Cl$_2$:Eu$^{2+}$, (Sr,Ca)$_{10}$(PO$_4$)$_6$Cl$_2$:Eu$^{2+}$, (Sr,Ca)$_{10}$(PO$_4$)$_6$·nB$_2$O$_3$:Eu$^{3+}$, (Sr, Ca,Mg)$_{10}$(PO$_4$)$_6$Cl$_2$:Eu$^{2+}$. The phosphate phosphors include by way of illustration Sr$_2$P$_2$O$_7$:Sn$^{2+}$, (Sr,Mg)$_3$(PO$_4$)$_2$:Sn$^{2+}$, Ca$_3$(PO$_4$)$_2$·Sn$^{2+}$, Ca$_3$(PO$_4$)$_2$:Tl$^{+}$, (Ca,Zn)$_3$(PO$_4$)$_2$:Tl$^{+}$, Sr$_2$P$_2$O$_7$:Eu$^{2+}$, SrMgP$_2$O$_7$:Eu$^{2+}$, Sr$_3$(PO$_4$)$_2$:Eu$^{2+}$, LaPO$_4$:Ce$^{3+}$, Tb$^{3+}$, La$_2$O$_3$·0.2SiO$_2$·0.9P$_2$O$_5$:Ce$^{3+}$·Tb$^{3+}$, BaO·TiO$_2$·P$_2$O$_5$. The silicate phosphors Zn$_2$SiO$_4$:Mn$^{2+}$, CaSiO$_3$:Pb$^{2+}$/Mn$^{2+}$, (Ba, Sr, Mg)$_3$Si$_2$O$_7$:Pb$^{2+}$, BaSi$_2$O$_5$:Pb$^{2+}$, Sr$_2$Si$_3$O$_8$·2SrCl$_2$:Eu$^{2+}$, Ba$_3$MgSi$_2$O$_8$:Eu$^{2+}$, (Sr,Ba)Al$_2$Si$_2$O$_8$:Eu$^{2+}$.

The aluminate phosphors include:

LiAlO$_2$:Fe$^{3+}$, BaAl$_8$O$_{13}$:Eu$^{2+}$, BaMg$_2$Al$_{16}$O$_{27}$:Eu$^{2+}$, BaMg$_2$Al$_{16}$O$_{27}$:Eu$^{2+}$/Mn$^{2+}$, Sr$_4$Al$_{14}$O$_{25}$:Eu$^{2+}$, CeMgAl$_{11}$O$_{19}$:Ce$^{3+}$/Tb$^{3+}$.

The borate phosphors include:

Cd$_2$B$_2$O$_5$:Mn$^{2+}$, SrB$_4$O$_7$F:Eu$^{2+}$, GdMgB$_5$O$_{10}$:Ce$^{3+}$/Tb$^{3+}$, GdMgB$_5$O$_{10}$:Ce$^{3+}$/Mn$^{3+}$, GdMgB$_5$O$_{10}$:Ce$^{3+}$/Tb$^{3+}$/Mn$^{2+}$.

The tungstate phosphors include:

CaWO$_4$, (Ca,Pb)WO$_4$, MgWO$_4$. Other phosphors Y$_2$O$_3$:Eu$^{3+}$, Y(V,P)O$_4$:Eu$^{2+}$, YVO$_4$:Dy$^{3+}$, MgGa$_2$O$_4$:Mn$^{2+}$, 6MgO·As$_2$O$_5$:Mn$^{2+}$, 3.5MgO·0.5MgF$_2$·GeO$_2$:Mn$^{4+}$.

Activators of relevance to the various doped phosphors include the following list:

Tl$^{+}$, Pb$^{2+}$, Ce$^{3+}$, Eu$^{2+}$, WO$_4^{2-}$, Sn$^{2+}$, Sb$^{3+}$, Mn$^{2+}$, Tb$^{3+}$, Eu$^{3+}$, Mn$^{4+}$, Fe$^{3+}$.

In various embodiments, the luminescence center Tl$^{+}$ can be used with a chemical composition such as:

(Ca,Zn)$_3$(PO$_4$)$_2$:Tl$^{+}$, Ca$_3$(PO$_4$)$_2$:Tl$^{+}$.

Similarly, the luminescence center Mn2+ can be used with chemical compositions such as MgGa$_2$O$_4$:Mn$^{2+}$, BaMg$_2$Al$_{16}$O$_{27}$:Eu$^{2+}$/Mn$^{2+}$, Zn$_2$SiO$_4$:Mn$^{2+}$, 3Ca$_3$(PO$_4$)$_2$·Ca(F,Cl)$_2$:Sb$^{2+}$/Mn$^{2+}$, CaSiO$_3$:Pb$^{2+}$/Mn$^{2+}$, Cd$_2$B$_2$O$_5$:Mn$^{2+}$, CdB$_2$O$_5$:Mn$^{2+}$, GdMgB$_5$O$_{10}$:Ce$^{3+}$/Mn$^{2+}$, GdMgB$_5$O$_{10}$:Ce$^{3+}$/Tb$^{3+}$/Mn$^{2+}$.

Further, the luminescence center Sn$^{2+}$ can be used with chemical compositions such as:

Sr$_2$P$_2$O$_7$:Sn$^{2+}$, (Sr,Mg)$_3$(PO$_4$)$_2$:Sn$^{2}$.

The luminescence center Eu$^{2+}$ can also be used with chemical compositions such as:

SrB$_4$O$_7$F:Eu$^{2+}$, (Sr,Ba)Al$_2$Si$_2$O$_8$:Eu$^{2+}$, Sr$_3$(PO$_4$)$_2$:Eu$^{2+}$, Sr$_2$P$_2$O$_7$:Eu$^{2+}$, Ba$_3$MgSi$_2$O$_8$:Eu$^{2+}$, Sr$_{10}$(PO$_4$)$_6$Cl$_2$:Eu$^{2+}$, BaMg$_2$Al$_{16}$O$_{27}$:Eu$^{2+}$/Mn$^{2+}$, (Sr,Ca)$_{10}$(PO$_4$)$_6$Cl$_2$:Eu$^{2+}$.

The luminescence center Pb$^{2+}$ can be used with chemical compositions such as:

(Ba,Mg,Zn)$_3$Si$_2$O$_7$:Pb$^{2+}$, BaSi$_2$O$_5$:Pb$^{2+}$, (Ba,Sr)$_3$Si$_2$O$_7$:Pb$^{2+}$.

The luminescence center Sb$^{2+}$ can be used with chemical compositions such as:

3Ca$_3$(PO$_4$)$_2$·Ca(F,Cl)$_2$:Sb$^{3+}$, 3Ca$_3$(PO$_4$)$_2$·Ca(F,Cl)$_2$:Sb$^{3+}$/Mn$^{2+}$.

The luminescence center Tb3+ can be used with chemical compositions such as:

CeMgAl$_{11}$O$_{19}$:Ce$^{3+}$/Tb$^{3+}$, LaPO$_4$:Ce$^{3+}$/Tb$^{3+}$, Y$_2$SiO$_5$:Ce$^{3+}$/Tb$^{3+}$, GdMgB$_5$O$_{10}$:Ce$^{3+}$/Tb$^{3+}$.

The luminescence center Eu$^{3+}$ can be used with chemical compositions such as:

Y$_2$O$_3$:Eu$^{3+}$, Y(V,P)O$_4$:Eu$^{3+}$.

The luminescence center Dy$^{3+}$ can be used with chemical compositions such as:

YVO$_4$:Dy$^{3+}$.

The luminescence center Fe$^{3+}$ can be used with chemical compositions such as:

LiAlO$_2$:Fe$^{3+}$.

The luminescence center Mn$^{4+}$ can be used with chemical compositions such as:

6MgO·As$_2$O$_5$:Mn$^{4+}$, 3.5MgO·0.5MgF$_2$·GeO$_2$:Mn$^{4+}$.

The luminescence center Ce$^{3+}$ can be used with chemical compositions such as:

Ca$_2$MgSi$_2$O$_7$:Ce$^{3+}$ and Y$_2$SiO$_5$:Ce$^{3+}$.

The luminescence center WO$_4^{2-}$ can be used with chemical compositions such as:

CaWO$_4$, (Ca,Pb)WO$_4$, MgWO$_4$.

The luminescence center TiO$_4^{4-}$ can be used with chemical compositions such as:

BaO·TiO$_2$·P$_2$O$_5$.

In various embodiments of this invention, the phosphor chemistry utilized in x-ray excitations can be used with or without energy augmentators. Of particular interest is the k-edge of these phosphors. Low energy excitation can lead to intense luminescence in materials with low k-edge. Some of these chemistries and the corresponding k-edge are included as follows:

| | |
|---|---|
| BaFCl:Eu$^{2+}$ | 37.38 keV |
| BaSO$_4$:Eu$^{2+}$ | 37.38 keV |
| CaWO$_4$ | 69.48 keV |
| Gd$_2$O$_2$S:Tb$^{3+}$ | 50.22 keV |
| LaOBr:Tb$^{3+}$ | 38.92 keV |
| LaOBr:Tm$^{3+}$ | 38.92 keV |
| La$_2$O$_2$S:Tb$^{3+}$ | 38.92 keV |
| Y$_2$O$_2$S:Tb$^{3+}$ | 17.04 keV |
| YTaO$_4$ | 67.42 keV |
| YTaO$_4$:Nb | 67.42 keV |
| ZnS:Ag | 9.66 keV |
| (Zn, Cd)S:Ag | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photostimulate reactions in a patient, simultaneous with irradiation by the high energy particles, there could be applied infrared irradiation to drive resonance in the energy augmentation structures described herein, where the x-ray phosphors would have enhanced light emissions when in the presence of the intensified electric fields. In another example, in medical or scientific instruments, for simultaneous with irradiation by the high energy particles, there could be applied electric fields to enhance emissions from these x-ray phosphors.

Electro Luminescent Materials: Various materials used for the electroluminescence in the present invention with or without energy augmentators can include but are not limited to:

4,4',4"-Tris[phenyl(m-tolyl)amino]triphenylamine (m-MTDATA)

N,N'-Bis(3-methylphenyl)-N,N'-diphenylbenzidine (TPD)

4,4',4"-Tris[phenyl(m-tolyl)amino]triphenylamine (m-MTDATA)

N,N'-Bis(3-methylphenyl)-N,N'-diphenylbenzidine (TPD)

Tris-(8-hydroxyquinoline)aluminum 2,4,6-Tris(2-pyridyl)-s-triazine (TPT)

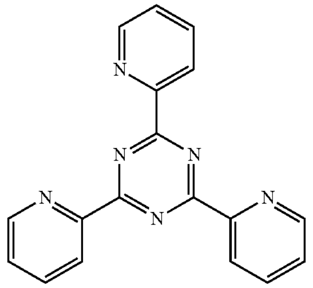 [SMILES: c1ccc(-c2nc(-c3ccccn3)nc(-c3ccccn3)n2)nc1]

2,2',2"-(1,3,5-Benzinetriyl)-tris(1-phenyl-1-H-benzimidazole) Alq

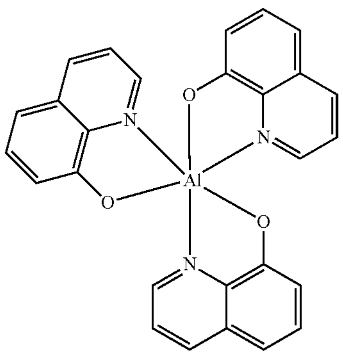

2,2',2"-(1,3,5-Benzinetriyl)-tris(1-phenyl-1-H-benzimidazole) TPBI

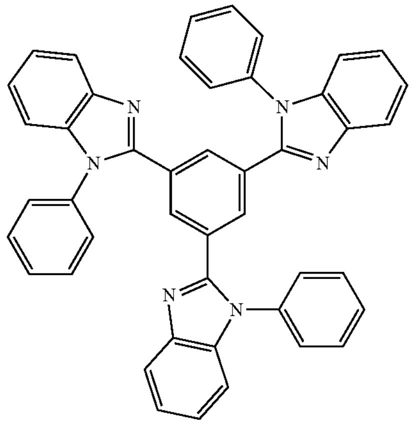 [SMILES: c1ccc(-n2c(-c3cc(-c4nc5ccccc5n4-c4ccccc4)cc(-c4nc5ccccc5n4-c4ccccc4)c3)nc3ccccc32)cc1]

2,9-Dimethyl-4,7-diphenyl-1,10-phenanthroline, BCP2,9-Dimethyl-4,7-diphenyl-1,10-phenanthroline, BCP

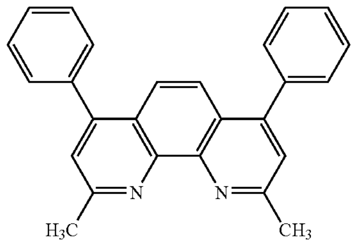 [SMILES: Cc1cc(-c2ccccc2)c2ccc3c(-c4ccccc4)cc(C)nc3c2n1]

Figure 26:
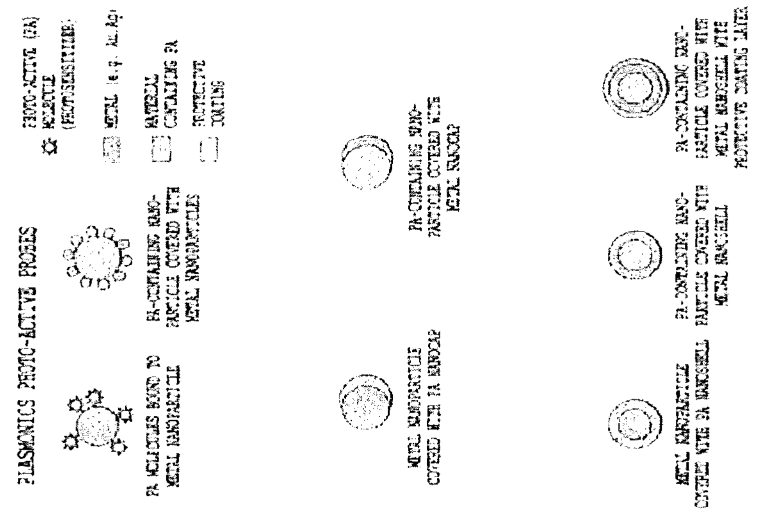
FIG. 26 is a schematic illustrating various converter structures of the invention.

Plasmonic enhancement structures: FIG. 26 is a schematic of a depiction of an upconverter or a down converter material (i.e., a photoactive material) according to one embodiment of the invention to be utilized in the color enhancement/augmentation structures noted herein with or without energy augmentators. FIG. 26 shows a number of structural configurations for placement of a dielectric core upconverter or a down converter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIG. 26, when a wavelength $\lambda_1$ interacts with a dielectric material core, three separate processes are well understood for the upconversion process involving trivalent rare earth ions. These three processes are:

1) excited state absorption whereby two photons are absorbed sequentially by the same ion to excite and populate one or more states;
2) energy transfer upconversion which is a transfer of excitation from one ion to another already in an excited state; and
3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion or down conversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by a NIR source to generate the resultant emission $\lambda_2$.

Hence, the invention in one embodiment provides an upconversion or a down conversion material configured, upon exposure to a first wavelength $\lambda_1$ of radiation, to generate a second wavelength $\lambda_2$ of radiation having an energy higher or lower than the first wavelength $\lambda_1$. The system can include a metallic structure disposed in relation to the nanoparticle (e.g. a metallic shell covering a fraction of the nanoparticle). The system may include a receptor disposed in the medium in proximity to the nanoparticle. The receptor upon activation by the second wavelength $\lambda_2$ may itself fluoresce producing visible light. In one embodiment of the invention, a physical characteristic of metallic structure (such as those described above and below in the drawings) is set to a value where a surface plasmon resonance in the metallic structure resonates at a frequency which provides spectral overlap with either the first wavelength $\lambda_1$ or the second wavelength $\lambda_2$. This system with a metallic structure disposed in relation to an up-conversion or a down-conversion nanoparticle becomes the converter utilized in the color enhancement/augmentation structures noted herein.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength $\lambda_1$ and the second wavelength $\lambda_2$. This capability permits radiation at $\lambda_1$ and $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and obloid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and obloid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures disposed in relation to an up-conversion or a down-conversion nanoparticle can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda_2$. In various embodiments, the metallic structures can be a metallic multi-layer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

As described above, a shell (or other structure) is in particular designed with a layer thickness (or for example a lateral dimension) to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by 980 nm NIR light, then the thickness of the shell is "tuned" in a thickness to where a plasmon resonance resonates at a frequency also of 980 nm (or in the neighborhood thereof as plasmon resonances are typically broad at these wavelengths).

Figure 27:
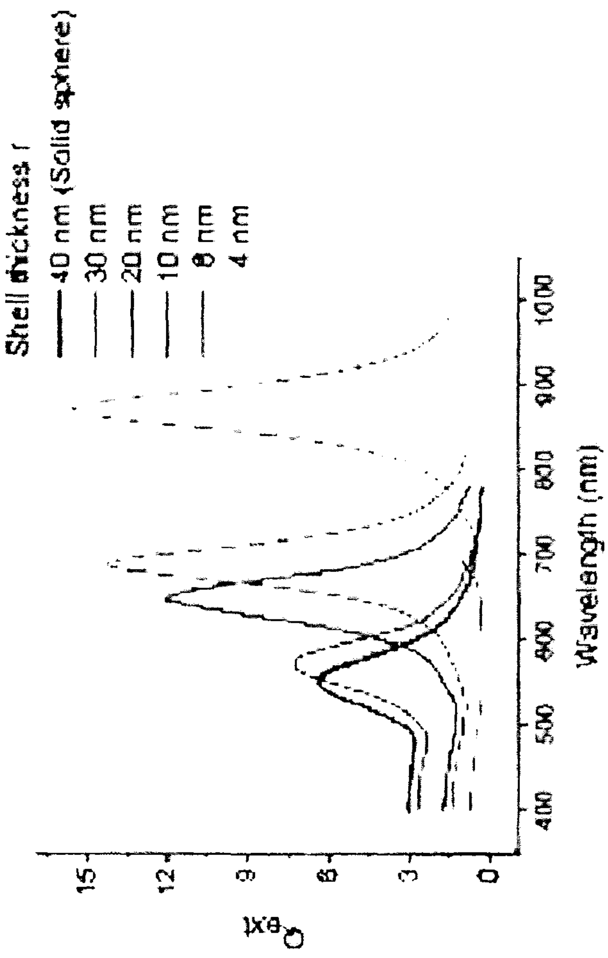
FIG. 27 is a schematic illustration of plasmon resonance as a function of shell thickness.

A plasmon resonating shell can be made of numerous transition metals, including though not limited to gold, silver, platinum, palladium, nickel, ruthenium, rhenium, copper, and cobalt or a combination or alloys or layers thereof. Such a plasmon resonating shell can be also made of a combination of metals and non-metals. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.) FIG. 27 is reproduced from Jain et al and illustrates the capability in the invention to "tune" the metal shell to have a spectral overlap with the excitation and/or emission radiation wavelengths.

In one embodiment of the invention, the metallic structures disposed in relation to an up-conversion or a down-conversion nanoparticle can be an alloy such as for example a Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the converter nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a predetermined surface plasmon resonance. In one embodiment of the invention, the zinc sulfide and cadmium sulfide nanoparticle alloy can have an alloy content is set to provide a predetermined surface plasmon resonance.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the thickness of the metal shell disposed in relation to an up-conversion or a down-conversion nanoparticle is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Additionally, plasmon-phonon coupling may be used to reduce a resonance frequency through the tuning of the bands to a degree off resonance. This may be useful in optimizing resonance energy transfer processes for the purpose of shifting the outputted color to a color desirable for a painted, colored, or displayed surface. In one example, FIG. 27 shows an example of the plasmon resonance shift as a function of shell thickness.

Here, in one embodiment of the invention, the capability to produce stimulated emission at a targeted wavelength or color or energy is complemented by the ability to design nanoparticles that have designed absorption bands. Such absorption materials could for example further serve to improve the monochromaticity of light observed from a paint, ink, dye, or otherwise reflecting surface treated with the color enhancing compositions of the invention.

Details of the preparation of this nanoparticle system are included in U.S. Ser. No. 12/725,108, the entire contents of which are incorporated herein by reference. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$ (upper trace), on the other hand, exhibit a strong absorption band at 546 nm, which is characteristic of the plasmonics resonance band due to the gold shell around the $Y_2O_3$ cores. The red-shifting of the plasmon absorption to 546 nm is consistent with the presence of a gold shell around a dielectric core.

In one embodiment of the invention, the converter materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence. suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teaching of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg. 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell, to enhance electron-phonon coupling and thereby increase up conversion or down conversion efficiency, as discussed above. In another embodiment of the invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. In another embodiment of the invention, the shell can include a $SiO_2$- and/or $TiO_2$-coating, and this coating is in one embodiment coated on doped $Y_2O_3$ down converting nanoparticles to thereby, in some instances, increase the down conversion efficiency relative to an uncoated nanocrystal. Further, in one embodiment of the invention, the coating can be a polymer. In one embodiment, this coating is provided on $NaYF_4$:Ln/$NaYF_4$ dielectric core. Such coatings can increase the upconversion efficiency relative to an uncoated upconverter.

In another embodiment of the invention, phonon modes of undoped host-lattice (e.g., $Y_2O_3$) nanocrystals are modulated, for example, by Au, Ag, Pt, and Pd shells of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure disposed in relation to an up-conversion or a down-conversion nanoparticle can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

In various embodiments of the invention, the upconverter or down converter dielectric core can be coated with thiol-terminated silanes to provide a coating of $SiO_2$ about the core of similar reactivity to $Y_2O_3$. In one embodiment of the invention, the above-described methodology is used to synthesize core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, the upconverter dielectric core can be mixed core-shell materials including for example semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and trioctylphosphine-oleic amine ($NaYF_4$ shell). All core-shell nanoparticles may further be solubilized into a colloidal suspension with the addition of triarginine peptide, polyethylene glycol, and polyethyleneimine surfactants.

Figure 28A:
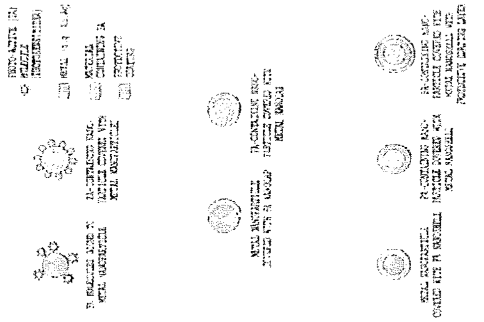
FIG. 28A is a schematic illustrating other various converter structures of the invention.

FIG. 28A shows some of the various embodiments of the converter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer.

Figure 28B:
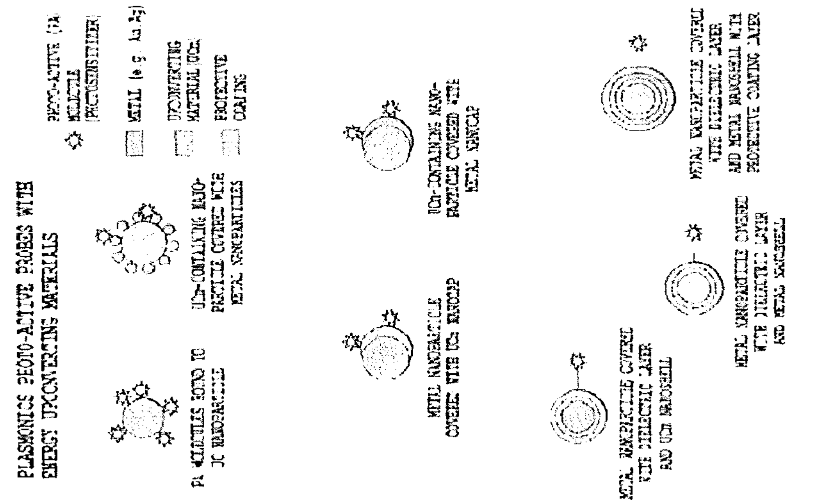
FIG. 28B is a further schematic illustrating other various converter structures of the invention.

The configurations (while shown in the FIG. 28A with UC-containing materials) would be applicable for enhancement for down converting materials such as the quantum dots or phosphors described herein. Moreover, in one embodiment of the invention, dielectric spacers (for examples silicates as discussed below) can be used with the structure of FIG. 6A-b to space apart the particle type metallic structures. In another embodiment of the invention, dielectric spacers can be used with the structure of FIG. 28A to space apart the metal layers, whether or not these layers are partial metal layers or continuous metal layers. See the schematics in FIG. 28B In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$. This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIG. 28A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The metal layer can be also made of a combination of metals and non-metals. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

As discussed below, the metallic shells in another embodiment of the invention serve as scattering centers for UV light where UV light which, even if absorbed in a paint or coating layer contributes at a minimum to localized heating of the paint or coating layer material, will be scattered from the paint or coated layer.

Figure 28C:
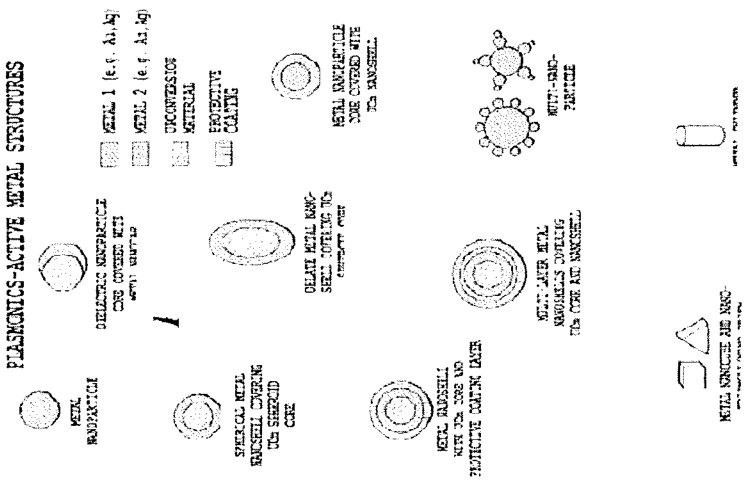
FIG. 28C is a schematic illustrating various plasmonics-active converter structures of the invention.

FIG. 28C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core, (d) an oblate metal nanoshell covering UC spheroid core, (e) a metal nanoparticle core covered with UC nanoshell, (f) a metal nanoshell with protective coating layer, (g) multi-layer metal nanoshells covering an UC spheroid core, (h) multi-nanoparticle structures, (i) a metal nanocube and nanotriangle/nanoprism, and (j) a metal cylinder.

Figure 28D:
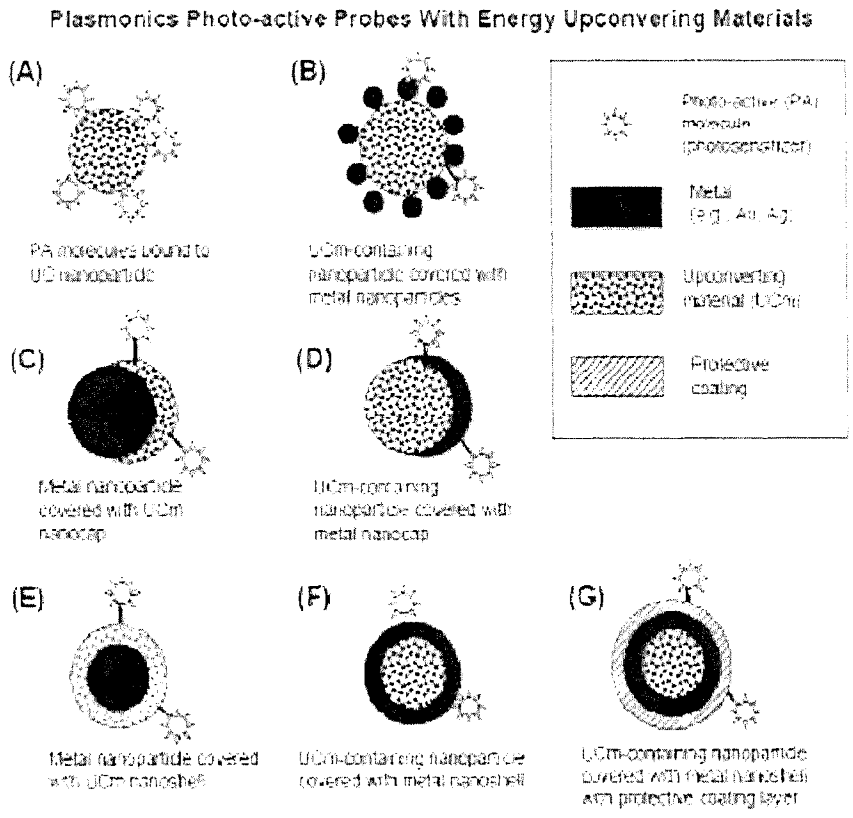
FIG. 28D is a schematic illustration of photo-active molecules linked to plasmonics-active upconverter structures of the invention.

FIG. 28D shows yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIG. 28D shows (a) PA molecules bound to an UC nanoparticle, (b) an UC material-containing a nanoparticle covered with metal nanoparticles, (c) a metal nanoparticle covered with UC material nanocap, (D) an UC material-containing nanoparticle covered with metal nanocap, (e) a metal nanoparticle covered with an UC material nanoshell, (f) an UC material-containing nanoparticle covered with metal nanoshell, (g) an UC material-containing nanoparticle covered with metal nanoshell with protective coating layer.

With the upconverter and down converter structures of the invention, a plasmonics effect is advantageous. A plasmonics effect can increase the local intensity of the received light or the local intensity of the emitted light from the up and/or down converter structures of the invention. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively.

In various embodiments, nanoparticles of neodymium and ytterbium doped yttrium oxide, europium and ytterbium doped yttrium oxide, and any combination of rare earth trivalent ions doped into a neodymium oxide nanocrystal can be used. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale. There are advantages offered by these yttrium oxide nanostructures of the invention. The small scale synthetic methodology for creating nanoscale yttrium oxide is easier to control and produce in yttrium oxide than in YAG. The host structure of yttrium oxide scintillates by down conversion. These combinations of dopants in yttrium oxide for example can provide predetermined emission colors for the yttrium oxide nanocrystal for the color shifting of the invention.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the visible and NIR spectral regions.

Up-conversion phosphors similar in chemical compositions to the down-conversion fluorescent materials discussed above can be used. The up-conversion phosphors can include laser dyes, e.g., the organic small molecules that can be excited by the absorption of at least two infrared photons with emission of visible light. The up-conversion phosphors can include fluorescent polymers, e.g., the class of polymers that can be excited by the absorption of at least two infrared photons with emission of visible light. The up-conversion phosphors can include inorganic or ceramic particles or nano-particles, including the conventional up-conversion phosphors (e.g. metal fluorides, metal oxides) that can be excited by the absorption of at least two infrared photons with emission of visible light. The up-conversion phosphors can include semiconductor particles, including nano-particles such as II-VI or III-V compound semiconductors, e.g. quantum dots, described in details in the "down-conversion" semiconductors above.

Fluorescent up-conversion inorganic phosphors can include but are not limited to metal oxides, metal halides, metal chalcogenides (e.g. sulfides), or their hybrids, such as metal oxo-halides, metal oxo-chalcogenides. Fluorescent up-conversion inorganic phosphors are usually doped with rare earth elements (e.g. $Yb^{3+}$, $Er^{3+}$, $Tm^{3+}$). Some host examples include, but are not limited to: $NaYF_4$, $YF_3$, $BaYF_5$, $LaF_3$, $La_2 MoO_8$, $LaNbO_4$, $LnO_2S$; where Ln is the rare earth elements, such as Y, La, Gd).

These converters (and the other energy converters described herein which receive energy and generate light or electron emission) can optionally include any of the energy augmentation structures described above.

In various embodiments of the invention, energy converters can be used with the energy augmentators described above for color enhancement. In some embodiments, the converters are up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without energy augmentators are included to enhance the color of the object being displayed. These application areas can include paints on signs, walls, cars, buildings, boats, airplanes. These application areas can include display monitors, computer monitors, telephone displays, watch dials, instrument dials to name but a few.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance a particular color of light observable to an observer. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance color emission can convert energy from one of ultraviolet light, x-rays, and high energy particles to visible light. The down conversion materials to enhance color emission can convert energy from higher energy visible light to lower energy visible light with or without the energy augmentators.

In one embodiment of the invention, a quantum dot mixture with or without the energy augmentators can be used for color enhancement. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted color emission, such as for example a green light emission. Quantum dots represent one way to down convert blue light of the spectrum to a targeted color emission, such as for example a green light emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

Specifically, in one embodiment of the invention, a quantum dot mixture (QDM) coating can be deposited using CVD and or sol-gel techniques using standard precipitation techniques to be used with or without the energy augmentators. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials here can be used with or without the energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{2+}$ or $Nd^{3+}$. Other suitable down conversion materials which would seem the most biocompatible are zinc sulfide, ZnS:$Mn^{2+}$, ferric oxide, titanium oxide, zinc oxide, zinc oxide containing small amounts of $Al_2O_3$, and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, BaFBr:$Eu^{2+}$ nanoparticles, Cesium Iodine, Bismuth Germanate, Cadmium Tungstate, and CsBr doped with divalent Eu.

In various embodiments of the invention, the following luminescent polymers are also suitable as conversion materials with or without the energy augmentators: poly(phenylene ethynylene), poly(phenylene vinylene), poly(p-phenylene), poly(thiophene), poly(pyridyl vinylene), poly (pyrrole), poly(acetylene), poly(vinyl carbazole), poly (fluorenes), and the like, as well as copolymers and/or derivatives thereof.

In various embodiments of the invention, the following materials can be used similar to that detailed in U.S. Pat. No. 7,090,355, the entire contents of which are incorporated herein by reference. For down-conversion, the following materials can be used with or without the energy augmentators. Inorganic or ceramic phosphors or nano-particles, including but not limited to metal oxides, metal halides, metal chalcogenides (e.g. metal sulfides), or their hybrids, such as metal oxo-halides, metal oxo-chalcogenides. Laser dyes and small organic molecules, and fluorescent organic polymers. Semiconductor nano-particles, such as II-VI or III-V compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_mA_{1-m})_3(Al_nB_{1-n})_5O$ 12, doped with Ce; where $0 \le m, n \le 1$, where A includes other rare earth elements, B includes B, Ga. In addition, phosphors containing metal silicates, metal borates, metal phosphates, and metal aluminates hosts can be used. In addition, nanoparticulates phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, Tl) as the fluorescent activators, can be used. Materials such as Ca, Zn, Cd in tungstates, metal vanadates, ZnO, etc. can be used with or without the energy augmentators.

The commercial laser dye materials obtained from several laser dye vendors, including Lambda Physik, and Exciton, etc. can also be used with or without the energy augmentators. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in opto-electronic devices, such as polymer light emitting diodes (PLED). Such fluorescent polymers can be used directly as the fluorescent layer of the transparent 2-D display screen.

As noted above, semiconductor nanoparticles (e.g., quantum dots) can be used with or without the energy augmentators. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nanoparticle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion materials with or without the energy augmentators. Such molecules include a metal center of rare earth elements including Eu, Tb, Er, Tm, Ce protected with organic chelating groups. The metal center may also include transitional elements such as Zn, Mn, Cr, Ir, etc. and main group elements such as B, Al, Ga. Such organometallic molecules can readily dissolve in liquid or transparent solid host media. Some examples of such fluorescent organometallic molecules include: 1. Tris(dibenzoylmethane)mono (phenanthroline)europium(III); 2. Tris(8-hydroxyquinoline) erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. A europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments with or without the energy augmentators, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue). In embodiments, the conversion materials can be light emitting particles made of pure organic or organo-metallic dyes with or without the energy augmentators.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials with or without the energy augmentators include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties, as noted above. Examples of doped (or alloyed) glass systems suitable for the include $Y_2O_3$:Gd, $Y_2O_3$:Dy, $Y_2O_3$:Tb, $Y_2O_3$:Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$:Eu (red), $Y_2O_3$:Eu (red), $YVO_4$:Eu (red), and $Zn_2SiO_4$:Mn (green).

With regard more specifically to down converter materials suitable for the invention with or without the energy augmentators, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without the energy augmentators.

In other embodiments of the invention, the down converter materials (or mixtures of down converters materials can include $Y_2O_3$:Li. Sun et al "Luminescent properties of Li+ doped nanosized $Y_2O_3$:Eu," Solid State Comm. 119 (2001) 393-396 (the entire contents of which are incorporated herein by reference) describe such materials. Hou et al "Luminescent properties nano-sized $Y_2O_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria ($Y_2O_3$) powders have been successfully synthesized by a co-precipitation method. The powders were well crystallized, and the grains were almost spherical with good dispersibility. The quenching concentration of $Eu^{3+}$ ions is 9 mol % which is much higher than micro-scaled powders. The incorporation of Li+ ions greatly improved the luminescence intensity. The highest emission intensity was observed with 4 mol % Li+ doped $Y_2O_3$:Eu powder ($(Y_{0.87}Eu_{0.09}Li_{0.04})_2O_3$) and the fluorescence intensity was increased by as much as 79%. Yi et al "Improved cathodoluminescent characteristics of $Y_2O_3$:$Eu^{3+}$ thin films by Li-doping," Appl. Phys. A 87, 667-671 (2007) (the entire contents of which are incorporated herein by reference) describe cathodoluminescent spectra for both $Y_2O_3$:$Eu^{3+}$ and Li-doped $Y_2O_3$:$Eu^{3+}$ films and methods for making these materials.

The invention in other embodiments can use a wide variety of up conversion materials (or mixtures of up converters) with or without the energy augmentators to enhance a particular color of light observable from reflective material or surface. These up conversion materials can include similar materials as discussed above with regard to down conversion but typically included doped or impurity states in a host crystal that provide a mechanism for up conversion pumping. Accordingly, the up conversion materials to enhance color emission can convert energy from one of near infrared, infrared, and microwave irradiation. The upconversion materials to enhance color emission can convert energy from lower energy visible light to higher energy visible light.

Upconversion materials with or without the energy augmentators can be used in various ways to enhance visible light emission by way of conversion of infrared light from a solar spectrum (as in daylight exposure) or a black body spectrum (as in an incandescent lamp). In one example, a nanoparticle of a lanthanide doped oxide can be excited with near infrared light such as laser light at 980 nm and 808 nm to produce visible light in different parts of the red, green, blue spectrum depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the $NaYF_4$ such that the $Yb^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention with or without the energy augmentators.

Further, materials specified for up conversion materials in the invention with or without the energy augmentators include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . 0<z≤1, o<q≤1).

Some nanoparticles such as ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn,$Er^{3+}$ are known in the art to function for both down-conversion luminescence and upconversion luminescence and would be suitable for the invention with or without the energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple colors from even the same dopants with or without the energy augmentators.

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a $Tm^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4$:$Yb^{3+}$, $Tm^{3+}$, and $YbPO_4$:$Er^{3+}$ nanocrystals in chloroform. Excitation at 975 nm has been shown by others to produce visible luminescence in the blue, green, or red spectral regions.

Tellurium and germanium oxides (tellurites and germinates) are also suitable upconverters. These glasses can be doped with Tm, Yb, Ho, Er, Pr, for example.

$Yb^{3+}$ doped $BaZrO_3$ is also suitable for upconversion. $Er^{3+}$ and/or $Tm^{3+}$ doping are also suitable for tailoring the emission wavelengths.

In another embodiment, $Nd^{3+}$:$Cs_2NaGdCl_6$ and $Nd^{3+}$, $Yb^{3+}$:$Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2-+4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^3$/$Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in $[Ru(dmb)_3]^{2+}$ (dmb=4,4'-dimethyl-2,2'-bipyridine) in the presence of anthracene or 9,10-diphenylanthracene have been reported converters and are suitable for the present invention.

Upconverted to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

The structures described herein for color enhancement with the energy augmentation structures are denoted as color enhancing/energy augmentation structures or as energy enhancing/augmentation structures.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/energy augmentation structures or the energy enhancing/augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

Accordingly, in one embodiment of the invention, the color enhancement structures described herein can receive polychromatic light from a variety of sources such as sunlight, incandescent bulbs, fluorescent tube, and LED light sources with each having different wavelengths or wavelength bands. For these wavelength different bands, the resonators are "matched" or "tuned" to those wavelengths such that an intense electric field is established especially between the external-electrode pairs, or the folded resonator electrode pairs if used. In those regions of intense electric field can be disposed color converters (up and/or down phosphors) which can take light from one of the different wavelengths or wavelength bands, and have light of another wavelength or of different wavelength bands be emitted therefrom. In one embodiment, the intense electric field increases the intensity of the emitted light from the phosphors. Moreover, unlike the above-noted plasmonics where the electric field enhancement is restricted to regions within 100 to 200 nm of the metal, the resonators establish an increased electric field within the volume of the external-electrode pair, or the folded resonator electrode pairs if used, such that the phosphor material in a vicinity and within the external-electrode pair (or the folded resonator electrode pairs) exhibits an intensity larger than if the converter were remote from the resonator.

In view of the above, this invention is directed in general to methods and systems for color enhancement utilizing a color enhancement structure having a) an energy collector comprising at least one energy augmentation structure, and b) an energy converter capable of converting a second wavelength/quantum of electromagnetic energy into and emitting therefrom a third wavelength of light shifted in wavelength/energy from the second wavelength/quantum of electromagnetic energy. In one embodiment, the energy converter is disposed in a vicinity of the at least one energy augmentation structure such that the light shifted in wavelength is emitted with an intensity larger than if the converter were remote from the at least one energy augmentation structure. For ease of understanding, the term "wavelength" will be used to describe the electromagnetic energy entering into the energy converter, even though that electromagnetic energy may be better described in certain embodiments based upon its energy level or strength.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/augmentation structures or the energy enhancing/augmentation structures of the invention are able to enhance the conversion of one form of energy to another, as a conversion from one or more wavelengths of light to other wavelengths of light, or as a conversion from the one or more wavelengths of light to electrical energy, or as a conversion from the one or more wavelengths of light to heat.

Conversion from the one or more wavelengths of light to other wavelengths of light is useful for color shifting and color enhancement applications. Conversion from the one or more wavelengths of light to electrical energy is useful for harvesting solar energy using for example photovoltaic cells. Conversion from the one or more wavelengths of light to heat is useful also for harvesting solar energy using for example thermoelectric cells or other heat-to-electrical energy devices such as thermoelectric generators.

In some embodiments of the color enhancing/energy augmentation structures, the color enhancing structure includes a multi-dimensional light collector comprising a first level of metallic patterns and a second level of metallic patterns offset in at least one of a lateral or axial direction from the first level of metallic patterns. At least one of the metallic patterns optionally comprises a first resonator dimensioned to be resonant with a first wavelength of light. The first resonator can be one of a folded structure or an external-electrode pair structure as noted above. The color enhancement structure has a converter capable of converting a second wavelength of light into and emitting therefrom a third wavelength of light shifted in wavelength from the second wavelength of light. The converter is disposed with the first resonator such that the light shifted in wavelength is emitted with an intensity larger than if the converter were remote from the first resonator.

In some embodiments, the energy converter being disposed in a vicinity of the at least one energy augmentation structure is conductively coupled the energy converter to the at least one energy augmentation structure.

For example, in some embodiments, the energy converter being disposed in a vicinity of the at least one energy augmentation structure comprises a physical conductive connection between the energy converter and the at least one energy augmentation structure.

In some embodiments of the color enhancing/energy augmentation structures, the color enhancing structure, the energy converter comprises a down converter converting ultraviolet or blue light into red, yellow, or green light. In some embodiments of the color enhancing/augmentation structures, the energy converter comprises an up converter converting infrared or red light into yellow, green light, or blue light.

In some embodiments of the color enhancing/energy augmentation structures, the metallic patterns referenced above comprises a folded resonator having opposing electrodes with electric fields directed in between, and the converter is positioned between the opposing electrodes or within fringing electric field of the opposing electrodes or otherwise in a vicinity of the opposing electrodes. In one example, the folded resonator is a % K folded resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the metallic patterns referenced above comprises an external external-electrode pair structure having opposing electrodes with electric fields directed in between, and the converter is positioned between the opposing electrodes or within fringing electric field of the opposing electrodes or otherwise in a vicinity of the opposing electrodes. In one example, the resonator is a ¾ λ external-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the color enhancing structure, there is an antireflection film disposed on at least one of the metallic patterns or on the converter.

In some embodiments of the color enhancing/energy augmentation structures, the color enhancing structure, the first resonator noted above comprises plural resonators, the converter noted above comprises plural converters, and the plural converters are disposed at multiple positions throughout the light collector. In one example, the plural converters are positioned to convert light being internally scattered within the light collector.

In some embodiments of the color enhancing/energy augmentation structures, the first level of metallic patterns noted above (or the second level of metallic patterns) comprises a metal core cladded with a high-K dielectric and a subsequent cladding of a low-K dielectric.

In some embodiments of the color enhancing/energy augmentation structures, the first level of metallic patterns noted above (or the second level of metallic patterns) comprises a radial pattern of conductors. In some embodiments of the color enhancing/energy augmentation structures, the first level of metallic patterns noted above (or the second level of metallic patterns) comprises a fractal pattern. In one example, the fractal pattern is embedded within a dielectric material.

In some embodiments of the color enhancing/energy augmentation structures, the first level of metallic patterns noted above (or the second level of metallic patterns) comprises a three-dimensional fractal structure.

In some embodiments of the color enhancing/energy augmentation structures, the light collector comprises a transparent panel with the first level of metallic patterns and the second level of metallic patterns and optionally multiple converters formed therein. In some embodiments of the color enhancing/augmentation structures, the light collector comprises a transparent sheet with the first level of metallic patterns and the second level of metallic patterns and optionally multiple converters formed therein.

In some embodiments of the color enhancing/energy augmentation structures, the first level of metallic patterns noted above (or the second level of metallic patterns) are of different sizes and/or orientations to each other of the first level of metallic patterns or with respect to the second level of metallic patterns.

Figure 29:
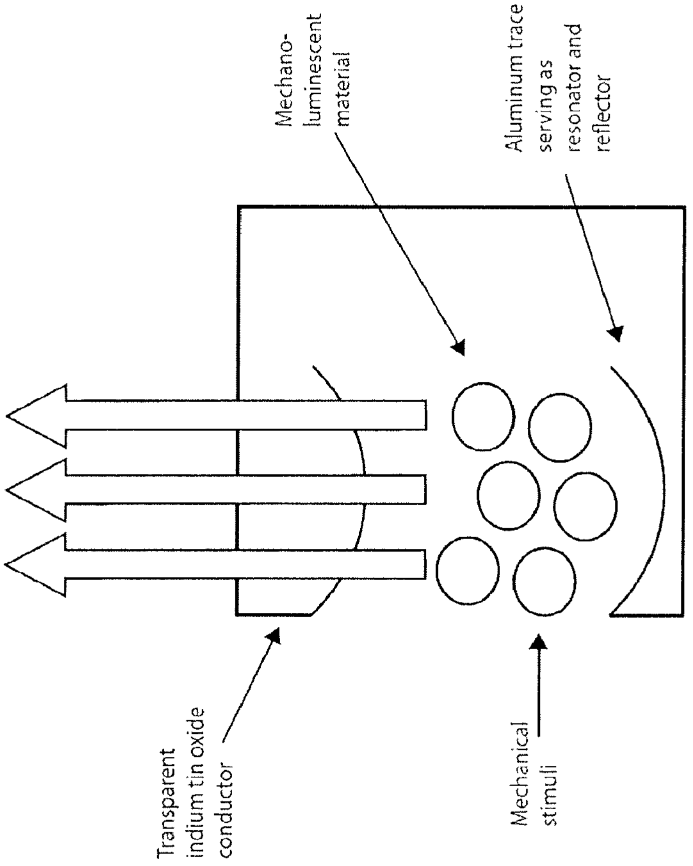
FIG. 29 is a diagram showing a mechanoluminescent emitter of the present invention.

Indeed, FIG. 29 is a schematic of a reflective resonator of this invention including mechano-luminescent materials, in this example the mechano-luminescent materials being placed between a folded resonator structure, although mechano-luminescent materials could be placed between an external electrode pair resonator structure. Thus, in one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

For example, the reflective resonator of FIG. 29 could be placed adjacent an exhaust stack of an engine or other waste heat dissipating machine. In one embodiment, the reflective resonator of FIG. 29 would be mounted on a stainless steel arm connected to the heat stack. The stainless steel would couple mechanical vibrations to the reflective resonator while thermally isolating the reflective resonator from the exhaust stack, thereby permitting even inorganic mechano-luminescent materials to be used.

When the engine began to show higher levels of vibration or vibrations at different frequencies, the intensity of the light emitted would change providing a visible light signal that the engine or machine was under stress from power loads or wear or mechanical failure.

In one embodiment of the invention, the reflective structure shown in FIG. 29 need not include the resonator and its resonating elements. In one embodiment of the invention, the reflective structure shown in FIG. 29 could be placed directly on a machine operating at a relatively cold temperature around 100° C. In this embodiment, the reflective structure need not include the resonator and its resonating elements. However, if the resonator and its resonating elements were present, a laser such as 656 nm laser could "probe" the resonator and intensify "on demand" the mechano-luminescence. In this way, early detection of developing mechanical problems could be detected.

Various mechano-luminescent materials suitable for the present invention include $ZnS:Mn^{2+}$, $SrAl_2O_4:Eu^{2+}$, ZnS: Cu, $SrAMgSi_2O_7:Eu^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_x$($x<1/4$), CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$ ($1\le n\le 2$), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ ($x<0.8$), $SrMg_2(PO_4)_2$, $Ba_{1-x}Ca_xTiO_3$ ($0.25<x<0.8$), $Ba_{1-x}Ca_xTiO_3$, $LiNbO_3$, $Sr_2SnO_4$, $(Ca, Sr, Ba)_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light. Details of various electroluminescent materials that can be used for the composite mechano-luminescent emitters are provided in the next section where electroluminescent materials alone are placed in vicinity of the opposing resonator electrodes.

Figure 30:
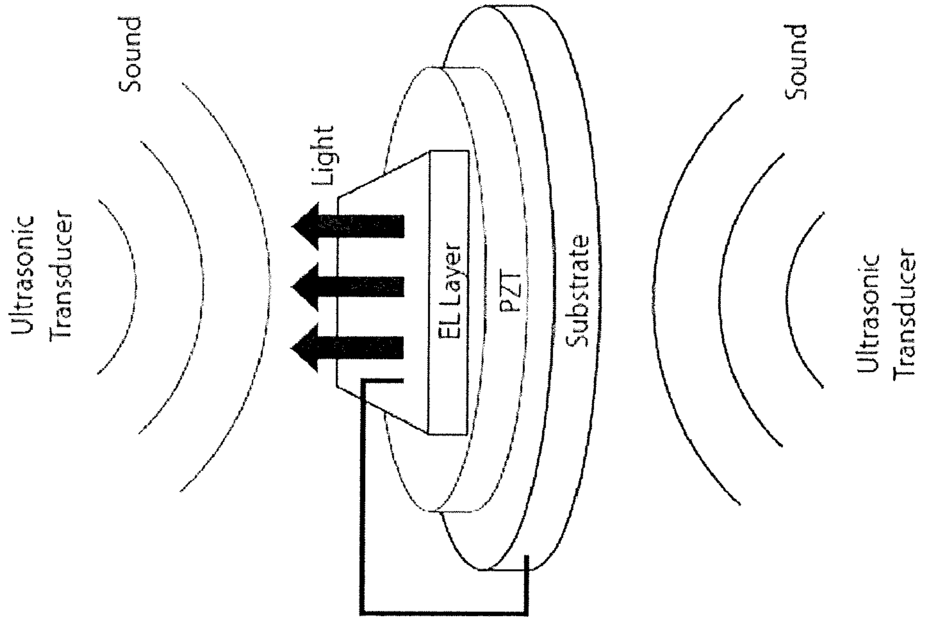
FIG. 30 is a diagram showing a composite piezoelectric/electroluminescent emitter of the present invention.

FIG. 30 is a schematic of composite mechano-luminescent emitter composed of a piezoelectric material and an electroluminescent material which, in one embodiment, could be mechano-luminescent light emitters in FIG. 29.

Figure 31:
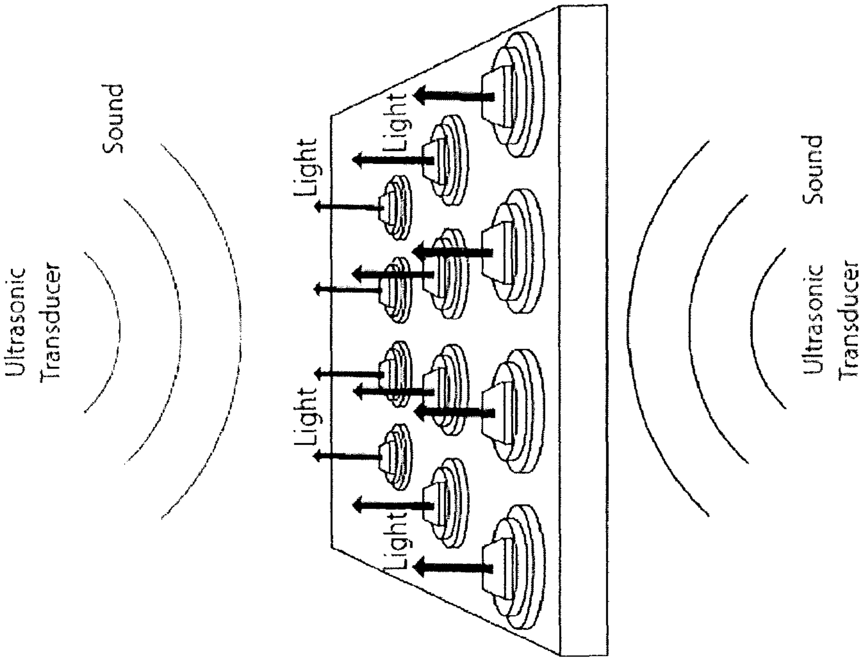
FIG. 31 is a diagram showing a distribution of the composite emitters of FIG. 30 across a surface for light emission.

In another embodiment, the composite mechano-luminescent emitters could be used without need for any resonator structure. FIG. 31 is schematic showing the composite mechano-luminescent emitters distributed across a sector of interest for generation of light therefrom. FIG. 31 shows that an ultrasonic transducer can be used for stimulation/activation of these composite mechano-luminescent emitters.

In color enhancement applications, application of ultrasonic energy could change the color emission from a surface. Such applications could be for security systems where an item would contain a pattern of the composite mechano-luminescent emitters. The pattern would not be apparent until it was activated with ultrasonic or acoustic energy upon which time light of a predetermined wavelength would be emitted. The light emitted might be visible or infrared light depending on the type of detector used to detect the emitted light.

Figure 32:
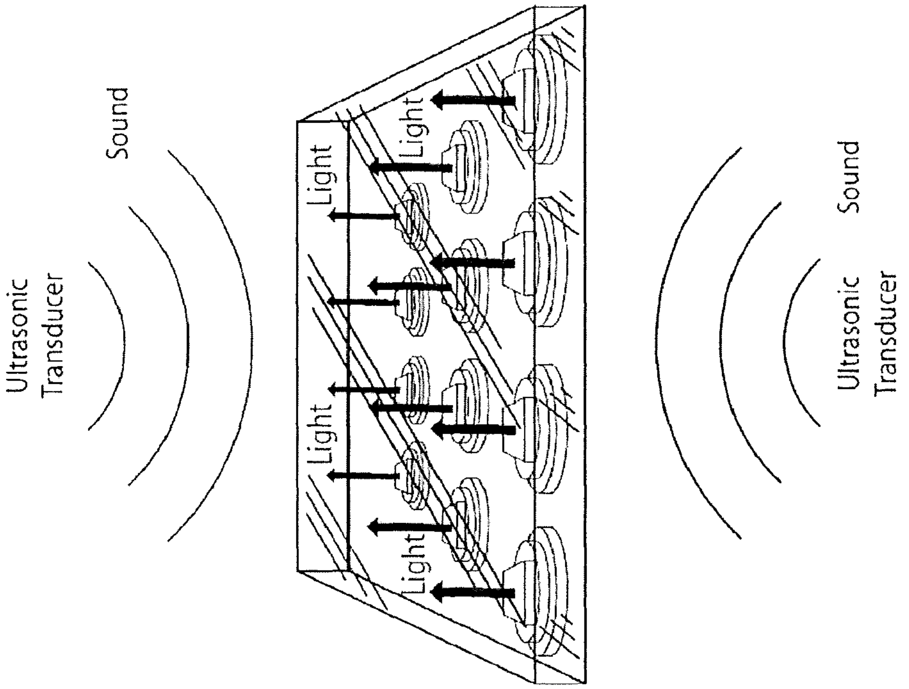
FIG. 32 is a diagram showing a distribution of the composite emitters of FIG. 30 within a target region for light emission.

In a related application of these composite mechano-luminescent emitters, FIG. 32 is schematic showing the composite mechano-luminescent emitters distributed inside a medium of interest for generation of light therein or therefrom. With the present invention, light can be turned on and off with the on/off status of an ultrasonic transducer and the intensity of the light can be varied. There are no power leads to run into the medium of interest. There is no space taken up by batteries or control elements to turn power on and off. The composite mechano-luminescent emitters can be miniaturized. The composite mechano-luminescent emitters could be agglomerated in a container. In some embodiments, the container would not be completely packed permitting the tilting of the container to relocate the composite mechano-luminescent emitters within the container.

Electroluminescent and phosphorescent materials (organic and inorganic): The present invention in various embodiments with or without energy augmentators can utilize in organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used in the resonating structures to enhance the color emission include but is not limited to the following inorganic electroluminescent phosphor materials:

$SrS:Ce^{3+}$
$CaGa_2S_4:Ce^{3+}$
$SrS:Cu^{+}$
$CaS:Pb^{2+}$
$BaAl_2S_4:Eu^{2+}$
$ZnS:Tb^{3+}$,
$ZnMgS:Mn^{2+}$
$SrGa_2S_4:Eu^{2+}$
$CaAl_2S_4:Eu^{2+}$
$BaAl_2S_4:Eu^{2+}$
$ZnS:Mn^{2+}$
$MgGa_2O_4:Eu^{3+}$
$(Ca, Sr)Y_2S_4:Eu^{2+}$
$BaAl_2S_4:Eu^{2+}$

The organic molecules that can phosphoresce under the influence of an electric field are also of interest in the present application. The organic fluorescent compounds with high quantum yield include by way of illustration:

Naphthalene,
Pyrene,
Perylene,
Anthracene,
Phenanthrene,
p-Terphenyl,
p-Quartphenyl,
Trans-stilbene,
Tetraphenylbutadiene,
Distyrylbenzene,
2,5-Diphenyloxazole,
4-Methyl-7-diethylaminocoumarin,
2-Phenyl-5-(4-biphenyl)-1,3,4-oxadiazole,
3-Phenylcarbostyryl,
1,3,5-Triphenyl-2-pyrazoline,
1,8-Naphthoylene-1',2'-bezimidazole,
4-Amino-N-phenyl-naphthalimide.

The inorganic fluorescent and phosphorescent materials detailed here are numerous, and various examples are given by way of illustration rather than limitation. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$.

Further included are alkali earth chalcogenide phosphors which are in turn exemplified by the following non-inclusive list:

$MgS:Eu^{3+}$, $CaS:Mn^{2+}$, CaS:Cu, CaS:Sb, $CaS:Ce^{3+}$, $CaS:Eu^{2+}$, $CaS:Eu^{2+}$ $Ce^{3+}$ $CaS:Sm^{3+}$, $CaS:Pb^{2+}$, $CaO:Mn^{2+}$, $CaO:Pb^{2+}$.

The examples include the ZnS type phosphors that encompass various derivatives:

ZnS:Cu,Al(Cl), ZnS:Cl(Al), ZnS:Cu,I(Cl), ZnS:Cu, ZnS:Cu,In.

Compound IIIb-Vb phosphors which include the group IIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1−y(Ga1−xAlx)yP (provides a simple example). Silicon Carbide SiC as a luminescent platform has commercial relevancy if the blue light emitting diodes. These include the polytypes 3C—SiC, 6H—SiC, 4H—SiC with donors such as N and Al and acceptors such as Ga and B.

Multiband luminescent materials suitable for converter materials include for example the following compositions:

$(Sr, Ca, Ba)_5(PO_4)_3Cl:Eu^{2+}$, $BaMg_2Al_{16}O_{27}:Eu^{2+}$, $CeMgAl_{11}O_{19}:Ce^{3+}:Tb^{3+}$, $LaPO_4:Ce^{3+}:Tb^{3+}$, $GdMgB_5O_{10}:Ce^{3+}:Tb^{3+}$, $Y_2O_3:Eu^{3+}$, $(Ba,Ca,Mg)_5(PO_4)_3Cl:Eu^{2+}$, $2SrO_{0.84}P_2O_5{\cdot}0.16B_2O_3:Eu^{2+}$, $Sr_4Al_{14}O_{25}:Eu^{2+}$.

Other materials suitable for converter materials include those materials used for fluorescent high pressure mercury discharge lamps can be excited with X-Ray and are exemplified by way of family designation as follows:

Phosphates $(Sr, M)(PO_4)_2:Sn^{2+}$, Mg or Zn activator, Germanate $4MgO{\cdot}GeO_2:Mn^{4+}$, $4(MgO, MgF_2)GeO_2:Mn^{4+}$, Yttrate $Y_2O_3:Eu^{3+}$, Vanadate $YVO_4:Eu^{3+}$, $Y(P,V)O_4:Eu^{3+}$, $Y(P,V)O_4:In^{+}$, Halo-Silicate $Sr_2Si_3O_8{\cdot}2SrCl_2:Eu^{2+}$, Aluminate $(Ba,Mg)_2Al_{16}O_{24}:Eu^{2+}$, $(Ba, Mg)_2Al_{16}O_{24}:Eu^{2+},Mn^{2+}$, $Y_2O_3Al_2O_3:Tb^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration:

$3Ca_3(PO_4)_2{\cdot}Ca(F,Cl)_2:Sb^{3+}$, $3Ca_3(PO_4)_2{\cdot}Ca(F,Cl)_2:Sb^{3+}$ $Mn^{2+}$, $Sr_{10}(PO_4)_6Cl_2:Eu^{2+}$, $(Sr,Ca)_{10}(PO_4)_6Cl_2:Eu^{2+}$, $(Sr,Ca)_{10}(PO_4)_6{\cdot}nB_2O_3:Eu^{3+}$, $(Sr, Ca,Mg)_{10}(PO_4)_6Cl_2:Eu^{2+}$. The phosphate phosphors include by way of illustration $Sr_2P_2O_7:Sn^{2+}$, $(Sr,Mg)_3(PO_4)_2:Sn^{2+}$, $Ca_3(PO_4)_2{\cdot}Sn^{2+}$, $Ca_3(PO_4)_2:Tl^{+}$, $(Ca,Zn)_3(PO_4)_2:Tl^{+}$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3{\cdot}0.2SiO_2{\cdot}0.9P_2O_5:Ce^{3+}{\cdot}Tb^{3+}$, $BaO{\cdot}TiO_2—P_2O_5$. The silicate phosphors $Zn_2SiO_4:Mn^{2+}$, $CaSiO_3:Pb^{2+}/Mn^{2+}$, $(Ba, Sr, Mg){\cdot}3Si_2O_7:Pb^{2+}$, $BaSi_2O_5:Pb^{2+}$, $Sr_2Si_3O_8{\cdot}2SrCl_2:Eu^{2+}$, $Ba_3MgSi_2O_8:Eu^{2+}$, $(Sr,Ba)Al_2Si_2O_8:Eu^{2+}$.

The aluminate phosphors include:

$LiAlO_2:Fe^{3+}$, $BaAl_8O_{13}:Eu^{2+}$, $BaMg_2Al_{16}O_{27}:Eu^{2+}$, $BaMg_2Al_{16}O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include:

$Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include:

$CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO{\cdot}As_2O_5:Mn^{2+}$, $3.5MgO{\cdot}0.5MgF_2{\cdot}GeO_2:Mn^{4+}$.

Activators of relevance to the various doped phosphors include the following list:

$Tl^+$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$.

In various embodiments, the luminescence center $Tl^+$ can be used with a chemical composition such as:

$(Ca,Zn)_3(PO_4)_2:Tl^+$, $Ca_3(PO_4)_2:Tl^+$.

Similarly, the luminescence center Mn2+ can be used with chemical compositions such as $MgGa_2O_4:Mn^{2+}$, $BaMg_2Al_{16}O_{27}:Eu^{2+}/Mn^{2+}$, $Zn_2SiO_4:Mn^{2+}$, $3Ca_3(PO_4)_2{\cdot}Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$.

Further, the luminescence center $Sn^{2+}$ can be used with chemical compositions such as:

$Sr_2P_2O_7:Sn^{2+}$, $(Sr,Mg)_3(PO_4)_2:Sn^{2+}$.

The luminescence center $Eu^{2+}$ can also be used with chemical compositions such as:

$SrB_4O_7F:Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$.

The luminescence center $Pb^{2+}$ can be used with chemical compositions such as:

$(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ can be used with chemical compositions such as:

$3Ca_3(PO_4)_2{\cdot}Ca(F,Cl)_2:Sb^{3+}$, $3Ca_3(PO_4)_2{\cdot}Ca(F,Cl)_2:Sb^{3+}/Mn^{2+}$.

The luminescence center Tb3+ can be used with chemical compositions such as:

$CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$.

The luminescence center $Eu^{3+}$ can be used with chemical compositions such as:

$Y_2O_3:Eu^{3+}$, $Y(V,P)O_4:Eu^{3+}$.

The luminescence center $Dy^{3+}$ can be used with chemical compositions such as:

$YVO_4:Dy^{3+}$.

The luminescence center $Fe^{3+}$ can be used with chemical compositions such as:

$LiAlO_2:Fe^{3+}$.

The luminescence center $Mn^{4+}$ can be used with chemical compositions such as:

$6MgO{\cdot}As_2O_5:Mn^{4+}$, $3.5MgO{\cdot}0.5MgF_2{\cdot}GeO_2:Mn^{4+}$.

The luminescence center $Ce^{3+}$ can be used with chemical compositions such as:

$Ca_2MgSi_2O_7:Ce^{3+}$ and $Y_2SiO_5:Ce^{3+}$.

The luminescence center $WO_4^{2-}$ can be used with chemical compositions such as:

$CaWO_4$, $(Ca,Pb)WO_4$, $MgWO_4$.

The luminescence center $TiO_4^{4-}$ can be used with chemical compositions such as:

$BaO{\cdot}TiO_2{\cdot}P_2O_5$.

In various embodiments of this invention, the phosphor chemistry utilized in X-Ray excitations can be used. Of particular interest is the k-edge of these phosphors. Low energy excitation can lead to intense luminescence in materials with low k-edge. Some of these chemistries and the corresponding k-edge are included as follows:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| ZnS:Ag | 9.66 keV |
| (Zn, Cd)S:Ag | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photostimulate reactions in a patient, simultaneous with irradiation by the high energy particles there could be applied infrared irradiation to drive resonance in the color enhancing structures/energy augmentation structures described herein, where the x-ray phosphors would have enhanced emissions when in the presence of the intensified electric fields. In another example, in medical or scientific instruments, simultaneous with irradiation by the high energy particles there could be applied electric fields to enhance emissions from these x-ray phosphors.

C. Solar Cells

In another embodiment, there is provided a distributed energy collector having separate light collection components branched together for collecting solar light for conversion into electrical power, such as shown in FIG. 25A, and discussed above.

In another embodiment, there is provided the above-noted distributed energy collector with separate light collection components collects solar light by directing the collected solar flux to a photovoltaic, thermoelectric, or thermionic emission cell, which would be optically coupled to output 766.

In another embodiment, there is provided a distributed energy collector integrated with a photovoltaic at separate light collection components within the collector in order to convert solar light into electrical power at the light collection components.

In another embodiment, there is provided the above-noted distributed energy collector with separate light collection components and/or the above-noted energy augmentation structure having the region of the intensified electromagnetic field such that solar light heats a thermionic emission cell. When the region of the intensified electromagnetic field is disposed in a vicinity of the thermionic emission cell, the intensified electromagnetic field enhances thermionic emission.

Figure 33:
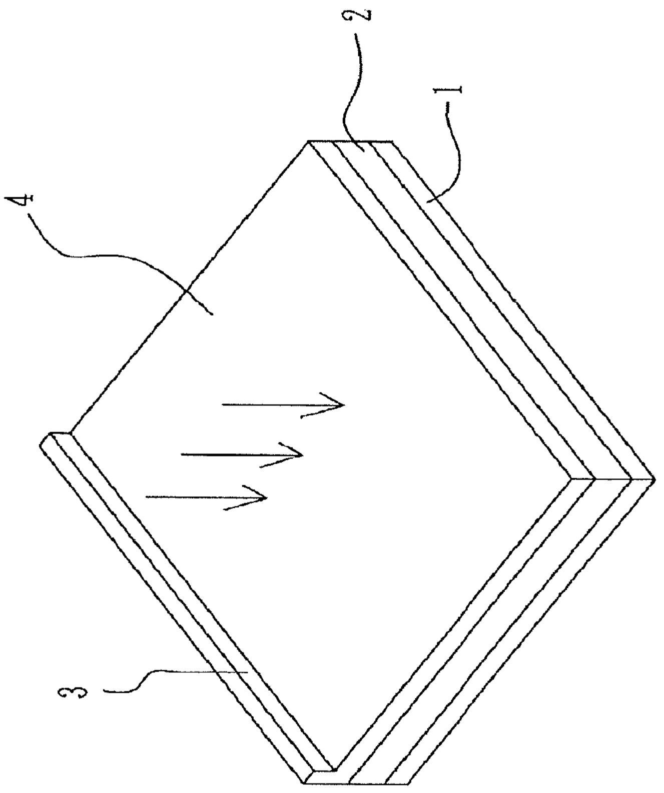
FIG. 33 schematically illustrates the basic framework of a conventional solar cell.

FIG. 33 shows the basic framework of a conventional solar cell, wherein 1 is a P-type monocrystalline silicon wafer, 2 is an n-type conductive layer, 3 is an electrode system, and 4 is an outer anti-reflection coating. The silicon wafer of the solar cell is usually covered with dustproof housing made of vinyl acetate or polycarbonate-like compound.

According to the solar radiation spectrum measured in the medium latitude region (at northern latitude 48°, for example), when the Sun is 450 above the horizon, the maximum-energy wavelength of the solar spectrum reaching the earth surface is between 290-1060 nm. When a solar cell works in the near-space environment, the complete spectrum also contains the short-wavelength radiation of UV and VIS and the medium-wavelength radiation of far-red longer than 1065 nm.

However, the energy distribution of the solar radiation spectrum is uneven. The maximum energy of the solar radiation appears in the blue light ($\lambda$=470 nm). The solar radiation is reduced by 20% in the main section of visible light between the wavelength 500-600 nm, and the corresponding radiation is half at $\lambda$=720 nm. Furthermore, the radiation at $\lambda$=1000 nm=1 μm is only ⅕ of the maximum value.

Figure 34:
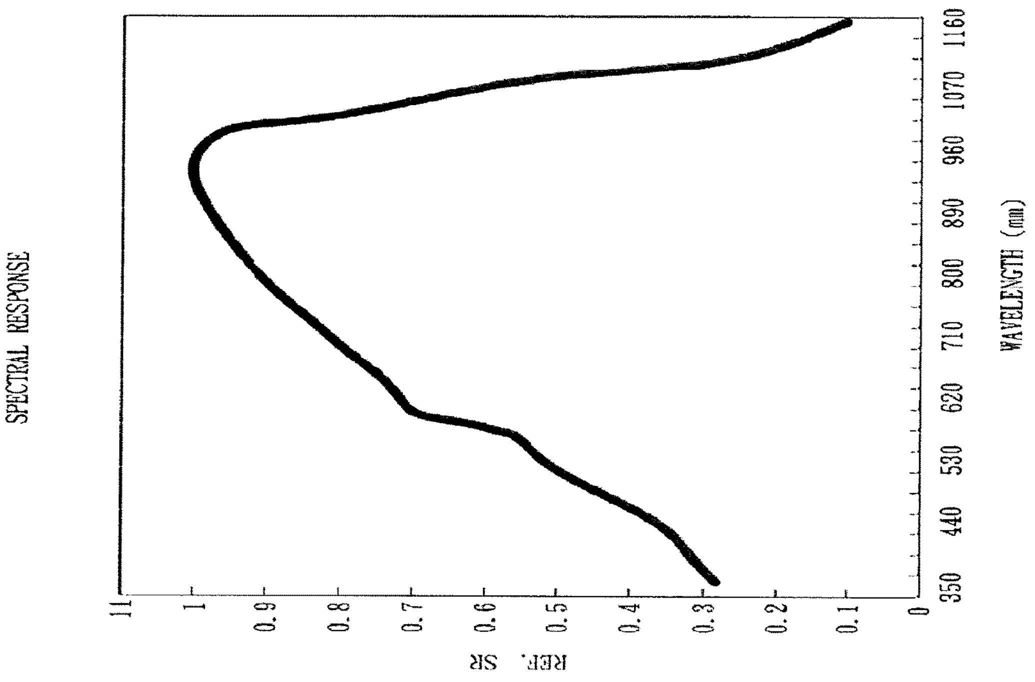
FIG. 34 schematically illustrates the sensitivity of the standard spectral curve of a solar cell sample at each wavelength range corresponding to the solar spectrum.

FIG. 34 shows the sensitivity of the standard spectral curve of a solar cell sample at each wavelength range corresponding to the solar spectrum. By inspection of the data in FIG. 2, at the wavelength range between $\lambda$=950~980 nm, a silicon solar cell assembly is most responsive with the maximum sensitivity because the energy band structure of the monocrystalline silicon has a bandgap Eg of 1.21 ev, which corresponds to the wavelength of $\lambda$=950 nm. On the other hand, a silicon solar cell assembly is virtually non-responsive to the ultraviolet ($\lambda$<4 00 nm), i.e. silicon cannot efficiently convert this ultraviolet light.

Figure 35:
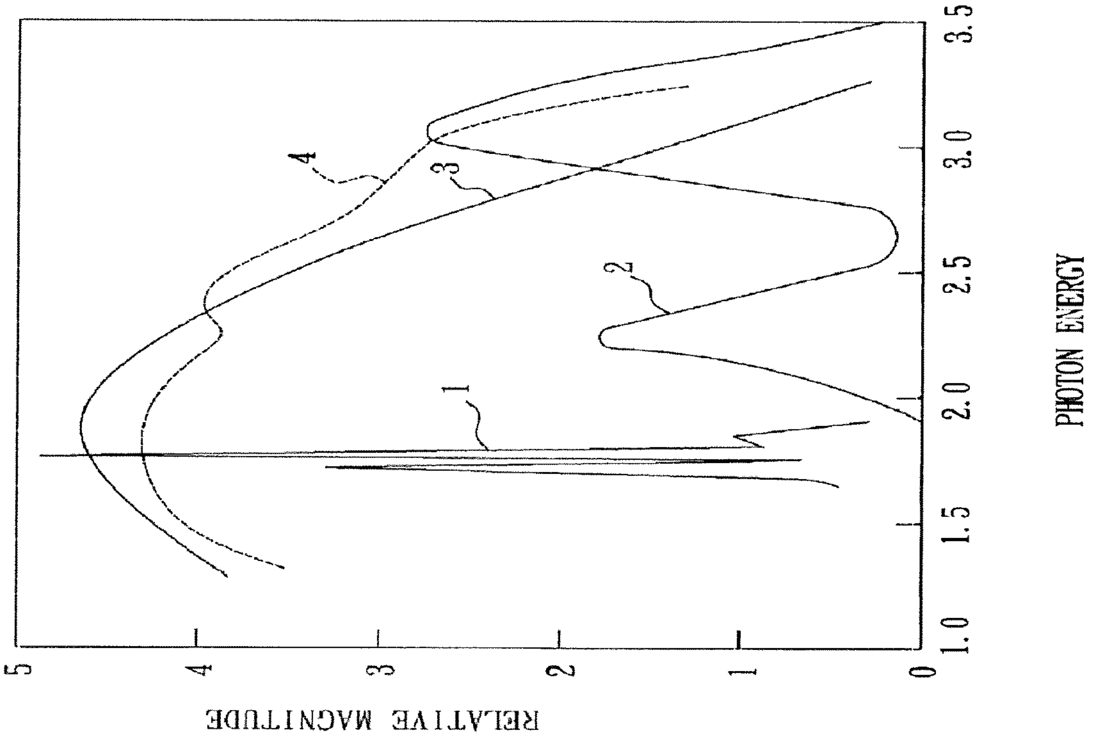
FIG. 35 schematically illustrates a solar cell covered with a layer of monocrystalline ruby, which can enhance the absorption of the solar radiation in the range of 2.3 ev~3.2 ev.

For a long time, researchers have strived to overcome the defects and limitations described above. FIG. 35 shows one prior approach in which a solar cell is covered with a layer of monocrystalline ruby including $Cr^{+3}$ which can enhance the absorption of the solar radiation in the wavelength range of 23 ev˜3.2 ev. The physical significance of this design is that, by coating a solar cell with a layer of monocrystalline ruby, the absorption of the solar radiation in the range of 2.3 ev˜3.2 ev will be enhanced, because the $Cr^{+3}$ will be excited to induce d-d transitions and then cause the narrow band to emit light. FIG. 35 plots photon energy verse absorptivity. Curve 2 is the absorptivity of the excited $Cr^{+3}$ and curve 1 is the light emission from the excited monocrystalline ruby. Consequently, the peak wavelength of $Cr^{+3}$ in the ruby corresponds to $\lambda$=695 nm, and thus the original solar radiation is "moved" to a longer wavelength range by way of the short-wavelength range of the radiation being absorbed and re-emitted in the wavelength range of $\lambda$=700 nm, FIG. 35 is also marked with the carrier assembly coefficient (curve 3) of a monocrystalline silicon cell coated with an excitable ruby. The carrier assembly coefficient varies with whether the ruby layer is present or not. The carrier assembly coefficient of the directly-excited short wavelength of the solar radiation is 10-20% higher than that of a light-emitting device operated by a ruby converter. Accordingly, the efficiency of a monocrystalline silicon solar cell may increased by 0.5-2% with a ruby converter. Despite this demonstration, the high cost of monocrystalline ruby distracts from this approach.

In solar cell applications of this invention, any of the energy converters described in the above section entitled "B. ENERGY CONVERTERS" can be used. Below is a more detailed discussion of specific energy converters that can be used for solar cell applications.

Figure 36:
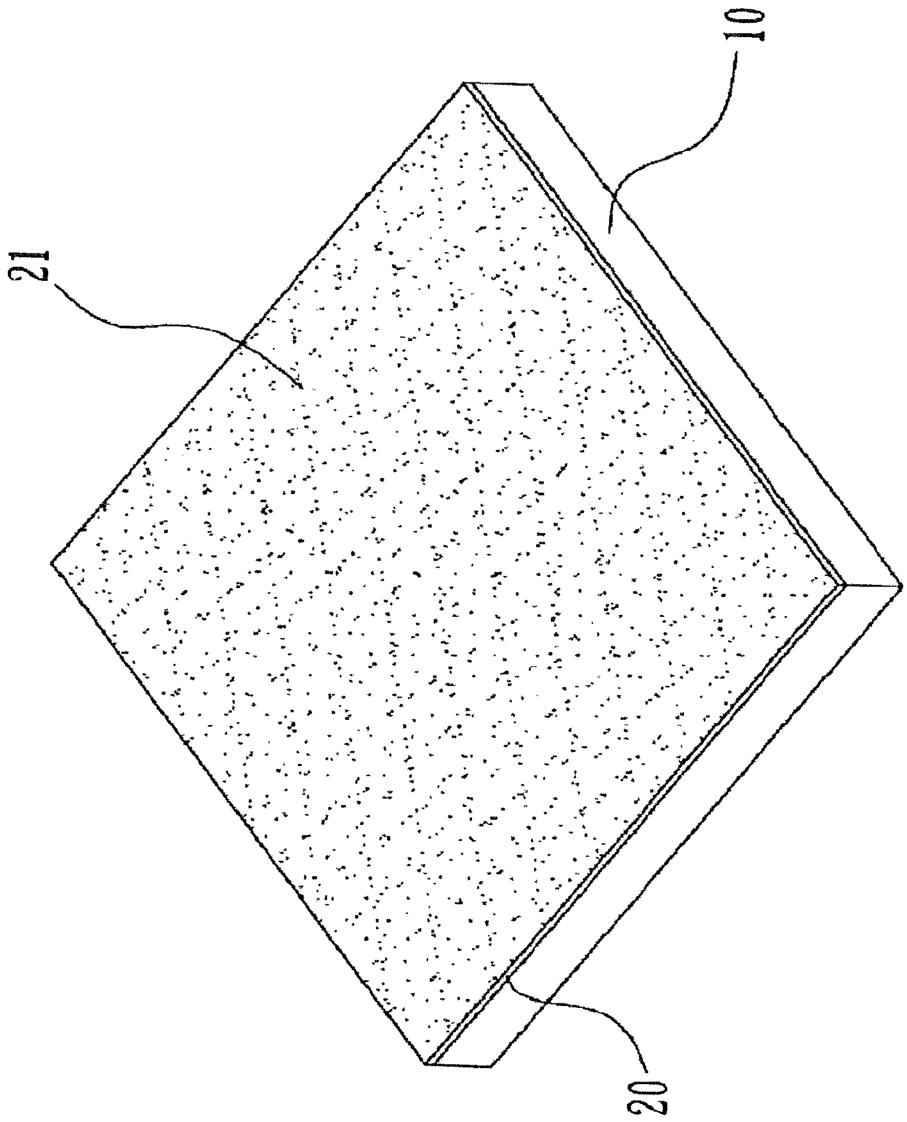
FIG. 36 schematically illustrates one solar cell structure of the present invention.

FIG. 36 illustrates a power conversion system according to the present invention. With reference to FIG. 36, the power conversion system comprises a conversion element 10 and a conversion film 20.

In one embodiment of the invention, the power conversion system is exposed to solar radiation in terrestrial or extraterrestrial settings, and the solar energy is converted by the conversion film 20 into a wavelength or wavelengths where the conversion element 10 is designed to operate (e.g., the solar energy is converted to wavelengths close to the band gap energy of a semiconductor material in the conversion element 10).

In another embodiment of the invention, the power conversion system is exposed to high energy or ionizing radiation, and the high energy or ionizing radiation is converted by the conversion film 20 into a wavelength or wavelengths where the conversion element 10 is designed to operate. Ionizing radiation has the ability to strip electrons from atoms and break chemical bonds. There are three types of ionizing radiation: alpha, beta, and gamma. Alpha radiation is composed of a helium nucleus (two protons and two neutrons bound together). Beta radiation is composed of high-speed electrons or their positively charged counterparts (positrons). Gamma radiation, highly energetic light, differs from alpha and beta radiation because it is massless and uncharged. Gamma radiation often accompanies the emission of alpha or beta radiation from a particular radioisotope. Typical radiation sources which could be used in the present invention include a Cobalt 60 source, a Cesium-137 source, an Iridium-192 source, a Krypton-85 source, a Radium-226 source, and a Strontium-90 source. Other high energy or ionizing radiation sources could be used. Indeed, the present invention could be used in the peripheral regions of nuclear cores at nuclear electric power generators.

In another embodiment of the invention, the power conversion system is exposed to infrared radiation from a waste heat source or a combustion source, and the infrared radiation is converted by the conversion film 20 into a wavelength or wavelengths where the conversion element 10 is designed to operate.

The conversion element 10 is typically a photoelectric element and can be for example a monocrystalline silicon wafer such as a p-type monocrystalline silicon wafer, a p-type polycrystalline silicon wafer, an n-type monocrystalline silicon wafer, or an n-type polycrystalline silicon wafer. A p-type monocrystalline silicon wafer is selected here as an example for explanation. However, other photoelectric conversion elements are equally usable in the invention. Also, the conversion element 10 can include multiple conversion elements such as for example 16-20 silicon wafers (e.g., 120 mm diam. wafers), forming a parallel circuit and covering a large percentage of the area of the conversion element 10.

The conversion film 20 can be made in the form of a thin polymer layer, in which a number of up and down conversion particles 21 are disposed. The filled polymer layer can be contacted with or disposed in close proximity to the outer surface of the conversion element 10. The filled polymer layer by way of a mixture of different or the same down conversion particles 21 can enhance the absorption for a first specific wavelength range of the solar radiation, for example but not limited to, $\lambda$<400 nm, and re-radiate in a second specific wavelength range, for example but not limited to, 500-780 nm where in this example a crystalline silicon solar cell would be the most efficient. The filled polymer layer by way of a mixture of different or the same up conversion particles 21 can enhance the absorption for a first specific wavelength range of the solar radiation, for example but not limited to, λ>1100 nm, and re-radiate in a second specific wavelength range, for example but not limited to, 500-780 nm where in this example a crystalline silicon solar cell would be the most efficient. In one embodiment of the invention, a glass structure is used instead of the polymer layer.

For use with solar radiation, a cover material on the conversion film 20 can be made of a polycarbonate, and/or polysiloxanes, and/or acrylate polymer. Alternatively, the cover material can be a glass compound including for example silica, phosphates, or metal oxides. The cover material on the conversion film 20 can have a high transmittance in a wide range of wavelength λ=400~1200 nm. For use with high energy radiation sources, the cover material can be a lead oxide glass to ensure that stray radiation not converted by the down conversion particles does not damage any of the components of the conversion element 10. For use with infrared radiation sources, the cover material can be an infrared transparent glass. For near-IR (NIR), from about 800 nm to 2500 nm, almost all silica-covered glasses as well as a variety of plastics and polycarbonates can be used. In fact, typical polycarbonates used in sunglasses are actually more transmissive in NIR than in the visible. For medium wavelength IR (MWIR), from 3000 to 5000 nm, sapphire, diamond, silicon, germanium, zinc selenide, zinc sulfide, magnesium fluoride, and other materials similar can be used. For long wavelength IR (LWIR), from 8000 to 14000 nm, germanium, silicon, zinc selenide, and some plastics can be used.

Down Converter Structures:

This invention in various embodiments uses a wide variety of down conversion materials (or mixtures of down converters) to produce a particular wavelength or spectrum of light which is well suited for electricity generation from a photoelectric conversion element.

In one embodiment of the invention, one class of down conversion materials can be the materials such as those described in Naum et al. The chemical composition of one phosphor powder down-converter is formulated as, for example but not limited to, $(Sr_{1-x}Ba_x)(BO_2)_2EuLiCl$, where $0 \leq x \leq 1$; that Sr and Ba are partial or total substitution can be deduced from the range of x.

A phosphor powder down-converter can further include Eu, Li, or Cl. The addition of Eu is, for example but not limited to, 0.1~15%; Li, 0~15%; and Cl, 0.1~30%. One process for formation of these phosphor powder down-converters would be to use $Sr(OH)_2$, $Ba(OH)_2$, $H_3BO_3$, $Eu_2O_3$, LiOH, $NH_4Cl$ as raw materials, and thoroughly mix these materials in a prescribed ratio. The mixture would then be fired in a module with different steps, e.g., a first step at temperature to 550-650° C. and remain isothermal for 1 to 2 hours; then in a second step, heating to 1000-1300° C. and remaining isothermal for 1 to 3 hours, for example. The material upon cooling would be a usable phosphor powder down-converter of the invention for inclusion with one of the other converter materials.

Other down converters known in the art include $TiO_2$, ZnO, $Fe_2O_3$, CdTe, CdSe, ZnS, CaS, BaS, SrS and $Y_2O_3$. Other suitable down conversion materials known in the art include zinc sulfide, $ZnS:Mn^{2+}$, ferric oxide, titanium oxide, zinc oxide, zinc oxide containing small amounts of $Al_2O_3$ and AgI nanoclusters encapsulated in zeolite. Other suitable down conversion materials include lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers known in the art are also suitable as conversion materials: poly(phenylene ethynylene), poly (phenylene vinylene), poly(p-phenylene), poly(thiophene), poly(pyridyl vinylene), poly(pyrrole), poly(acetylene), poly (vinyl carbazole), poly(fluorenes), and the like, as well as copolymers and/or derivatives thereof.

In various embodiments of the invention, the following particles can be used similar to that detailed in U.S. Pat. No. 7,090,355, the entire contents of which are incorporated herein by reference. For down-conversion, the following materials can be used: inorganic or ceramic phosphors or nano-particles, including but not limited to metal oxides, metal halides, metal chalcoginides (e.g. metal sulfides), or their hybrids, such as metal oxo-halides, metal oxo-chalcoginides; laser dyes and small organic molecules, and fluorescent organic polymers; semiconductor nano-particles, such as II-VI or III-V compound semiconductors, e.g. fluorescent quantum dots; organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The Garnet series of phosphors can be used: $(Y_mA_{1-m})_3(Al_nB_{1-n})_5O_{12}$, doped with Ce; where $0 \leq m$, $n \leq 1$, where A includes other rare earth elements, B includes B, Ga. In addition, phosphors containing metal silicates, metal borates, metal phosphates, and metal aluminates hosts can be used. In addition, phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, Tl) as the fluorescent activators, can be used. Materials such as Ca, Zn, Cd in tungstates, metal vanadates, ZnO, etc. can be used.

Commercial laser dyes obtainable from several laser dye vendors, including Lambda Physik, and Exciton, etc can be used. A partial list of laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc have been used in opto-electronic devices, such as polymer light emitting diodes (PLED).

As noted above, quantum dots or semiconductor nanoparticles can be used. The term "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nano-particle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion. Such molecules include a metal center of rare earth elements including Eu, Tb, Er, Tm, Ce protected with organic chelating groups. The metal center may also include transitional elements such as Zn, Mn, Cr, Ir, etc and main group elements such as B, Al, Ga. Such organometallic molecules can readily dissolved in liquid or transparent solid host media. Some examples of such fluorescent organometallic molecules include: 1. Tris(dibenzoylmethane)mono (phenanthroline)europium(III); 2. Tris(8-hydroxyquinoline) erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-converting particles for red emission (e.g., near the band gap of a crystalline silicon solar cell) include those discussed above and europium complexes such as those described in JP Laid-open Patent Publication (Kokai) No. 2003-26969, which were constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. An europium (Eu) complex is capable of emitting red fluorescence when irradiated with ultraviolet rays having a wavelength ranging from 365 nm to 410 nm. Terbium (Tb) is capable of emitting green or yellow fluorescence when irradiated with ultraviolet rays having a wavelength of 365 nm and may be useful for example in higher bandgap solar cells, such as for example amorphous silicon solar cells or GasAs based or other II-V-based solar cells.

In other down-conversion embodiments, light emitting particles which emit red light can include europium, light emitting particles which emit green light can include Terbium, and light emitting particles which emit blue or yellow light can include cerium (and/or thulium). In embodiments, light emitting particles can be included in pure organic or organo-metallic dyes.

In addition to the combinations of rare earth complexes, such as a combination of a europium complex and a terbium complex, it is also possible employ a combination of a europium substance and a green-emitting fluorescent substance which is not a complex, or a combination of a terbium substance and a red-emitting fluorescent substance which is not a complex.

Other down converters include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties. Examples of doped (or alloyed) glass systems suitable for the include $Y_2O_3$:Gd, $Y_2O_3$:Dy, $Y_2O_3$:Tb, $Y_2O_3$:Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$:Eu (red), $Y_2O_3$:Eu (red), $YVO_4$:Eu (red), and $Zn_2SiO_4$:Mn (green).

Alternatively, quantum dots can be used to tailor the down conversion process. As described in U.S. Pat. No. 6,744,960 (the entire contents of which are incorporated by reference), different size quantum dots produce different wavelength emissions. As applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot, may range from about 2 to 10 nm. Since the size of these particles is so small, quantum physics governs many of the electrical and optical properties of the quantum dot. One such result of the application of quantum mechanics to the quantum dot is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots, light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm.

In other embodiments of the invention, the down converters (or mixtures of down converters) can include $Y_2O_3$; Li (5%). This material is an especially well suited material for x-ray stimulated emissions in the ultraviolet to violet region of the light spectrum and may be used in power conversion systems of the invention which generate power from for example radioactive sources.

The converters in one embodiment can include a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$, alkali lead silicate including compositions of $SiO_2$, $B_2O_3$, $Na_2O$, $K_2O$, PbO, MgO, or Ag, and combinations or alloys or layers thereof.

Upconverter Structures:

The invention in various embodiments uses a wide variety of up conversion materials (or mixtures of up converters) to produce a particular wavelength or spectrum of light which is well suited for electricity generation from a photoelectric conversion element optically coupled to a conversion device converting the light into electrical power. These up conversion materials can include similar materials as discussed above with regard to down conversion but typically included doped or impurity states in a host crystal that provide a mechanism for up conversion pumping. Accordingly, the up conversion materials can convert energy from one of near infrared, infrared, and microwave irradiation into light more suited for photoelectric conversion. The upconversion materials in one embodiment can convert energy from lower energy visible light to higher energy visible light more suited for photoelectric conversion. In up-conversion embodiments, light emitting particles of rare earth element complexes which emit red light may include praseodymium, light emitting particles which emit green light may include erbium, and light emitting particles which emit blue light may include thulium.

With regard more specifically to up converters suitable for the invention, U.S. Pat. No. 4,705,952 (the contents of which are hereby incorporated herein by reference) describes an infrared-triggered phosphor that stores energy in the form of visible light of a first wavelength and releases energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention.

The synthesis of oxide nanoparticles such as those that are covered on the lanthanides have been achieved by a number of processes including solid-gel (sol-gel) techniques, gas phase condensation or colloidal chemical methods. While efforts to make concentrated colloidal solutions of highly uniform size luminescent nanoparticles have met with some technical difficulties, synthesis of useful amounts of some 5 nanometer sized lanthanide doped oxides have been achieved as shown in a paper by Bazzi et al entitled *Synthesis and luminescent properties of sub 5-nm lanthanide oxide particles*, in the Journal of Luminescence 102 (2003) pages 445-450, the entire contents of which are incorporated herein by reference. Materials such as these and the other materials discussed below are useful materials for upconversion. The work by Bazzi et al concentrated on understanding the properties on lanthanide oxide nanoparticles with an emphasis on the microstructural properties and optical emission properties (i.e. concentrated on the fluorescence and down conversion properties of these materials). Nevertheless, the materials described by Bazzi et al are useful in various embodiments of this invention.

In one example of others to be described below, up conversion and down conversion materials can be used in the conversion film 20 of the present invention. In one example of others to be described below, a nanoparticle of a lanthanide doped oxide can be excited with near infrared light such as for example light of a wavelength range greater than 1000 nm in the solar spectrum and produce visible light more tuned for the band gap of the conversion element 10. Such nanoparticles would have application in the solar concentrators discussed above.

Other work reported by Suyver et al in *Upconversion spectroscopy and properties of $NaYF_4$ doped with $Er^{3+}$, $Tm^{3+}$ and or $Yb^{3+}$*, in Journal of Luminescence 117 (2006) pages 1-12, the entire contents of which are incorporated herein by reference, recognizes in the $NaYF_4$ material system upconversion properties. The materials described by Suyver et al are useful in various embodiments of this invention.

Figure 37:
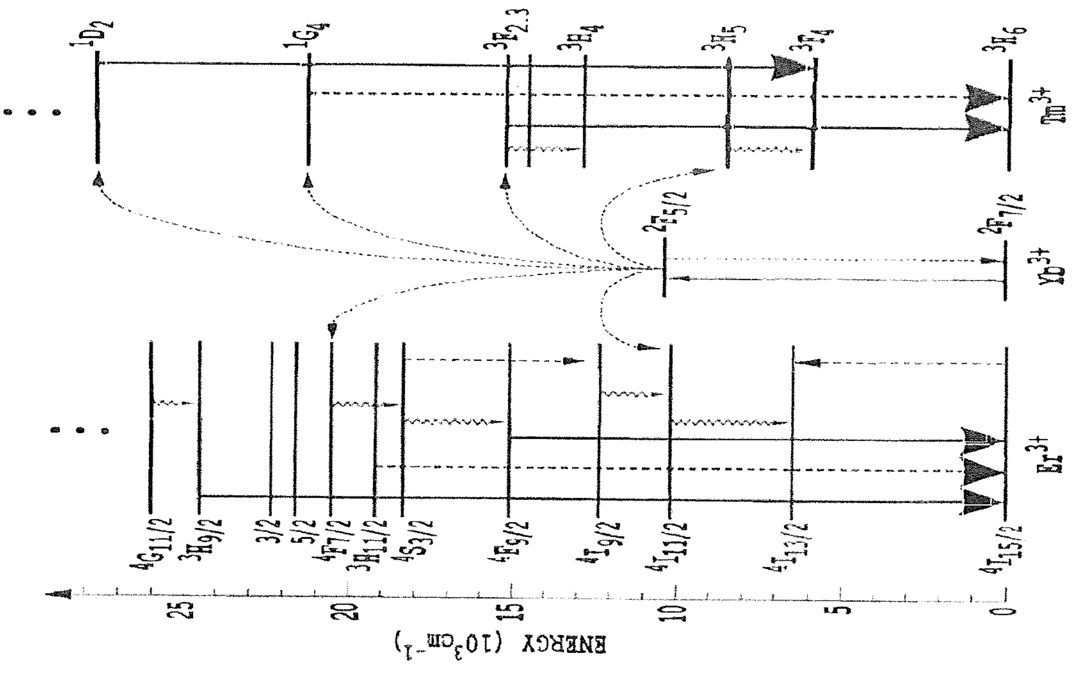
FIG. 37 is a schematic energy level diagram showing upconversion excitation and visible emissions schemes for $Er^{3+}$, $Tm^{3+}$ and or $Yb^{3+}$ ions.

FIG. 37 is a schematic reproduced from Suyver et al shows a schematic energy level diagram of upconversion excitation and visible emissions schemes for $Er^{3+}$, $Tm^{3+}$ and or $Yb^{3+}$ ions. Full, dotted, dashed, and curly arrows indicate respectively radiative, non-radiative energy transfer, cross relaxation and other relaxation processes.

The lanthanide doped oxides differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the $NaYF_4$ such that the $Yb^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

Figure 38:
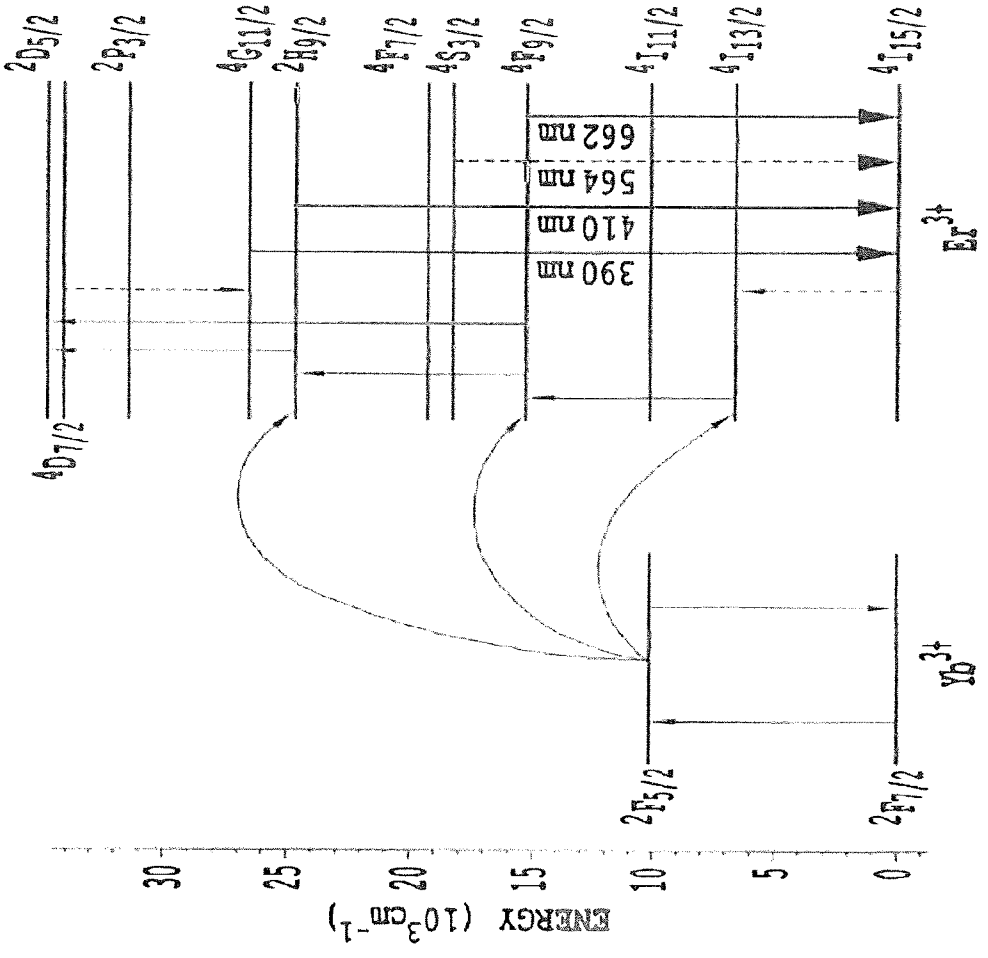
FIG. 38 is an energy diagram showing energy states for a four-photon upconversion process in $Y_2O_3$ nanocrystals.

Chen et al have described a four photon upconversion in *Four-photon upconversion induced by infrared diode laser excitation in rare-earth-ion-doped $Y_2O_3$ nanocrystals*, Chemical Physics Letters, 448 (2007) pp. 127-131 In that paper, emissions at 390 nm and at 409 nm were associated with a four-photon upconversion process in the $Y_2O_3$ nanocrystals. FIG. 38 reproduced below from Chen et al shows a ladder of states by which an infrared light source can progressively pump until the $^4D_{7/2}$ state is reached. From this upper state, transitions downward in energy occur until the $^4G_{1/2}$ state is reached, where a transition downward in energy emits a 390 nm photon. The materials described by Chen et al are useful in various embodiments of this invention.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of this invention.

Further materials specified for up conversion in the present invention include CdTe, CdSe, ZnO, CdS, $Y_2O_3$, MgS, CaS, SrS and BaS. Such up conversion materials may include any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, 0; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . $0<z\leq1$, $o<q\leq1$).

Up-conversion phosphors similar in chemical compositions to the down-conversion fluorescent materials discussed above can also be used. The up-conversion phosphors can include laser dyes, e.g., the organic small molecules that can be excited by the absorption of at least two infrared photons with emission of visible light. The up-conversion phosphors can include fluorescent polymers, e.g., the class of polymers that can be excited by the absorption of at least two infrared photons with emission of visible light. The up-conversion phosphors can include inorganic or ceramic particles or nano-particles, including the conventional up-conversion phosphors (e.g. metal fluorides, metal oxides) that can be excited by the absorption of at least two infrared photons with emission of visible light. The up-conversion phosphors can include semiconductor particles, including nano-particles such as II-VI or III-V compound or Group IV semiconductors, described in details in the "down-conversion" semiconductors above.

Fluorescent up-conversion inorganic phosphors can include but are not limited to metal oxides, metal halides, metal chalcoginides (e.g. sulfides), or their hybrids, such as metal oxo-halides, metal oxo-chalcoginides. Fluorescent up-conversion inorganic phosphors are usually doped with rare earth elements (e.g. $Yb^{3+}$, $Er^{3+}$, $Tm^{3+}$). Some host examples include, but are not limited to: $NaYF_4$, $YF_3$, $BaYF_5$, $LaF_3$, $La_2MoO_8$, $LaNbO_4$, $LnO_2S$; where Ln is the rare earth elements, such as Y, La, Gd).

Some nanoparticles such as ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$ are known in the art to function for both down-conversion luminescence and upconversion luminescence.

Figure 39A:
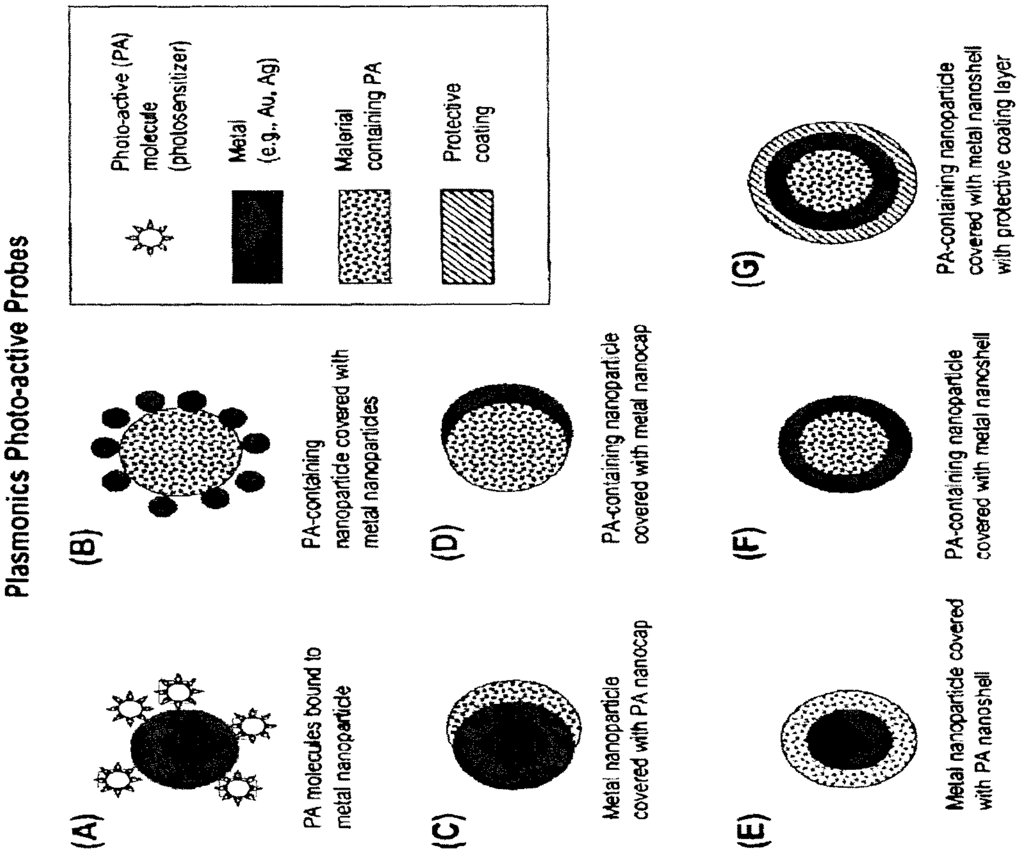
FIG. 39A is a schematic illustration of various upconverter structures of the invention.
Figures 1, 39A:
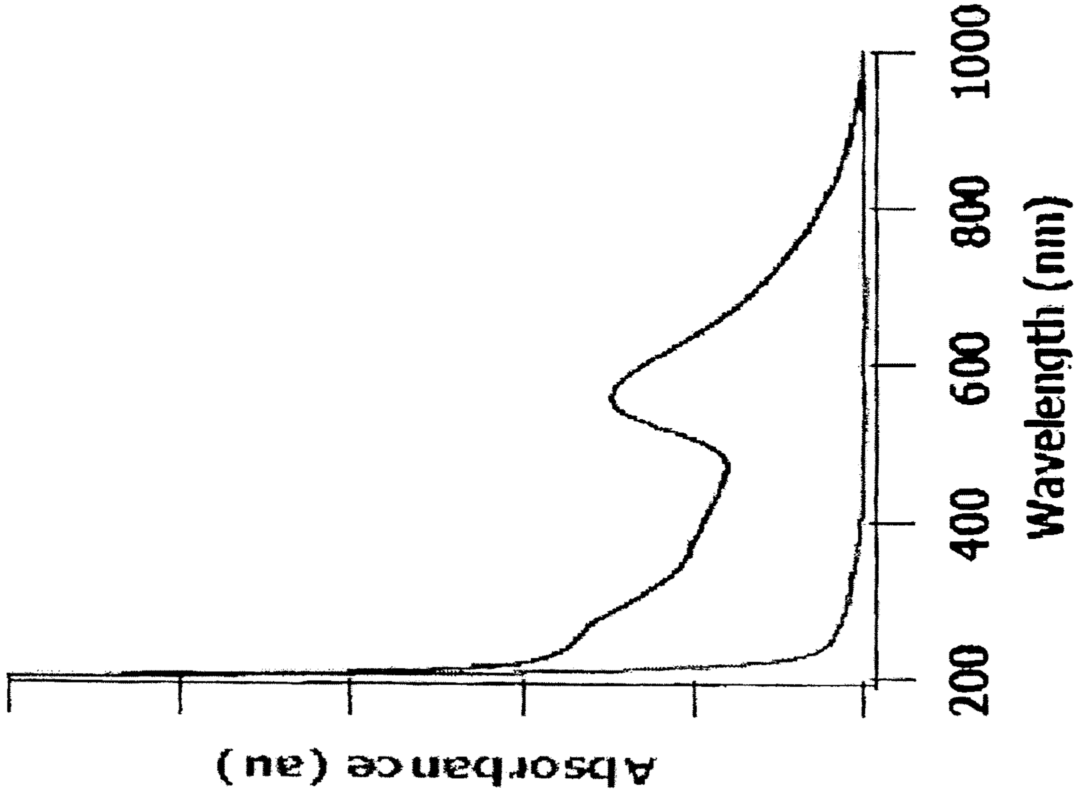

FIG. 39A is a schematic of a depiction of a converter material (i.e., a photoactive material) according to one embodiment of the invention. FIG. 39A shows a number of structural configurations for placement of a dielectric core upconverter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion are critical to the invention, for the purposes for discussion and illustration, the following explanation is offered.

In the context of FIG. 39A, when a wavelength $\lambda_1$ interacts with a dielectric material core, three separate processes are well understood for the upconversion process involving trivalent rare earth ions. These three processes are:

1) excited state absorption whereby two photons are absorbed sequentially by the same ion to excite and populate one or more states;
2) energy transfer upconversion which is a transfer of excitation from one ion to another already in an excited state; and
3) a cooperative process of mutiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion process.

Therefore, the particular ion being activated (whether it be a dopant ion or a host ion of a lattice such as in the neodymium oxide) will be chosen covered on the host material being processed, in order that the dopant ion or the host ion in the dielectric core provide ion states which are pumpable by the NIR source to generate the resultant emission $\lambda_2$.

In one embodiment of this invention, the dielectric core is coated, such as for example with a metallic shell, to enhance electron-phonon coupling and thereby increase upconversion efficiency, as discussed above. In another embodiment of this invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. Further, in one embodiment of this invention, the coating can be a polymer. In one embodiment, this coating is provided on $NaYF_4$:Ln/$NaYF_4$ dielectric core. Such coatings can increase the upconversion efficiency relative to an uncoated upconverter. Similarly, such a coating may increase the down conversion efficiency relative to an uncoated down converter.

In another embodiment of the invention, phonon modes of an undoped host-lattice (e.g., $Y_2O_3$) nanocrystals are modulated, for example, by Au, Ag, Pt, and Pd shells of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure can exist inside the dielectric and the relative position of the metal structure to the dielectric structure can enhance plasmon resonance for both down and up conversion materials. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

In general, the metallic shell is designed with a layer thickness to enhance the photon upconversion or down conversion process through plasmonic enhancement. The thickness of the shell is "tuned" in its thickness to the absorption process by having a dimension in which plasmons (i.e., electrons oscillations) in shell have a resonance in frequency which provides spectral overlap with the absorption band of the incident light targeted. Thus, if the upconversion is to be stimulated by NIR light such as for example centered around 1000 nm NIR light, then the thickness of the shell is "tuned" in a thickness to where a plasmon resonance resonates at a frequency also of 1000 nm (or in the neighborhood thereof as plasmon resonances are typically broad at these wavelengths).

Such a plasmon resonating shell can be made of numerous transition metals, including though not limited to gold, silver, platinum, palladium, nickel, ruthenium, rhenium, copper, and cobalt. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.)

FIG. 39A-1 is reproduced from Jain et al and illustrates the capability in the present invention to "tune" the metal shell to have a spectral overlap with the excitation and/or emission radiation wavelengths. This capability of matching or tuning of the frequencies provides an enhancement of the absorption which would not be present with a dielectric core alone.

In one embodiment of this invention, the thickness of the metal shell is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall conversion process.

Figure 39B:
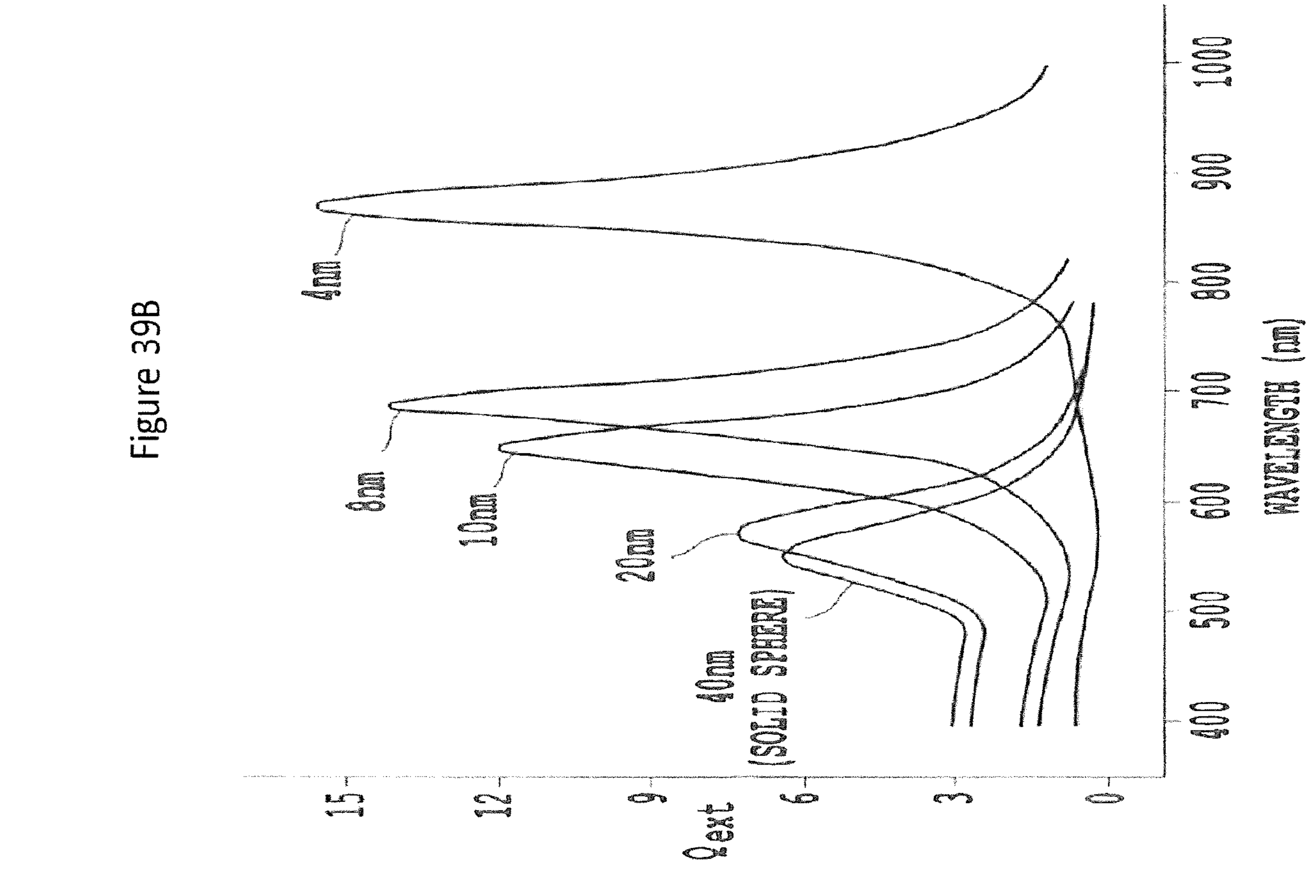
FIG. 39B is a schematic illustration of plasmon resonance as a function of shell thickness.

FIG. 39B is a schematic illustration of plasmon resonance as a function of shell thickness.

Additionally, plasmon-phonon coupling may be used to reduce a resonance frequency through the tuning of the bands to a degree off resonance. This may be useful in optimizing resonance energy transfer processes for the purpose of coupling the core-shell nanoparticles to sensitive chromophores or drug targets. Accordingly, when a recipient is outside of the shell, the recipient will receive enhanced light $\lambda_2$ by the above-described plasmonic effect than would occur if the shell were absent from the structure.

In one embodiment of this invention, the metallic structures can be an alloy such as for example a Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

Such metallic structures in various embodiments of this invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Accordingly, with the upconverter or down converter structures of this invention, a plasmonics effect is advantageous. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively.

In one embodiment of the invention, Ln-doped $Y_2O_3$ cores for example may be shelled with $NaYF_4$, $Nd_2O_3$, $Ga2O_3$, $LaF_3$, undoped $Y_2O_3$, or other low phonon mode dielectric material using a secondary polyol approach following silyl protection of the core nanocrystal. It has been shown that low phonon mode host lattices (such as $Y_2O_3$, $NaYF_4$, etc.) are useful for aiding in the upconversion process. This has been attributed to the nature of electron-phonon coupling to low phonon modes and the removal of non-radiative decay processes within the host-lattice/ion crystal. Accordingly, in one embodiment of the present invention, the dielectric core materials are made of low mode phonon host lattices (such as $Y_2O_3$, $NaYF_4$, $Nd_2O_3$, $LaF_3$, $LaCl_3$ $La_2O_3$, $TiO_2$, $SiO_2$ etc.).

In various embodiments of the invention, the upconverter dielectric core can be coated with thiol-terminated silanes to provide a coating of $SiO_2$ about the core of similar reactivity to $Y_2O_3$. These thiolated nanoparticles are then exposed to colloidal Au (1-2 nm) which associates to the nanoparticle surface and, with addition of $HAuCl_4$ and a reducing agent, Ostwald ripening coalesces the Au surface into a uniform shell of a designated thickness. Solubility enhancement of $NaYF_4$ and other $CaF_2$ lattices can be increased by the use of coupled trioctylphosphine-oleic amine, polyethylene glycol, and polyethyleneimine surfactants. These surfactants associate to the surface of the nanoparticles with functional head groups and are soluble in either organic or aqueous solvents to permit colloidal suspension of the nanoparticles.

In one embodiment of the invention, this methodology is used to synthesize upconverting core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag, Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, this methodology is used to synthesize novel mixed core-shell materials can include semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and trioctylphosphine-oleic amine ($NaYF_4$ shell). All core-shell nanoparticles may further be solubilized into a colloidal suspension with the addition of triarginine peptide, polyethylene glycol, and polyethyleneimine surfactants.

Gold nanoshells can be prepared using the method described in Hirsch L R, Stafford R J, Bankson J A, Sershen S R, Price R E, Hazle J D, Halas N J, West J L (2003) *Nanoshell-mediated near infrared thermal therapy of tumors under MR Guidance*. Proc Natl Acad Sci 100:13549-13554, the entire contents of which are incorporated herein by reference. This method uses a mechanism involving nucleation and then successive growth of gold nanoparticles around a dielectric core. Gold nanoparticles and the seed can be prepared using the Frens method to grow the gold shell. Dielectric nanoparticles (100 nm or less) used for the core of the nanoshells can then be monodispersed in solution of 1% APTES in EtOH. The gold "seed" colloid can then be synthesized using the Frens method to deposit gold onto the surface of nanoparticles via molecular linkage of silyl terminated, amine groups. The "seed" covers the aminated nanoparticle surface, first as a discontinuous gold metal layer gradually growing forming a continuous gold shell.

In a further embodiment of the invention, the upconverter structures of the invention can be incorporated into a material (e.g., biocompatible polymer) that can form a nanocap onto the metal (gold) nanoparticles. Suitable gel or biocompatible polymers include, but are not limited to poly(esters) covered on polylactide (PLA), polyglycolide (PGA), polycarpolactone (PCL), and their copolymers, as well as poly (hydroxyalkanoate)s of the PHB-PHV class, additional poly (ester)s, natural polymers, particularly, modified poly (saccharide)s, e.g., starch, cellulose, and chitosan, polyethylene oxides, poly(ether)(ester) block copolymers, and ethylene vinyl acetate copolymers.

In one embodiment of the invention, the materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y, atomic no. 39) and scandium (Sc). Hence, suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above. Doping concentrations in the invention can range from 0.2% to 20% roughly per ion into the host lattice or in a weight or mol % variation. The efficiency of the up and down conversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teachings of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of this invention, the dielectric core is coated, such as for example with a metallic shell, to enhance electron-phonon coupling and thereby increase upconversion efficiency, as discussed above. In another embodiment of this invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. Further, in one embodiment of this invention, the coating can be a polymer. In one embodiment this coating is provided on $NaYF_4$:Ln/$NaYF_4$ dielectric core. Such coatings can increase the upconversion efficiency relative to an uncoated upconverter. Similarly, such a coating may increase the down conversion efficiency relative to an uncoated down converter.

In another embodiment of the invention, phonon modes of an undoped host-lattice (e.g., $Y_2O_3$) nanocrystals are modulated, for example, by Au, Ag, Pt, and Pd shells 4 of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

Figure 39C:
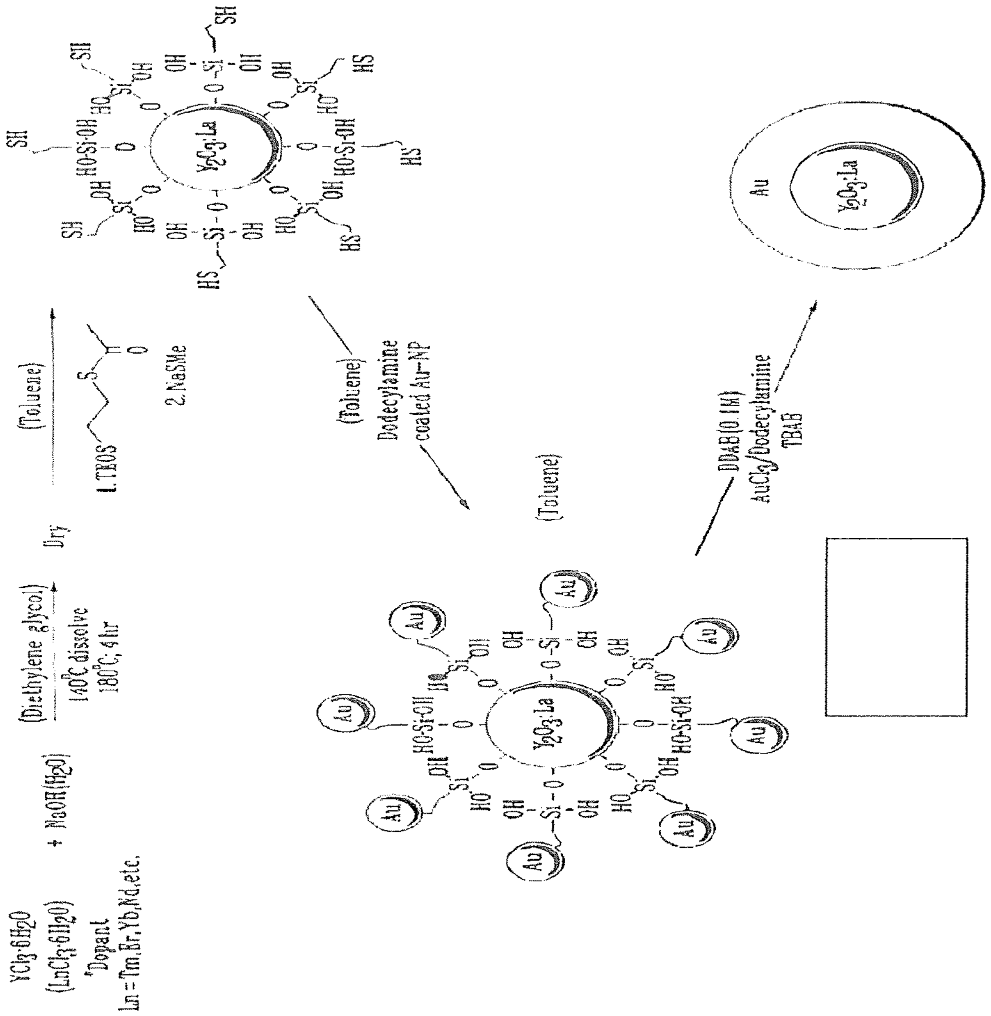
FIG. 39C is a schematic illustration of a process for forming and a resultant Ln-doped $Y_2O_3$ core with a Au shell.

FIG. 39C is a schematic illustration of a process for forming and a resultant Ln-doped $Y_2O_3$ core with a Au shell. One illustrative method for producing sub-10 nm Ln-doped $Y_2O_3$ nanoparticles with a metal shell can be achieved through the polyol method See Bazzi, R. et al *Journal of Luminescence,* 2003, 102-103, 445-450, the entire contents of which are incorporated by reference. In this approach, yttrium chloride hexahydrate and lanthanum-series chloride hexahydrates are combined in an appropriate ratio with respect to their cation concentration into suspension with diethylene glycol (0.2 mol chloride per liter of DEG). To this suspension is added a solution of NaOH and water (0.2 mol/L and 2 mol/L, respectively). The suspension is heated to 140° C. in a solvent recondensing/reflux apparatus for a period of 1 hour. Upon completion of the 1 hour of heating the solution has become transparent and nucleation of the desired nanoparticles has occurred. The temperature is then increased to 180° C. and the solution is boiled/refluxed for 4 hours yielding $Y_2O_3$:Ln nanoparticles. This solution is then dialyzed against water to precipitate the nanoparticles or solvent is distilled off and excess water added to precipitate the same. The nanoparticles are collected through centrifugation and dried in vacuo.

The dried nanoparticles are then calcined at 900° C. for 2 hours to afford single phase, cubic $Y_2O_3$ nanocrystals with lanthanide dopants equally distributed through the $Y_2O_3$ nanocrystal. This methodology may be modified to allow for synthesis in a pressurized environment, thereby allowing for complete expression in the cubic phase, allowing for a shorter calcining times and lower temperatures leading to less nanoparticle agglomeration and size growth.

Nanocrystals are then resuspended in toluene with sonication and treated with 2-triethoxysilyl-1-ethyl thioacetate (300 mM) in toluene. Volatile components of the reaction mixture are removed in vacuo and the remaining residue is resuspended in toluene and treated with NaSMe. Volatile components of the reaction mixture are again removed in vacuo and the remaining residue is purified through reprecipitation, centrifugation, and drying. The thiol-terminated, surface-modified nanocrystals are then resuspended in 0.1 M DDAB (didodecylammonium bromide) in toluene and a solution of colloidal gold nanoparticles (~1 nm in diameter) coated in dodecylamine (prepared as per Jana, et al. *J. Am. Chem. Soc.* 2003, 125, 14280-14281, the entire contents of which are incorporated herein by reference) is added. The gold shell is then completed, and grown to the appropriate shell thickness through additions of $AuCl_3$ and dodecylamine in the presence of reducing equivalents of tetrabutylammonium borohydride. Thiol terminated organic acids may then be added to allow for increased water solubility and the completed gold metal shell, Ln-doped, $Y_2O_3$ nanoparticles may be separated in the presence of water through extraction or dialysis.

Figure 39D:
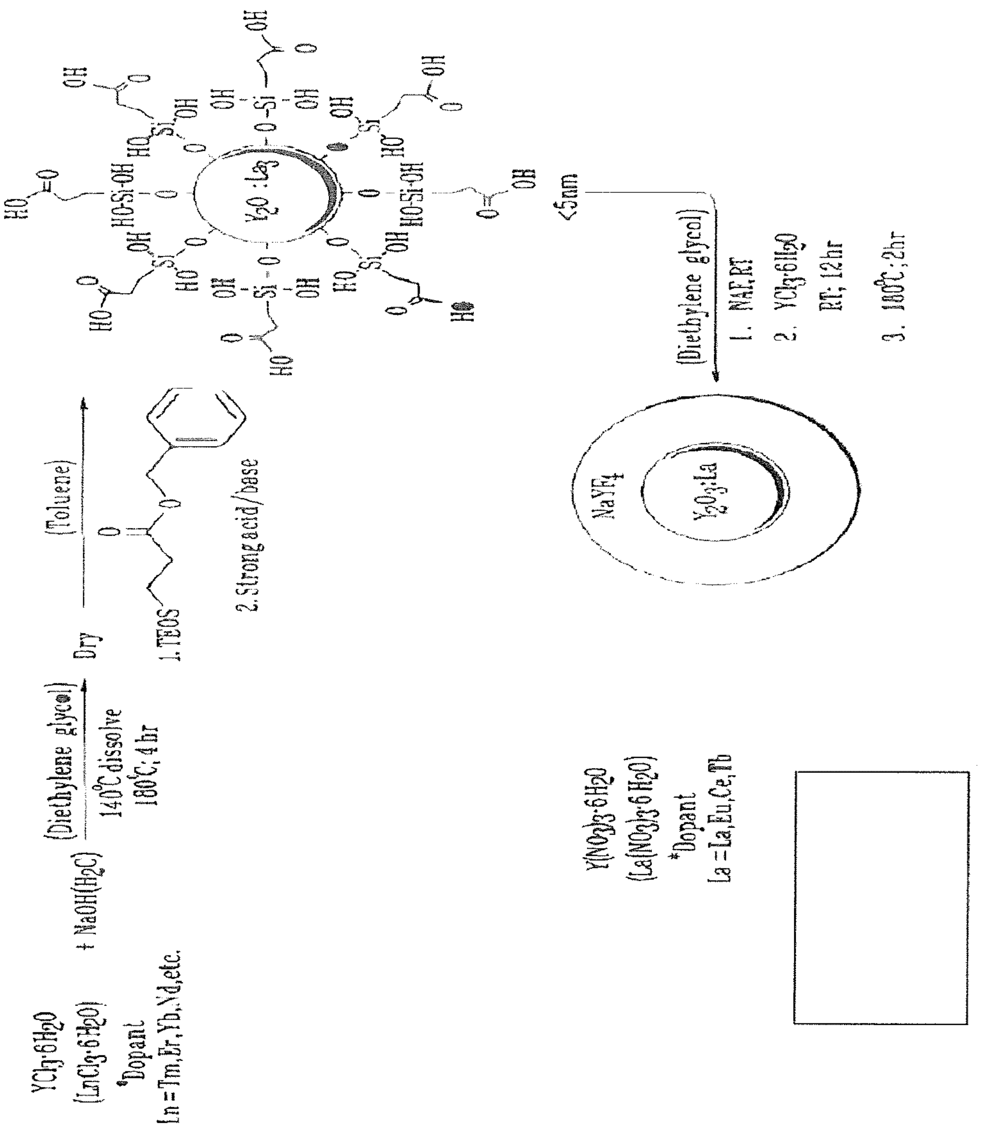
FIG. 39D is a schematic illustration of a process for forming and a resultant Ln-doped $Y_2O_3$ core with a $NaYF_4$ shell.

FIG. 39D is a schematic illustration of a process for forming and a resultant Ln-doped $Y_2O_3$ core with a $NaYF_4$ shell. In this embodiment of the present invention, Ln-doped $Y_2O_3$ cores for example may be shelled with $NaYF_4$, $Nd_2O_3$, $Ga_2O_3$, $LaF_3$, undoped $Y_2O_3$, or other low phonon mode dielectric material using a secondary polyol approach following silyl protection of the core nanocrystal. It has been shown that low phonon mode host lattices (such as $Y_2O_3$, $NaYF_4$, etc.) are useful for aiding in the upconversion process. This has been attributed to the nature of electron-phonon coupling to low phonon modes and the removal of non-radiative decay processes within the host-lattice/ion crystal. Accordingly, in one embodiment of the present invention, the dielectric core materials are made of low mode phonon host lattices (such as $Y_2O_3$, $NaYF_4$, $Nd_2O_3$, $LaF_3$, $LaCl_3$ $La_2O_3$, $TiO_2$, $SiO_2$ etc.).

Dried $Y_2O_3$ nanoparticles are resuspended in toluene with sonication and treated with 2-triethoxysilyl-1-propionic acid, benzyl ester (300 mM) in toluene Volatile components of the reaction mixture are removed in vacuo and the remaining residue is resuspended in toluene and treated with a strong cover. Volatile components of the reaction mixture are again removed in vacuo and the remaining residue is purified through reprecipitation, centrifugation, and drying. The carboxyl-terminated, surface-modified nanocrystals are then resuspended in a solution of sodium fluoride in DEG and treated with yttrium nitrate hexahydrate at room temperature, stirring for 12 hours (for $NaYF_4$ exemplar). The reaction mixture is then brought to 180° C. for 2 hours to grow the $NaYF_4$ shell through Ostwald ripening. Nanoparticles are purified through reprecipitation, as described previously. Organic acid terminated polymers, polyethylene glycol, polyethyleneimine, or other FDA approved, bioavailable polymer may then be added to allow for increased water solubility and the completed $NaYF_4$ shell. Ln-doped, $Y_2O_3$ nanoparticles may be resuspended in water for medical use.

In various embodiments of the invention, the upconverter dielectric core can be coated with thiol-terminated silanes to provide a coating of $SiO_2$ about the core of similar reactivity to $Y_2O_3$. These thiolated nanoparticles are then exposed to colloidal Au (1-2 nm) which associates to the nanoparticle surface and, with addition of $HAuCl_4$ and a reducing agent, Ostwald ripening coalesces the Au surface into a uniform shell of a designated thickness Solubility enhancement of $NaYF_4$ and other $CaF_2$ lattices can be increased by the use of coupled trioctylphosphine-oleic amine, polyethylene glycol, and polyethyleneimine surfactants. These surfactants associate to the surface of the nanoparticles with functional head groups and are soluble in either organic or aqueous solvents to permit colloidal suspension of the nanoparticles.

In one embodiment of the invention, this methodology is used to synthesize upconverting core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells. $NaYF_4$:Ln with Au(Ag, Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, this methodology is used to synthesize novel mixed core-shell materials can include semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag, Pt, Pd) or undoped $Y_2O_3$ and $NaYF_4$ matrices which have the potential to enhance or tune the phonon modes needed for energy transfer in the upconversion process Solubility can be enhanced, for example, by addition of thiolated organics (Au shell), organic chain triethanolsilane ($Y_2O_3$ shell), and trioctylphospine-oleic amine ($NaYF_4$ shell). All core-shell nanoparticles may further be solubilized into a colloidal suspension with the addition of triarginine peptide, polyethylene glycol, and polyethyleneimine surfactants.

Figure 40:
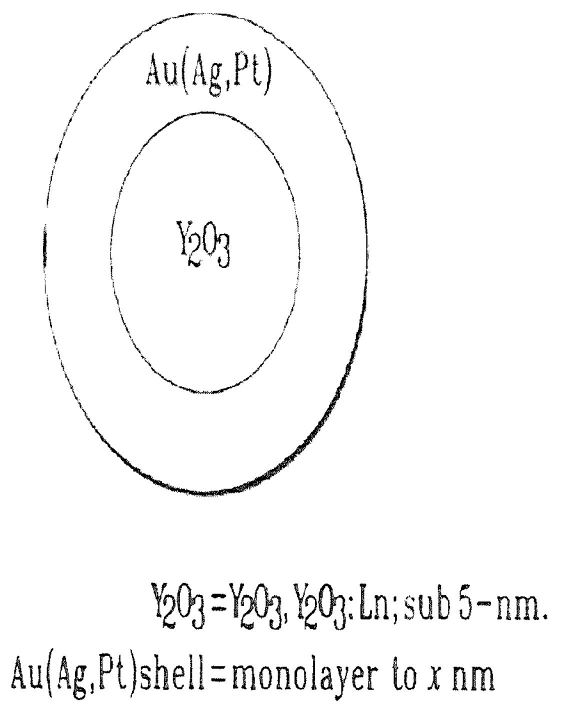
FIG. 40 is a schematic illustration of a particular nanometer sized upconverter structure of the invention.

In one embodiment of the invention, small nanocrystals of these materials are prepared using rare-earth (RE) precursors (e.g. chloride, nitrate, alkoxides) which are mixed with a defined amount of water in a high boiling polyalcohol (e.g., diethylene glycol) solvent. The dehydrating properties of the alcohol and the high temperature of the solution promote a non-aqueous environment for the formation of oxide particles, as opposed to hydroxide, particles. Other solvents which can be used include: ethylene glycol, triethylene glycol, propylene glycol, dipropylene glycol, tripropylene glycol, etc. (thereby providing solvents with different boiling points). With these procedures, one expects sub-5 nm nanocrystals to be coated with Au, Ag, Pt, Pd (or combinations thereof) layers. FIG. 40 illustrates one such coated sub-5 nm nanocrystal.

Accordingly, the synthesis of these nanocrystals and other dielectric core elements can follow the methods described below.

In particular, one method of forming yttrium oxide nanocrystals is to obtain precursors of the yttrium and rare earth ions in their salt forms, preferably in a chloride salt of the hexahydrate form, which is more soluble than non-hexahydrate forms. These salts are then combined in the correct molar ratios as listed below to create a yttrium oxide containing solution in a high boiling polyalcohol solvent with an added cover of the correct proportion. An initial cation concentration of 0.2 moles per liter is mixed with a sodium hydroxide solution in water (0.2 moles per liter of sodium hydroxide per liter of reaction solution: 2 moles of $H_2O$ per liter per solution). The precursors were added together in the polyalcohol solvent, stirred for one hour at 140° C. After the salts are completely dissolved, the solution is brought to reflux at 180° C. and heated for four hours. The reaction is then cooled to room temperature yielding a transparent colloidal suspension of rare earth doped, yttrium oxide nanocrystals. The metallic shell can then be prepared using the processes described below.

Similar methods can be employed for the preparation of the other upconversion materials described above, such as for example for the preparation of 1) nanoparticles of 2% neodymium and 8% ytterbium doped yttrium oxide,
2) europium and ytterbium doped yttrium oxide, and
3) any combination of rare earth trivalent ions doped into a neodymium oxide nanocrystal.

FIGS. 41A-41D show some of the various embodiments of converter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer.

Figure 41A:
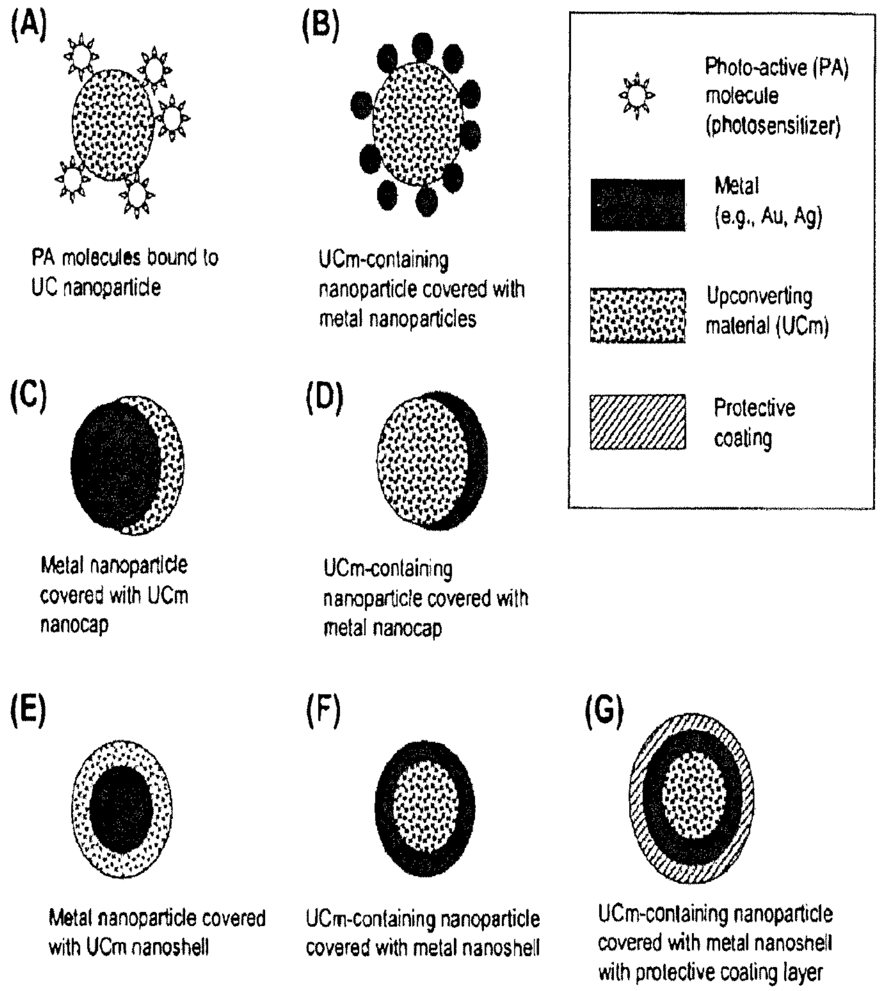
FIG. 41A is a schematic illustration of other various upconverter structures of the invention.

Accordingly, FIG. 41A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

FIG. 41B shows yet other embodiments of conversion structures that have a dielectric layer between the metal and the UC materials.

Figure 41C:
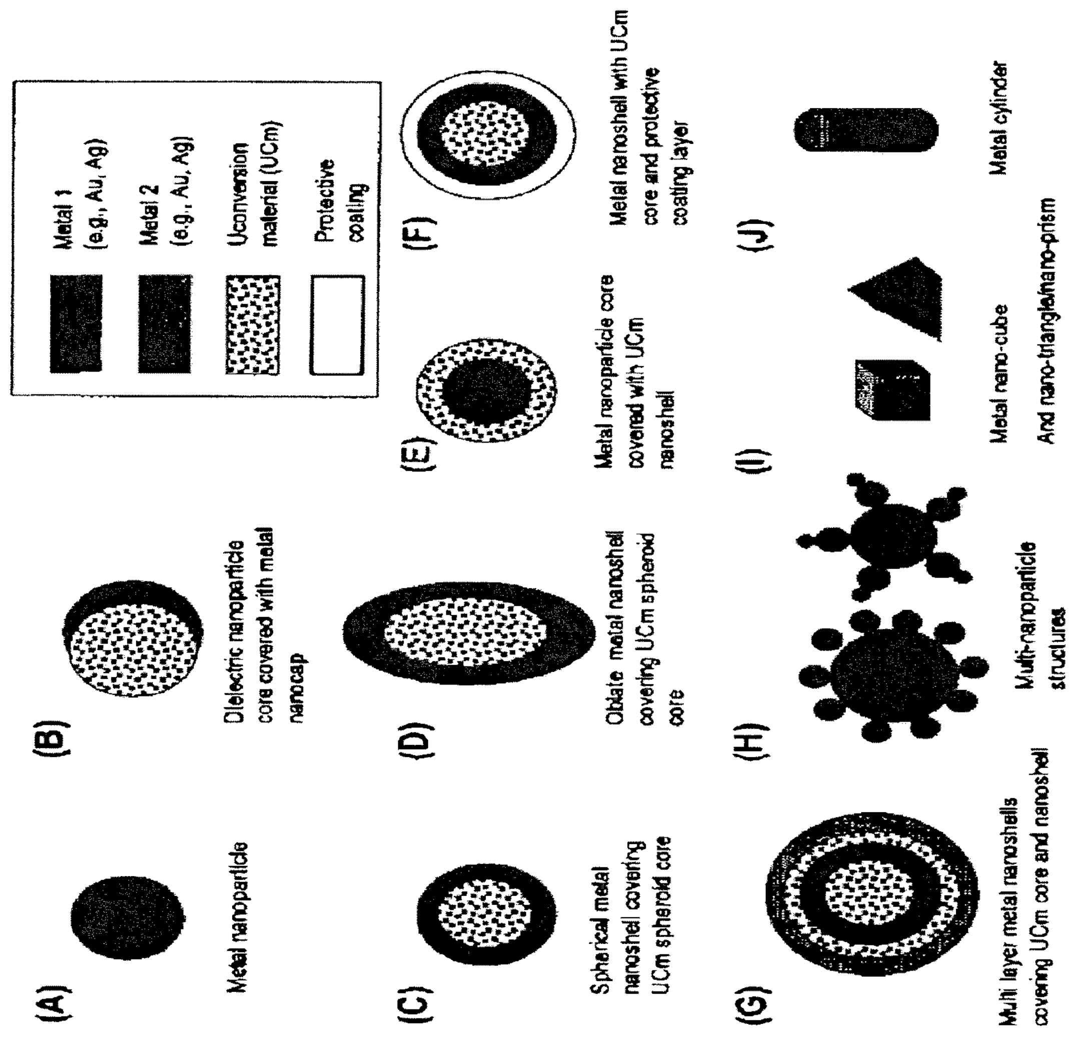
FIG. 41C is a schematic illustration of plasmonics-active upconverter structures of the invention.

FIG. 41C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core. (d) an oblate metal nanoshell covering UC spheroid core, (e) a metal nanoparticle core covered with UC nanoshell, (f) a metal nanoshell with protective coating layer, (g) multi layer metal nanoshells covering an UC spheroid core. (h) multi-nanoparticle structures, (i) a metal nanocube and nanotriangle/nanoprism, and (j) a metal cylinder.

FIG. 41D shows yet other embodiments of plasmonics-active nanostructures having upconverting materials with linked photo-active (PA) molecules that can be designed. For example, the length of the linker between the PA molecule and the UC material or the metal surface is tailored such that it is sufficiently long to allow the PA molecules to be active and short enough to allow efficient excitation of light from the UC to efficiently excite the PA molecules. FIG. 41D shows (a) PA molecules bound to an UC nanoparticle, (b) an UC material-containing a nanoparticle covered with metal nanoparticles, (c) a metal nanoparticle covered with UC material nanocap. (D) an UC material-containing nanoparticle covered with metal nanocap, (e) a metal nanoparticle covered with an UC material nanoshell, (f) an UC material-containing nanoparticle covered with metal nanoshell, (g) an UC material-containing nanoparticle covered with metal nanoshell with protective coating layer.

Gold nanoshells can be prepared using the method described in Hirsch L R, Stafford R J, Bankson J A, Sershen S R. Price R E, Hazle J D. Halas N J, West J L (2003) *Nanoshell-mediated near infrared thermal therapy of tumors under MR Guidance*. Proc Natl Acad Sci 100:13549-13554, the entire contents of which are incorporated herein by reference. This method uses a mechanism involving nucleation and then successive growth of gold nanoparticles around a dielectric core. Gold nanoparticles and the seed can be prepared using the Frens method to grow the gold shell. Dielectric nanoparticles (100 nm or less) used for the core of the nanoshells can then be monodispersed in solution of 1% APTES in EtOH. The gold "seed" colloid can then be synthesized using the Frens method to deposit gold onto the surface of nanoparticles via molecular linkage of silyl terminated, amine groups. The "seed" covers the aminated nanoparticle surface, first as a discontinuous gold metal layer gradually growing forming a continuous gold shell.

In a further embodiment of the invention, the upconverter structures of the invention can be incorporated into a material (e.g., biocompatible polymer) that can form a nanocap onto the metal (gold) nanoparticles. Suitable gel or biocompatible polymers include, but are not limited to poly(esters) covered on polylactide (PLA), polyglycolide (PGA), polycarpolactone (PCL), and their copolymers, as well as poly (hydroxyalkanoate)s of the PHB-PHV class, additional poly (ester)s, natural polymers, particularly, modified poly (saccharide)s, e.g., starch, cellulose, and chitosan, polyethylene oxides, poly(ether)(ester) block copolymers, and ethylene vinyl acetate copolymers.

Neodymium oxide is a dielectric nanostructural material that can also be synthesized by the same polyalcohol method described above with regard to yttrium oxide nanocrystal preparation. Doped neodymium oxide is expected to also show upconversion processes. Neodymium oxide as a host structure possesses lower optical phonon modes than all other oxide covered materials. Lower frequency of phonon may be best suited for electronic transfer between ions. In general, phonon modes are vibrations in a crystal lattice whose frequencies are dependent on the crystal lattice structure and materials. Energy released by upconversion (effectively atomic emission) is transmitted through the photons. With photons, energy can be transferred via Forster, Dexter, or photon capture pathways. Meanwhile, for holes and electrons, charge tunneling is one mechanism for energy transfer. For photons, lower phonon modes typically exhibit less destructive interference, thereby being more suitable for upconverted emission. Accordingly, in one embodiment of the invention, the lower energy phonon modes for neodymium oxide are expected to provide for a stronger electron phonon coupling transfer to occur between the dopants inside of the neodymium oxide. Neodymium oxide has also shown the same low toxic effects as yttrium oxide.

Accordingly, the upconversion emitters of this invention involve a number of configurable structures and materials which will permit their use in a variety of photoelectric conversion applications. Further, many of the dielectric cores described in the invention for up conversion also exhibit down conversion properties.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm), one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)].

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. For glasses with a $Tm^{3+}$ concentration of 0.2 mol % and greater, cross-relaxation processes occur which decrease the up-conversion efficiency. The emission of blue light (while not optimum) can still be used by the photoelectric conversion element of this invention to produce electricity, whereas without up conversion the red or infrared or otherwise below band gap light would lead only to waste heat upon absorption in the photoelectric conversion element.

The emission of visible light upon excitation in the near-infrared (NIR) has been observed in optically clear colloidal solutions of $LuPO_4$:$Yb^{3+}$, $Tm^{3+}$, and $YbPO_4$:$Er^{3+}$ nanocrystals in chloroform. Excitation at 975 nm has been shown by others to produce visible luminescence in the blue, green, or red spectral regions.

Tellurium and germanium oxides (tellurites and germinates) are also suitable upconverters. These glasses can be doped with Tm, Yb, Ho, Er, Pr, for example. $Yb^{3+}$ doped $BaZrO_3$ is also suitable for upconversion. $Er^{3+}$ and/or $Tm^{3+}$ doping is also suitable for tailoring the emission wavelengths.

In another embodiment, $Nd^{3+}$:$Cs_2NaGdCl_6$ and $Nd^{3+}$, $Yb^{3+}$:$Cs_2NaGdCl_6$ polycrystalline powder samples have been reported to be up converters and are suitable for this invention. These materials, under 785 nm irradiation, have shown upconversion emissions near 538 nm (Green), 603 nm (Orange), and 675 nm (Red) were observed and assigned to 4G7/2-4I9/2, (4G7/2-4I11/2; 4G5/2-+4I9/2), and (4G7/2-+4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for this invention. Among the up-conversion luminescences for the $ZrF_4$ fluoride glasses, the green emission was seen to be extremely strong, and the blue and red emission intensities were very weak.

In another embodiment, $Tm^{3+}$/$Yb^{3+}$-codoped $TeO_2$—$Ga_2O_3$—$R_2O$ (R═Li, Na, K) glasses have been reported to be up converters and are suitable for this invention. These materials, under excitation at 977 nm, showed intense blue upconversion emission centered at 476 nm along with a weak red emission at 650 nm. Once again, the emission of blue light (while not optimum) can still be used by the photoelectric conversion element of this invention to produce electricity, whereas without up conversion the red or infrared or otherwise below band gap light would lead only to waste heat upon absorption in the photoelectric conversion element.

In another embodiment, metal-to-ligand charge transfer (MLCT) transition in $[Ru(dmb)_3]^{2+}$ (dmb=4,4'-dimethyl-2,2'-bipyridine) in the presence of anthracene or 9,10-diphenylanthracene have been reported to be up converters and are suitable for this invention. Upconverted singlet fluorescence resulting from triplet-triplet annihilation at low excitation power has been reported. In particular, 9,10-diphenylanthracene (DPA) (substituted for anthracene) showed higher efficiencies for upconversion.

Other Converter Structures:

This invention in various embodiments uses a wide variety of up and/or down conversion materials (or mixtures of up and down converters) to produce a particular wavelength or a spectrum of light which is well suited for electricity generation from one or photoelectric conversion elements optically coupled to the conversion film 20. In various embodiments, the mixtures of up and down converters can include a first plurality of particles which upon radiation from a radiant source at a first radiation energy radiate at a higher energy than the first radiation energy. In various embodiments, the mixtures of up and down converters can include a second plurality of particles which upon radiation from the radiant source at a second radiation energy radiate at a lower energy than the second radiation energy.

Moreover, the first and second radiation energies need not be (but can be) the same wavelength of energy. In the case of different wavelengths for the first and second radiation energies, the power conversion devices can include tandem conversion devices with respective ones of the conversion devices designed to produce electricity from the different wavelengths.

Hence, the present invention in one embodiment provides a conversion system for producing light of an energy more readily converted by conversion element 10. The system includes one or more nanoparticles configured, upon exposure to a first wavelength $\lambda_1$ of radiation, to generate a second wavelength $\lambda_2$ of radiation having a, higher or lower energy than the first wavelength $\lambda_1$. The system includes a metallic shell encapsulating at least a fraction of the nanoparticles. In one embodiment of the invention, a radial dimension of the metallic shell is set to a value where a surface plasmon resonance in the metallic shell resonates at a frequency which provides spectral overlap with either the first wavelength $\lambda_1$ or the second wavelength $\lambda_2$.

In another embodiment, the present invention provides a nanoparticle structure including a sub 10 nm dielectric core and a metallic shell encapsulating at least a fraction of the nanoparticle. The dielectric core includes at least one of $Y_2O_3$, $NaYF_4$, YAG, YAP, or $Nd_2O_3$. Such nanoparticle structures can exhibit in certain embodiments surface plasmon resonance in the metallic shell to enhance upconversion of light from a first wavelength $\lambda_1$ to a second wavelength $\lambda_2$.

As described above, shell is in particular designed with a layer thickness to enhance the photon upconversion process through plasmonic enhancement. The thickness of the shell is "tuned" in its thickness to the absorption process by having a dimension in which plasmons (i.e., electrons oscillations) in shell have a resonance in frequency which provides spectral overlap with the absorption band of the incident light targeted. Thus, if the upconversion is to be stimulated by NIR light such as for example centered around 1000 nm NIR light, then the thickness of the shell is "tuned" in a thickness to where a plasmon resonance resonates at a frequency also of 1000 nm (or in the neighborhood thereof as plasmon resonances are typically broad at these wavelengths).

Such a plasmon resonating shell can be made of numerous transition metals, including though not limited to gold, silver, platinum, palladium, nickel, ruthenium, rhenium, copper, and cobalt. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.) FIG. 7A-1 is reproduced from Jain et al and illustrates the capability in the present invention to "tune" the metal shell to have a spectral overlap with the excitation and/or emission radiation wavelengths. This capability of matching or tuning of the frequencies provides an enhancement of the absorption which would not be present with a dielectric core alone.

In one embodiment of this invention, the thickness of the metal shell is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall conversion process.

Additionally, plasmon-phonon coupling may be used to reduce a resonance frequency through the tuning of the bands to a degree off resonance. This may be useful in optimizing resonance energy transfer processes for the purpose of coupling the core-shell nanoparticles to sensitive chromophores or drug targets. Accordingly, when a recipient is outside of the shell, the recipient will receive enhanced light X by the above-described plasmonic effect than would occur if the shell were absent from the structure.

Accordingly, with the upconverter or down converter structures of this invention, a plasmonics effect is advantageous. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively. The converter structures of this invention include in various embodiments nanoparticles of neodymium and ytterbium doped yttrium oxide, europium and ytterbium doped yttrium oxide, and any combination of rare earth trivalent ions doped into a neodymium oxide nanocrystal. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale There are a number of advantages offered by these yttrium oxide nanostructures of the invention. The small scale synthetic methodology for creating nanoscale yttrium oxide is easier to control and produce in yttrium oxide than in YAG.

In one embodiment of this invention, a dual dopant permits excitation of either ion in the host glass. For instance, excitation by 980 nm light excites a ytterbium ion, where through transfer of energy from one excited state of the ytterbium ion to another dopant provides a mechanism for upconversion emission of light in the visible spectral region.

Accordingly, this invention can use a wide variety of up conversion and down conversion materials and alternatively mixtures of different up conversion materials and/or mixtures of different down conversion materials. These conversion materials can include quantum dots, semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties.

Indeed, in one example, for power conversion, the energy source need not be the Sun. The energy source can be from a radiation source such as a Cobalt 60 source whose gamma radiation is converted to visible light for photoelectric conversion. Other sources include a Cesium-137 source, an Iridium-192 source, a Krypton-85 source, a Radium-226 source, and a Strontium-90 source. Further, as noted above, the high energy radiation source may come from an active nuclear core generating power in an electric plant.

Indeed, in another example, for power conversion, the energy source can be from a radiation source such as a waste heat source from a combustion process whose infrared radiation is to be converted to visible light for photoelectric conversion. Presently, many conventional steam plants driving electric generators use combustion burners to provide the energy to convert water into steam. Infrared radiation from these sources generally is wasted into the environment where air conditioning or other means to moderate the temperature have to be used. With the present invention, a part of the radiated heat would be captured, converted to visible-type light and the converted to electric power.

Thus, the first problem encountered in solar cell conversion is that the Sun is a broad spectrum source while the basic semiconductor p-n junction is a device where there is an optimum energy (i.e., the semiconductor band gap) for the generation of an electron-hole pair. This presents a power matching problem, where a large part of the solar spectral is not converted into electric power. Higher energy light above the band gap makes an electron hole pair, but the excess energy is converted into heat. Lower energy light below the band gap is not converted and only results in heating of the solar cell conversion material. Moreover, the heat generated reduces the efficiency of the solar cell. Especially, in approaches where the sun light is being concentrated or there is no ready way to cool the solar cell assemblies, reduced efficiency due to waste heat affects solar cell performance.

As shown above, for a silicon solar cell assembly, the maximum sensitivity because the energy band structure of the monocrystalline silicon is at or near the bandgap Eg of 1.21 ev, which corresponds to the wavelength of $\lambda$=950 nm. On the other hand, the silicon solar cell assembly is virtually non-responsive to the ultraviolet ($\lambda$<400 nm), i.e. silicon cannot efficiently convert this ultraviolet light.

As noted above, Naum et al in U.S. Pat. Appl. Publ. No. 2009/0156786 describe a transparent light conversion film including phosphor materials added to increase the overall efficiency of converting the incident solar light into electricity. Specifically, Naum et al focused on the problem that, when the sunlight reaches the earth, about 6~8% of the energy is ultraviolet. The energy carried by ultraviolet cannot be absorbed by a solar cell to generate electric energy. Moreover, this energy degrades and heats up the solar cell assembly, resulting in damaging the assembly and lowering its efficiency. Naum et al used a transparent phosphor powder which absorbed the ultraviolet in the wavelength $\lambda<400$ nm and re-radiated red light in the wavelength range $\lambda=500$~780 nm, thereby generating extra electricity and enhancing the conversion efficiency of the solar cell assembly. Naum et al thus used a singular type down conversion phosphor in their process to convert higher energy light to a lower energy light that was closer to that which the crystalline silicon cell would optimally convert.

Yet, in one embodiment of this invention, nanotechnology engineering can permit a wide degree of engineering to permit nanostructures to be fabricated into sophisticated optical components whose optical transfer function can be tailored to more closely match the optical input needed by the underlying photoelectric conversion element.

In one embodiment of this invention, conversion materials and/or mixtures of these conversion materials are applied to solar cells included in solar concentrator units where for example 1000 sun intensities are present. In one embodiment of the invention, these conversion materials and/or mixtures of these conversion materials include up converters which do not require as high a power flux in order to exhibit up conversion. These more efficient conversion materials can also be applied to solar cells, and may or may not be included in solar concentrator units. Regardless of approach, another level of solar cell efficiency increase can be expected when the IR and/or NIR part and/or visible part of the solar light is converted to a light more optimized to the fundamental energy of the solar cell converter itself (i.e., to more closely match the optical input needed by the underlying photoelectric conversion element).

In one embodiment of this invention, a light conversion device such conversion film 20 has first converters configured to emit, upon exposure to an energy source, light at a first wavelength in response to absorption of energy across a first band of wavelengths, and has second converters configured to emit, upon exposure to the energy source, light at a second wavelength in response to absorption of energy across a second band of wavelengths.

In this embodiment, a power conversion device such as conversion element 10 is a conversion device designed with an optimum excitation wavelength, and the first wavelength and the second wavelength (generated by the first and second converters) are matched to the optimum excitation wavelength. By matching, the light generated by the first and second converters is within +/−20%, and more preferably +/−10%, and more preferably +/−5%, and more preferably +/−2%, and more preferably +/−1% of the optimum excitation wavelength.

In another embodiment of this invention, a light conversion device such conversion film 20 has first converters configured to emit, upon exposure to an energy source, light at a first wavelength in response to absorption of energy across a first band of wavelengths, and has second converters configured to emit, upon exposure to the energy source, light at a second wavelength in response to absorption of energy across a second band of wavelengths.

In this embodiment, a power conversion device such as conversion element 10 comprises plural conversion devices designed with respective optimum excitation wavelengths; and the first wavelength and the second wavelength are matched to the respective optimum excitation wavelengths. By matching, the light generated by the first and second converters is within +/−20%, and more preferably +/−10%, and more preferably +/−5%, and more preferably +/−2%, and more preferably +/−1% of a respective one of the optimum excitation wavelengths.

Moreover, the ability to form nanostructures of different elemental doped crystals and the ability to form controlled shells of metallic, semiconductive, and insulating materials on conversion materials provide other solar converter designs for the invention. As the nanostructures technology have developed, plasmonic shells (e.g., Au shells) have been shown to enhance optical absorption and emission and to further tailor the optical properties.

Electrons in semiconductor quantum dots tend to make transitions near the edges of the bandgap. With quantum dots, the size of the bandgap is controlled simply by adjusting the size of the dot. Because the emission frequency of a dot is dependent on the bandgap, it is therefore possible to control the output wavelength of a dot with extreme precision. In effect, it is possible to tune the bandgap of a dot, and therefore specify its "color" output.

Accordingly, in one embodiment of the invention, a composite of different size quantum dot emitters (or a composite of different down converter materials including materials better suited than quantum dots to convert ultraviolet light to more closely match the optical input needed by the underlying photoelectric conversion element) would provide another possible way to further alter the optical transfer function of a nanostructure optical component to permit a better solar match to the underlying photo-electric conversion device.

Thus, according to the invention, the advances in nanotechnology now permit nanostructure-covered optical components to have an optical transfer function which is not merely a property of the real and imaginary index of refraction components of the nanostructures, but which also is a product of the luminescent properties of the nanostructures, whose type, size, shell structure, and mix represent engineering parameters for more closely "matching" the solar spectrum to the photo-electric conversion device. This engineering capability offers the possibility to engineer an optical transfer function of a solar converter plate to more selectively transform the broad solar spectrum into energies at or near the band gap of the photoelectric element. These improvements will apply whether or not these nanostructured covered optical components are in front of an amorphous Si solar cell on a stainless steel sheet for a roof top installation, in front of a single crystal GaAs concentrator cell exposed to 1000 suns, or in front of a remote terrestrial or outer space solar cell.

As described above, a shell (or other structure) in one embodiment of this invention can be designed with a layer thickness to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by NIR or IR light, then the thickness of the shell is "tuned" in a thickness to where a plasmon resonance resonates at these NIR or IR wavelengths.

In one embodiment of this invention, the metallic structures can be an alloy such as for example a Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance In one embodiment of the invention, the metallic structures can be an alloy such as for example a Pt:Au alloy. The alloy content can be set to adjust the frequency of the surface plasmon resonance.

In one embodiment of the invention, the nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a predetermined surface plasmon resonance. In one embodiment of the invention, the zinc sulfide and cadmium sulfide nanoparticle alloy can have an alloy content is set to provide a predetermined surface plasmon resonance. Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of this invention, the nanoparticle can be a dielectric or semiconductor configured to generate an up converted or down converted wavelength $\lambda_2$. In one embodiment of the invention, the nanoparticle can include multiple dielectrics or semiconductors respectively configured to emit at different wavelengths for $\lambda_2$, which for example might correspond to respective cells in a cascade or tandem solar cell structure. In one embodiment of this invention, multiple nanoparticles having different dielectrics or semiconductors can be included in a mixture of the nanoparticles dispersed in the medium.

In one embodiment of this invention, the thickness of the metal shell is set depending on the absorption frequency (or in some cases the emission frequency) of the particular dopant ions in the dielectric core to enhance the total efficiency of the emission process of the down converted or upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Additionally, plasmon-phonon coupling may be used to reduce a resonance frequency through the tuning of the bands to a degree off resonance.

The plasmonic properties of various metallic structures, which have been investigated in the art and are suitable for this invention, include metallic nanoshells of spheroidal shapes [S. J. Norton and T. Vo-Dinh, "*Plasmonic Resonances of Nanoshells of Spheroidal Shape", IEEE Trans. Nanotechnology,* 6, 627-638 (2007)], oblate metal nanospheres [S. J. Norton, T. Vo-Dinh, "*Spectral bounds on plasmon resonances for Ag and Au prolate and oblate nanospheroids", J. Nanophotonics,* 2, 029501 (2008)], linear chains of metal nanospheres [S. J. Norton and T. Vo-Dinh, "*Optical response of linear chains of metal nanospheres and nanospheroids", J. Opt. Soc. Amer.,* 25, 2767 (2008)], gold nanostars [C. G. Khoury and T Vo-Dinh, "*Gold Nanostars for Surface-Enhanced Raman Scattering: Synthesis, Characterization and Applications", J. Phys. Chem C.* 112, 18849-18859 (2008)], nanoshell dimmers [C. G. Khoury. S. J. Norton. T. Vo-Dinh, "*Plasmonics of 3-D Nanoshell Dimers Using Multipole Expansion and Finite Element Method, ACS Nano.* 3, 2776-2788 (2009)], and multi-layer metallic nanoshells [S. J. Norton, T. Vo-Dinh, "*Plasmonics enhancement of a luminescent or Raman-active layer in a multilayered metallic nanoshell". Applied Optics.* 48, 5040-5049 (2009)]. The entire contents of each of the above noted references in this paragraph are incorporated herein by reference. In various embodiments of this invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$ This feature also can be used in the down converting to enhance primarily the emission at wavelength $\lambda_2$ and potentially the excitation at wavelength $\lambda_1$.

Such metallic structures in various embodiments of this invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

In one embodiment, a mixture of converters can include a first material configured to emit a first wavelength in response to absorption of ultraviolet light and a second material configured to emit a second wavelength in response to absorption of near infrared or infrared light. The second wavelength can be substantially the same color as the first wavelength. The mixture of converters can include a third material configured to emit a third wavelength in response to absorption of the ultraviolet light. The third wavelength can be different from the first wavelength and the second wavelength or the same color as the first wavelength and the second wavelength. Alternatively or in addition, the mixture of converters can include a third material configured to emit a third wavelength in response to absorption of the infrared light. The third wavelength can be different from the first wavelength and the second wavelength or the same color as the first wavelength and the second wavelength.

The converters can be a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof. The dielectric up converter can have a particle diameter ranging from at least one of 2-1000 nm. 2-100 nm, 2-50 nm, 2-20 nm, or 2-10 nm. The dielectric up converter can include a dopant of at least one of Er, Eu, Yb, Tm, Nd, Tb, Ce, Y, U, Pr, La, Gd and other rare-earth species or a combination thereof. The dopant can have a concentration of 0.01%-50% by mol concentration. A metallic structure can be disposed in relation to the dielectric up converter, and the metallic structure includes at least one of Au, Ag, Cu, Ni, Pt, Pd, Co, Ru, Rh, Al, Ga, or a combination of alloys or layers thereof. The metallic structure can be a metallic shell including at least one of a spherical shell, an oblate shell, a crescent shell, or a multilayer shell. The dielectric up converter can be configured to exhibit visible emission upon interaction with NIR light.

Solar Cell and Power Converters:

Using up converters and down converters to capture more sun energy in this invention make use of the intensity and efficacy with which ultra-nano particles in the configurations shown above perform conversion.

In one embodiment of the invention, ultra-nano-materials (e.g., below 10 nm) can be phosphorescent or fluorescent and are able to take portions of the sun's spectral output and match it with a photovoltaic PV cell input without scattering and shadowing effects. Significant down conversion efficiencies from UV to green light can be achieved and the ultra-nano-materials can be tunable through the proper doping to other wavelength outputs. This breakthrough is significant and is backward compatible and adaptable to various PV installed panels of different technologies including crystalline silicon, polycrystalline silicon, amorphous silicon single junction (aSi (1×)), amorphous silicon tandum junction (aSi (2×)), amorphous silicon triple junction (aSi (3×)). CdTe and CIGS cells.

These nano converters can be surface treated to both tune and further intensify light outputs Phosphorescent and fluorescent ultra-nano-materials that are surface treated (or coated as discussed in detail above) add another degree of control over both color and intensity.

The conversion modules of the invention including the phosphorescent and fluorescent ultra-nano-materials described herein are applicable to multiple entry points across a spectrum of potential end users. Specifically, these conversion modules are applicable to residential, commercial and solar farms.

Moreover, these conversion modules have utility in hybrid lighting applications for residential and commercial users. Natural sunlight along with the traditional electric lighting can be converted to brighter light for interior spaces or light more suited to the human eye perception. In one embodiment, a fiber bundle with nano particles at their input can be used to concentrate the sunlight spectrum into a spectrum of energy more suited for white light illumination, to thereby enhance interior lighting.

Figure 42A:
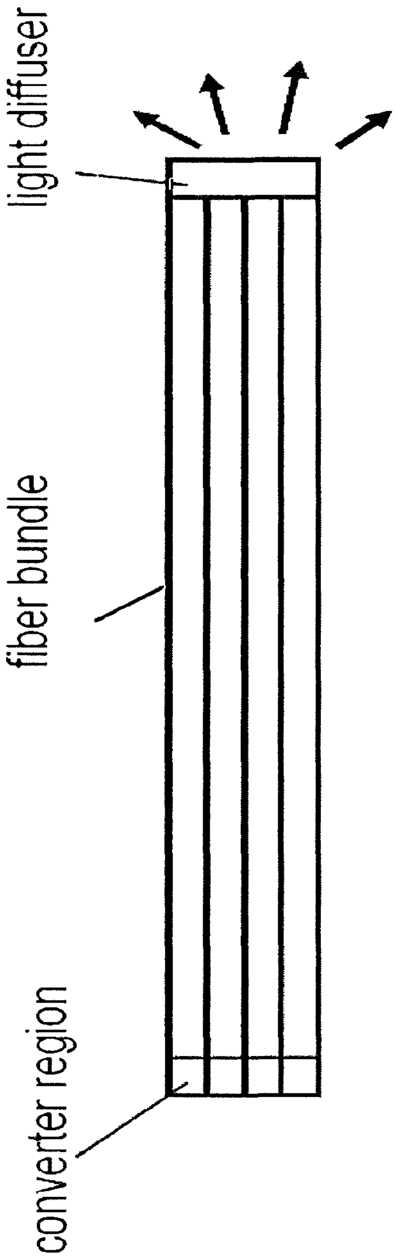
FIG. 42A is a schematic illustration of a fiber bundle of the invention showing an input converter section including the converters of the invention.

FIG. 42A is a schematic illustration of a fiber bundle of the invention showing an input converter section including the converters of the invention. In one embodiment, the optical fibers are routed into an interior space (which may or may not be close to windows). In one embodiment, these fiber bundles can be coupled with rods or flat screen to diffuse the light for illumination of the interior space.

In one aspect of this invention, the fiber bundles of the invention provide for a nominally heat free light source, as compared to directed "pure" sun light into a building where significant amounts of infrared light is transmitted with the visible. In this aspect, the fiber bundles of the invention provide for a significant energy savings against air conditioning cost. The light sources in one embodiment of the invention have boosted light intensity outputs by virtue of the plasmonic effects discussed above, and can be made available at the workplace as well as residential areas. This would help alleviate the net cost of electricity. The light inside the interior spaces carried in by the fiber bundles of the invention, m one embodiment, can be regulated and modulated, using simple controllers.

Figure 42B:
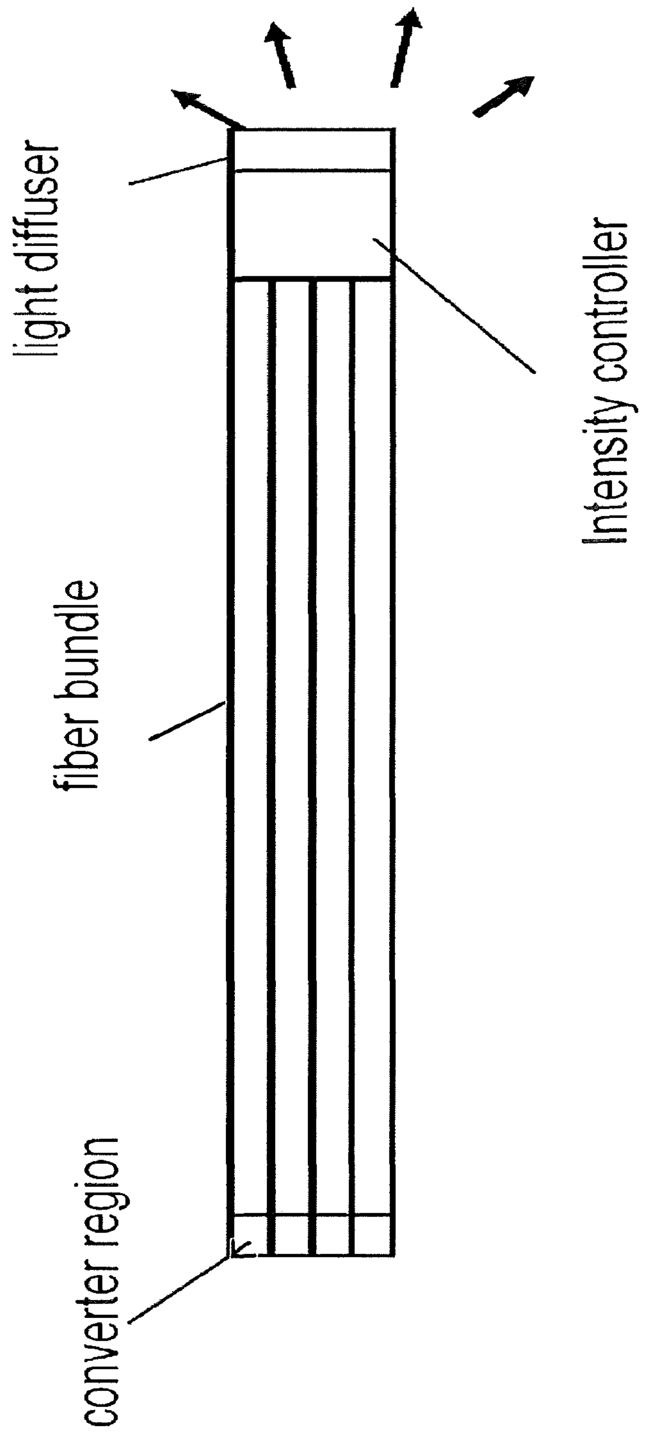
FIG. 42B is a schematic illustration of a fiber bundle of the invention showing a controller to stabilize light emission.

FIG. 42B is a schematic illustration of a fiber bundle of the invention showing a controller to stabilize light emission. In this embodiment, the controller can lower the intensity transmitted into the interior space so that the combined light source and fiber bundle have a stable output in a work place or so that the lighting level can be dimmed if needed.

In one embodiment of the invention, solar panels (e.g. on a roof top) can be made to combine electricity generation and fiber light bundling functions so that, in one embodiment, a fully integrated panel can be produced (including a power converter and a light converter).

Figure 42C:
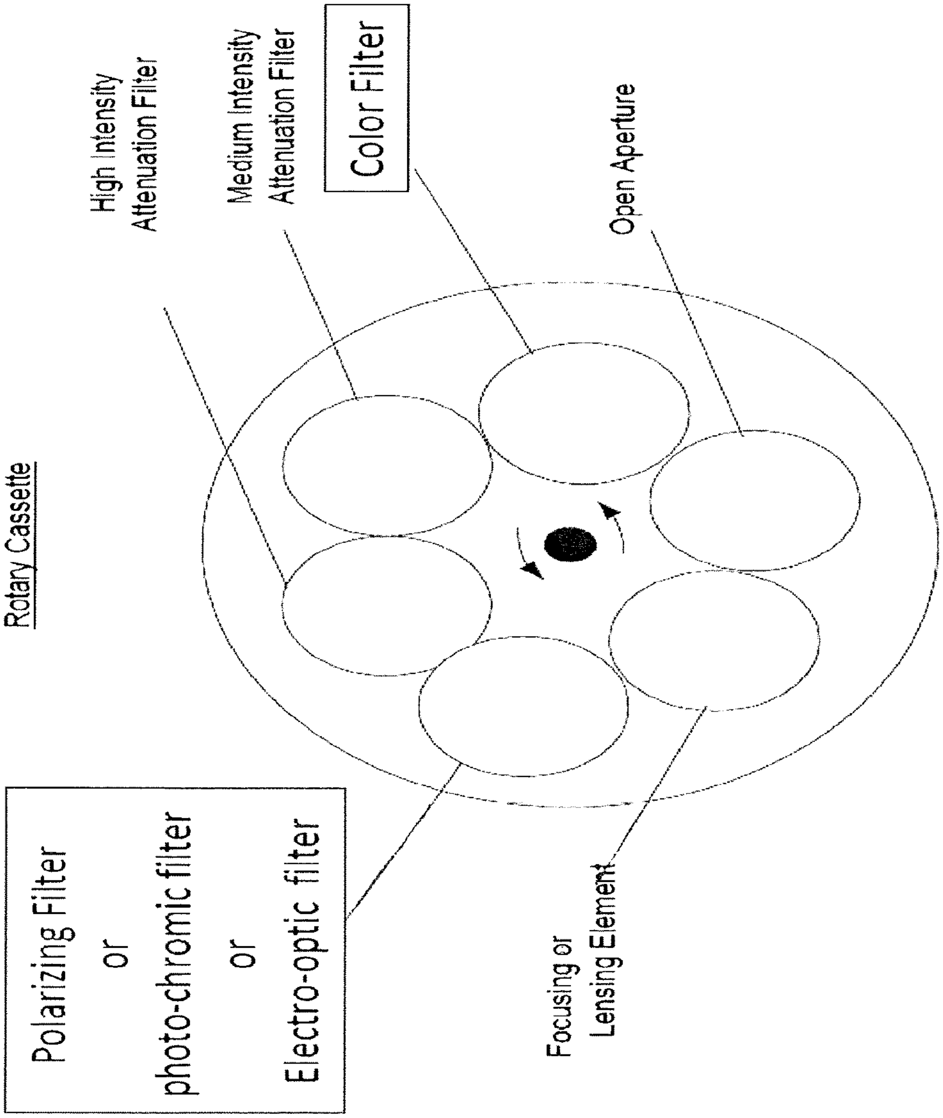
FIG. 42C is a schematic illustration showing a top view of a rotary cassette placed proximate to a solar panel level where light is transferred to a fiber bundle of the invention.

FIG. 42C is a schematic illustration of another embodiment where a light control mechanism, including for example a rotary cassette, is placed proximate to a solar panel level and includes multiple apertures for modifying light entering a fiber bundle.

Figure 42D:
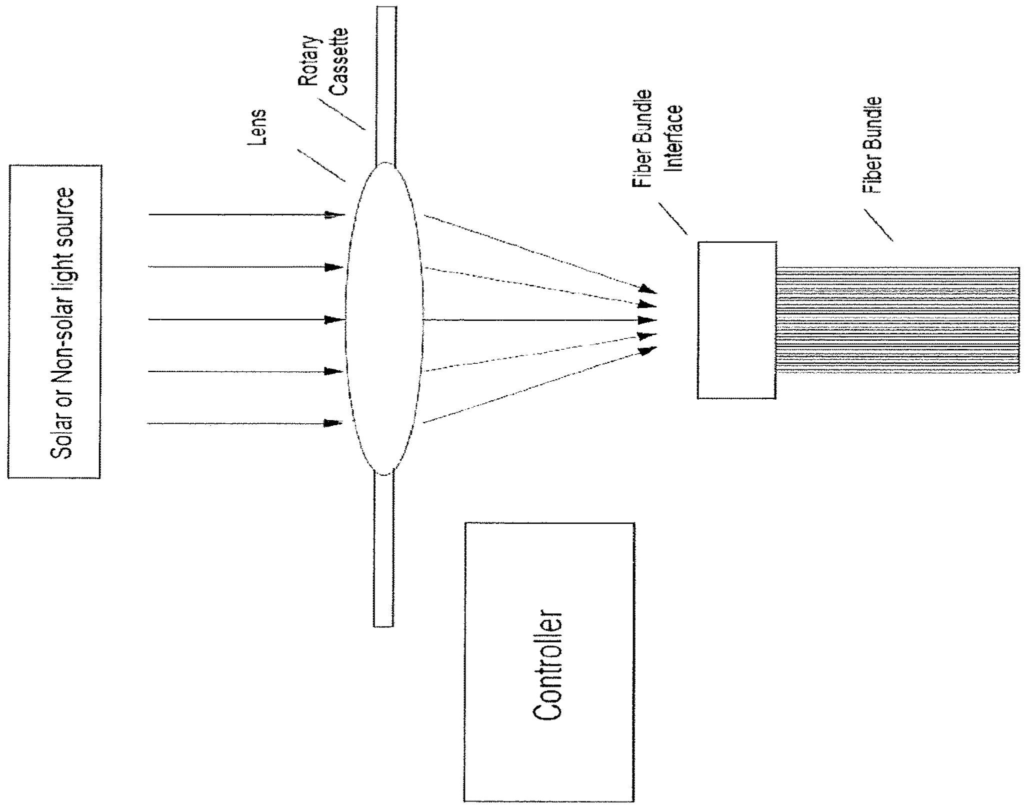
FIG. 42D is a schematic illustration showing a side view of the rotary cassette of FIG. 42C.

FIG. 42D is a schematic illustration showing a side view of the rotary cassette of FIG. 42C. In one embodiment, a controller may control the elements of the rotary cassette described below.

In one embodiment, the light control mechanism of FIGS. 42C and 42D is placed at the power converter or solar panel level In one embodiment, the rotary cassette has multiple apertures, although a single aperture and an optical light block could be used Each aperture modifies light in color, intensity, or path in order to direct altered or unaltered light into the fiber bundle. In one embodiment, one aperture in the rotary cassette is left unpopulated to have no influence of sun light prior to entering the fiber bundle. In one embodiment, the intensity can be modulated up and down by using a lens in one case and an attenuation filter in another case. In one embodiment, a color feeding the fiber bundle can be changed by a color filter. In one embodiment, a photo-chromic filter can be added to change and modulate light. In one embodiment, an electro-optic filter can be added to change the attenuation or the polarization of the light. In one embodiment, the electro-optic filter can be triggered by a switch connected to a circuit electrically connected to the electro-optic material.

The rotary cassette is but one mechanism of altering the light characteristics. Altering of the light characteristics can be controllable, in one embodiment, through a programmable interface accessible by an end user. In turn, in one embodiment, the control interface can be in communication with a wireless network. Remote control and light alteration are therefore made possible.

While described with respect to the control of solar light distribution, in one embodiment, the light control mechanism of FIGS. 42C and 42D can be used to distribute light from non-solar light sources, such as for example, a centralized bank of halogen lamps, arc-lamps, or LED light sources.

Figure 42E:
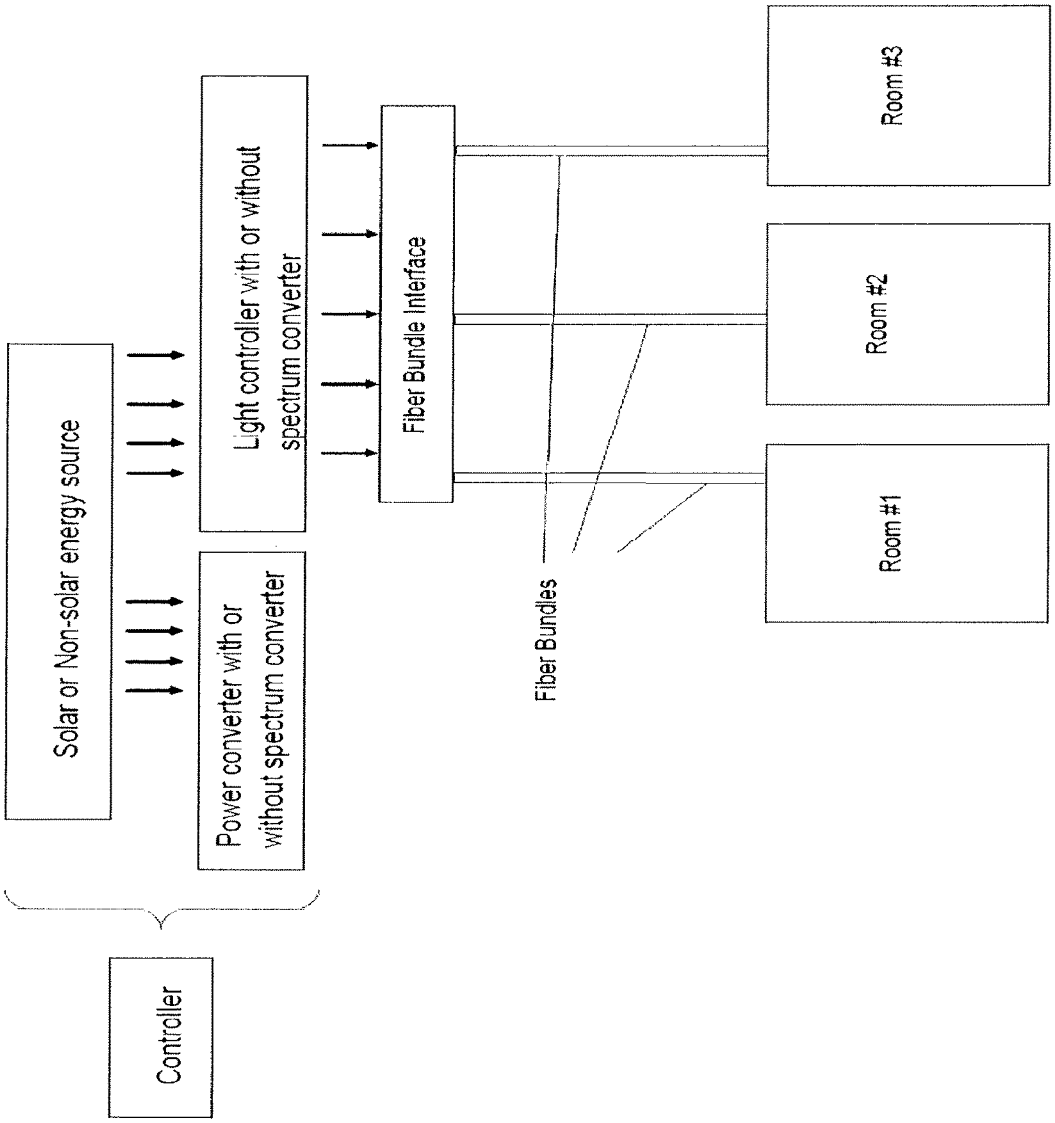
FIG. 42E is a schematic illustration of a system for lighting distribution from solar or non-solar light sources.

FIG. 42E is a schematic illustration of a system for lighting distribution from solar or non-solar energy sources. FIG. 42E shows that light or radiation from a solar or non-solar energy source can also be directed to a power converter (e.g., a solar cell or solar cell array).

As shown in FIG. 42E, light or radiation from a solar or non-solar energy source is directed to a light controller with or without a converter. The light controller/converter in one embodiment can include the above-described light control mechanism. The light controller/converter in one embodiment can include a spectrum or color converter (e.g., using the up and/or down converters of this invention described above). Light from the light controller/converter is directed to a fiber bundle interface and then distributed to various "rooms" as shown. Here, the use of the word "rooms" designates some lighted compartment or area lighted separately or in one embodiment lighted from multiple ones of the fiber bundles. A controller as shown can be used to control for example the power to the non-solar light source and/or to control a rotary cassette included in the In another embodiment, a fiber bundle would interface with the Sun in its inputs and yield e.g. green light in its output (for aesthetic viewing purposes). The various fibers can then be optically coupled to a glass screen (covering up to the size of a wall) to diffuse green light over the entire wall. Similarly, another fiber bundle doped with fluorescent nano-materials in their input can be built and directed to the same or different wall.

The aesthetic lighting is an attractive, value adding attribute for both residential and commercial properties. Moreover, with the combined embodiment shown above, the cost of panel installation will be amortized by these two independent uses.

The introduction of renewable and environmentally friendly sources of energy hinges, among others, on their cost and reliability in comparison to standard energy sources. Competition over the next 15 years is with traditional means of electricity generation (i.e. coal, natural gas, nuclear). Furthermore, the cost of solar energy/PV will be compared to other renewable form of energy including wind, geothermal, hydroelectric and tide and ocean current.

Ultimately, the cost of electricity (i.e.; $/kWh) is the final metric with which to gauge the competitiveness of solar PV technologies.

The PV market itself fragments into various technologies that are briefly highlighted in the current document. All of these leading PV candidates have two common areas for improvement: light trapping and the potential to convert more of the available sunlight spectrum into useable electricity.

The nano particles and materials discussed above are expected to convert UVA (close 10 to 7%) of the sun output into useable energy at the Si-junction level.

The PV market is also impacted but the competitive offering of the existing technologies with emphasis on. (1) module cost per watt. (2) system cost per watt profiles (which factors in the maintenance in the field) and (3) the levelized cost of electricity (LCOE) compared to grid pricing. Crystalline silicon is the dominant technology; however, amorphous silicon offers much better scalability potential over time Thin film technologies include (1) single junction amorphous silicon (a-Si 1×) on glass (2) dual junction amorphous silicon (a-Si 2×) on glass, (3) triple junction amorphous silicon (a-Si 3×) on a flexible stainless steel substrate, (4) cadmium telluride (CdTe) on glass, (5) copper indium gallium selenium (CIGS) on glass, and (6) CIGS on a flexible stainless steel substrate. A summary of the cost per watt per module time over time for the various PV technologies is provided in the Table of FIG. 43.

The nano particles and materials discussed above are expected to boost the efficiency of the PV technologies by 5% to 9% depending whether both up and down conversion are used.

To understand better the efficacy of the nano particles and materials discussed above to boost the efficiency of the PV technologies, remember that the Sun is a broad spectrum source while the basic semiconductor p-n junction is a device where there is an optimum energy (i.e., the semiconductor band gap) for the generation of an electron-hole pair. This presents a power matching problem, where a large part of the solar spectral is not converted into electric power. Higher energy light above the band gap makes an electron hole pair, but the excess energy is converted into heat. Lower energy light below the band gap is not converted and only results in heating of the solar cell conversion material. Moreover, the heat generated reduces the efficiency of the solar cell. Especially, in approaches where the sun light is being concentrated or there is no ready way to cool the solar cell assemblies, reduced efficiency due to waste heat effects solar cell performance.

As discussed above, advances in nanotechnology now permit nanostructures to be fabricated into sophisticated optical components whose optical transfer function can be tailored to more closely match the optical input needed by the underlying photoelectric conversion element. Moreover, the ability to form nanostructures of different elemental doped crystals and the ability to form controlled shells of metallic, semiconductive, and insulating materials on conversion materials (as detailed above) provides opportunities for solar converter improvement, including but not limited to the plasmonic shells and effects discussed above. The plasmonic effect offers the capability of matching or tuning a specific particle emitter to provide an enhancement of the absorption (and/or the emission) properties of conversion materials which would not be present without the plasmonic shell structure.

Thus, in short, the advances in nanotechnology now permit nanostructure-based optical components to have an optical transfer function which is not merely a property of the real and imaginary index of refraction components of the nanostructures, but which also is a product of the luminescent properties of the nanostructures, whose type, size, shell structure, and mix represent engineering parameters for more closely "matching" the solar spectrum to the photoelectric conversion device. This engineering capability offers the possibility to alter the optical transfer function of a solar converter plate to more selectively transform the broad solar spectrum into energies (e.g., a spectrum of energies) at or near the band gap of the photoelectric element. These improvements of the invention will apply whether or not these nanostructured based optical components of the invention are in front of an amorphous Si solar cell on a stainless steel sheet for a roof top installation, or in front of a single crystal GaAs concentrator cell exposed to 1000 suns, or in front of a remote terrestrial or outer space solar cell.

Energy Augmentators

In solar cell applications of this invention, any of the energy augmentators described in the section entitled "A. ENERGY AUGMENTATORS" can be used. Below is a more detailed discussion of specific augmentators that can be used for solar cell applications and that can be used with the embodiments described above in FIGS. 33-34, and the embodiments described below.

As noted above, in the field of solar cells, the addition of plasmonics, photonics band gap, and up and down conversion is known in the literature. Additionally, antireflection coatings and concentrators are well known in the literature. The problem with the plasmonics effect is that, as noted above, the plasmons and the electric field enhancement decays rapidly with distance away from the metal structure meaning that the effect is only useful for a small volume of interaction. The problem with antireflection coatings is that, although sun light is not scattered away as much as if there were no coatings, the light transmitted is still predominantly that of wavelengths that are not optimum for power generation. The problem with concentrators is that, besides concentrating light which can be converted to power, a concentrator also concentrates light which does not generate power, which in general makes for waste heat. While photonic band gap structures can serve to reflect or confine light, they have no effective way to gain power from the discarded light.

Accordingly, one problem encountered in solar cell conversion is that the Sun is a broad spectrum source while the basic semiconductor p-n junction is a device where there is an optimum energy (i.e., the semiconductor band gap) for the generation of an electron-hole pair. This presents an energy matching problem, where a large part of the solar spectral is not converted into electric power. Higher energy light above the band gap makes an electron hole pair, but the excess energy is converted into heat. Lower energy light below the band gap is not converted and only results in heating of the solar cell conversion material. Moreover, the heat generated reduces the efficiency of the solar cell. Especially, in approaches where the sun light is being concentrated or there is no ready way to cool the solar cell assemblies, reduced efficiency due to waste heat affects solar cell performance.

For a silicon solar cell assembly, the maximum sensitivity because the energy band structure of the monocrystalline silicon is at or near the bandgap Eg of 1.21 ev, which corresponds to the wavelength of $\lambda$=950 nm. On the other hand, the silicon solar cell assembly is virtually non-responsive to the ultraviolet ($\lambda$<400 nm), i.e. silicon cannot efficiently convert this ultraviolet light.

Yet, in one embodiment of this invention, nanotechnology engineering can permit a wide degree of engineering to permit energy augmentation structures to be fabricated into sophisticated optical components whose optical transfer function can be tailored to more closely match the optical input needed by the underlying photoelectric conversion element.

In another power conversion application, the energy source need not be the Sun. The energy source can be from a radiation source such as a Cobalt 60 source whose gamma radiation is converted to visible light for photoelectric conversion. Other sources include a Cesium-137 source, an Iridium-192 source, a Krypton-85 source, a Radium-226 source, and a Strontium-90 source. Further, as noted above, the high energy radiation source may come from an active nuclear core generating power in an electric plant.

In another power conversion application, the energy source can be from a radiation source such as a waste heat source from a combustion process whose infrared radiation is to be converted to visible light for photoelectric conversion. Presently, many conventional steam plants driving electric generators use combustion burners to provide the energy to convert water into steam. Infrared radiation from these sources generally is wasted into the environment where air conditioning or other means to moderate the temperature have to be used. With the present invention, a part of the radiated heat would be captured and used to produce electric power.

Figure 44A:
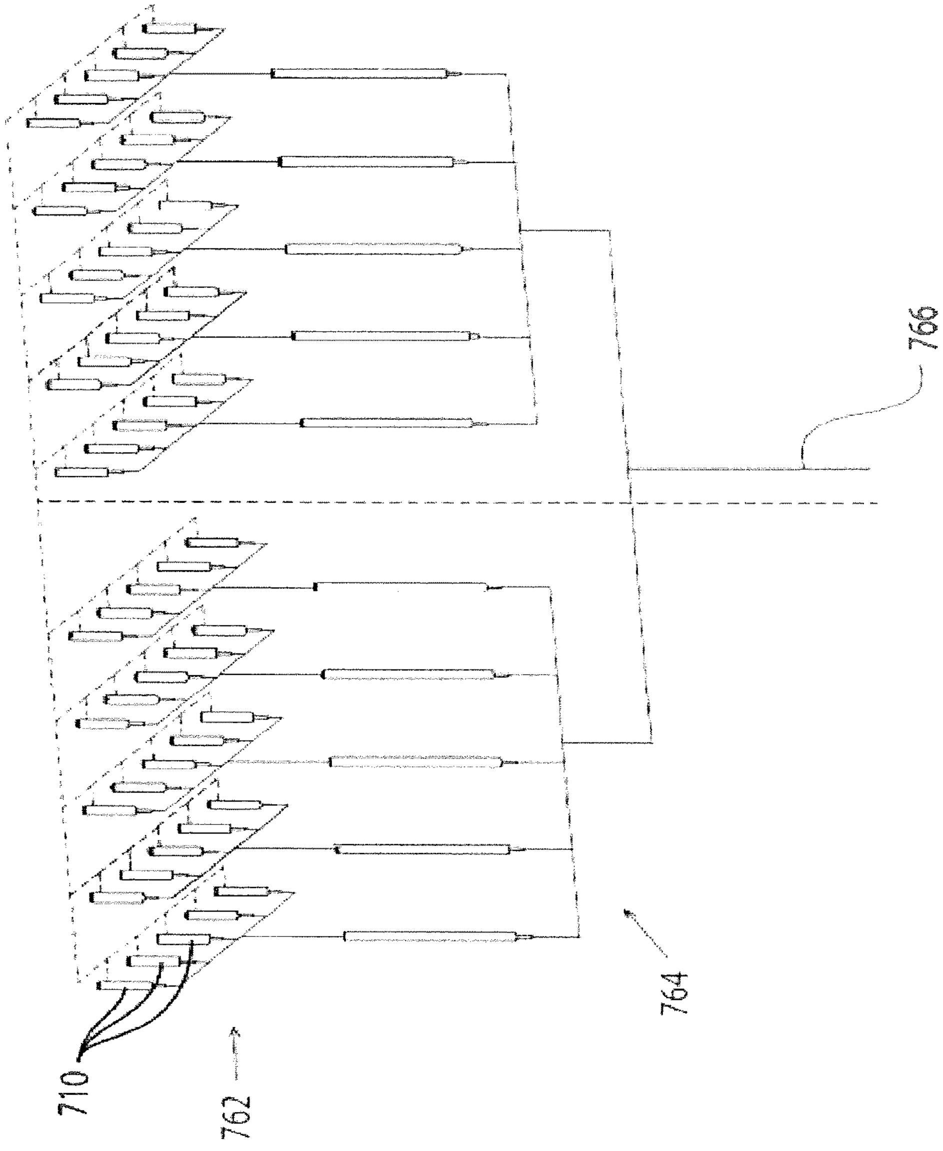
FIG. 44A is a schematic illustration of a distributed solar collector according to one embodiment.

To address these and other needs, in one embodiment of the invention, there is provided a distributed energy collector 762 having separate light collection components branched together for collecting solar light (or other energy) for conversion into electrical power, such as shown in FIG. 44A. In this embodiment, light is collected at the different collector elements 710 distributed spatially in x-y at at least two different levels z.

In one embodiment, there is provided the above-noted distributed energy collector with separate light collection components which collect solar light by directing the collected solar flux to a conversion cell such as photovoltaic, thermoelectric, or thermionic emission cell, which would be optically coupled to the output.

In one embodiment, the light collectors 710 each include a metal core sandwiched by a high k dielectric and low k dielectric material and an optional light conversion material. When the light collector is used as a concentrator, the light conversion material is omitted, and light is collected concentrated at the common trunk 766, where a photovoltaic, thermoelectric, or thermionic emission cell would convert the concentrated light. When the light collector is used as a distributed photovoltaic converter, the light conversion material is present, and incident light collected at each collector is converted into a photovoltage feed along the metal to the common trunk 766.

The fabrication of this light collector can be performed using well known semiconductor processes for build-up of small metallic features, including, but not limited to, low-k $SiO_2$ dielectric, and high-k $SiO_2$ dielectric. The growth of various layers could be done through a sequential build-up process. The metallized features can be achieved through metal atomic layer deposition (ALD) or through other metal deposition processes known in the art such as sputtering or evaporation, with photo-resist processing used to pattern the deposited metal layer(s) leaving the appropriate metallized patterns of interest. The metallic pattern in one embodiment would be surrounded by a high-k dielectric in contact with the metal, and that structure embedded inside a low k dielectric to a form a sensitive optical waveguide that is capable of detecting the stimulus of a weak electric field from the bio-photonic activity.

Metallic features are considered in electromagnetic theory to have an infinite dielectric constant, and are therefore able to pick up an oscillating electric field such as light from the solar spectrum. The electromagnetic energy propagates along the path of the highest dielectric constant which in this case is the metal. The light can and will propagate along a path with the high k $SiO_2$ dielectric, as shown. However, due to internal scattering, the light will remain confined between the high-k $SiO_2$ dielectric and the metal. Any time the electromagnetic energy approaches the boundary interface between the high-k $SiO_2$ and the low-k $SiO_2$, it will bend back and confine itself to the intended waveguide area formed by the metallic path as surrounded by the high k dielectric material.

Unlike conventional panels or collectors, the solar light in this configuration travels by internal reflection along a length of the conversion material (if present) as it is absorbed (i.e., converted into electron-hole pairs). Unlike conventional panels or collectors, if the absorbing conversion material is not present, the solar light travels by internal reflection along a length of the collector to the common trunk In the conversion material configuration with the absorbing conversion material present, the high k dielectric material could comprise a conducting transparent metal oxide such as indium tin oxide (forming one electrode of the photocell collecting voltage/current). Indium tin oxide has a refractive index of around 1.9. In this configuration, the low k dielectric material could be silicon dioxide with a refractive index of 1.48. (Low k and high k are used as relative terms here in this description, and is not restricted to a particular range of dielectric constant.)

Figure 44B:
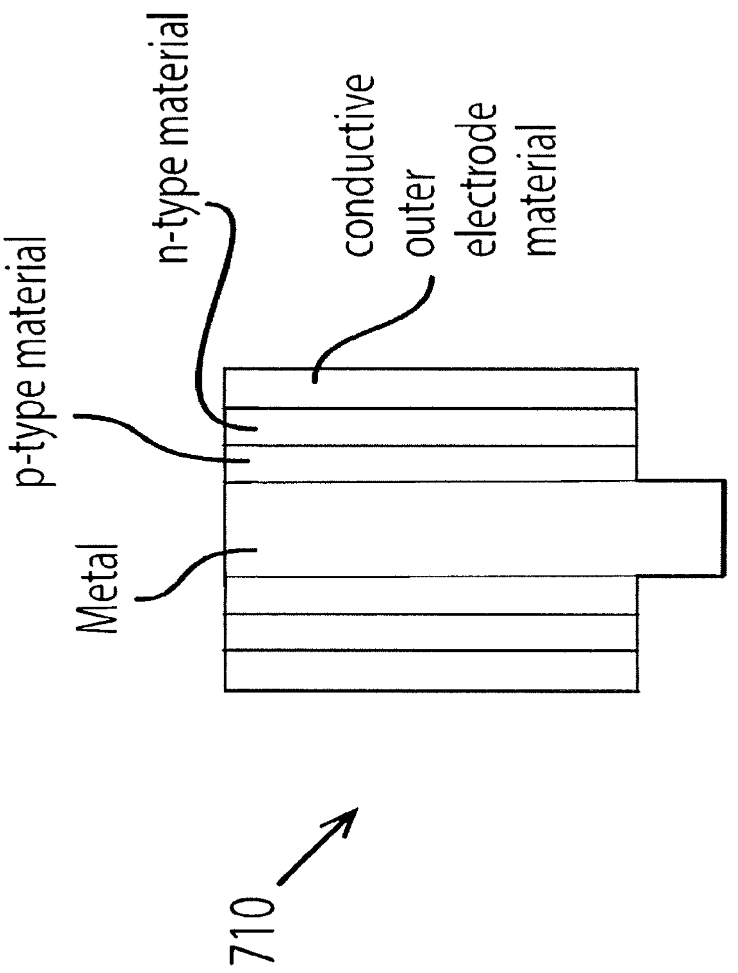
FIG. 44B is an expanded schematic illustration of one of the solar collector elements on FIG. 44A.

In another configuration as shown in FIG. 44B, with the absorbing conversion material present as p-type and n-type materials, the low k dielectric material would not be required, and the outermost layer could be a transparent conductive electrode such as a transparent metal oxide.

Thus, in one embodiment, there is provided a distributed energy collector integrated with a conversion material or a photovoltaic at separate light (or other received energy) collection positions within the collector in order to convert the light (or the other received energy) into electrical power at the light collection components.

In one embodiment, the metal core would also be formed of a transparent metal oxide. As such, the ends of the collectors 710 facing the incident light do not appear as reflective surfaces. In some sense, the collectors of the present invention mimic that of a plant in which the leaves (the light collectors) are not oriented perfectly planar to the sunlight, and sun light passes through and along a length and a thickness of the conversion cell (the leaf).

Unlike conventional panels, the thickness of the conversion material can be made thin as the solar light is absorbed not in an optical path transiting a thickness of the solar cell, but rather in an optical path along the length of the converted material. Accordingly, the collecting the electron-hole pairs by transport of the electrons and holes across the thickness of the conversion material to their respective electrodes can be enhanced in the present configuration where the respective electrode can be spaced with a separation distance even smaller than an absorption depth. In amorphous silicon solar cells, a 200 to 300 nm thickness of an absorptive i-layer is used for generation of the electron hole pairs therein. Here, the conversion layer thickness could be even smaller.

Another advantage of the present configuration compared to conventional panels is that, in conventional panels, photons of an energy significantly greater than the band gap of the converter material are absorbed in the initial region of the material, and the electrons or holes generated in those initial regions are far removed from one collector or another, and are often loss from power generation. Here, as shown in FIG. 45A, the high energy photons as well as the lower energy photons are absorbed at positions in the converter material where the respective collection electrodes are at the same distance from the points of the generation of the electron-hole pairs.

In one embodiment of the invention, organic materials can also be used for solar cell conversion. The use of organic materials facilitates the fabrication of the three-dimensional type structures such as the one illustrated in FIG. 45A.

Figure 45A:
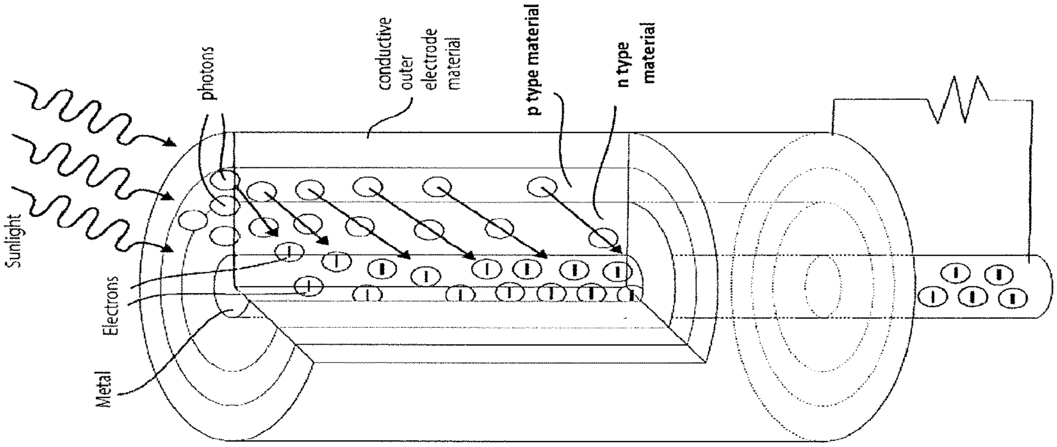
FIG. 45A is a schematic illustration of a coaxial solar collector element according to one embodiment.
Figure 45B:
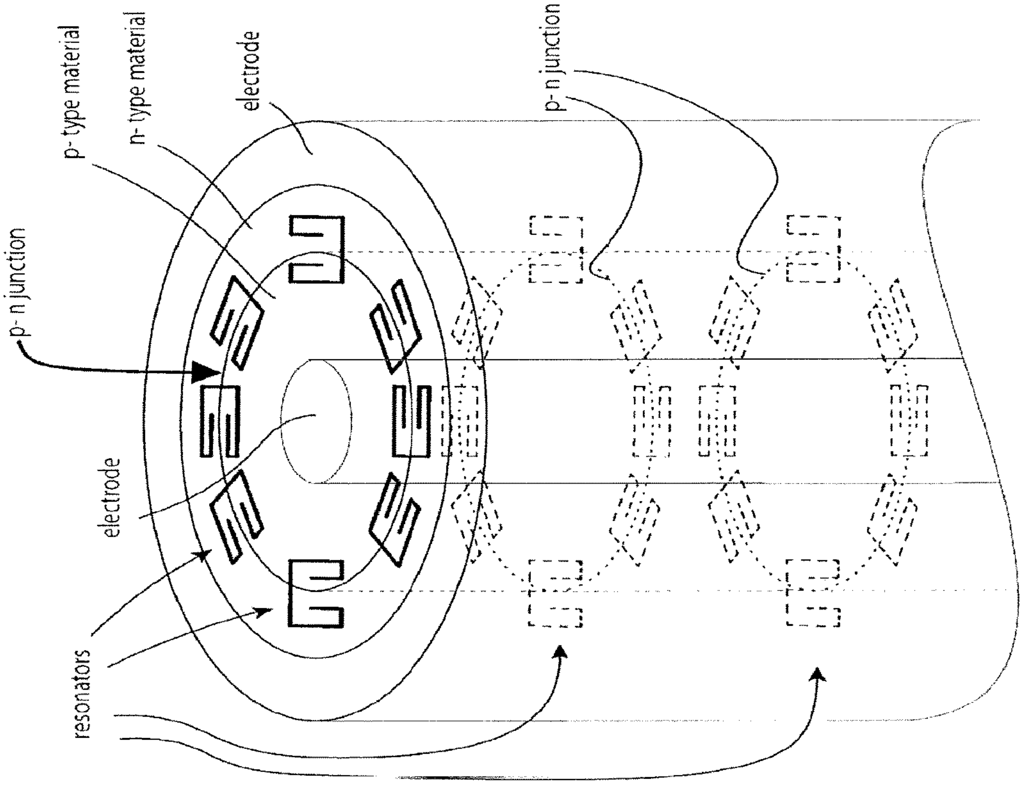
FIG. 45B is a schematic illustration of another coaxial solar collector element according to one embodiment.

In another embodiment of the invention, the converter device in FIG. 45A includes a plurality of folded resonators as shown in FIG. 45B (although the invention is not so limited). Here, the dimensions of the folded resonator are set to resonate at frequencies in the solar IR spectrum. The electrodes of the folded resonator are electrically isolated from the p- and n-materials and from the collection electrodes of the converter (i.e., electrically isolated from the core metal and conductive outer electrode. As shown, a circular array of the folded resonators may reside on top surface of the solar converter where the circular track of the array places the opposing electrodes of each folded resonator over a p-n junction region. As illustrated, multiple circular arrays of the folded resonators can be disposed at different heights within the converter device.

The embodiment shown in FIGS. 45A and 45B with the cylindrical configuration is an example where fabricating the solar conversion cells of the invention with a semiconducting polymer would have distinct advantages. One problem encountered with organic polymers is that the diffusion length of excitons in organic electronic materials is typically on the order of 10 nm. In order for most excitons to diffuse to the interface of layers and split into carriers, the layer thickness should be in the same range as the diffusion length. However, a polymer layer typically needs a thickness of at least 100 nm to absorb enough light. At such a large thickness, only a small fraction of the excitons can reach the heterojunction interface. Here, in the cylindrical configuration of either FIGS. 45A and 45B, thin organic polymer layers can be used to enhance collection efficiency, while solar light is absorbed along the axial direction, and not lost from generating excitons.

Thus, as discussed above, the solar cell configurations described herein can be made with organic semiconductor materials. In that case, the folded resonator of the invention can assist the electric field in the organic layer resulting from the difference of work function between the two collection conductors. In one embodiment of the invention, when the potential created by the different work functions separates the exciton pairs, pulling electrons to a positive electrode and holes to a negative electrode, electrons (traversing the "built-in" electric field across the organic semiconductor materials) will be accelerated by the intensified electric field from the opposing electrodes of the folded resonator and reduce the chance of the separated electron recombining with the exciton, and thereby improve collection efficiency. While it is preferred that the acceleration direct the electron toward one of the collection electrodes (i.e., toward the central metal electrode or the outer electrode), any displacement of the electron away from the exciton should reduce the chance of the separated electron recombining with the exciton, and thus improving collection efficiency.

Returning to a discussion of FIG. 45A, it is possible in a more miniaturized version of the converter cell that the metallic structures in FIG. 45 1000 μm. For example, the outer cylindrical conductor and the central electrode could be dimensioned to form a resonant coaxial structure where the distance from the central electrode to the outer cylindrical conductor would be on the order of 1000 μm to support a radially-directed standing wave for solar wavelengths of 1000 μm. In these embodiments, like that of the folded resonator embodiment in FIG. 45B, one part of the solar spectrum (near the visible spectrum) is absorbed in the p-n materials to generate power and another part of the solar spectrum (toward the infrared) produces regions of intensified electric field to enhance electron-hole pair separation and thereby increase the efficiency of the cell. The structures shown in FIGS. 45A and 45B may work in other ways than the ways described, and the invention is not necessarily limited to the mechanisms described herein.

While discussed above as part of the distributed energy collector 762, in one embodiment of the present invention, a simple array of the converters shown above offers the advantages described above and need not be of the configuration shown for the distributed energy collector 762. Each of these converters is itself unique for being able to use thin converter materials for absorbing the sunlight as it propagates along the axial direction while at the same time collecting electron-hole pairs (transiting the converter material) in the radial direction by the presence of a central conductor and an outer cylindrical conductor.

Figure 46:
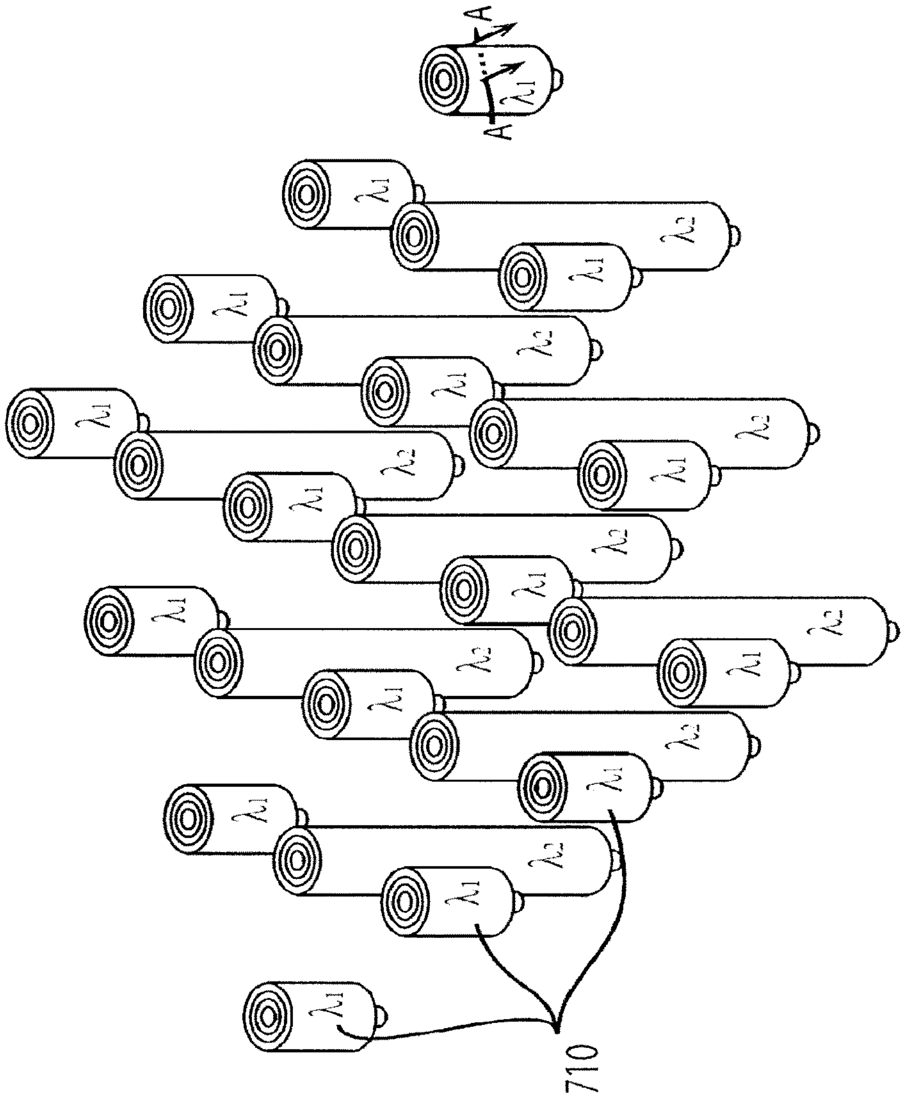
FIG. 46 is a schematic illustration of a coaxial solar collector element according to one embodiment where the elements are resonant at different wavelengths.

In another embodiment depicted in FIG. 46, the collectors 710 are resonant structures. An array of resonant structures (such as for example two different resonant structures resonant at $\lambda 1$ and $\lambda 2$, respectively) could be provided. The array could include even more resonant structures resonating at different wavelengths such that the resonant structures of the array "map" to the wavelengths of the solar spectrum. The length of each resonator would be set to be that of a target wavelength λ.

Figure 47:
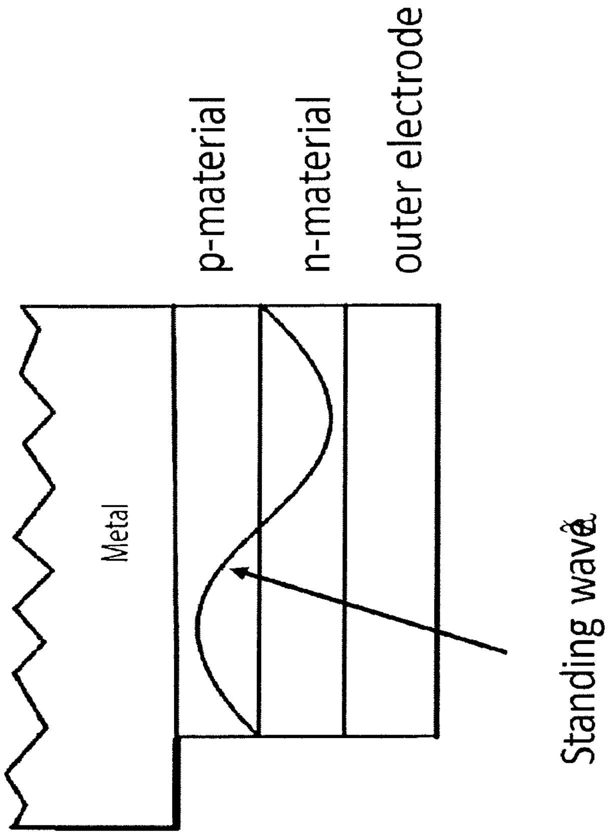
FIG. 47 is an expanded schematic illustration of one of the solar collector elements on FIG. 46.

As shown in FIG. 47, this structure with its discontinuity in the index of refraction, where the p- and n-materials end and are exposed to air or a passivation layer (not shown), may establish a standing wave structure along the length of the collector 710 with anti-node regions of intensified electric field in the converter material (i.e., in the p- and n-materials). Moreover, in one embodiment, the cylindrical shapes of the collectors 710 can couple better to the circularly polarized natural sun light, as the rotating polarization vector is always coupled between the metal core and outer indium tin oxide conductor, the high k dielectric.

Thus, in one embodiment, axial heights (lengths) of each of the collector elements can be set to a dimension which would form a standing wave along the axial length (as illustrated in FIG. 47).

In one embodiment, the standing wave structure acts in a similar manners as a semiconductor laser cavity in that the standing wave structure upon receiving incoherent light from the sun would produce therefrom coherent oscillating waveforms therein, producing enhanced electric fields at the anti-node positions which, in one embodiment, would facilitate absorption and generation of electron-hole pairs in the conversion layer in the conversion materials.

In one embodiment of this invention, the standing wave established by this configuration provides a region of intensified electric field, especially at the antinodes. In one embodiment of the invention, because of this field, electrons of any separated electron-hole pair (a pair that is being normally separated by the "built-in" electric field across the p-n junction) will be accelerated by the electric field reducing the chance of the separated electron-hole pairs recombining, and thus improving collection efficiency. While it is preferred that the acceleration direct the electron toward one of the collection electrodes (i.e., toward the central metal electrode or the outer electrode), any displacement of the electron away from the hole of the electron-hole pair should reduce the chance of the separated electron-hole pairs recombining, and thus improving collection efficiency.

Similarly, in another embodiment, there is provided an energy augmentation structure (such as a fractal antenna or a folded resonator) having a region of the intensified electromagnetic field such that solar energy (or other energy) is better coupled into a conversion cell than if the energy augmentation structure were not present.

Accordingly, there is provided in one embodiment of the invention a power conversion cell comprising a) at least one energy augmentation structure configured to resonate at a first wavelength λ1 which is a frequency included within a radiant source of energy from which power is to be harvested, and b) at least one converter capable of converting the energy from the radiant source into electrical power, wherein electric fields from the augmentation structure permeate into a region of the converter and augment energy conversion.

Moreover, the converter may comprise an array of solar collectors comprising a first set and a second set of photovoltaic cells, the at least one energy augmentation structure may comprises a first resonator dimensioned to be resonant with a first spectrum of solar radiation and a second resonator dimensioned to be resonant with a second spectrum of solar radiation. Under this circumstance of including these element, the first set of photovoltaic cells would be capable of converting the first spectrum of solar radiation into electrical power, and the second set of photovoltaic cells would be capable of converting the second spectrum of solar radiation into electrical power.

Furthermore, as apparent from FIG. 46, the first set and the second set of photovoltaic cells are disposed at different levels whereby solar radiation scattered from one photovoltaic cell can be collected by another photovoltaic cell at the same or a lower level.

Figure 48:
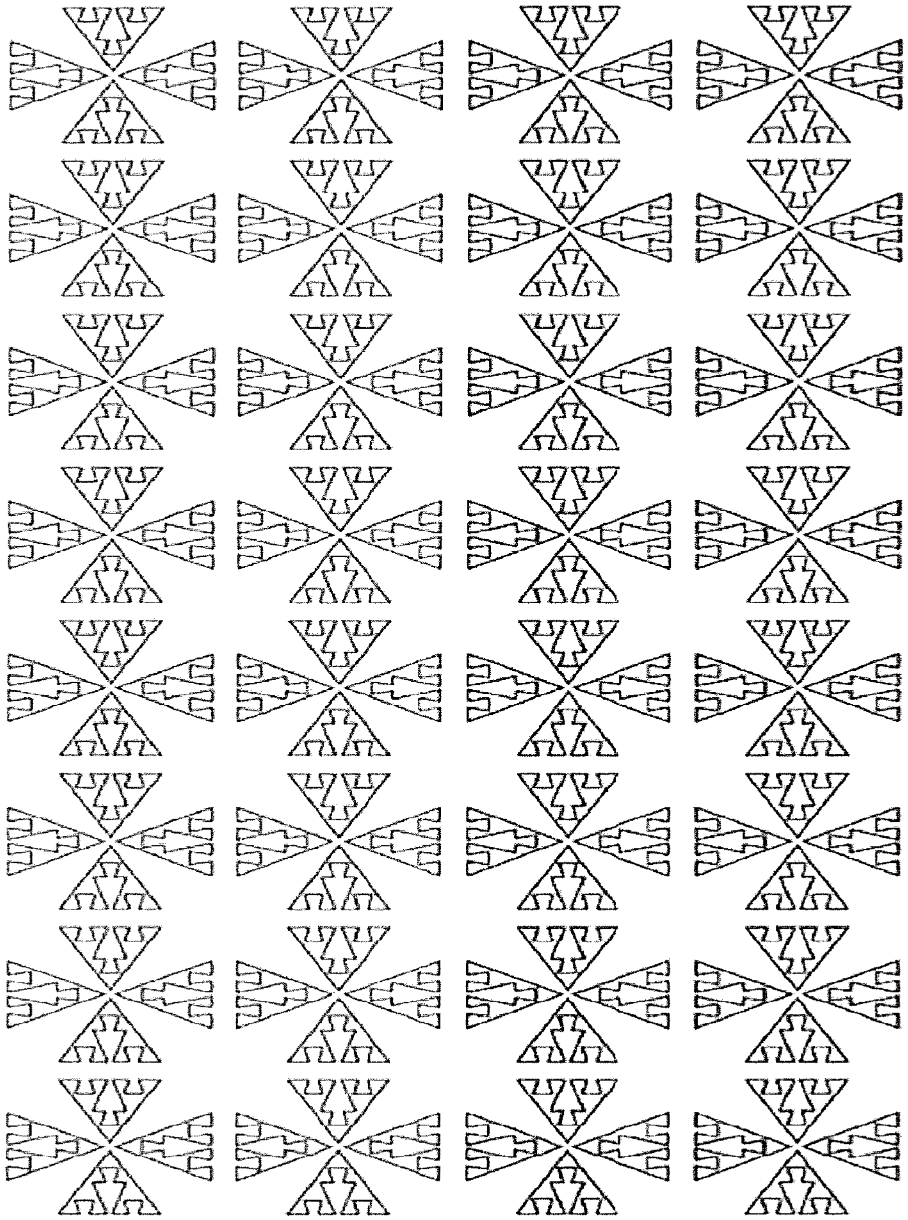
FIG. 48 is a schematic illustration of a fractal antennae element useful in various embodiments.

FIG. 48 depicts a fractal antenna using a self-repeating design such as self-repeating design, or other fractal patterns. In general, fractal antennas are compact and have a wide band of operation because a fractal antenna resonates at many different resonances, meaning it can act as an antenna for many different electromagnetic frequencies. The different resonances arise because the fractal nature of the antenna acts as a virtual network of capacitors and inductors. Here, in one embodiment, the fractal antenna would be designed to resonate about the infrared wavelengths of the solar spectrum and enhance absorption of solar energy at those wavelengths.

In one embodiment of the invention, a fractal antenna could be printed (or otherwise formed) onto the external surface of a conversion cell (e.g. an up conversion cell), whereby solar energy would be collected and enhanced for conversion. Accordingly, in regions of intensified electric fields around the fractal antennas up conversion or down conversion materials could be placed to shift parts of the solar spectrum (significantly greater than the band gap energy of the semiconductor converter or significantly lower than the band gap energy) to energies where the semiconductor can then generate a photovoltage from photons of the solar spectrum that normally would have not been converted or poorly converted into electrical power.

Figure 49:
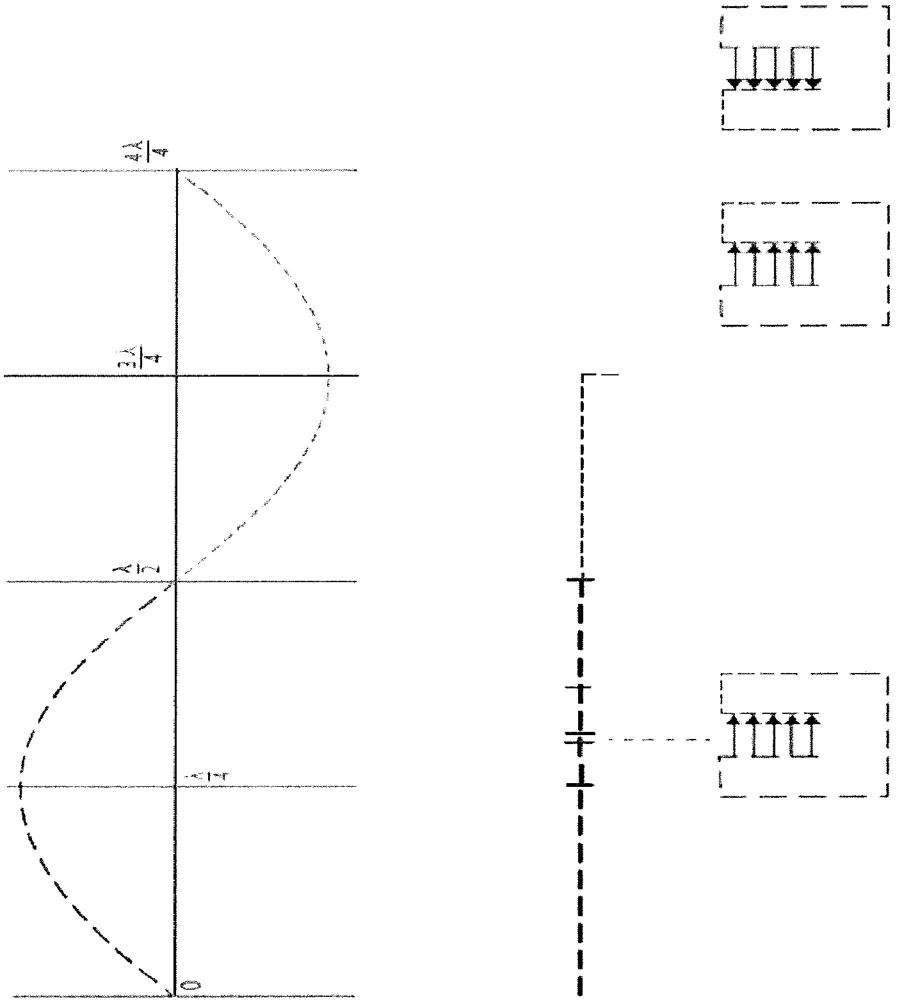
FIG. 49 is a schematic illustration of a folded resonator useful in various embodiments.

In one embodiment of the invention, as depicted in FIG. 49, a folded resonator could be printed (or otherwise formed) onto the external surface of a conversion cell, whereby solar energy would be collected and enhanced for conversion. A sinusoidal wave representing for example an instantaneous waveform of a light wave (an incident energy flux 12) when incident on a ¾ λresonator, having a length of % of the wavelength λ, with the open ends of the resonator "folded" together couples energy into this resonant structure. The folded ends form a region of an intensified, amplified electric field denoted by the horizontally directed arrows between the opposing open ends.

When light nominally of a wavelength λ(or harmonics thereof 2λ, 3λ, 4λ, etc.) is incident on the folded antenna structure, a fraction of the light will be coupled into this structure establishing the amplified electric field. Since the light from sun comes continuously and at different rotational polarizations, subsequent light waves will continue to "pump" the electric fields in the resonant structure until some "loss" mechanism caps the strength of the electric fields. For resonators made of low loss materials, high Q-factors are obtained which, in this case, could mean that the electric field strength between the opposing electrodes may be for example 100 to 1000 times the peak amplitude of the electric field vector of the incident waveform.

Figure 50:
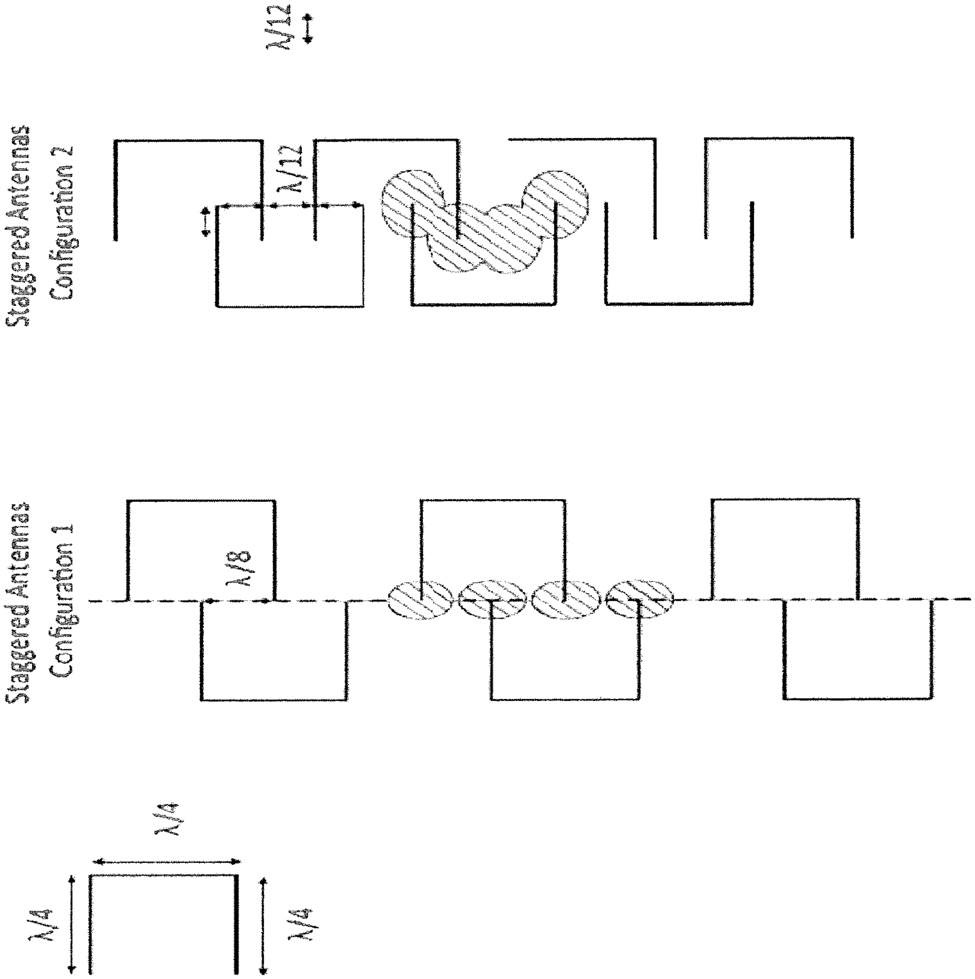
FIG. 50 is a schematic illustration of another interleaved resonators pattern useful in various embodiments.

In another embodiment, a resonating antenna could have the configuration shown in FIG. 50 in which the ¾ λ structures oppose and are interdigitated together without a "folded" structure. In this configuration, the horizontal stubs are ¼ λlong, the vertical extending connectors are ¼ long, and the vertical spacing between the horizontal stubs and the extend of interdigitation varies as shown between configuration 1 and configuration 2.

While the ¾ λfolded resonator in one embodiment could be designed to resonate at blue light (λ=420 to 440 nm) for photovoltaic conversion, the resonator could also be designed to resonate at frequencies of infrared light from the solar spectrum (e.g. λ=700 to 1000 nm) for thermionic or thermoelectric conversion of this energy into power.

Figure 51:
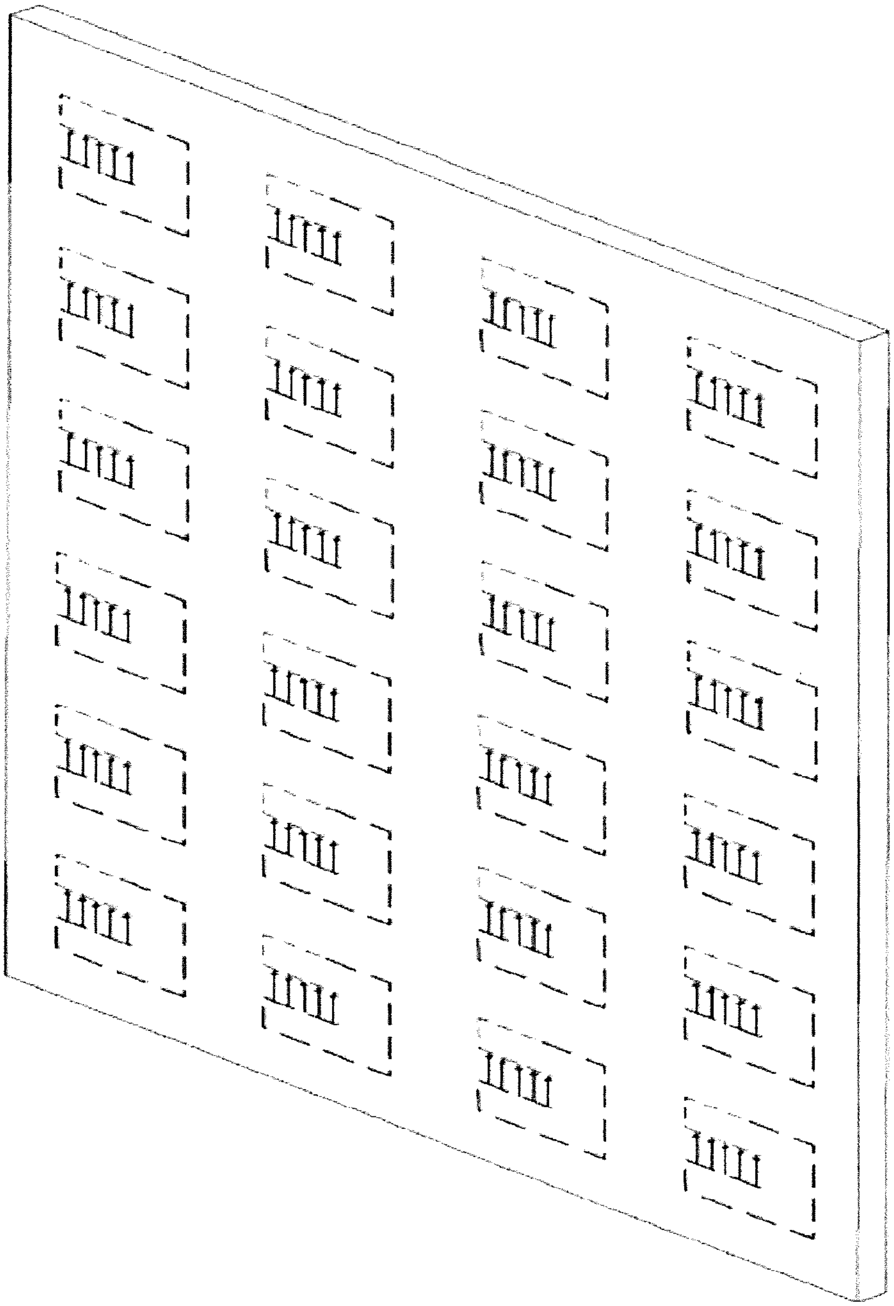
FIG. 51 is a schematic illustration of an array of folded resonators useful in various embodiments.

FIG. 51 is diagram showing a pattern of ¾ λfolded resonators 22 distributed in space. As to be discussed in more detail later, there are numerous ways to distribute the ¾ λfolded resonators. The present invention is not limited to the regular, uniformly spaced and sized resonators shown in FIG. 51. There is no requirement that the distribution be regular, uniformly spaced, uniformly sized, or uniformly oriented. Differently sized, spaced, and oriented resonators may provide better utilization of the full spectrum of the sun or any other light source incident on the object.

In one embodiment, this pattern could be formed by lithographic or stamping processes onto a planar surface such as a glass plate or onto a curved sheet type product. Upon solar irradiation, the infrared part of the solar spectrum (normally only heating the surface) would generate the intensified electric field regions. In those regions, down converting phosphors converting deep blue and ultraviolet light to visible light would convert the deep blue and ultraviolet light of the solar spectrum to visible light better suited for photovoltaic conversion.

Figure 52:
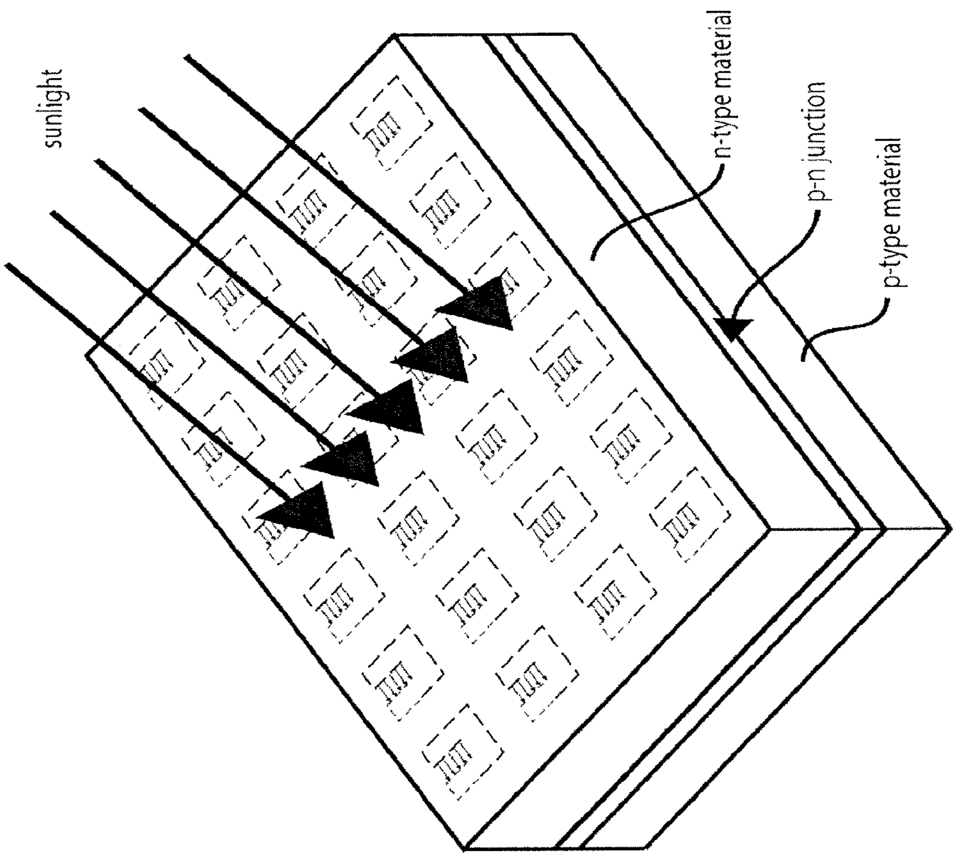
FIG. 52 is a schematic illustration of an array of folded resonators coupling power to a photovoltaic cell.

FIG. 52 shows an array of folded resonators disposed on a solar panel including an n-type material and a p-type material. Similar to that above, in regions of intensified electric fields around or in between the opposing electrodes of the folded resonators, up conversion or down conversion materials could be placed to shift parts of the solar spectrum (significantly greater than the band gap energy of the semiconductor converter or significantly lower than the band gap energy) to energies where the semiconductor can then generate a photovoltage from photons of the solar spectrum that normally would have not been converted or poorly converted into electrical power.

Figure 53:
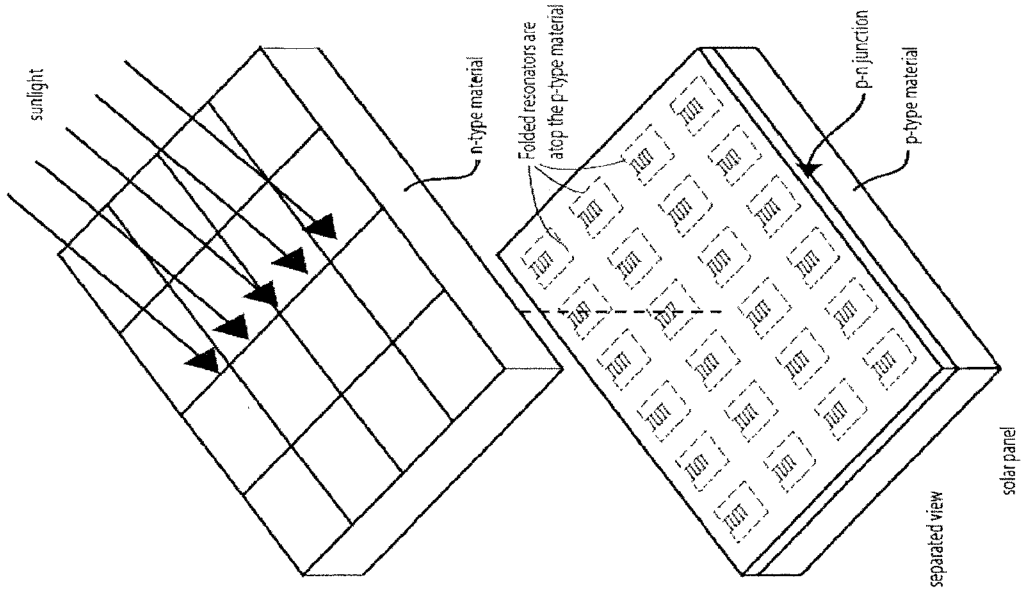
FIG. 53 is a schematic illustration of an array of folded resonators coupling power to a photovoltaic cell by enhancing up conversion of infrared light not absorbed by the photovoltaic cell.

Additionally, in one embodiment, the folded resonators (with or without the upconverters and down converters) could be fabricated as an integral part of the p-n junction, as shown in FIG. 53. Sub-band gap light (which would normally pass through the solar cell and provide no electrical power) could be upconverted (by phosphors existing in or in proximity to the regions of intensified electric field at the opposing electrodes of the folded resonators) with the upconverted light emitted at the band gap energy and emitted within the p-n material and absorbed by the semiconductor material without substantial loss of the upconverted photons from the conversion cell.

Figure 54:
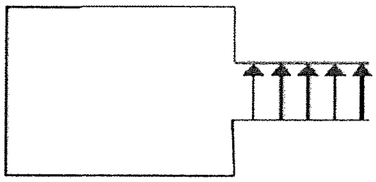
FIG. 54 is a schematic illustration of a folded resonator useful in various embodiments and having external electrodes.

In other embodiments of the invention, the ¾ λfolded resonators need not to have the "folded sections" which fold inwards. Instead, as shown in FIG. 54, the ¾ λresonators of the invention can have folded sections which fold outward with the regions of intensified electric field being outside of the "loop" of the resonator. The distal ends of the antenna protrude outwardly while maintaining parallelism.

Figure 55:
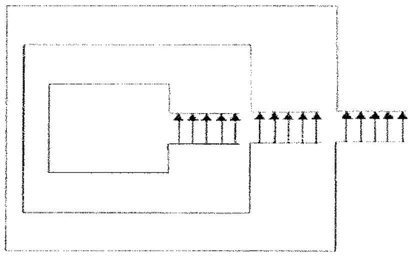
FIG. 55 is another schematic illustration of an array of folded resonators each having external electrodes which are useful in various embodiments.

In one embodiment of the invention, the ¾ λexternal-electrode folded resonator 22 provides the capability to be packed in a concentric-type arrangement with progressively increasing or decreasing size resonators. These resonators are maintained in plane with no overlapping distal ends. FIG. 55 is a schematic of a plurality of concentric-type ¾ λ external-electrode folded resonators 22.

Since each of the ¾ λexternal-electrode folded resonators has a different electrical length, the plurality of concentric-type ¾ λexternal-electrode resonators will be "tuned" to the different wavelengths associated with the respective electrical lengths. Three different frequencies are therefore focused between the distal ends of the antennas.

Figure 56:
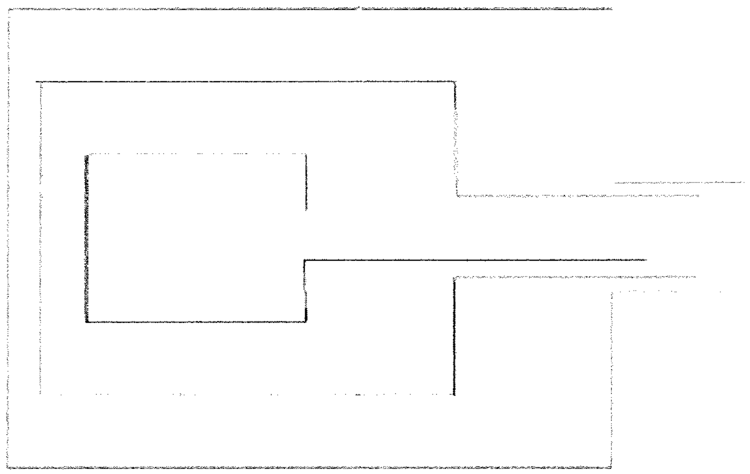
FIG. 56 is another schematic illustration of an array of folded resonators each having external electrodes which are useful in various embodiments.

In another embodiment, FIG. 56 is a schematic of a plurality of concentric-type ¾ λexternal-electrode folded resonators 22 with overlapping electrodes. In one embodiment, the overlapping provides a more concentrated/enhanced field region than in the non-overlapping arrangement.

Figure 57:
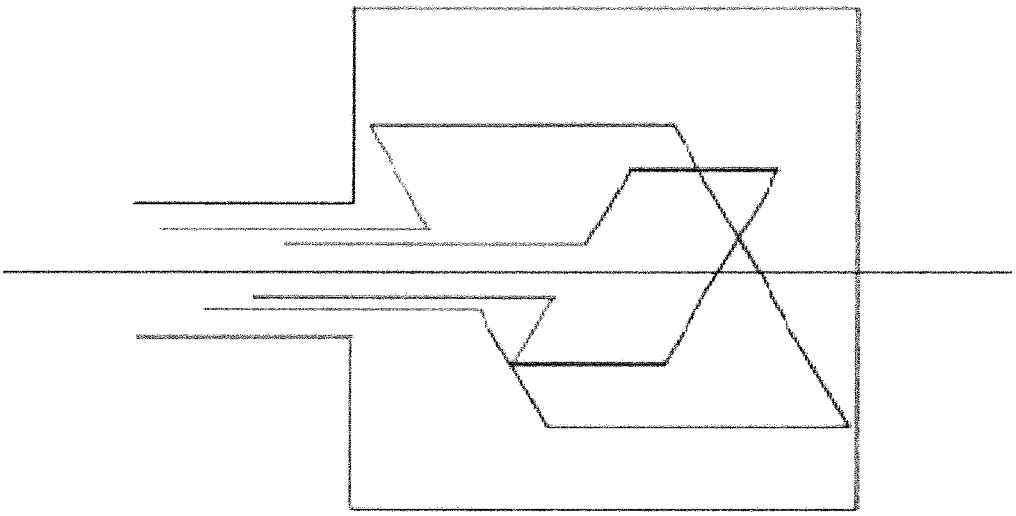
FIG. 57 is another schematic illustration of a cluster of folded resonators each having external electrodes which are useful in various embodiments.

The present invention is not limited to planar concentric type packing arrangements. In one embodiment, the present invention utilizes an off plane configuration with axial symmetry where the antennas are in an axially rotated, multiple frequency, interleaved % wave resonator structure. FIG. 57 is a schematic of an axially rotated, multiple frequency, interleaved % wave resonators 22 showing (in this example) three differently sized resonators for multiple frequency resonance disposed about/along a common axis but axially rotated. In one embodiment, in this configuration, the resultant electric field is concentrated without one electrode section perturbing the electric fields from another.

Figure 58:
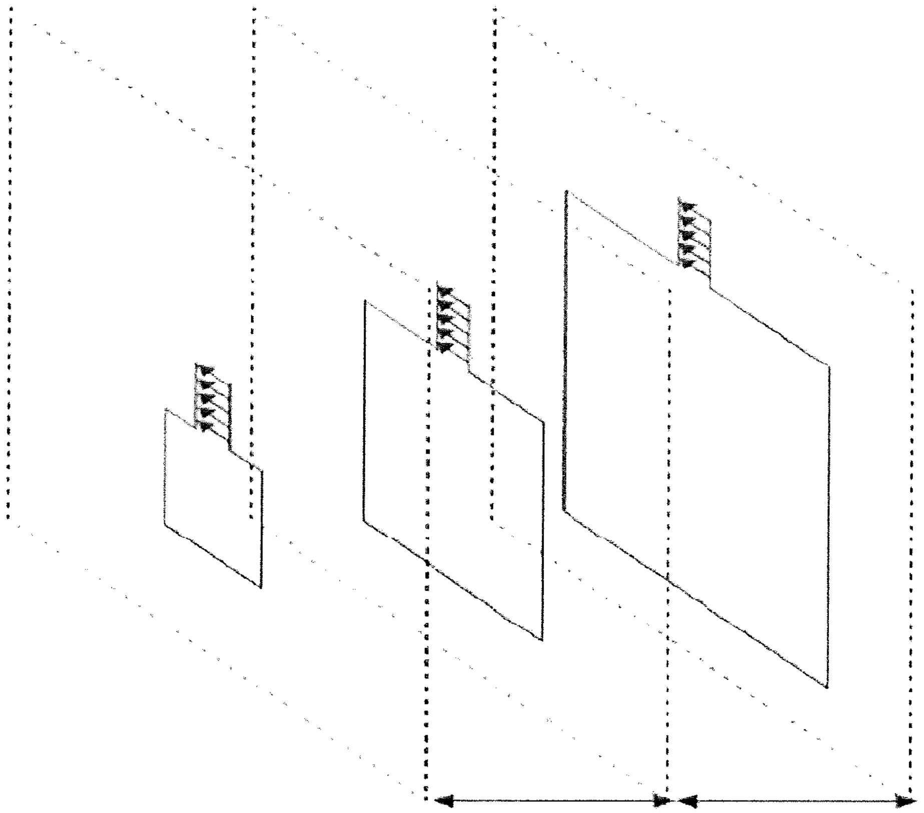
FIG. 58 is yet another schematic illustration of an array of resonators s each having external electrodes which are useful in various embodiments.
Figure 59:
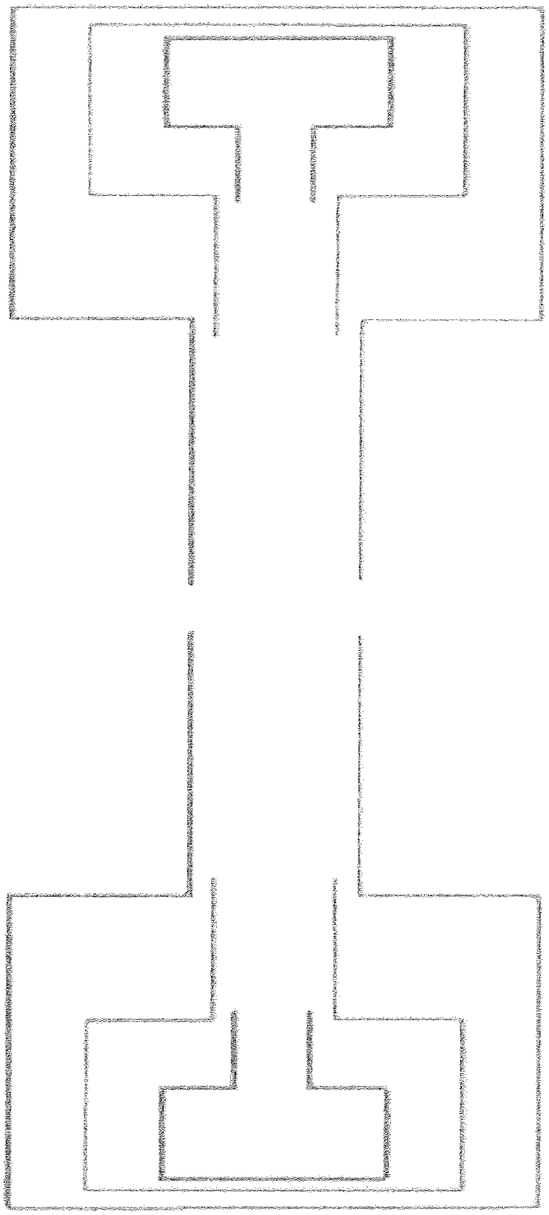
FIG. 59 is still another schematic illustration of an array of folded resonators each having external electrodes which are useful in various embodiments.
Figure 60:
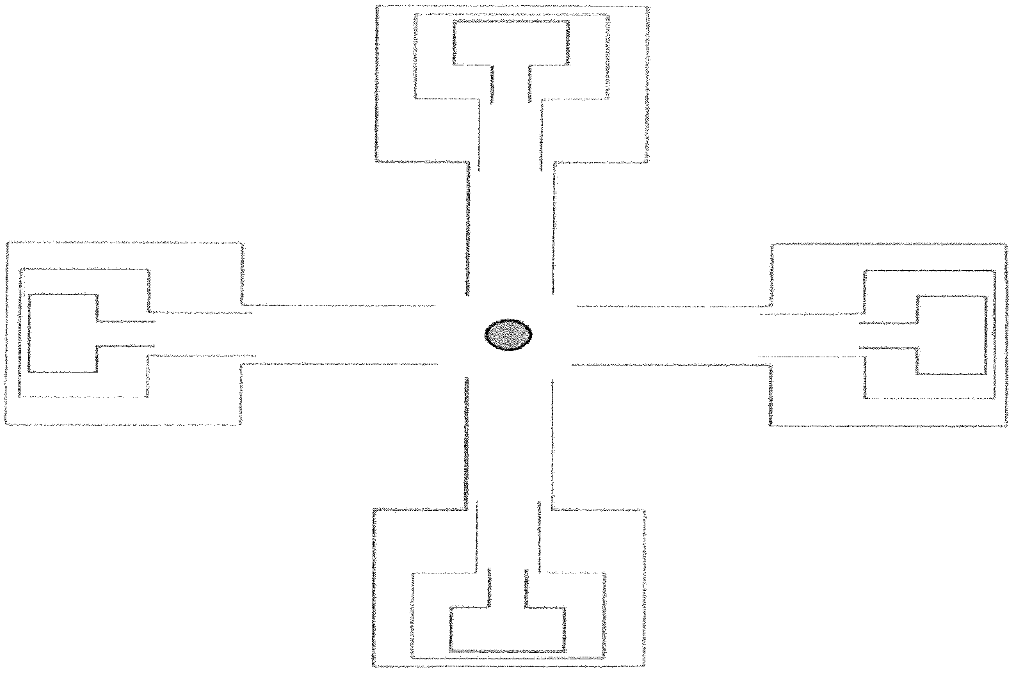
FIG. 60 is further another schematic illustration of an array of folded resonators each having external electrodes which are useful in various embodiments.

Other packing arrangements of the folded resonators are possible as shown in FIGS. 58-60.

These configurations of fractal antennas or folded resonators can be used with a number of other conversion cells other than just the photovoltaic organic and inorganic cells discussed above.

Figure 61:
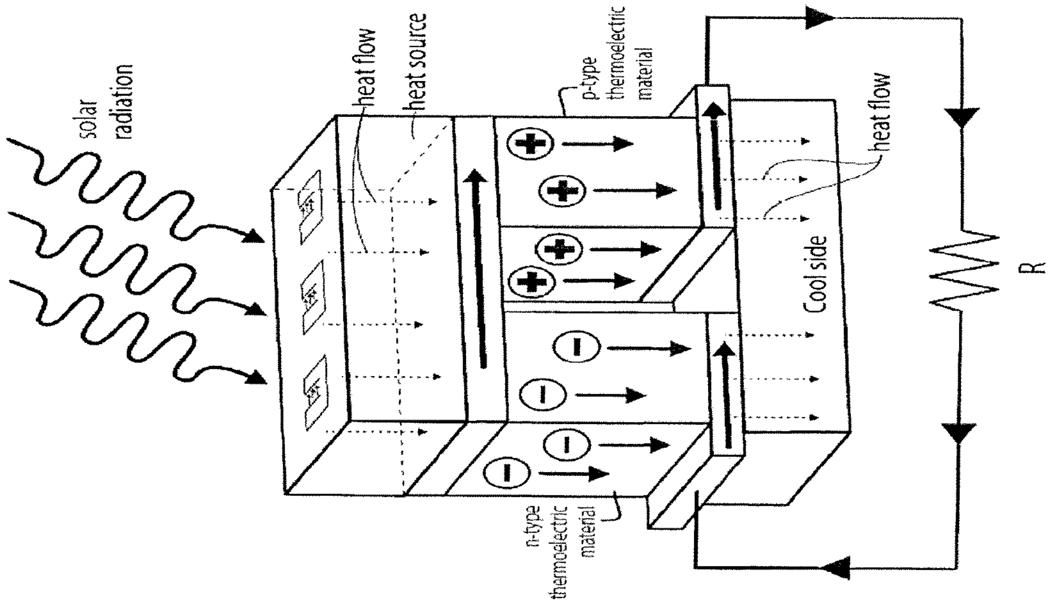
FIG. 61 is a schematic illustration of an array of folded resonators coupling power to a thermoelectric converter.

In one example illustrated with the folded resonators (but also useable with fractal antennas), the folded resonators of this invention are used with a thermoelectric converter, as shown in FIG. 61. The folded resonators are disposed on a top plate of the thermoelectric converter exposed to solar radiation or radiation from other black body sources (such as waste heat from combustion or waste heat from industrial processes). The folded resonators are designed to resonate at a primary wavelength or many wavelengths of the radiation source and thereby absorb the radiation and heat the top plate. The design of the thermoelectric cell is conventional and can follow the layout of known thermoelectric cells but with the addition of the folded resonator or fractal antennas to the solar energy absorbing surface. In a conventional layout, as shown in FIG. 61, two legs (one of an n-type material and the other of a p-type material) transport their majority carriers away from the heated top plate (the majority carriers diffuse from the hotter top side). This current flow forms a circuit as shown through a resistive load R and develops a voltage across the resistive load R which can be used as a source of power. The bottom plate dissipates the heat in order to maintain a temperature differential between the top plate and the bottom plate by which the majority carriers continue to diffuse from the hotter top side.

Figure 62:
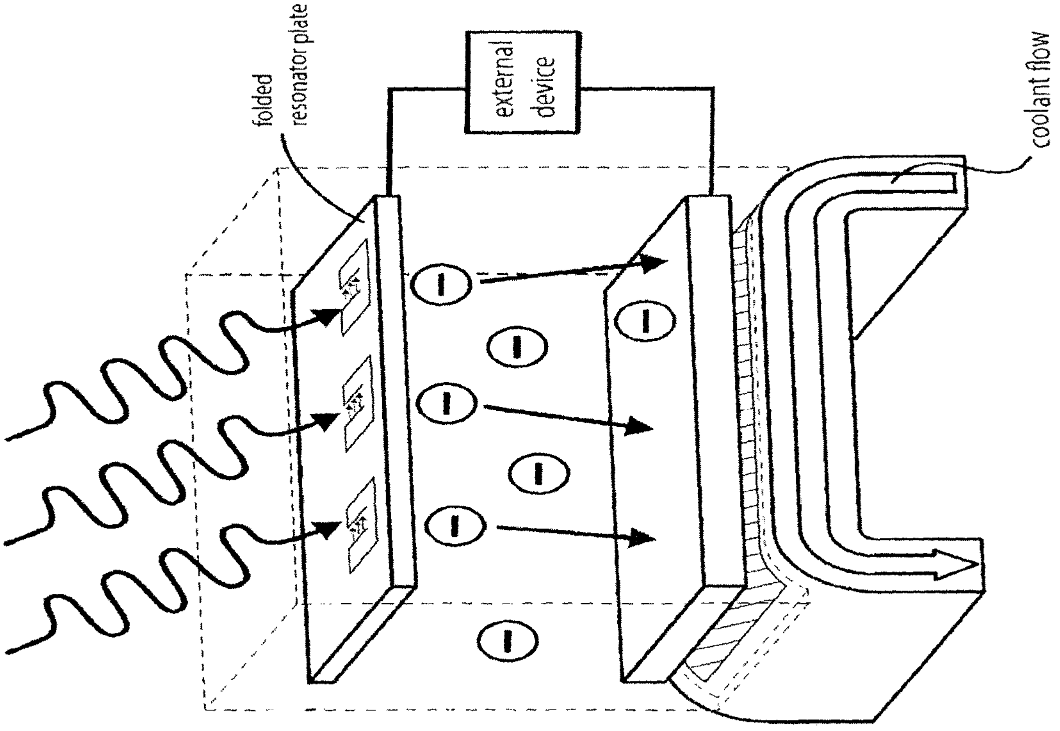
FIG. 62 is a schematic illustration of an array of folded resonators coupling power to a thermionic converter.

In one example illustrated with the folded resonators but also useable with fractal antennas, the folded resonators of this invention are used with a thermionic converter. Thermionic energy conversion (TEC) is the direct conversion of heat into electricity by the mechanism of thermionic emission, the spontaneous ejection of hot electrons from a surface. Electrons thermally emitted from a hot surface traverse a gap, and are collected by another surface. This process, starting with thermionic emission, produces a current of electrons that can subsequently drive an electrical load R. In this example, there are a number of ways that the folded resonators and/or the fractal antennas of this invention can improve the efficiency. FIG. 62 shows a thermionic converter in which a heated upper plate (containing folded resonators) emits electrons into a vacuum for collection at a lower plate.

Here, in this embodiment, the folded resonators can have many different resonances, matched to the infrared spectrum of the sun, and allow the top plate to heat to a higher temperature than if the folded resonators were not present.

Figure 63:
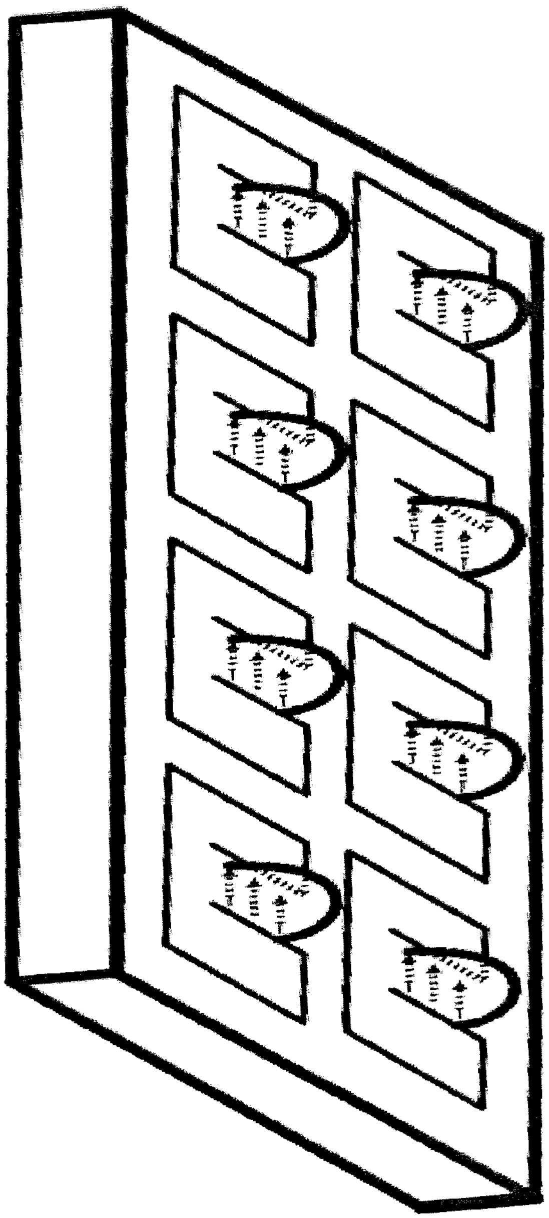
FIG. 63 is a schematic illustration of an array of folded resonators locally heating tips of a thermionic converter.

In another embodiment, the upper plate is a high temperature and infrared transparent material such as a silicon wafer or an infrared transmitting glass wafer in which protrusions are patterned onto the underside and folded resonators provide a region of an intensified electric field for the protrusions. The protrusions could be made of a negative electron affinity material such as carbon or diamond-like carbon, or diamond. A negative electron affinity material is a material that presents no barrier to electron emission therefrom. These materials have been used in the past to supply electrons to vacuum with little energy loss. In one aspect of this invention, the intensified electric field provided by the fractal antennas or the folded resonators can be used to either 1) locally heat the protrusions to a higher temperature than the top plate, and thereby assist in electron emission. In this case, the protrusions need not necessarily be a negative electron affinity material, but mere needs to be a high temperature conductive material which will be heated in the intensified electric field oscillating at infrared frequencies. Useful materials for the protrusions include but are not limited to refractory metals, graphite, diamond-like carbon, diamond, low bad gap semiconductors such as germanium, and combinations thereof. FIG. 63 below shows the use of folded resonators to produce an intensified electric field in vicinity of the protrusions to locally heat the protrusions.

Figure 64:
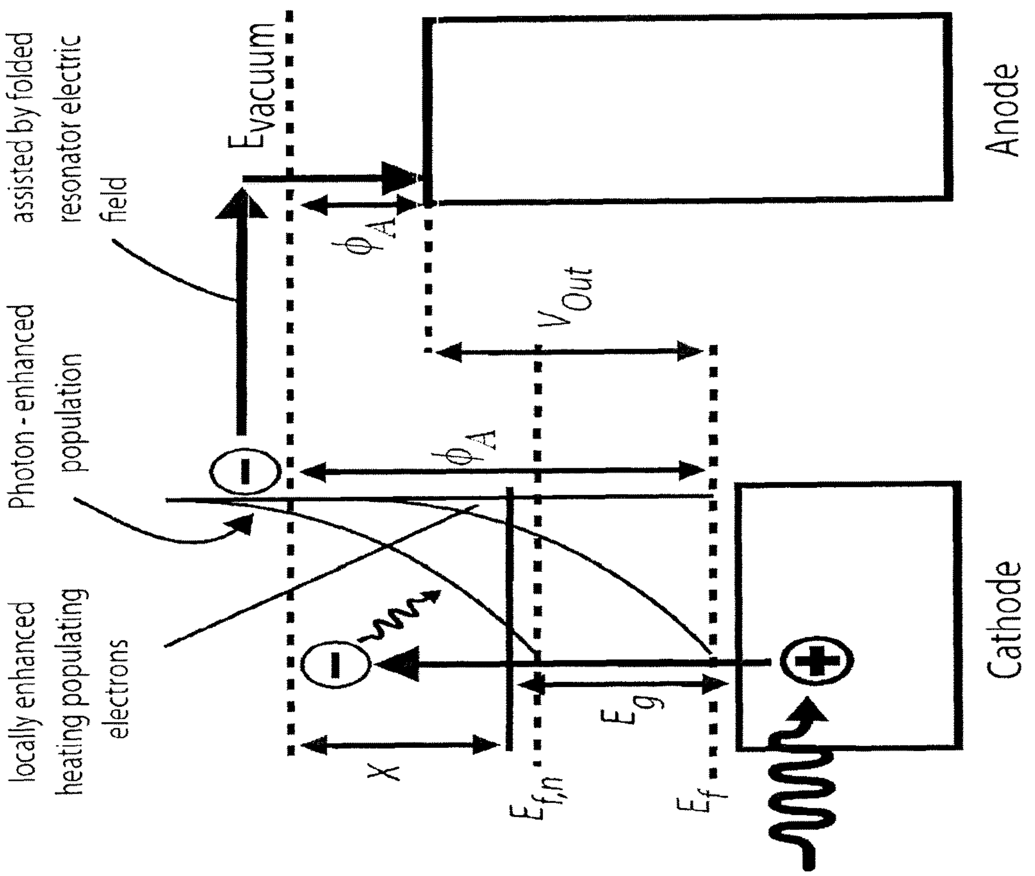
FIG. 64 is a band diagram of a thermionic converter.

In another embodiment, the fractal antennas and folded resonators can be disposed onto a semiconductor top plate material to assist in heating the top plate. Here, part of the solar spectrum not in the infrared will be absorbed by the semiconductor material. Below in FIG. 64 is a band diagram showing the processes used in this embodiment to "drive" electron emission into the vacuum.

Here, in this embodiment, electrons are "pumped" by the enhanced heating from a folded resonator absorbing IR radiation from the solar spectrum will tend tends to populate electrons into the bent conduction band near the vacuum surface. In this embodiment, absorption of visible parts of the solar spectrum will also populate electrons into the bent conduction band near the vacuum surface. These population enhancements drive emission into the vacuum, for collection by the anode. The emission and collection of electrons may be assisted by the instantaneous electric field on the folded resonator if for example the fringing field lines diverging from between the opposing electrodes induce electron emission.

Indeed, in one aspect of the invention, the high frequency signal on the folded resonator during one half of the AC signal is negatively biased which would drive electrons emitted into the vacuum and toward the opposing (grounded) collector. When the bias during the other half of the AC signal occurs, as seen in the band diagram, there is barrier because of the peaked curvature of the conduction band for return of the electrons back into the cathode. In effect, the action is that of a diode.

Figure 65:
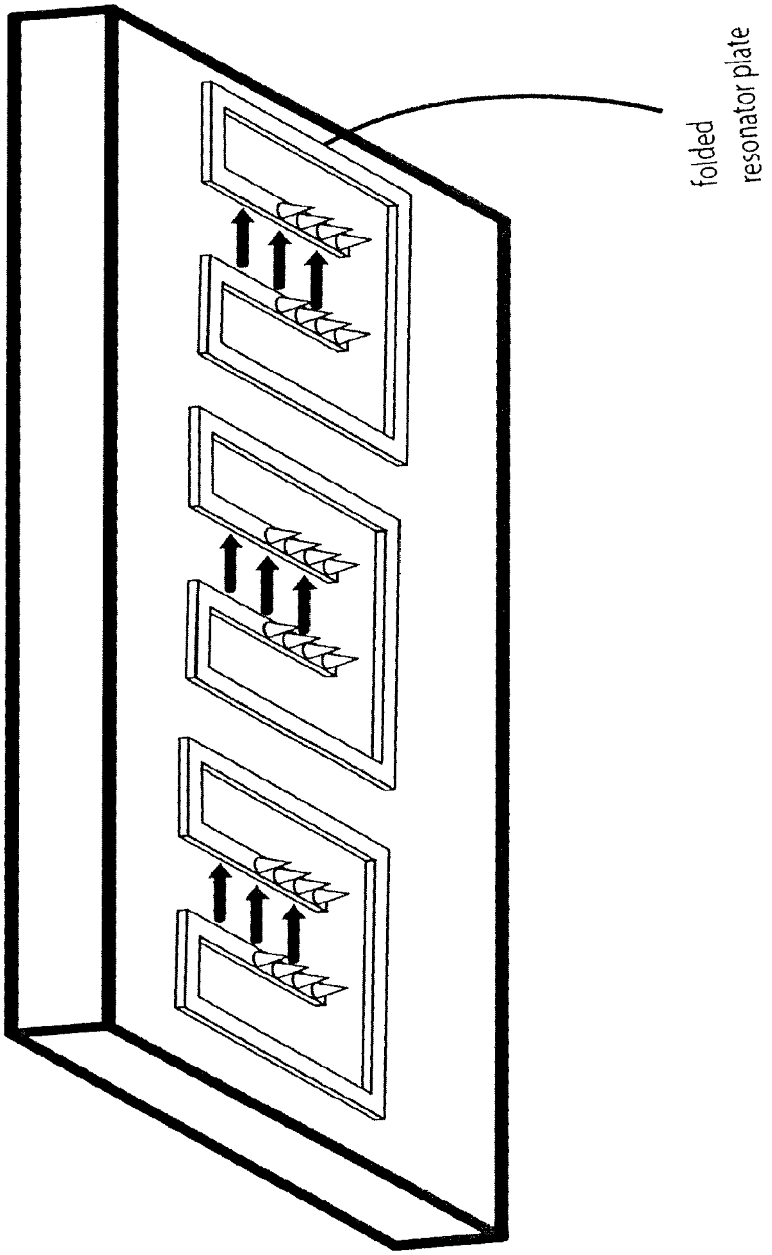
FIG. 65 is a schematic illustration of an array of folded resonants having thereon tips of a thermionic converter for electron emission.

Accordingly, in one embodiment, there is provided a thermionic emitter structure in which (by the diode action described above) energy coupled into the folded resonator can be directly turned into a rectified current waveform having a time-averaged, non-zero voltage. FIG. 65 shows a folded resonator plate for use in the thermionic conversion device described above in FIG. 62. In FIG. 65, the depicted top plate of the thermionic conversion device could be a silicon or quartz wafer transparent to IR radiation from the solar spectrum. A high temperature metal such as tungsten would be patterned on the underside of the top plate for the folded resonator. DC leads not shown would be connected at the opposite of side of the folded electrode at the AC voltage node position in order to supply electrons back to the folded resonator following their emission into the vacuum and collection by the opposing collector electrode (as for example the lower electrode in FIG. 62). Furthermore, as shown in FIG. 65, the high temperature metal could be patterned to have protrusions extending from the base metal toward the collector (not shown). Incoherent infrared light from the sun would set up a standing wave on the % wavelength resonator.

Here, the electron emission into the vacuum occurs both from pure thermionic emission from the heated folded resonator into the vacuum and toward the grounded collector and from emissions induced by the intense electric field during the negative cycle of the standing wave induced on the folded resonator. As above, return of electrons to the heated folded resonator during the positive cycle of the standing wave is inhibited by the vacuum barrier, thus providing a rectified high frequency current flow.

Figure 66:
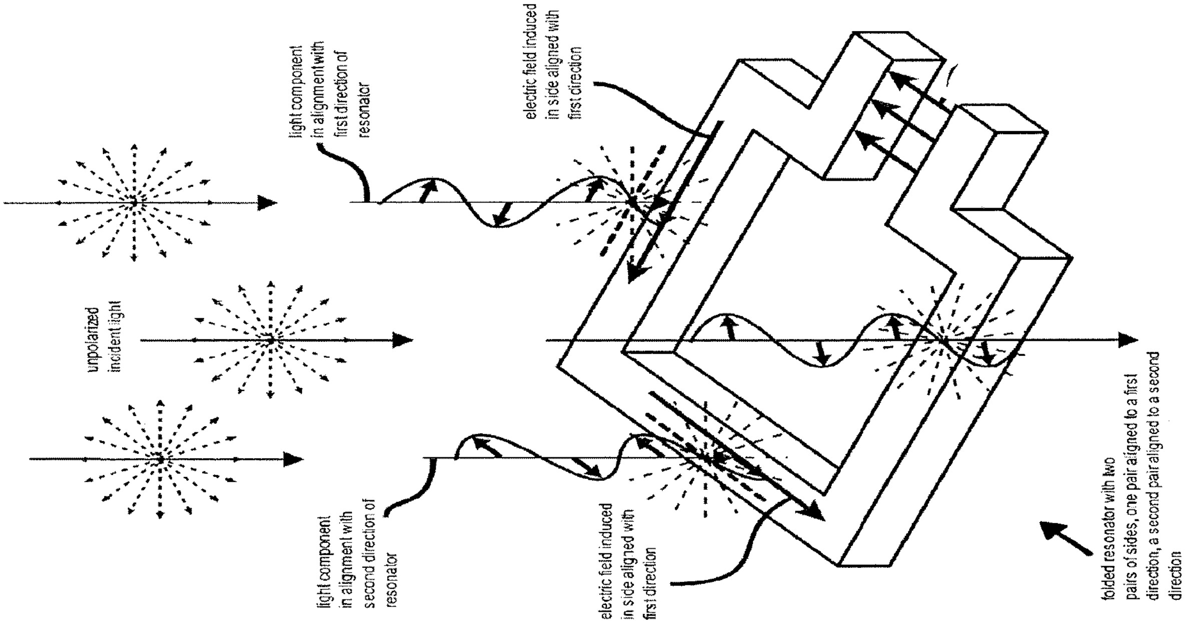
FIG. 66 is a schematic illustration depicting coupling of circularly polarized light such as sunlight into a folded antenna.

In the following non-limiting discussion, some of the advantages of the folded resonator for coupling to circularly polarized sun light is expounded. As shown in FIG. 66, the "loop" of the folded resonator presents sets of electrodes that are orthogonal to each other (i.e., a first pair aligned in a first direction, and a second pair aligned in a second direction orthogonal to the first direction).

This orthogonality means that, at some point in time, the circularly polarized wave has its oscillation plane aligned with one side, and at another point in time, the circularly polarized wave has its oscillation plane aligned with the orthogonal sides. At any time in between, a projection of the circularly polarized wave will be coupled in one side, while its complement is projected into the orthogonal side. Thus, as the polarization vector of natural sunlight rotates, the loop will always couple to the circularly polarized wave.

Figure 67:
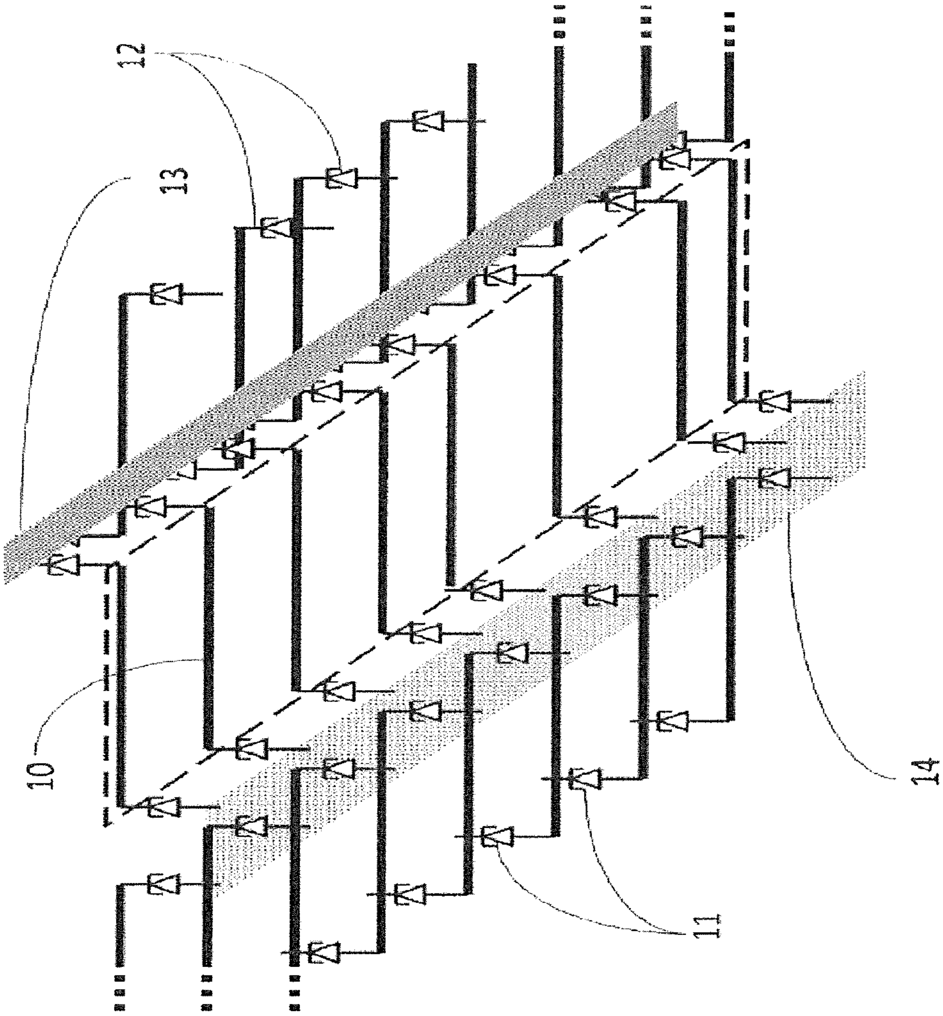
FIG. 67 is a schematic illustration of a prior art drawing of a ¼ wave carbon nanotube antenna for solar power conversion.

Prior work such as reported in U.S. Pat. No. 9,917,217 (the entire contents of which are incorporated herein by reference) used carbon nanotube ¼-wavelength straight-length antennas that varied in length from 80 to 620 nm. In an apparent attempt to improve coupling, the '217 patent used an array of randomly placed carbon nanotube antennas to convert sunlight into electrical power. FIG. 67 is a reproduction of a drawing from the '217 patent showing the core of a solar antenna array having rows of antennas 10, separated by power lines 13 and ground lines 14.

In the '217 patent, the power and ground lines may be respectively coupled to the antennas by tunnel diodes 11 and 12. When the antennas are excited by visible light, the current may flow from the ground line to the power line, thus producing half-rectified electrical energy. In the '217 patent and applicable here, the diodes can be a MIIM diode or a point contact diode.

MIM diodes use quantum tunneling to operate at terahertz frequencies. The quantum tunneling reportedly permits electrons to jump from one metal electrode to the other without interacting with the intervening insulator layer. Oregon State University (OSU) researchers in 2013 added a second insulator layer to produce an MIIM device that aims to solve the problems with the older MIM devices. By using two different metals on the opposing electrodes, one is limited by the work function difference between the different metals, but "by using two different insulators—one with a large bandgap and one with a smaller bandgap—" the extra asymmetry overshadows the asymmetry of the different metals. In the OSU work and applicable in the present invention, hafnium oxide and aluminum oxide—permitted "step tunneling," precise control of the diode asymmetry, and rectification at low voltages.

Figure 68A:
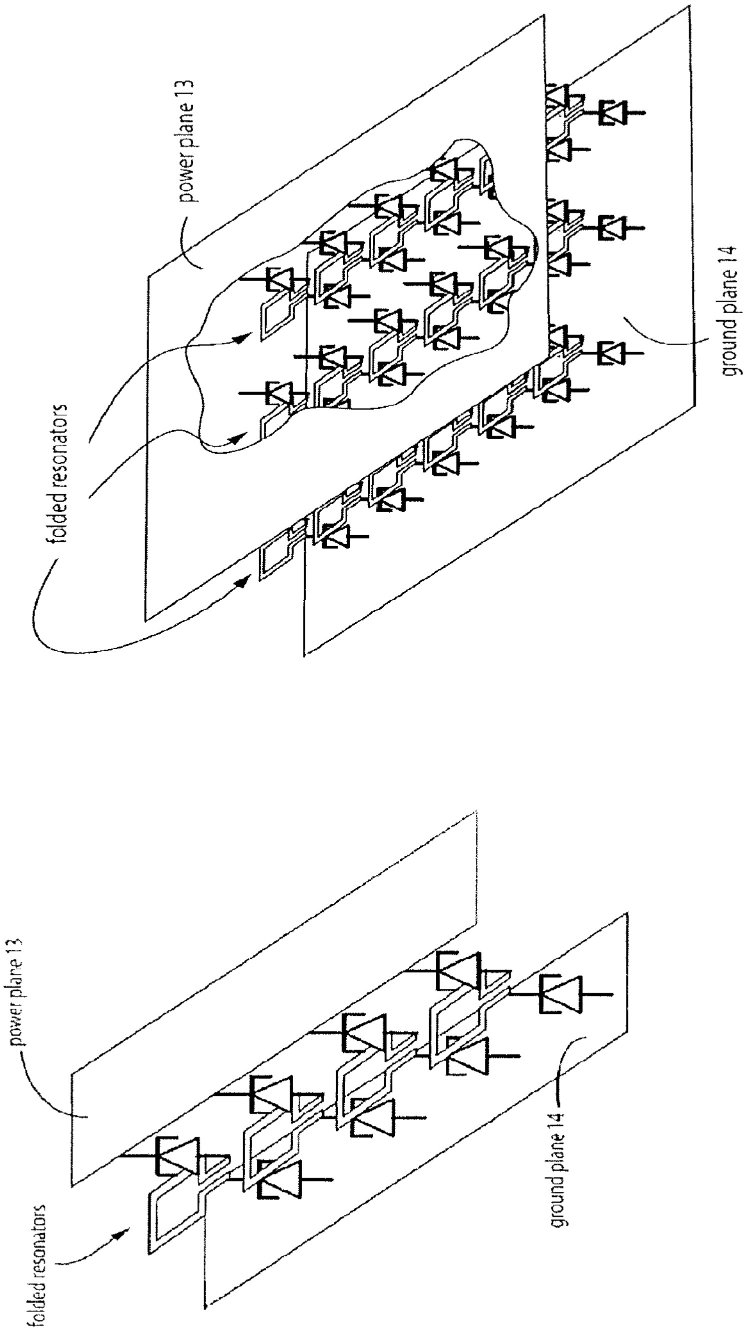
FIG. 68A is a schematic illustration of an array of folded resonators configured for direct solar power conversion through rectification of induced current on the resonators.

Unlike, the '217 patent, the folded resonators need not be placed in random directions in order to couple to circularly polarized sunlight. FIG. 68A shows an array of folded resonators arranged in a configuration with a) a ground plane, b) for every folded resonator, a diode is attached connecting the ground plane to the folded resonator, c) another diode attached to other side of the folded resonator, and 6) a power plane attached to this other diode. Indeed, FIG. 68A is a schematic illustration of an array of folded resonators configured for direct solar power conversion through rectification of induced current on the resonators. In this configuration (although the invention is not so limited), the ground plane, the array of folded resonators, and the power plane exist in different planes.

On forward bias during one half cycle of the solar radiation wave, electrons move from ground into resonator, and electrons in the resonator move to the power plane. On the other half cycle of the solar radiation wave, the diodes are reverse biased, and the electrons are blocked from returning back to ground. Thus, the power plane becomes charged with electrons, i.e., becomes a charge source which can be connected to an external load to drive current through the load back to ground. The substrate(s) which support the diodes and the folded resonator are preferably insulators for both electrical isolation and reducing any capacitance that could compromise the speed of the diode switching.

Figure 68B:
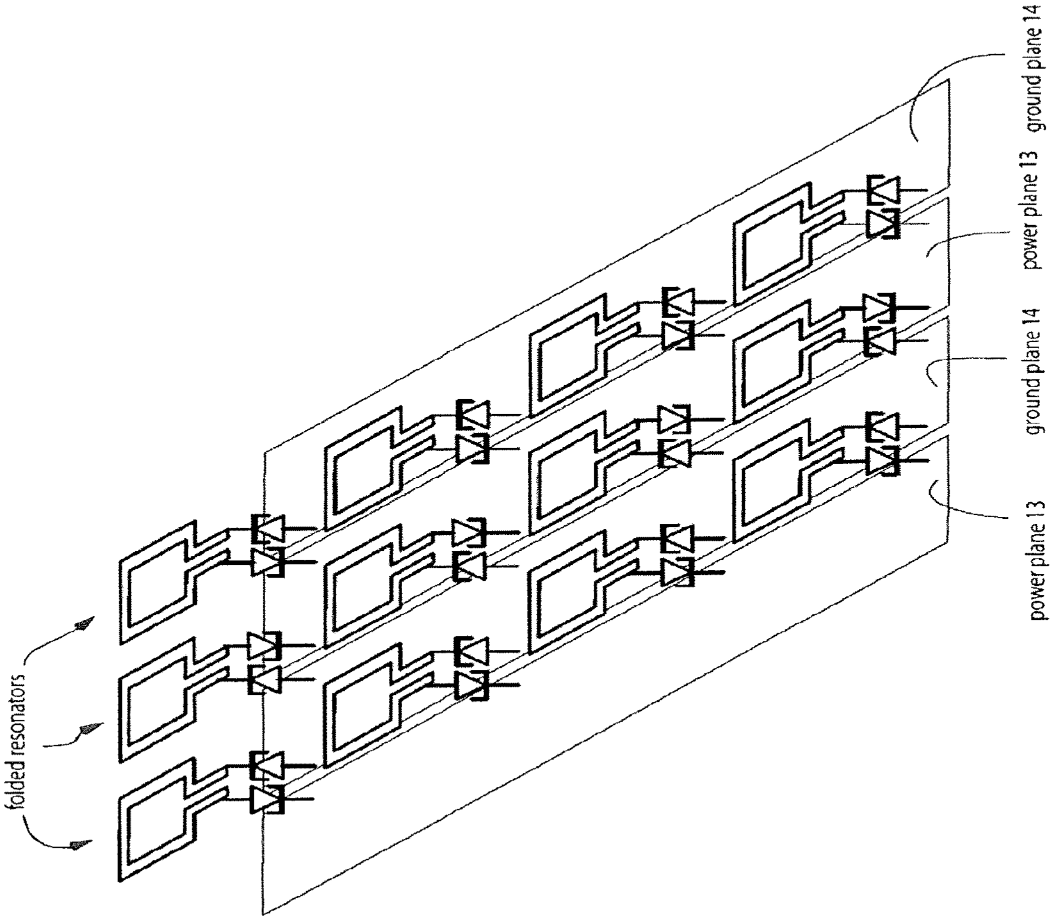
FIG. 68B is a schematic illustration of another array of folded resonators configured for direct solar power conversion through rectification of induced current on the resonators.

FIG. 68B is a schematic illustration of another array of folded resonators configured for direct solar power conversion through rectification of induced current on the resonators. In this configuration (although the invention is not so limited), the power plane and the ground plane are in the same plane, and the array of folded resonators exists above that plane.

Figure 69:
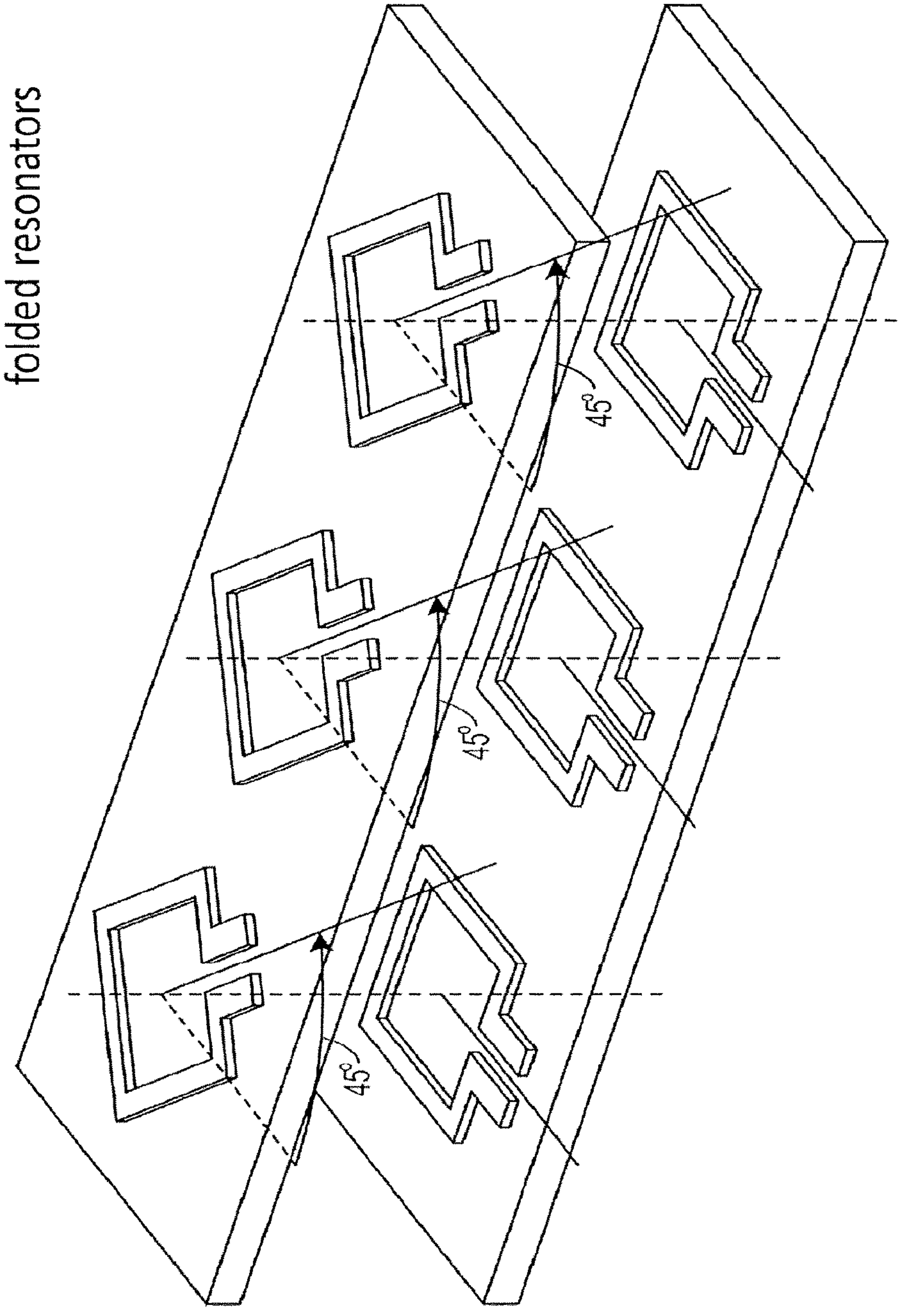
FIG. 69 is a schematic illustration of stacked array of folded resonators having a predetermined angular offset.

Furthermore, as shown in FIG. 69, stacked arrays of folded resonators can be used with the resonators for example on the top substrate rotated for example 45° from the folded resonators in the lower substrate. What is shown in FIG. 69 is an exploded view of two successively stacked planes of folded resonators disposed on two different substrates. The resonators are predominantly rectangular within the respective planes, having a having a first pair of sides extending in a primary direction and a second pair of sides extending in a secondary direction. The directionality of the resonators are indicated by an angular-alignment line extending from a central point between the sides. Within each plane, the angular alignment lines of the resonators are parallel to one another. Here, the central point of each resonator of the uppermost layer is coaxially-aligned with the central point of a corresponding resonator of the lowermost resonator, defining a central axis. The alignment axis of the resonator of the uppermost layer is angularly offset a desired offset angle from the alignment axis of the resonator of the lowermost layer about the central axis. Here, the offset angle is 45 degrees.

Angles other than 45° can be used, and more than one pair of substrates can be used. In this way, the likelihood that a solar wave will pass through the stacked array of folded resonators without coupling its energy into one of the folded resonators is reduced. Vertical interconnects (not shown) can be used to connect individual ones of the folded resonators to respective ground and power planes.

Figure 70:
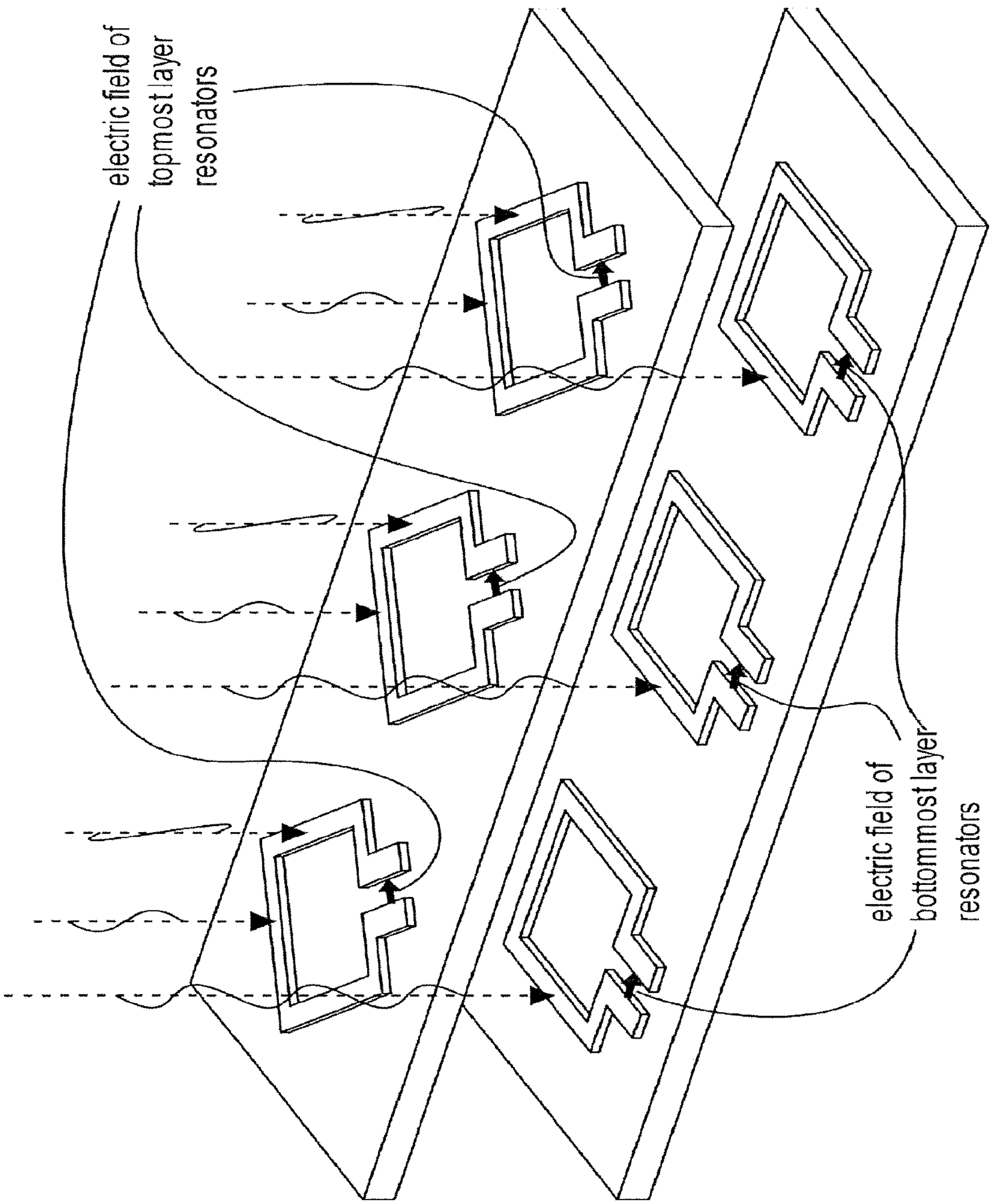
FIG. 70 is a schematic illustration of light coupling to the stacked array of folded resonators of FIG. 69.

FIG. 70 is a depiction of components of circularly polarized light interacting with stacked arrays of folded resonators. Here, by way of example, a first set of vertical interconnects would connect the all the left-side opposing electrodes to a ground plane, and a second set of vertical interconnects would connect all the right-side opposing electrodes to a power plane.

Figure 71:
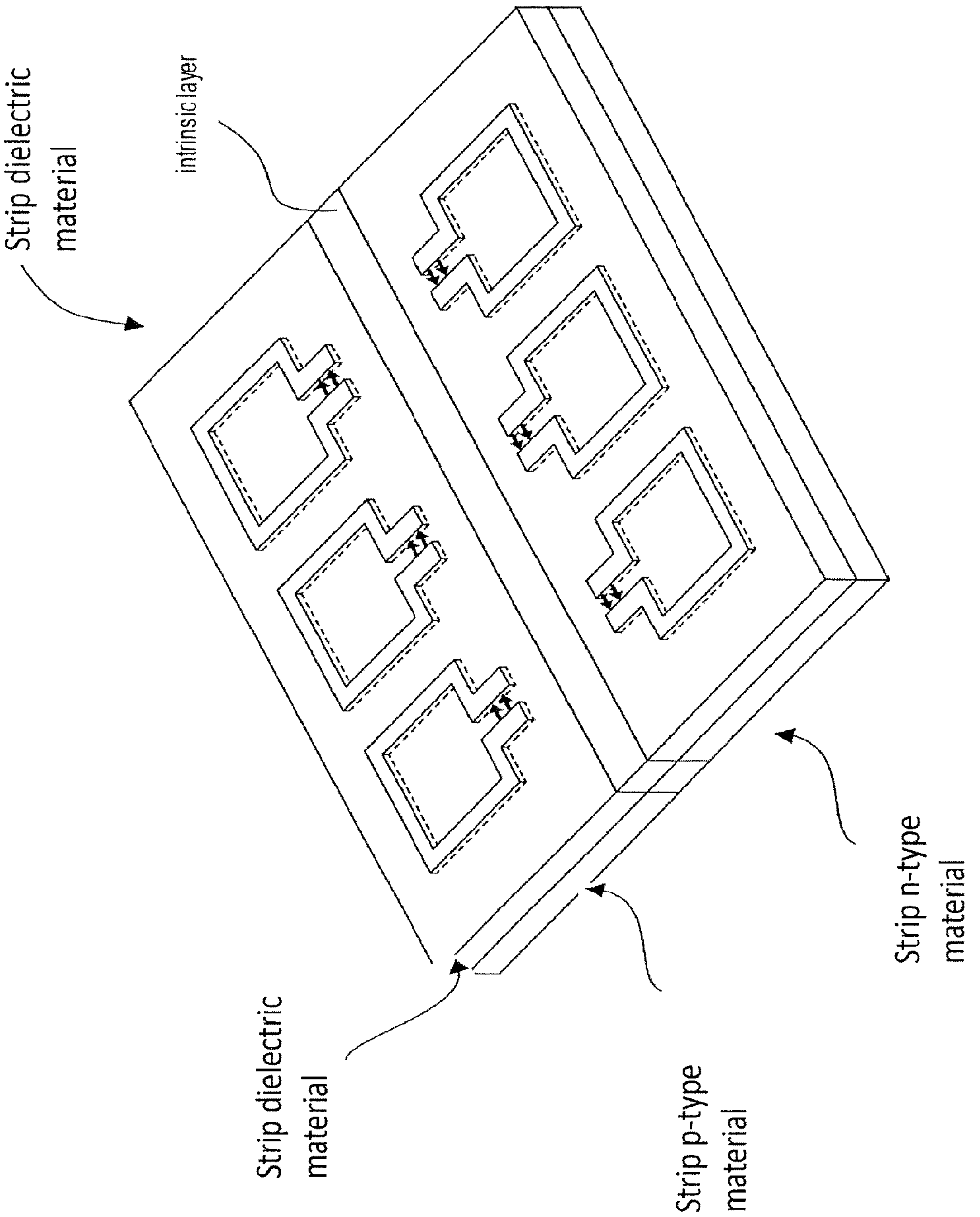
FIG. 71 is a schematic illustration of an array of folded resonators disposed on a photovoltaic panel.

Returning now to a consideration of photoelectric conversion cells converting sunlight into electric power, the folded resonators of the invention can be used to generate the above-noted intensified electric fields in regions at least proximate to the p-i-n junctions, as discussed with regards to FIGS. 45B and 53. FIG. 71 depicts one example an array of folded resonators placed on a solar panel, where the folded resonators are isolated from the p-type and n-type materials by a dielectric material.

Figure 72:
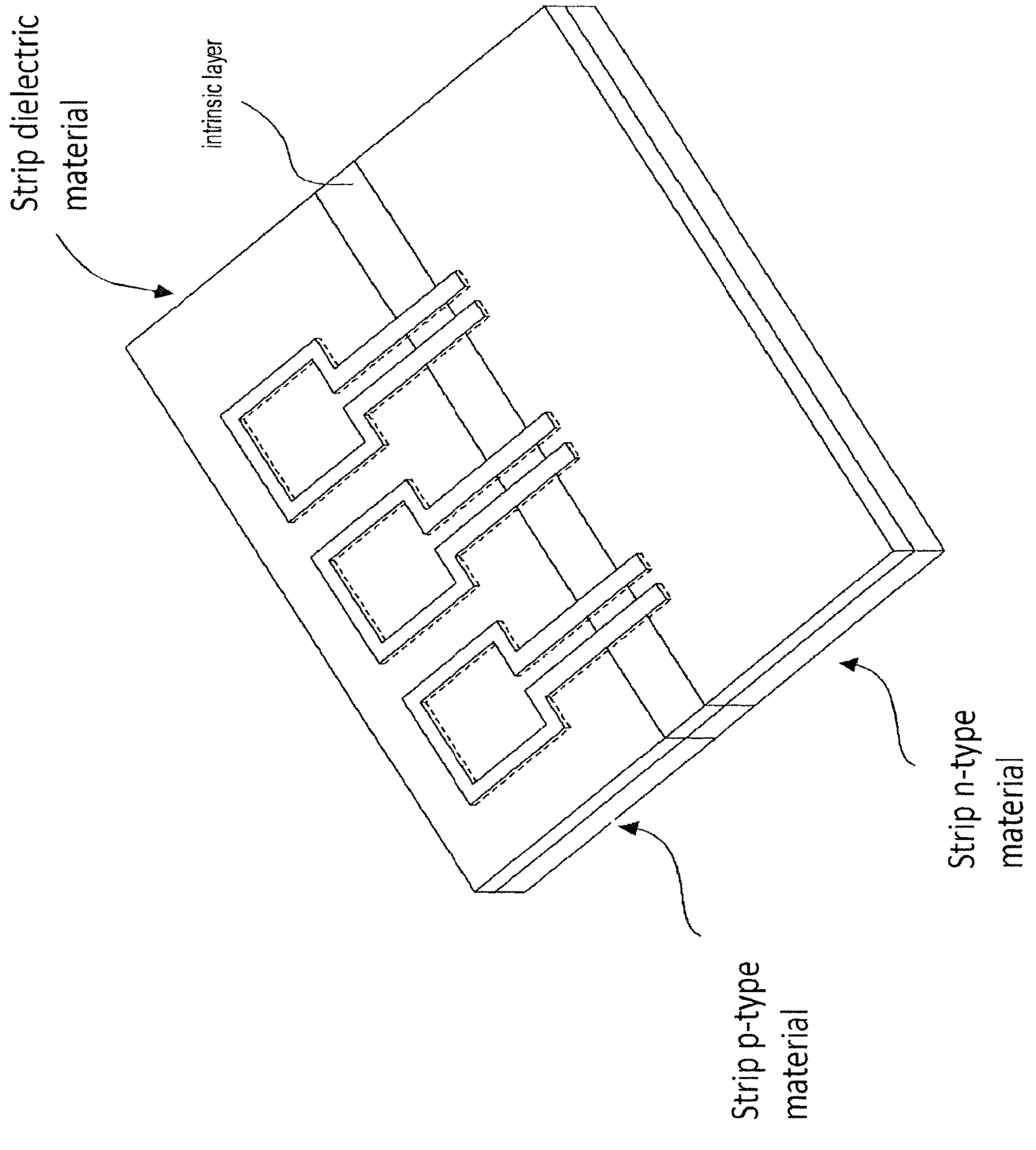
FIG. 72 is a schematic illustration of another array of folded resonators disposed on a photovoltaic panel.

FIG. 72 depicts another example an array of folded resonators placed on a solar panel, where the opposing electrodes of each folded resonator extends over the intrinsic layer.

Figure 73:
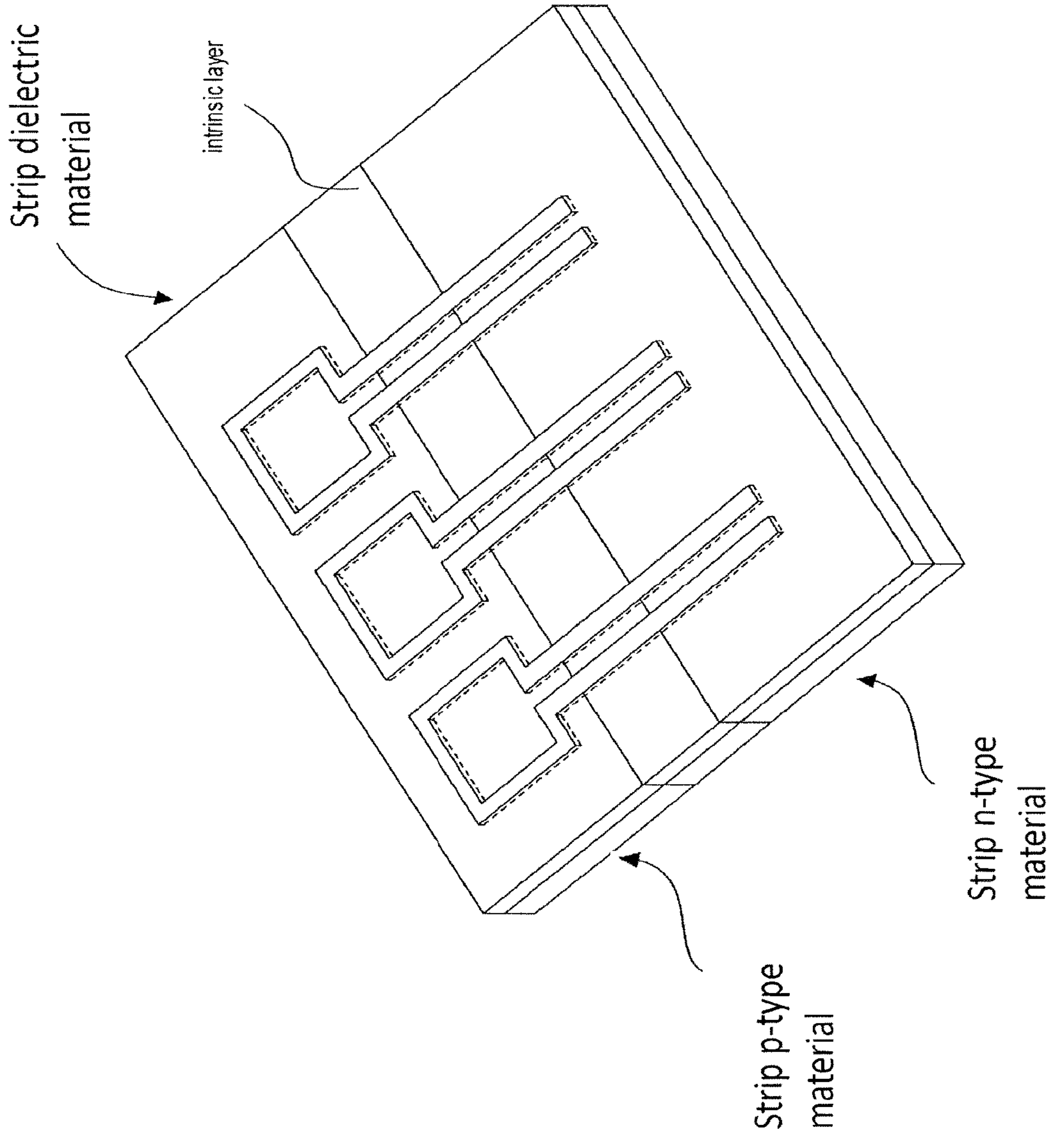
FIG. 73 is a schematic illustration of yet another array of folded resonators disposed on a photovoltaic panel.

FIG. 73 depicts another example an array of folded resonators placed on a solar panel, where the opposing electrodes of each folded resonator extends over the intrinsic layer and over above the n-type layer.

Figure 74:
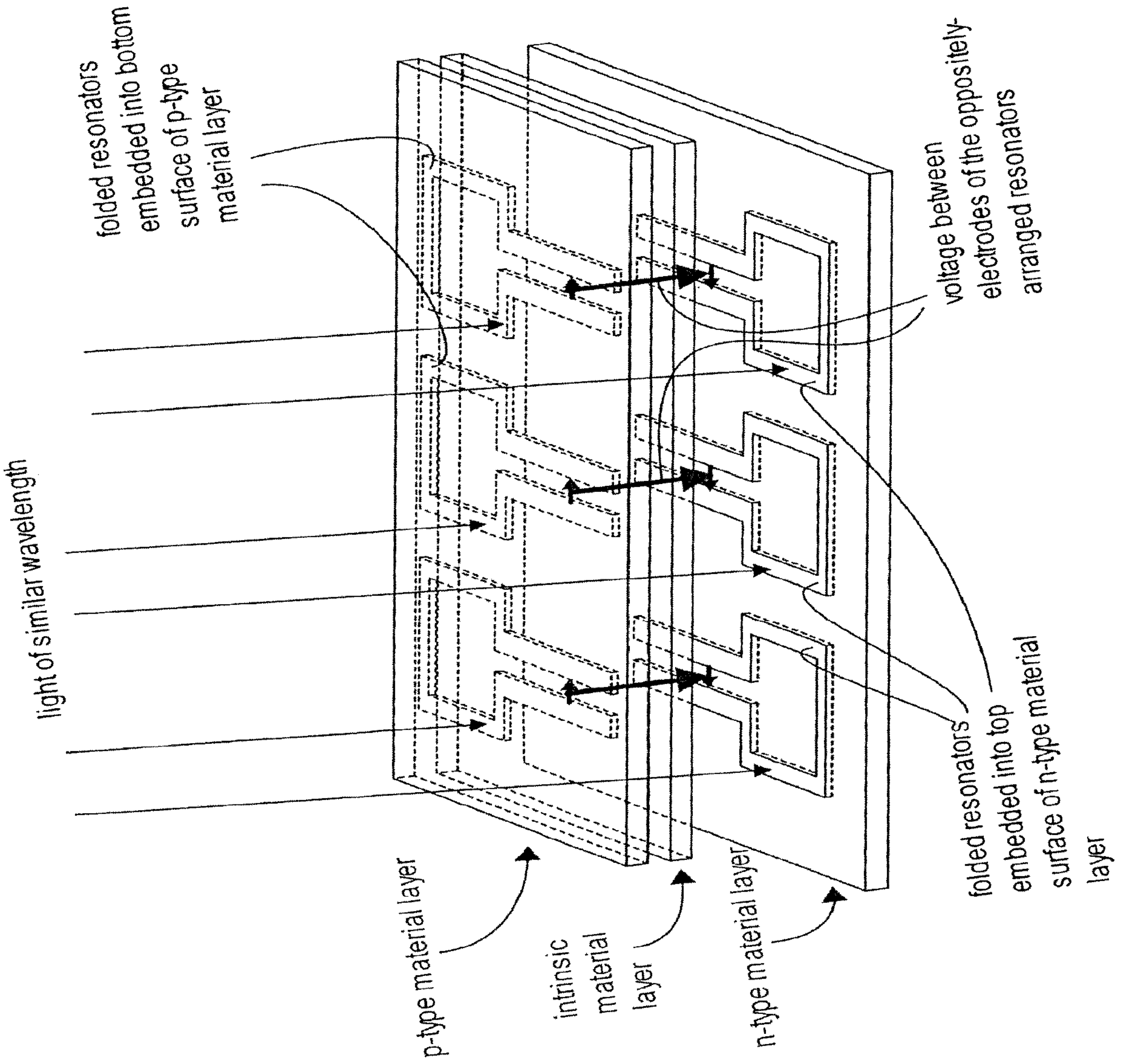
FIG. 74 is a schematic illustration of an embedded array of folded resonators disposed in a photovoltaic panel.
Figure 75:
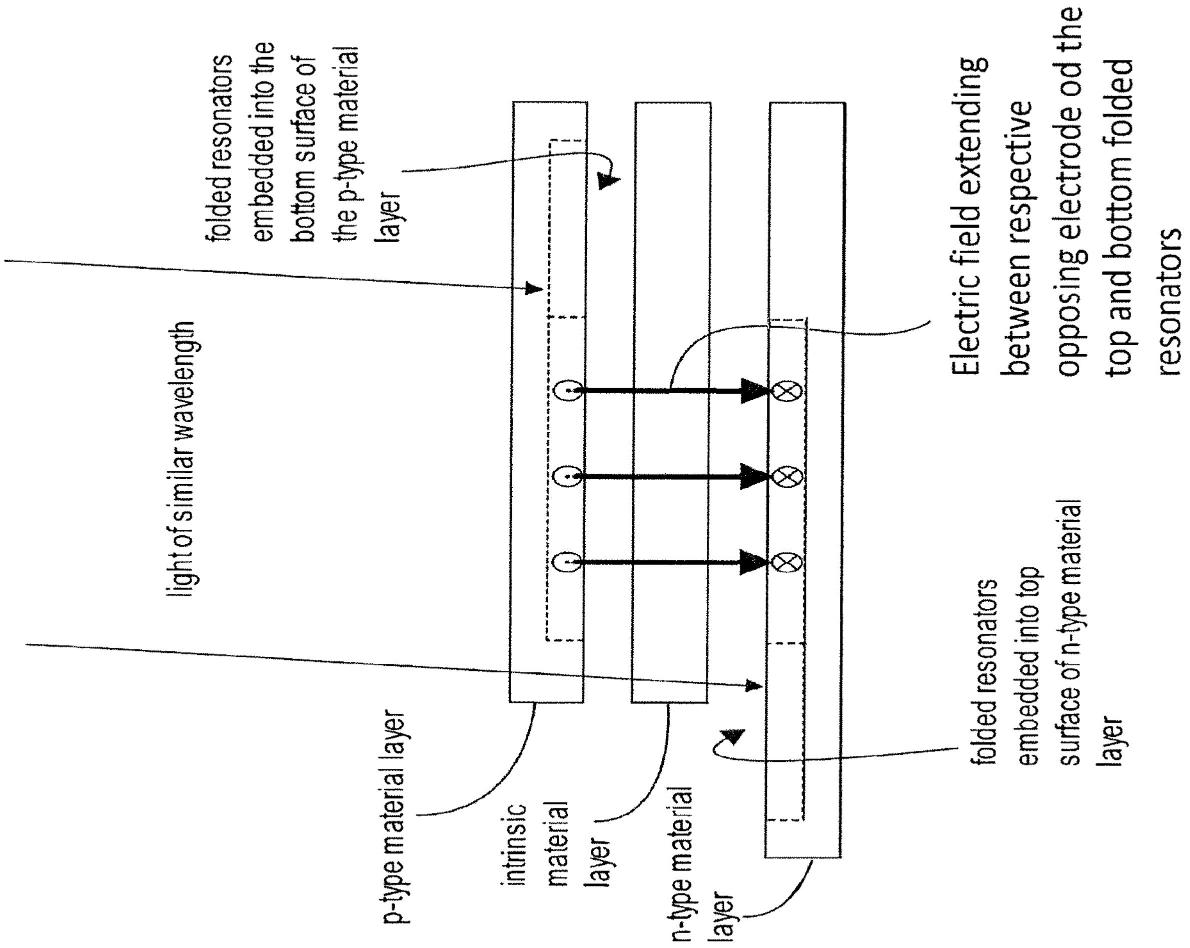
FIG. 75 is a schematic illustration of a sectional view of the embedded array of folded resonators of FIG. 74.

FIG. 74 depicts another example an array of folded resonators embedded in a solar panel. FIG. 74 is shown as an exploded view showing a p-type material layer block, an intrinsic material layer block, and an n-type material layer separating the p-type and n-type materials. FIG. 75 depicts a sectional view of the embedded array of folded resonators of FIG. 74 Figure. In these figures, a first plurality of folded resonators embedded into the bottom surface of the p-type material layer are arranged with their electrodes extending in a first direction in parallel with one another. Another plurality of folded resonators embedded into the top surface of the n-type material layer are arranged with their electrodes extending oppositely to the first direction of the first plurality of folded resonators, in parallel with one another. In this illustration, the length of the electrodes of the first plurality of folded resonators overlaps the length of the second plurality of folded resonators. In this illustration, the p-type material layer contacts the top surface of the intrinsic material layer, and the n-type material layer contacts the bottom surface of the intrinsic material layer such that the resonators are separated by the intrinsic material layer.

Because the resonators of the top layer are oppositely aligned to the resonators in the bottom layer, for a given incident light passing through the layers, the first plurality of resonators should create a field in the top layer that is opposite the field created in the bottom layer. (With both of the folded resonators having one opposed electrode or the other as node, there will always exist an instantaneous electric field from one electrode of the top folded resonators to one electrode of the bottom folded resonator and across the intrinsic material layer.) In one embodiment of the invention, because of this field across the intrinsic material layer, electrons of any separated electron-hole pair (a pair that is being normally separated by the "built-in" electric field across the p-i-n material) will be accelerated by the electric field reducing the chance of the separated electron-hole pairs recombining, and improving collection efficiency. While it is preferred that the acceleration direct the electron toward one of the collection electrodes, any displacement of the electron away from the hole of the electron-hole pair should reduce the chance of the separated electron-hole pairs recombining, and thus improving collection efficiency.

Accordingly, the energy augmentation structures of the present invention can be used in conjunction with the energy converters described herein in a wide variety of applications, including but not limited to, medical treatments using energy generated in situ within a subject being treated (whether using an energy converter or not), solar cells, adhesives and other resins, sterilization treatment for various materials (such as wastewater, beverages, etc). The use of energy converters in such applications has been described in the following: US Published Application No. 2008/0248001; US Published Application No. 2009/0104212; US Published Application No. 2009/0294692; US Published Application No. 2010/0003316; US Published Application No. 2010/0016783; US Published Application No. 2010/0261263; US Published Application No. 2010/0266621; US Published Application No. 2011/0021970; US Published Application No. 2011/0117202; US Published Application No. 2011/0126889; US Published Application No. 2011/0129537; US Published Application No. 2011/0263920; US Published Application No. 2012/0064134; US Published Application No. 2012/0089180; US Published Application No. 2013/0102054; US Published Application No. 2013/0129757; US Published Application No. 2013/0131429; US Published Application No. 2013/0156905; US Published Application No. 2013/0171060; US Published Application No. 2013/0240758; US Published Application No. 2014/0134307; US Published Application No. 2014/0163303; US Published Application No. 2014/0166202; US Published Application No. 2014/0222117; US Published Application No. 2014/0242035; US Published Application No. 2014/0243934; US Published Application No. 2014/0272030; US Published Application No. 2014/0323946; US Published Application No. 2014/0341845; US Published Application No. 2014/0343479; US Published Application No. 2015/0182934; US Published Application No. 2015/0202294; US Published Application No. 2015/0246521; US Published Application No. 2015/0251016; US Published Application No. 2015/0265706; US Published Application No. 2015/0283392; US Published Application No. 2015/0290614; US Published Application No. 2016/0005503; US Published Application No. 2016/0067524; US Published Application No. 2016/0159065; US Published Application No. 2016/0243235; US Published Application No. 2016/0263393; US Published Application No. 2016/0325111; US Published Application No. 2016/0331731; US Published Application No. 2016/0354467; US Published Application No. 2016/0362534; US Published Application No. 2017/0027197; US Published Application No. 2017/0043178; US Published Application No. 2017/0050046; US Published Application No. 2017/0096585; US Published Application No. 2017/0113061; US Published Application No. 2017/0121472; US Published Application No. 2017/0154866; US Published Application No. 2017/0157418; US Published Application No. 2017/0162537; US Published Application No. 2017/0173350; US Published Application No. 2017/0186720; US Published Application No. 2017/0190166; US Published Application No. 2017/0196977; US Published Application No. 2017/0239489; US Published Application No. 2017/0239637; US Published Application No. 2017/0240717; US Published Application No. 2017/0258908; US Published Application No. 2017/0319868; US Published Application No. 2017/0319869; US Published Application No. 2018/0036408; US Published Application No. 2018/0154171; US Published Application No. 2018/0154178; US Published Application No. 2018/0169433; US Published Application No. 2018/0170028; US Published Application No. 2018/0269174; US Published Application No. 2018/0271121; US Published Application No. 2018/0304225; US Published Application No. 2018/0311355; US Published Application No. 2018/0317307; US Published Application No. 2018/0344850; US Published Application No. 2018/0358327; US Published Application No. 2019/0016869; US Published Application No. 2019/0022221; US Published Application No. 2019/0100680; US Published Application No. 2019/0134419; US Published Application No. 2019/0134595; US Published Application No. 2019/0134596; US Published Application No. 2019/0157234; US Published Application No. 2019/0168015; US Published Application No. 2019/0184190; US Published Application No. 2019/308030; US Published Application No. 2019/0336605; US Published Application No. 2019/0336785; US Published Application No. 2019/0336786; US Published Application No. 2019/0341364; U.S. application Ser. No. 16/074,707, filed Aug. 1, 2018; U.S. application Ser. No. 16/516,463, filed Jul. 19, 2019; U.S. application Ser. No. 16/554,831, filed Aug. 29, 2019 U.S. application Ser. No. 16/599,732, filed Oct. 11, 2019; U.S. application Ser. No. 16/674,435, filed Nov. 5, 2019; and U.S. application Ser. No. 16/728,803, filed Dec. 27, 2019; the contents of each of which are hereby incorporated by reference in their entireties. The energy augmentation structures and/or energy converters described herein have uses with the subject matter in the above noted published and unpublished US patent applications.

The following are exemplary embodiments of the present invention:

Embodiment 1. An energy emitter comprising:

at least one energy augmentation structure; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present.

Embodiment 2. The emitter of Embodiment 1, wherein the at least one energy augmentation structure comprises a structure in which a locally intensified electric field exists in one part of the structure when the structure receives electromagnetic energy.

Embodiment 3. The emitter of Embodiment 1 or 2, wherein the at least one energy augmentation structure comprises at least one resonator dimensioned to be resonant with the applied electromagnetic energy.

Embodiment 4. The emitter of any one of Embodiments 1-3, wherein the resonator comprises a folded resonator.

Embodiment 5. The emitter of Embodiment 4, wherein the folded resonator comprises electrical conductors configured as a fractal pattern.

Embodiment 6. The emitter of Embodiment 4, wherein the folded resonator comprises a ¾ wavelength resonator having opposing ends folded inwards from a center of the folded resonator with a gap in between the opposing ends.

Embodiment 7. The emitter of Embodiment 6, wherein the locally intensified electric field exists in a vicinity of the opposing ends.

Embodiment 8. The emitter of Embodiment 4, wherein the folded resonator comprises a ¾ wavelength resonator having opposing ends folded outwards from a center of the folded resonator with a gap in between the opposing ends.

Embodiment 9. The emitter of Embodiment 8, wherein the locally intensified electric field exists in a vicinity of the opposing ends.

Embodiment 10. The emitter of Embodiment 4, wherein the resonator comprises a fractal pattern.

Embodiment 11. The emitter of Embodiment 10, wherein the fractal pattern comprises a three-dimensional fractal pattern.

Embodiment 12. The emitter of Embodiment 4, wherein the at least one resonator comprises a plurality of resonators.

Embodiment 13. The emitter of Embodiment 12, wherein the resonators are disposed on a sheet.

Embodiment 14. The emitter of Embodiment 13, wherein the sheet comprises a sheet for disposal within a medium to be treated.

Embodiment 15. The emitter of Embodiment 13, wherein the sheet comprises a flexible sheet for disposal within a medium to be treated.

Embodiment 16. The emitter of Embodiment 13, wherein the sheet comprises a rigid sheet for disposal within a medium to be treated.

Embodiment 17. The emitter of Embodiment 13, wherein the plurality of resonators comprises an array of the resonators disposed on a sheet.

Embodiment 18. The emitter of Embodiment 12, wherein each of the resonators comprises a free-standing resonator.

Embodiment 19. The emitter of Embodiment 18, wherein the free-standing resonator is disposed within a medium to be treated.

Embodiment 20. The emitter of any one of Embodiments 1 to 19, wherein the at least one energy augmentation structure comprises a first level of metallic patterns and a second level of metallic patterns offset in in at least one of a lateral or axial direction from the first level of metallic patterns.

Embodiment 21. The emitter of Embodiment 20, wherein at least one of the metallic patterns comprises a first resonator dimensioned to be resonant with an applied electromagnetic energy.

Embodiment 22. The emitter of Embodiment 21, wherein the at least one of the metallic patterns comprises a folded resonator having opposing electrodes with electric fields directed in between, and the energy converter is positioned between the opposing electrodes or within fringing electric field of the opposing electrodes.

Embodiment 23. The emitter of Embodiment 22, wherein the opposing electrodes are directed external to the folded resonator and parallel to one another.

Embodiment 24. The emitter of Embodiment 22, wherein the opposing electrodes are directed internal to the folded resonator and parallel to one another.

Embodiment 25. The emitter of any one of Embodiments 22-24, wherein the folded resonator comprises a % k folded resonator.

Embodiment 26. The emitter of Embodiment 20, wherein the at least one of the metallic patterns comprises a plurality of the folded resonators concentrically arranged and optionally co-planar to one another, such that the external opposing electrodes of each folded resonator do not overlap spatially with the external opposing electrodes of the other of the plurality of folded resonators.

Embodiment 27. The emitter of Embodiment 20, wherein the at least one of the metallic patterns comprises a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 28. The emitter of any one of Embodiments 1 to 27, wherein the at least one energy augmentation structure comprises at least one of Au, Ag, Cu, Al, transparent metal oxides or refractory metals.

Embodiment 29. The emitter of any one of Embodiments 1 to 28, further comprising an antireflection film disposed on the at least one energy augmentation structure or the energy converter.

Embodiment 30. The emitter of any one of Embodiments 1 to 29, wherein the at least one energy augmentation structure is disposed in vicinity of a down conversion material comprising the energy converter.

Embodiment 31. The emitter of any one of Embodiments 1 to 29, wherein the at least one energy augmentation structure is disposed in vicinity of an up-conversion material comprising the energy converter.

Embodiment 32. The emitter of any one of Embodiments 1 to 29, wherein the at least one energy augmentation structure is disposed in vicinity of a phosphor comprising the energy converter.

Embodiment 33. The emitter of any one of Embodiments 1 to 29, wherein the at least one energy augmentation structure is disposed in vicinity of a piezoelectric device comprising the energy converter.

Embodiment 34. The emitter of Embodiment 33, wherein the piezoelectric device is configured to receive sonic or acoustic energy and emit at least one of ultraviolet or visible light in response to absorbing the sonic or acoustic energy.

Embodiment 35. The emitter of any one of Embodiments 1 to 29, wherein the at least one energy augmentation structure is disposed in vicinity of a mechanoluminescent device comprising the energy converter.

Embodiment 36. The emitter of Embodiment 35, wherein the mechanoluminescent device is configured to receive sonic or acoustic energy and emit at least one of ultraviolet or visible light in response to absorbing the sonic or acoustic energy.

Embodiment 37. The emitter of any one of Embodiments 1 to 36, wherein the at least one energy augmentation structure is disposed inside a plasma capsule device comprising the energy converter.

Embodiment 38. The emitter of Embodiment 37, wherein the plasma capsule device is configured to receive radio frequency or microwave energy and emit at least one of ultraviolet or visible light in response to absorbing the radio frequency or microwave energy.

Embodiment 39. The emitter of any one of Embodiments 1 to 29, wherein the at least one energy augmentation structure is disposed in vicinity of an x-ray stimulated phosphor comprising the energy converter.

Embodiment 40. The emitter of Embodiment 39, wherein the x-ray stimulated phosphor emits one of ultraviolet or visible light in response to absorbing x-rays.

Embodiment 41. The emitter of Embodiment 40, wherein the x-ray stimulated phosphor emits the one of ultraviolet or visible light for at least a time of 1 minute after x-ray stimulation.

Embodiment 42. The emitter of Embodiment 40, wherein the x-ray stimulated phosphor emits the one of ultraviolet or visible light for at least a time of 10 minutes after x-ray stimulation.

Embodiment 43. The emitter of Embodiment 40, wherein the x-ray stimulated phosphor emits the one of ultraviolet or visible light for at least a time of 60 minutes after x-ray stimulation.

Embodiment 44. The emitter of Embodiment 39, wherein the x-ray stimulated phosphor emits lower energy x-rays in response to absorbing higher energy x-rays.

Embodiment 45. The emitter of any one of Embodiments 1 to 44, wherein the energy received from the energy source is one or more selected from acoustic waves, sound waves, radio waves, microwaves, far infrared, near infrared, visible light, UV, x-rays, gamma rays, electron beams, and proton beams.

Embodiment 46. The emitter of any one of Embodiments 1 to 45, wherein the energy converter being disposed in a vicinity of the at least one energy augmentation structure comprises a conductive coupling of the energy converter to the at least one energy augmentation structure.

Embodiment 47. The emitter of Embodiment 46, wherein the conductive coupling comprises a physical conductive connection between the energy converter and the at least one energy augmentation structure.

Embodiment 48. The emitter of any one of Embodiments 1 to 29, wherein the energy converter comprises either one or both of (i) a down converter converting ultraviolet or blue light into red, yellow, or green light, or (ii) an up converter converting infrared or red light into yellow, green light, or blue light.

Embodiment 49. The emitter of any one of Embodiments 1 to 29, wherein the at least one energy augmentation structure comprises a plurality of energy collectors.

Embodiment 50. The emitter of Embodiment 49, wherein the energy converters are positioned to convert energy being internally scattered within the energy collectors.

Embodiment 51. The emitter of Embodiment 49, wherein the energy collectors comprise a metal core cladded with a high-K dielectric and a subsequent cladding of a low-K dielectric.

Embodiment 52. The emitter of Embodiment 49, wherein the energy collectors comprise a radial pattern of collectors.

Embodiment 53. The emitter of Embodiment 7, wherein the energy collectors comprise a fractal pattern.

Embodiment 54. The emitter of Embodiment 53, wherein the fractal pattern is embedded within a dielectric material.

Embodiment 55. The emitter of any one of Embodiments 1 to 54, wherein the at least one energy augmentator comprises metallic conductors including at least one of Au, Ag, Cu, Ni, Pt, Pd, Co, Ru, Rh, Al, Ga, or a combination or alloys or layers thereof.

Embodiment 56. The emitter of any one of Embodiments 1 to 54, wherein the energy converter comprises at least one of Y2O3, Y2O2S, NaYF4, NaYbF4, YAG, YAP, Nd2O3, LaF3, LaCl3, La2O3, TiO2, LuPO4, YVO4, YbF3, YF3, Na-doped YbF3, or SiO2 or alloys or layers thereof.

Embodiment 57. The emitter of Embodiment 56, wherein the energy converter further comprises a dopant including at least one of Er, Eu, Yb, Tm, Nd, Tb, Ce, Y, U, Pr, La, Gd and other rare-earth species or a combination thereof.

Embodiment 58. The emitter of Embodiment 57, wherein the dopant is included at a concentration of 0.01%-50% by mol concentration.

Embodiment 59. The emitter of any one of Embodiments 1 to 54, wherein the energy converter comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+, Er3+; ZnS:$Tb^{3+}$; Y2O3:$Tb^{3+}$; Y2O3:Tb3+, Er3+; ZnS: Mn2+; ZnS:Mn,Er3+.

Embodiment 60. The emitter of any one of Embodiments 1 to 54, wherein the energy converter comprises an up converter including at least one of Y2O3, Y2O2S, NaYF4, NaYbF4, YAG, YAP, Nd2O3, LaF3, LaCl3, La2O3, TiO2, LuPO4, YVO4, YbF3, YF3, Na-doped YbF3, or SiO2 or alloys or layers thereof.

Embodiment 61. The emitter of any one of Embodiments 1 to 54, wherein the energy converter comprises an up converter including at least one of Tm3+ doped flourozirconate glasses, LuPO4:Yb3+, $Tm^{3+}$, and YbPO4:Er3+ nanocrystals, tellurium and germanium oxides, tellurium and germanium oxides doped with at least one Tm, Yb, Ho, Er, or Pr, Yb3+ doped $BaZrO_3$, $Nd^{3+}$:Cs2NaGdCl6, $Nd^{3+}$, $Yb^{3+}$:Cs2NaGdCl6, $Nd^{3+}$ and Ho3+ co-doped-based ZrF4 fluoride glasses, $Tm^{3+}$/$Yb^{3+}$-codoped TeO2-Ga2O3-R2O (R=Li, Na, K) glasses, and metal-to-ligand charge transfer (MLCT) transition materials, and MLCT transition materials including [Ru(dmb)3]2+ (dmb=4,4-dimethyl-2,2-bipyridine).

Embodiment 62. An energy augmentation structure capable of capturing one or more wavelengths of electromagnetic energy, and augmenting the one or more wavelengths of electromagnetic energy in at least one property.

Embodiment 63. The energy augmentation emitter of Embodiment 62, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 64. The energy augmentation structure of Embodiment 62, comprising a folded resonator having opposing electrodes with electric fields directed in between.

Embodiment 65. The energy augmentation structure of Embodiment 64, wherein the opposing electrodes are directed external to the folded resonator and parallel to one another.

Embodiment 66. The energy augmentation structure of Embodiment 64, wherein the opposing electrodes are directed internal to the folded resonator and parallel to one another.

Embodiment 67. The energy augmentation structure of any one of Embodiments 64 to 66, wherein the folded resonator comprises a % k folded resonator.

Embodiment 68. The energy augmentation structure of Embodiment 64, wherein the folded resonator is a plurality of the folded resonators concentrically arranged and optionally co-planar to one another, such that the external opposing electrodes of each folded resonator do not overlap spatially with the external opposing electrodes of the other of the plurality of folded resonators.

Embodiment 69. The energy augmentation structure of Embodiment 64, wherein the folded resonator is a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 70. An energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Embodiment 71. The energy collector of Embodiment 70, wherein the at least one energy converter is at least one member selected from the group consisting of phosphors, lumiphors, electroluminescent particles, up-converters, down-converters, and scintillators.

Embodiment 72. The energy collector of Embodiment 70 or 71, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 73. The energy collector of any one of Embodiments 70 to 72, wherein having the energy converter disposed in a vicinity of the at least one energy augmentation structure comprises conductively coupling the at least one energy converter to the at least one energy augmentation structure.

Embodiment 74. The energy collector of Embodiment 73, wherein conductively coupling comprises having the at least one energy converter be proximate the at least one energy augmentation structure, physically located within the at least one energy augmentation structure, or located within a generated electric field of the at least one energy augmentation structure.

Embodiment 75. The energy collector of Embodiment 73, wherein conductively coupling comprises a physical conductive connection between the at least one energy converter and the at least one energy augmentation structure.

Embodiment 76. The energy collector of Embodiment 70, wherein the applied electromagnetic energy is selected from radio waves, microwaves, far infrared, near infrared, visible light, UV, x-rays, gamma rays, electron beams, and proton beams.

Embodiment 77. The energy collector of Embodiment 70, wherein the at least one energy augmentation structure comprises a first resonator dimensioned to be resonant with the applied electromagnetic energy, said first resonator optionally comprising a fractal pattern.

Embodiment 78. The energy collector of Embodiment 70, wherein the energy augmentation structure comprises a folded resonator having opposing electrodes with electric fields directed in between.

Embodiment 79. The energy collector of Embodiment 76, wherein the opposing electrodes are directed external to the folded resonator and parallel to one another.

Embodiment 80. The energy collector of Embodiment 76, wherein the opposing electrodes are directed internal to the folded resonator and parallel to one another.

Embodiment 81. The energy collector of any one of Embodiments 78-80, wherein the folded resonator comprises a ¾ λfolded resonator.

Embodiment 82. The energy collector of Embodiment 78, wherein the folded resonator is a plurality of the folded resonators concentrically arranged and optionally co-planar to one another, such that the external opposing electrodes of each folded resonator do not overlap spatially with the external opposing electrodes of the other of the plurality of folded resonators.

Embodiment 83. The energy collector of Embodiment 78, wherein the folded resonator is a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 84. An energy collector comprising:

at least one energy augmentation structure of any one of Embodiments 62-69, wherein the at least one energy augmentation structure is configured to resonate at a first wavelength λ1 which is a frequency included within a radiant source of energy from which power is to be harvested;

a conversion device capable of converting the energy from the radiant source into electrical power, wherein electric fields from the augmentation structure permeate into a region of the converter and augment energy conversion.

Embodiment 85. The collector of Embodiment 84, wherein the at least one energy augmentation structure comprises a folded resonator.

Embodiment 86. The collector of Embodiment 85, wherein the folded resonator comprises a ¾ λfolded resonator.

Embodiment 87. The collector of Embodiment 84, wherein the at least one energy augmentation structure comprises a fractal antenna.

Embodiment 88. The collector of any one of Embodiments 84-87, wherein the conversion device comprises a photovoltaic device converting the energy from the radiant source into electricity.

Embodiment 89. The collector of any one of Embodiments 84-87, wherein the conversion device comprises a thermoelectric device converting the energy from the radiant source into electricity.

Embodiment 90. The collector of any one of Embodiments 84-87, wherein the conversion device comprises a thermionic device converting the energy from the radiant source into electricity.

Embodiment 91. The collector of any one of Embodiments 84-91, wherein the conversion device comprises at least one rectifying device connected in series with the at least one energy augmentation structure for rectifying oscillating current induced in the at least one energy augmentation structure from the energy absorbed from the radiant source.

Embodiment 92. The collector of Embodiment 91, wherein the at least one energy augmentation structure comprises a folded resonator; and the at least one rectifying device comprises a tunneling or vacuum diode.

Embodiment 93. The collector of Embodiment 84, wherein the conversion device comprises a photovoltaic converter having, a first collector, a p-type material, a n-type material, a second collector, at least one of the p-type material or the n-type material is in contact with the first collector, a remaining one of the p-type material or the n-type material, not in contact with the first collector, is in contact with the second collector, the p-type material and the n-type material form an intrinsic layer there in between, and the one energy augmentation structure comprises a folded resonator having opposing electrodes producing the electric fields, and the electric fields permeate into one or more of the p-type material, the n-type material, and the intrinsic layer.

Embodiment 94. The collector of Embodiment 84, wherein the conversion device comprises a cylindrical photovoltaic converter having, a first collector extending along a longitudinal axis of the cylindrical photovoltaic converter, a p-type material disposed around the collection electrode, a n-type material disposed around the collection electrode, a peripheral second collector, at least one of the p-type material or the n-type material is in contact with the first collector, a remaining one of the p-type material or the n-type material, not in contact with the first collector, is in contact with the second collector, the p-type material and the n-type material form a cylindrical intrinsic layer disposed around the longitudinal axis and extending along the longitudinal axis, and the at least one energy augmentation structure comprises a folded resonator having opposing electrodes producing the electric fields, and the electric fields permeate into one or more of the p-type material, the n-type material, and the cylindrical intrinsic layer.

Embodiment 95. The collector of Embodiment 84, wherein the conversion device comprises a thermoelectric device having a radiant absorber including the at least one energy augmentation structure, a first leg of n-type material, the first leg connected to a first side of the absorber, a second leg of p-type material, the second leg connected to a second side of the absorber, and a heat sink coupled to the first leg and the second leg to cool the first and second legs.

Embodiment 96. The collector of Embodiment 95, wherein the at least one energy augmentation structure comprises a folded resonator.

Embodiment 97. The collector of Embodiment 96, wherein the folded resonator comprises a ¾λfolded resonator.

Embodiment 98. The collector of Embodiment 84, wherein the conversion device comprises a thermionic device having a radiant absorber including the at least one energy augmentation structure, an electron emitter for emitting electrons from therefrom, and an electron collector for collecting the emitted electrons.

Embodiment 99. The collector of Embodiment 98, further comprising a heat sink coupled to the electron collector to cool the electron collector.

Embodiment 100. The collector of Embodiment 98 or 99, wherein a vacuum exists between the electron emitter and the electron collector.

Embodiment 101. The collector of any one of Embodiments 98-100, wherein the at least one energy augmentation structure comprises a folded resonator.

Embodiment 102. The collector of Embodiment 101, wherein the folded resonator comprises a ¾λfolded resonator.

Embodiment 103. The collector of any one of Embodiments 84-102, further comprising at least one of an upconverter or a downconverter absorbing the energy from the radiant source and emitting respectfully light upconverted to higher energy or down converted to lower energy, and wherein the at least one energy augmentation structure is disposed in a vicinity of the upconverter or the downconverter, and the electric fields permeate into the upconverter or the downconverter.

Embodiment 104. The collector of any one of Embodiments 84-103, wherein the conversion device comprises an array of solar collectors comprising a first set and a second set of photovoltaic cells, the at least one energy augmentation structure comprises a first resonator dimensioned to be resonant with a first spectrum of solar radiation and a second resonator dimensioned to be resonant with a second spectrum of solar radiation, the first set of photovoltaic cells is capable of converting the first spectrum of solar radiation into electrical power, and the second set of photovoltaic cells is capable of converting the second spectrum of solar radiation into electrical power.

Embodiment 105. The collector of Embodiment 104, wherein the first set and the second set of photovoltaic cells are disposed such that the solar radiation scattered from one photovoltaic cell is collected by another photovoltaic cell.

Embodiment 106. The collector of Embodiment 104, wherein the first set and the second set of photovoltaic cells are disposed at different levels whereby the solar radiation scattered from one photovoltaic cell is collected by another photovoltaic cell at a lower level.

Embodiment 107. The collector of any one of Embodiments 84-106, wherein the conversion device comprises an inorganic semiconductor or an organic semiconductor.

Embodiment 108. The collector of any one of Embodiments 84-106, wherein the conversion device comprises amorphous, polycrystalline, of monocrystalline silicon photovoltaic cell.

Embodiment 109. The collector of any one of Embodiments 84-106, wherein the conversion device comprises a direct gap material photovoltaic cell.

Embodiment 110. The collector of Embodiment 109, wherein the direct gap material photovoltaic cell comprises at least one of GaAs, AlGaAs, and InGaAs.

Embodiment 111. The collector of any one of Embodiments 84-106, wherein the conversion device further comprises:

an upconverter including at least one of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}:Cs_2NaGdCl_6$, $Nd^{3+}$, $Yb^{3+}:Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2—Ga_2O_3—R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 112. The collector of any one of Embodiments 84-106, wherein the conversion device comprises:

a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$.

Embodiment 113. The collector of any one of Embodiments 84-106, wherein the conversion device comprises:

a mixture including, 1) at least one of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine), and 2) at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 114. The collector of any one of Embodiments 84-106, wherein the conversion device comprises:

a mixture including at least two or more of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 115. The collector of any one of Embodiments 84-106, wherein the conversion device comprises:

a mixture including at least two or more of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 116. The collector of any one of Embodiments 84-115, wherein the conversion device is configured to down-converts a radiant source of energy from a high energy source of x-rays, gamma rays, and other high energy particles into a specific energy spectrum for power conversion.

Embodiment 117. The collector of Embodiment 116, wherein the radiant source of energy comprises a radioactive source including at least one of a Cobalt 60 source, a Cesium-137 source, an Iridium-192 source, a Krypton-85 source, a Radium-226 source, and a Strontium-90 source.

Embodiment 118. The collector of any one of Embodiments 84-117, wherein the conversion device comprises a plurality of particles which upon radiation from the radiant source of energy radiate at higher or lower energies.

Embodiment 119. The collector of Embodiment 118, wherein the particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

Embodiment 120. The collector of Embodiment 119, comprising the metallic shell, and a radial dimension of the metallic shell is set to a value where a surface plasmon resonance in the metallic shell resonates at a frequency which provides spectral overlap with either an absorption band or an emission band of the particle.

Embodiment 121. The collector of Embodiment 120, wherein the metallic shell comprises a plasmonic shell configured to enhance at least one of said absorption or said emission.

Embodiment 122. The collector of Embodiment 121, wherein the metallic shell covers said dielectric core and comprises at least one of a spherical shell, an oblate shell, a crescent shell, or a multilayer shell.

Embodiment 123. The collector of Embodiment 122, wherein said shell comprises at least one of Au, Ag, Cu, Ni, Pt, Pd, Co, Ru, Rh, or a combination thereof.

Embodiment 124. The collector of Embodiment 118, wherein the particles comprise down-converting particles including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 125. The collector of Embodiment 118, wherein the particles comprise a dopant including at least one of Er, Eu, Yb, Tm, Nd, Tb, Ce, or a combination thereof.

Embodiment 126. The collector of Embodiment 125, wherein the dopant is included at a concentration of 0.01%-50% by mol concentration.

Embodiment 127. The collector of any one of Embodiments 84-106, wherein the radiant source comprises an infrared source.

Embodiment 128. The collector of any one of Embodiments 84-106, wherein the radiant source comprises a solar concentrator.

Embodiment 129. An energy collector comprising:

a conversion device capable of converting the energy from a radiant source into electrical power, the conversion device comprising a cylindrical photovoltaic converter having, a first collector extending along a longitudinal axis of the cylindrical photovoltaic converter, a p-type material disposed around the collection electrode, a n-type material disposed around the collection electrode, a peripheral second collector, at least one of the p-type material or the n-type material is in contact with the first collector, a remaining one of the p-type material or the n-type material, not in contact with the first collector, is in contact with the second collector, and the p-type material and the n-type material form a cylindrical intrinsic layer disposed around the longitudinal axis and extending along the longitudinal axis.

Embodiment 130. An energy collector comprising:

a conversion device capable of converting the energy from a radiant source into electrical power, the conversion device comprising a thermionic device having a radiant absorber comprising a folded resonator, the folded resonator having opposing electrodes, an electron emitter for emitting electrons therefrom and disposed on the opposing electrodes or in a vicinity of the opposing electrodes, and an electron collector for collecting the emitted electrons.

Embodiment 131. An energy collector comprising:

a conversion device capable of converting the energy from a radiant source into electrical power;

the conversion device comprising a folded resonator and at least one rectifying device connected in series with the folded resonator; and the at least one rectifying device configured to rectify oscillating current induced in the folded resonator from energy absorbed from a radiant source.

Embodiment 132. The collector of Embodiment 131, wherein the at least one rectifying device comprises a tunneling or vacuum diode.

Embodiment 133. The collector of Embodiment 132, comprising the tunneling diode, wherein the tunneling diode comprises a metal-insulator-metal diode.

Embodiment 134. A power conversion system comprising:

a power conversion device which produces electric power upon illumination;

at least one energy augmentation structure of any one of Embodiments 62-69; and a light conversion device which (i) down-converts, (ii) up-converts, or (iii) both down-converts and up-converts a radiant source of energy into a specific energy spectrum for said illumination of the power conversion device.

Embodiment 135. The system of Embodiment 134, wherein the radiant source comprises solar light.

Embodiment 136. The system of Embodiment 134 or 135, wherein the light conversion device comprises:

a first plurality of particles which upon radiation from the radiant source at a first radiation energy radiate at a higher energy than the first radiation energy; and a second plurality of particles which upon radiation from the radiant source at a second radiation energy radiate at a lower energy than the second radiation energy.

Embodiment 137. The system of Embodiment 136, wherein at least one of the first and second plurality of particles comprises at least one of a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

Embodiment 138. The system of Embodiment 137, wherein a radial dimension of the metallic shell is set to a value where a surface plasmon resonance in the metallic shell resonates at a frequency which provides spectral overlap with either an absorption band or an emission band of the particles.

Embodiment 139. The system of Embodiment 137, wherein the metallic shell comprises a plasmonic shell configured to enhance at least one of said absorption or said emission.

Embodiment 140. The system of Embodiment 136, wherein at least one of the first and second plurality of particles comprises a dielectric material including elements having energetic states for absorption of a first wavelength $\lambda_1$ and recombination states for emission of a second wavelength $\lambda_2$.

Embodiment 141. The system of Embodiment 136, wherein at least one of the first and second of the plurality of particles comprises particles having a dielectric core.

Embodiment 142. The system of Embodiment 141, wherein a metallic shell covers said dielectric core and comprises at least one of a spherical shell, an oblate shell, a crescent shell, or a multilayer shell.

Embodiment 143. The system of Embodiment 142, wherein said shell comprises at least one of Au, Ag, Cu, Ni, Pt, Pd, Co, Ru, Rh, or a combination thereof.

Embodiment 144. The system of Embodiment 136, wherein at least one of the first and second of the plurality of particles comprises down-converting particles including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn, $Er^{3+}$.

Embodiment 145. The system of Embodiment 136, wherein at least one of the first and second of the plurality of particles comprises up-converting particles including at least one of $Y_2O_3$, $Y_2O_2S$, $NaYF_4$, YAG, YAP, or $Nd_2O_3$, $LaF_3$, $LaCl_3$ $La_2O_3$, $TiO_2$, $SiO_2$.

Embodiment 146. The system of Embodiment 145, wherein at least one of the first and second of the plurality of particles comprises a dopant including at least one of Er, Eu, Yb, Tm, Nd, Tb, Ce, or a combination thereof.

Embodiment 147. The system of Embodiment 146, wherein the dopant is included at a concentration of 0.01%-50% by mol concentration.

Embodiment 148. The system of Embodiment 136, wherein the first plurality of particles is configured to exhibit visible emission upon interaction with a first wavelength $\lambda_1$ at a lower energy than visible light.

Embodiment 149. The system of Embodiment 136, wherein the second plurality of particles is configured to exhibit visible emission upon interaction with a first wavelength $\lambda_1$ at a higher energy than visible light.

Embodiment 150. The system of Embodiment 136, wherein:

the first plurality of particles is configured to exhibit visible emission upon interaction with a first wavelength $\lambda_1$ at a lower energy than visible light; and the second plurality of particles is configured to exhibit visible emission upon interaction with a first wavelength $\lambda_1$ at a higher energy than visible light.

Embodiment 151. The system of Embodiment 134, wherein the light conversion device comprises:

a cover material transparent to solar radiation; and a plurality of particles which upon radiation from an energy range of the solar radiation removed from said specific energy spectrum radiate in the specific energy spectrum.

Embodiment 152. The system of Embodiment 151, wherein the plurality of particles are dispersed in the cover material.

Embodiment 153. The system of Embodiment 151, wherein the plurality of particles are disposed on a side of the cover material.

Embodiment 154. The system of Embodiment 134, wherein the light conversion device comprises:

first converters configured to emit, upon exposure to an energy source, light at a first wavelength in response to absorption of energy across a first band of wavelengths; and second converters configured to emit, upon exposure to the energy source, light at a second wavelength in response to absorption of energy across a second band of wavelengths.

Embodiment 155. The system of Embodiment 154, wherein:

the power conversion device comprises a conversion device designed with an optimum excitation wavelength; and the first wavelength and the second wavelength are matched to the optimum excitation wavelength.

Embodiment 156. The system of Embodiment 154, wherein:

the power conversion device comprises plural conversion devices designed with respective optimum excitation wavelengths; and the first wavelength and the second wavelength are matched to the respective optimum excitation wavelengths.

Embodiment 157. The system of Embodiment 154, wherein the first and second converters comprise:

a first material configured to emit in response to absorption of ultraviolet light; and a second material configured to emit in response to absorption of infrared light.

Embodiment 158. The system of Embodiment 134, wherein the light conversion device comprises:

an upconverter including at least one of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}:Cs_2NaGdCl_6$, $Nd^{3+}$, $Yb^{3+}:Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 159. The system of Embodiment 134, wherein the light conversion device comprises:

a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$.

Embodiment 160. The system of Embodiment 134, wherein the light conversion device comprises:

a mixture including, 1) at least one of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}:Cs_2NaGdCl_6$, $Nd^{3+}$, $Yb^{3+}:Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine), and 2) at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+ Er3+. $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$.

Embodiment 161. The system of Embodiment 134, wherein the light conversion device comprises:

a mixture including at least two or more of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}:Cs_2NaGdCl_6$, $Nd^{3+}$, $Yb^{3+}:Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 162. The system of Embodiment 134, wherein the light conversion device comprises:

a mixture including at least two or more of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$.

Embodiment 163. The system of Embodiment 134, wherein the power conversion device comprises at least one of:

a conversion device designed with an optimum excitation wavelength; or plural conversion devices designed with respective optimum excitation wavelengths.

Embodiment 164. A power conversion system comprising:

a power conversion device which produces electric power upon illumination;

at least one energy augmentation structure of any one of Embodiments 62-69; and a light conversion device which down-converts a radiant source of energy from a high energy source of x-rays, gamma rays, and other high energy particles into a specific energy spectrum for said illumination of the power conversion device.

Embodiment 165. The system of Embodiment 164, wherein the radiant source of energy comprises a radioactive source including at least one of a Cobalt 60 source, a Cesium-137 source, an Iridium-192 source, a Krypton-85 source, a Radium-226 source, and a Strontium-90 source.

Embodiment 166. The system of Embodiment 164 or 165, wherein the light conversion device comprises a plurality of particles which upon radiation from an energy range removed from said specific energy spectrum radiate at lower energies in the specific energy spectrum.

Embodiment 167. The system of Embodiment 166, wherein the plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

Embodiment 168. The system of Embodiment 167, wherein a radial dimension of the metallic shell is set to a value where a surface plasmon resonance in the metallic shell resonates at a frequency which provides spectral overlap with either an absorption band or an emission band of the particle.

Embodiment 169. The system of Embodiment 167, wherein the metallic shell comprises a plasmonic shell configured to enhance at least one of said absorption or said emission.

Embodiment 170. The system of Embodiment 166, wherein the particles comprise a dielectric material including elements having energetic states for absorption of a first wavelength $\lambda_1$ and recombination states for emission of a second wavelength $\lambda_2$.

Embodiment 171. The system of Embodiment 166, wherein the particles comprises particles having a dielectric core.

Embodiment 172. The system of Embodiment 171, wherein a metallic shell covers said dielectric core and comprises at least one of a spherical shell, an oblate shell, a crescent shell, or a multilayer shell.

Embodiment 173. The system of Embodiment 172, wherein said shell comprises at least one of Au, Ag, Cu, Ni, Pt, Pd, Co, Ru, Rh, or a combination thereof.

Embodiment 174. The system of Embodiment 166, wherein the particles comprise down-converting particles including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 175. The system of Embodiment 166, wherein the particles comprise a dopant including at least one of Er, Eu, Yb, Tm, Nd, Tb, Ce, or a combination thereof.

Embodiment 176. The system of Embodiment 175, wherein the dopant is included at a concentration of 0.01%-50% by mol concentration.

Embodiment 177. The system of Embodiment 176, wherein the particles are configured to exhibit visible emission upon interaction with a first wavelength $\lambda_1$ at a higher energy than visible light.

Embodiment 178. The system of Embodiment 164, wherein the light conversion device comprises:

a cover material transparent to the radiant source; and a plurality of particles which upon radiation from the radiant source radiate at lower energies in the specific energy spectrum.

Embodiment 179. The system of Embodiment 178, wherein the plurality of particles are dispersed in the cover material.

Embodiment 180. The system of Embodiment 178, wherein the plurality of particles are disposed on a side of the cover material.

Embodiment 181. The system of Embodiment 164, wherein the light conversion device comprises:

a mixture including at least two or more of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 182. The system of Embodiment 164, wherein the power conversion device comprises at least one of:

a conversion device designed with an optimum excitation wavelength; or plural conversion devices designed with respective optimum excitation wavelengths.

Embodiment 183. A power conversion system comprising:

a power conversion device which produces electric power upon illumination;

at least one energy augmentation structure of any one of Embodiments 62-69; and a light conversion device which up-converts a radiant source of energy from a low energy source of radiation into a specific energy spectrum for said illumination of the power conversion device.

Embodiment 184. The system of Embodiment 183, wherein the radiant source comprises an infrared source.

Embodiment 185. The system of Embodiment 183, wherein the light conversion device comprises a plurality of particles which upon radiation from an energy range removed from said specific energy spectrum radiate at higher energies in the specific energy spectrum.

Embodiment 186. The system of Embodiment 185, wherein the plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

Embodiment 187. The system of Embodiment 186, wherein a radial dimension of the metallic shell is set to a value where a surface plasmon resonance in the metallic shell resonates at a frequency which provides spectral overlap with either an absorption band or an emission band of the particle.

Embodiment 188. The system of Embodiment 186, wherein the metallic shell comprises a plasmonic shell configured to enhance at least one of said absorption or said emission.

Embodiment 189. The system of Embodiment 185, wherein the particles includes a dielectric material including elements having energetic states for absorption of the first wavelength $\lambda_1$ and recombination states for emission of the second wavelength $\lambda_2$.

Embodiment 190. The system of Embodiment 185, wherein the particles comprises particles having a dielectric core.

Embodiment 191. The system of Embodiment 190, wherein a metallic shell covers said dielectric core and comprises at least one of a spherical shell, an oblate shell, a crescent shell, or a multilayer shell.

Embodiment 192. The system of Embodiment 190, wherein said shell comprises at least one of Au, Ag, Cu, Ni, Pt, Pd, Co, Ru, Rh, or a combination thereof.

Embodiment 193. The system of Embodiment 185, wherein the particles comprise at least one of $Y_2O_3$, $Y_2O_2S$, $NaYF_4$, YAG, YAP, or $Nd_2O_3$, $LaF_3$, $LaCl_3$ $La_2O_3$, $TiO_2$, $SiO_2$.

Embodiment 194. The system of Embodiment 185, wherein the particles comprise a dopant including at least one of Er, Eu, Yb, Tm, Nd, Tb, Ce, or a combination thereof.

Embodiment 195. The system of Embodiment 194, wherein the dopant is included at a concentration of 0.01%-50% by mol concentration.

Embodiment 196. The system of Embodiment 185, wherein the particles are configured to exhibit visible emission upon interaction with a first wavelength $\lambda_1$ at a lower energy than visible light.

Embodiment 197. The system of Embodiment 183, wherein the light conversion device comprises:

a cover material transparent to infrared radiation; and a plurality of particles which upon radiation from the infrared radiation radiate at higher energies in the specific energy spectrum.

Embodiment 198. The system of Embodiment 197, wherein the plurality of particles are dispersed in the cover material.

Embodiment 199. The system of Embodiment 197, wherein the plurality of particles are disposed on a side of the cover material.

Embodiment 200. The system of Embodiment 183, wherein the light conversion device comprises:

a mixture including at least two or more of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 201. The system of Embodiment 183, wherein the power conversion device comprises at least one of:

a conversion device designed with an optimum excitation wavelength; or plural conversion devices designed with respective optimum excitation wavelengths.

Embodiment 202. A conversion element comprising:

at least one energy augmentation structure of any one of Embodiments 62-69;

a first plurality of particles which upon radiation from a first radiation source radiate at a first energy than the first radiation source;

a second plurality of particles which upon radiation from the first radiation source radiate at a second energy; and at least one of the first plurality of particles and the second plurality of particles is at least partially coated with a shell material including at least one of a metallic, a semiconductive, or an insulative material.

Embodiment 203. The element of Embodiment 202, further comprising:

a cover material transparent to solar radiation;

said first plurality of particles which upon radiation from wavelengths of the solar radiation lower than a specific energy range of the solar spectrum radiate at the specific energy range; and said second plurality of particles which upon radiation from wavelengths of the solar radiation higher than the specific energy range of the solar spectrum radiate at the specific energy range.

Embodiment 204. The element of Embodiment 203, wherein the plurality of particles are dispersed in the cover material or on a side of the cover material.

Embodiment 205. The element of Embodiment 202, wherein the plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the first radiation source; and quantum dots of a distributed size.

Embodiment 206. The system of Embodiment 202, wherein the plurality of particles comprises:

a mixture including, 1) at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine), and 2) at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+ Er3+. ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 207. The system of Embodiment 202, wherein the plurality of particles comprises:

a mixture including at least two or more of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 208. The system of Embodiment 202, wherein the plurality of particles comprises:

a mixture including at least two or more of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+, $Er^{3+}$; ZnS:$Tb^{3+}$; $Y_2O_3$:$Tb^{3+}$; $Y_2O_3$:$Tb^{3+}$, $Er^{3+}$; ZnS:Mn2+; ZnS:Mn,$Er^{3+}$.

Embodiment 209. A conversion element comprising:

at least one energy augmentation structure of any one of Embodiments 62-69; and a plurality of particles at least partially metal coated, which upon radiation from a high energy radiant source radiate at a lower energy than the high energy radiant source.

Embodiment 210. The element of Embodiment 209, further comprising:

a cover material transparent to a high energy radiation.

Embodiment 211. The element of Embodiment 210, wherein the plurality of particles are dispersed in the cover material or on a side of the cover material.

Embodiment 212. The element of Embodiment 210, wherein the plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

Embodiment 213. The system of Embodiment 209, wherein the plurality of particles comprises:

a mixture including, 1) at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine), and 2) at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb3+ $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 214. The system of Embodiment 209, wherein the plurality of particles comprises:

a mixture including at least two or more of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R═Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 215. The system of Embodiment 209, wherein the plurality of particles comprises:

a mixture including at least two or more of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn,$Er^{3+}$.

Embodiment 216. A conversion element comprising:

at least one energy augmentation structure of any one of Embodiments 62-69; and a plurality of particles at least partially metal coated, which upon radiation from an infrared radiation source radiate at a higher energy than the infrared radiation source.

Embodiment 217. The element of Embodiment 216, further comprising:

a cover material transparent to infrared radiation.

Embodiment 218. The system of Embodiment 217, wherein the plurality of particles are dispersed in the cover material or on a side of the cover material.

Embodiment 219. The system of Embodiment 217, wherein the plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

Embodiment 220. The system of Embodiment 216, wherein the plurality of particles comprises:

a mixture including, 1) at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R═Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine), and 2) at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$ $Er^{3+}$. ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

Embodiment 221. The system of Embodiment 216, wherein the plurality of particles comprises:

a mixture including at least two or more of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R═Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

Embodiment 222. The system of Embodiment 216, wherein the plurality of particles comprises:

a mixture including at least two or more of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn,$Er^{3+}$.

Embodiment 223. A light carrier comprising:

at least one energy augmentation structure of any one of Embodiments 62-69;

at least one fiber optic for transmission of light along a length of the fiber optic; and a converter on a first end to the fiber optic, said converter (i) down-converts, (ii) up-converts, or (iii) both down-converts and up-converts a radiant energy from a radiant source into a specific energy spectrum for illumination of an object downstream from a second end of the fiber optic.

Embodiment 224. The carrier of Embodiment 223, further comprising:

a diffuser to diffuse light exiting the second end of the fiber optic.

Embodiment 225. The carrier of Embodiment 223, further comprising:

a controller disposed in relation to the at least one fiber to control a light intensity exiting the fiber optic.

Embodiment 226. The carrier of Embodiment 224, wherein the converter comprises:

a first plurality of particles which upon radiation from the radiant source at a first radiation energy radiate at a higher energy than the first radiation energy; and a second plurality of particles which upon radiation from the radiant source at a second radiation energy radiate at a lower energy than the second radiation energy.

Embodiment 227. The carrier of Embodiment 226, wherein at least one of the first and second plurality of particles comprises at least one of a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

Embodiment 228. The carrier of Embodiment 227, wherein a radial dimension of the metallic shell is set to a value where a surface plasmon resonance in the metallic shell resonates at a frequency which provides spectral overlap with either an absorption band or an emission band of the particles.

Embodiment 229. The carrier of Embodiment 227, wherein the metallic shell comprises a plasmonic shell configured to enhance at least one of said absorption or said emission.

Embodiment 230. The carrier of Embodiment 226, wherein at least one of the first and second plurality of particles comprises a dielectric material including elements having energetic states for absorption of a first wavelength $\lambda_1$ and recombination states for emission of a second wavelength $\lambda_2$.

Embodiment 231. The carrier of Embodiment 226, wherein at least one of the first and second of the plurality of particles comprises particles having a dielectric core.

Embodiment 232. The carrier of Embodiment 231, wherein a metallic shell covers said dielectric core and comprises at least one of a spherical shell, an oblate shell, a crescent shell, or a multilayer shell.

Embodiment 233. The carrier of Embodiment 232, wherein said shell comprises at least one of Au, Ag, Cu, Ni, Pt, Pd, Co, Ru, Rh, or a combination thereof.

Embodiment 234. The system of Embodiment 226, wherein at least one of the first and second of the plurality of particles comprises down-converting particles including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn, $Er^{3+}$.

Embodiment 235. The carrier of Embodiment 226, wherein at least one of the first and second of the plurality of particles comprises up-converting particles including at least one of $Y_2O_3$, $Y_2O_2S$, $NaYF_4$, YAG, YAP, or $Nd_2O_3$, $LaF_3$, $LaCl_3$ $La_2O_3$, $TiO_2$, $SiO_2$.

Embodiment 236. The carrier of Embodiment 235, wherein at least one of the first and second of the plurality of particles comprises a dopant including at least one of Er, Eu, Yb, Tm, Nd, Tb, Ce, or a combination thereof.

Embodiment 237. The carrier of Embodiment 236, wherein the dopant is included at a concentration of 0.01%-50% by mol concentration.

Embodiment 238. The carrier of Embodiment 226, wherein the first plurality of particles is configured to exhibit visible emission upon interaction with a first wavelength $\lambda_1$ at a lower energy than visible light.

Embodiment 239. The carrier of Embodiment 226, wherein the second plurality of particles is configured to exhibit visible emission upon interaction with a first wavelength $\lambda_1$ at a higher energy than visible light.

Embodiment 240. The carrier of Embodiment 226, wherein:

the first plurality of particles is configured to exhibit visible emission upon interaction with a first wavelength $\lambda_1$ at a lower energy than visible light; and the second plurality of particles is configured to exhibit visible emission upon interaction with a first wavelength $\lambda_1$ at a higher energy than visible light.

Embodiment 241. The carrier of Embodiment 224, wherein the converter comprises:

a plurality of particles which upon radiation from an energy range of the solar radiation removed from said specific energy spectrum radiate in the specific energy spectrum.

Embodiment 242. A system for power conversion and lighting, comprising:

a power conversion device which produces electric power upon illumination by light from a light source;

at least one energy augmentation structure of any one of Embodiments 62-69;

at least one fiber optic for transmission of the light along a length of the fiber optic; and a light conversion device on a first end to the fiber optic, said light conversion device (i) down-converts, (ii) up-converts, or (iii) both d own-converts and up-converts the light into a second specific energy spectrum for illumination of an object downstream from a second end of the fiber optic.

Embodiment 243. The system of Embodiment 242, further comprising:

a light control mechanism configured to modify the light entering the at least one fiber optic.

Embodiment 244. The system of Embodiment 242, wherein the light control mechanism is placed at a level proximate the power conversion device.

Embodiment 245. The system of Embodiment 243, wherein the light control mechanism comprises a rotary cassette having at least one aperture for directing the light into the at least one fiber optic.

Embodiment 246. The system of Embodiment 245, wherein the rotary cassette comprises multiple apertures configured to modify at least one of a color, an intensity, or a path of the light.

Embodiment 247. The system of Embodiment 246, wherein at least one of the multiple apertures comprises an open aperture wherein the light is directed unaltered into the at least one fiber optic.

Embodiment 248. The system of Embodiment 246, wherein at least one of the multiple apertures comprises a lens to modulate an intensity of the light directed into the at least one fiber optic.

Embodiment 249. The system of Embodiment 246, wherein at least one of the multiple apertures comprises a color filter to change a color of the light directed into the at least one fiber optic.

Embodiment 250. The system of Embodiment 246, wherein at least one of the multiple apertures comprises an electro-optic filter configured to change an attenuation or polarization of the solar light directed into the at least one fiber optic.

Embodiment 251. The system of Embodiment 250, further comprising a controller configured to control the electro-optic filter.

Embodiment 252. The system of Embodiment 242, wherein the power conversion device is configured to produce power from solar light.

Embodiment 253. The system of Embodiment 242, further comprising a solar light source for said light source.

Embodiment 254. The system of Embodiment 253, wherein the solar light source comprises a solar concentrator.

Embodiment 255. The system of Embodiment 242, further comprising a non-solar light source for said light source.

Embodiment 256. The system of Embodiment 255, wherein the non-solar light source comprises at least one of a halogen lamp source, an arc-lamp source, or a diode light source.

Embodiment 257. A system for lighting distribution, comprising:

a receptor of light from a light source; and at least one fiber optic for transmission of the light along a length of the fiber optic;

at least one energy augmentation structure of any one of Embodiments 62-69; and a light conversion device on a first end to the fiber optic, said light conversion device (i) down-converts, (ii) up-converts, or (iii) both d own-converts and up-converts the light into a second specific energy spectrum for illumination of an object downstream from a second end of the fiber optic.

Embodiment 258. The system of Embodiment 257, further comprising:

a light control mechanism configured to modify the light entering the at least one fiber optic.

Embodiment 259. The system of Embodiment 258, wherein the light control mechanism comprises a rotary cassette having at least one aperture for directing the light into the at least one fiber optic.

Embodiment 260. The system of Embodiment 259, wherein the rotary cassette comprises multiple apertures configured to modify at least one of a color, an intensity, or a path of the light.

Embodiment 261. The system of Embodiment 260, wherein at least one of the multiple apertures comprises an open aperture wherein the light is directed unaltered into the at least one fiber optic.

Embodiment 262. The system of Embodiment 260, wherein at least one of the multiple apertures comprises a lens to modulate an intensity of the light directed into the at least one fiber optic.

Embodiment 263. The system of Embodiment 260, wherein at least one of the multiple apertures comprises a color filter to change a color of the light directed into the at least one fiber optic.

Embodiment 264. The system of Embodiment 260, wherein at least one of the multiple apertures comprises an electro-optic filter configured to change an attenuation or polarization of the solar light directed into the at least one fiber optic.

Embodiment 265. The system of Embodiment 264, further comprising a controller configured to control the electro-optic filter.

Embodiment 266. The system of Embodiment 257, further comprising a solar light source for said light source.

Embodiment 267. The system of Embodiment 266, wherein the solar light source comprises a solar concentrator.

Embodiment 268. The system of Embodiment 257, further comprising anon-solar light source for said light source.

Embodiment 269. The system of Embodiment 268, wherein the non-solar light source comprises at least one of a halogen lamp source, an arc-lamp source, or a diode light source.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The invention claimed is:

1. A power conversion system comprising:

a power conversion device which produces electric power upon illumination;

at least one energy augmentation structure capable of capturing one or more wavelengths of electromagnetic energy, and augmenting the one or more wavelengths of electromagnetic energy in at least one property, wherein the at least one energy augmentation structure comprises a 3/4λfolded resonator; and a light conversion device which (i) down-converts, (ii) up-converts, or (iii) both down-converts and up-converts a radiant source of energy into a specific energy spectrum for said illumination of the power conversion device.

2. The system of claim 1, wherein the radiant source comprises solar light.

3. The system of claim 1, wherein the light conversion device comprises:

a first plurality of particles which upon radiation from the radiant source at a first radiation energy radiate at a higher energy than the first radiation energy; and a second plurality of particles which upon radiation from the radiant source at a second radiation energy radiate at a lower energy than the second radiation energy.

4. The system of claim 3, wherein at least one of the first and second plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

5. The system of claim 4, wherein a radial dimension of the metallic shell is set to a value where a surface plasmon resonance in the metallic shell resonates at a frequency which provides spectral overlap with either an absorption band or an emission band of the particles.

6. The system of claim 4, wherein the metallic shell comprises a plasmonic shell configured to enhance at least one of said absorption or said emission.

7. The system of claim 3, wherein at least one of the first and second plurality of particles comprises a dielectric material including elements having energetic states for absorption of a first wavelength $\lambda_1$ and recombination states for emission of a second wavelength $\lambda_2$.

8. The system of claim 3, wherein at least one of the first and second of the plurality of particles comprises particles having a dielectric core.

9. The system of claim 8, wherein a metallic shell covers said dielectric core and comprises at least one of a spherical shell, an oblate shell, a crescent shell, or a multilayer shell.

10. The system of claim 9, wherein said shell comprises at least one of Au, Ag, Cu, Ni, Pt, Pd, Co, Ru, Rh, or a combination thereof.

11. The system of claim 3, wherein at least one of the first and second of the plurality of particles comprises down-converting particles including at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

12. The system of claim 3, wherein at least one of the first and second of the plurality of particles comprises up-converting particles including at least one of $Y_2O_3$, $Y_2O_2S$, $NaYF_4$, YAG, YAP, or $Nd_2O_3$, $LaF_3$, $LaCl_3$ $La_2O_3$, $TiO_2$, $SiO_2$.

13. The system of claim 12, wherein at least one of the first and second of the plurality of particles comprises a dopant including at least one of Er, Eu, Yb, Tm, Nd, Tb, Ce, or a combination thereof.

14. The system of claim 13, wherein the dopant is included at a concentration of 0.01%-50% by mol concentration.

15. The system of claim 3, wherein the first plurality of particles is configured to exhibit visible emission upon interaction with a first wavelength $\lambda_1$ at a lower energy than visible light.

16. The system of claim 3, wherein the second plurality of particles is configured to exhibit visible emission upon interaction with a first wavelength $\lambda_1$ at a higher energy than visible light.

17. The system of claim 3, wherein:

the first plurality of particles is configured to exhibit visible emission upon interaction with a first wavelength $\lambda_1$ at a lower energy than visible light; and the second plurality of particles is configured to exhibit visible emission upon interaction with a first wavelength $\lambda_1$ at a higher energy than visible light.

18. The system of claim 1, wherein the light conversion device comprises:

a cover material transparent to solar radiation; and a plurality of particles which upon radiation from an energy range of the solar radiation removed from said specific energy spectrum radiate in the specific energy spectrum.

19. The system of claim 18, wherein the plurality of particles are dispersed in the cover material.

20. The system of claim 18, wherein the plurality of particles are disposed on a side of the cover material.

21. The system of claim 1, wherein the light conversion device comprises:

first converters configured to emit, upon exposure to an energy source, light at a first wavelength in response to absorption of energy across a first band of wavelengths; and second converters configured to emit, upon exposure to the energy source, light at a second wavelength in response to absorption of energy across a second band of wavelengths.

22. The system of claim 21, wherein:

the power conversion device comprises a conversion device designed with an optimum excitation wavelength; and the first wavelength and the second wavelength are matched to the optimum excitation wavelength.

23. The system of claim 21, wherein:

the power conversion device comprises plural conversion devices designed with respective optimum excitation wavelengths; and the first wavelength and the second wavelength are matched to the respective optimum excitation wavelengths.

24. The system of claim 21, wherein the first and second converters comprise:

a first material configured to emit in response to absorption of ultraviolet light; and a second material configured to emit in response to absorption of infrared light.

25. The system of claim 1, wherein the light conversion device comprises:

an upconverter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

26. The system of claim 1, wherein the light conversion device comprises:

a down converter including at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$: $Tb^{3+}$; $Y_2O_3$:$Tb^{3+}$, $Er^{3+}$; ZnS:$Mn^{2+}$; ZnS:Mn, $Er^{3+}$.

27. The system of claim 1, wherein the light conversion device comprises:

a mixture including,

1) At least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine), and 2) At least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$: $Tb^{3+}$; $Y_2O_3$:$Tb^{3+}$, $Er^{3+}$; ZnS:$Mn^{2+}$; ZnS:Mn, $Er^{3+}$.

28. The system of claim 1, wherein the light conversion device comprises:

a mixture including at least two or more of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

29. The system of claim 1, wherein the light conversion device comprises:

a mixture including at least two or more of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$: $Tb^{3+}$; $Y_2O_3$:$Tb^{3+}$, $Er^{3+}$; ZnS:$Mn^{2+}$; ZnS:Mn, $Er^{3+}$.

30. The system of claim 1, wherein the power conversion device comprises at least one of:

a conversion device designed with an optimum excitation wavelength; or plural conversion devices designed with respective optimum excitation wavelengths.

31. The system of claim 1, wherein the at least one energy augmentation structure comprises a fractal antenna.

32. A power conversion system comprising:

a power conversion device which produces electric power upon illumination;

at least one energy augmentation structure capable of capturing one or more wavelengths of electromagnetic energy, and augmenting the one or more wavelengths of electromagnetic energy in at least one property, wherein the at least one energy augmentation structure comprises a 3/4λfolded resonator; and a light conversion device which down-converts a radiant source of energy from a high energy source of x-rays, gamma rays, and other high energy particles into a specific energy spectrum for said illumination of the power conversion device.

33. The system of claim 32, wherein the radiant source of energy comprises a radioactive source including at least one of a Cobalt 60 source, a Cesium-137 source, an Iridium-192 source, a Krypton-85 source, a Radium-226 source, and a Strontium-90 source.

34. The system of claim 32, wherein the light conversion device comprises a plurality of particles which upon radiation from an energy range removed from said specific energy spectrum radiate at lower energies in the specific energy spectrum.

35. The system of claim 34, wherein the plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

36. The system of claim 35, wherein a radial dimension of the metallic shell is set to a value where a surface plasmon resonance in the metallic shell resonates at a frequency which provides spectral overlap with either an absorption band or an emission band of the particle.

37. The system of claim 35, wherein the metallic shell comprises a plasmonic shell configured to enhance at least one of said absorption or said emission.

38. The system of claim 34, wherein the particles comprise a dielectric material including elements having energetic states for absorption of a first wavelength $\lambda_1$ and recombination states for emission of a second wavelength $\lambda_2$.

39. The system of claim 34, wherein the particles comprises particles having a dielectric core.

40. The system of claim 39, wherein a metallic shell covers said dielectric core and comprises at least one of a spherical shell, an oblate shell, a crescent shell, or a multilayer shell.

41. The system of claim 40, wherein said shell comprises at least one of Au, Ag, Cu, Ni, Pt, Pd, Co, Ru, Rh, or a combination thereof.

42. The system of claim 34, wherein the particles comprise down-converting particles including at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$: $Tb^{3+}$; $Y_2O_3$:$Tb^{3+}$, $Er^{3+}$; ZnS:$Mn^{2+}$; ZnS:Mn, $Er^{3+}$.

43. The system of claim 34, wherein the particles comprise a dopant including at least one of Er, Eu, Yb, Tm, Nd, Tb, Ce, or a combination thereof.

44. The system of claim 43, wherein the dopant is included at a concentration of 0.01%-50% by mol concentration.

45. The system of claim 44, wherein the particles are configured to exhibit visible emission upon interaction with a first wavelength $\lambda_1$ at a higher energy than visible light.

46. The system of claim 32, wherein the light conversion device comprises:

a cover material transparent to the radiant source; and a plurality of particles which upon radiation from the radiant source radiate at lower energies in the specific energy spectrum.

47. The system of claim 46, wherein the plurality of particles are dispersed in the cover material.

48. The system of claim 46, wherein the plurality of particles are disposed on a side of the cover material.

49. The system of claim 32, wherein the light conversion device comprises:

a mixture including at least two or more of $Y_2O_3$; ZnS; ZnSe; MgS; CaS; Mn, Er ZnSe;

Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$: $Tb^{3+}$; $Y_2O_3$:$Tb^{3+}$, $Er^{3+}$; ZnS:$Mn^{2+}$; ZnS:Mn, $Er^{3+}$.

50. The system of claim 32, wherein the power conversion device comprises at least one of:

a conversion device designed with an optimum excitation wavelength; or plural conversion devices designed with respective optimum excitation wavelengths.

51. The system of claim 32, wherein the at least one energy augmentation structure comprises a fractal antenna.

52. A power conversion system comprising:

a power conversion device which produces electric power upon illumination;

at least one energy augmentation structure capable of capturing one or more wavelengths of electromagnetic energy, and augmenting the one or more wavelengths of electromagnetic energy in at least one property, wherein the at least one energy augmentation structure comprises a 3/4λfolded resonator; and a light conversion device which up-converts a radiant source of energy from a low energy source of radiation into a specific energy spectrum for said illumination of the power conversion device.

53. The system of claim 52, wherein the radiant source comprises an infrared source.

54. The system of claim 52, wherein the light conversion device comprises a plurality of particles which upon radiation from an energy range removed from said specific energy spectrum radiate at higher energies in the specific energy spectrum.

55. The system of claim 54, wherein the plurality of particles comprises at least one of:

a metallic shell encapsulating at least a fraction of a surface of the particles;

a semiconductor shell encapsulating at least a fraction of a surface of the particles;

an insulator shell encapsulating at least a fraction of a surface of the particles;

particles having a size less than a wavelength of the radiant source; and quantum dots of a distributed size.

56. The system of claim 55, wherein a radial dimension of the metallic shell is set to a value where a surface plasmon resonance in the metallic shell resonates at a frequency which provides spectral overlap with either an absorption band or an emission band of the particle.

57. The system of claim 55, wherein the metallic shell is present and comprises a plasmonic shell configured to enhance at least one of said absorption or said emission.

58. The system of claim 54, wherein the particles includes a dielectric material including elements having energetic states for absorption of the first wavelength $\lambda_1$ and recombination states for emission of the second wavelength $\lambda_2$.

59. The system of claim 54, wherein the particles comprises particles having a dielectric core.

60. The system of claim 59, wherein a metallic shell covers said dielectric core and comprises at least one of a spherical shell, an oblate shell, a crescent shell, or a multilayer shell.

61. The system of claim 59, wherein said shell comprises at least one of Au, Ag, Cu, Ni, Pt, Pd, Co, Ru, Rh, or a combination thereof.

62. The system of claim 54, wherein the particles comprise at least one of $Y_2O_3$, $Y_2O_2S$, $NaYF_4$, YAG, YAP, or $Nd_2O_3$, $LaF_3$, $LaCl_3$ $La_2O_3$, $TiO_2$, $SiO_2$.

63. The system of claim 54, wherein the particles comprise a dopant including at least one of Er, Eu, Yb, Tm, Nd, Tb, Ce, or a combination thereof.

64. The system of claim 63, wherein the dopant is included at a concentration of 0.01%-50% by mol concentration.

65. The system of claim 54, wherein the particles are configured to exhibit visible emission upon interaction with a first wavelength $\lambda_1$ at a lower energy than visible light.

66. The system of claim 52, wherein the light conversion device comprises:

a cover material transparent to infrared radiation; and a plurality of particles which upon radiation from the infrared radiation radiate at higher energies in the specific energy spectrum.

67. The system of claim 66, wherein the plurality of particles are dispersed in the cover material.

68. The system of claim 66, wherein the plurality of particles are disposed on a side of the cover material.

69. The system of claim 52, wherein the light conversion device comprises:

a mixture including at least two or more of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}:Cs_2NaGdCl_6$, $Nd^{3+}$, $Yb^{3+}:Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2$—$Ga_2O_3$—$R_2O$ (R═Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

70. The system of claim 52, wherein the power conversion device comprises at least one of:

a conversion device designed with an optimum excitation wavelength; or plural conversion devices designed with respective optimum excitation wavelengths.

71. The system of claim 52, wherein the at least one energy augmentation structure comprises a fractal antenna.

* * * * *